United States Patent
Lu et al.

(10) Patent No.: US 10,098,951 B2
(45) Date of Patent: Oct. 16, 2018

(54) ANTIBODY/T-CELL RECEPTOR CHIMERIC CONSTRUCTS AND USES THEREOF

(71) Applicant: EUREKA THERAPEUTICS, INC., Emeryville, CA (US)

(72) Inventors: Jingwei Lu, Union City, CA (US); Zhiyuan Yang, Albany, CA (US); Cheng Liu, Emeryville, CA (US); Hong Liu, El Sobrante, CA (US); Yiyang Xu, Pleasanton, CA (US); Su Yan, State College, PA (US); Vivien Wai-Fan Chan, Emeryville, CA (US); Lucas Horan, Emeryville, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 0 days.

(21) Appl. No.: 15/829,793

(22) Filed: Dec. 1, 2017

(65) Prior Publication Data
US 2018/0085457 A1    Mar. 29, 2018

Related U.S. Application Data

(63) Continuation of application No. PCT/US2016/058305, filed on Oct. 21, 2016.

(60) Provisional application No. 62/245,944, filed on Oct. 23, 2015, provisional application No. 62/304,918, filed on Mar. 7, 2016, provisional application No. 62/345,649, filed on Jun. 3, 2016, provisional application No. 62/369,694, filed on Aug. 1, 2016.

(51) Int. Cl.
| | |
|---|---|
| C07K 16/00 | (2006.01) |
| A61K 39/395 | (2006.01) |
| A61K 35/17 | (2015.01) |
| C12N 15/62 | (2006.01) |
| C07K 14/725 | (2006.01) |
| C07K 16/28 | (2006.01) |
| A61K 38/00 | (2006.01) |
| A61K 39/00 | (2006.01) |

(52) U.S. Cl.
CPC ........ *A61K 39/39558* (2013.01); *A61K 35/17* (2013.01); *A61K 38/00* (2013.01); *C07K 14/7051* (2013.01); *C07K 16/2809* (2013.01); *C12N 15/62* (2013.01); *A61K 2039/505* (2013.01); *C07K 2317/522* (2013.01); *C07K 2317/55* (2013.01); *C07K 2317/56* (2013.01); *C07K 2317/622* (2013.01); *C07K 2317/73* (2013.01); *C07K 2319/00* (2013.01); *C07K 2319/03* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | |
|---|---|---|
| 3,753,357 A | 8/1973 | Schwartz |
| 4,199,022 A | 4/1980 | Senkan et al. |
| 4,559,298 A | 12/1985 | Fahy |
| 4,816,567 A | 3/1989 | Cabilly et al. |
| 5,229,275 A | 7/1993 | Goroff |
| 5,350,674 A | 9/1994 | Boenisch et al. |
| 5,399,346 A | 3/1995 | Anderson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,580,859 A | 12/1996 | Feigner et al. |
| 5,585,358 A | 12/1996 | Bialer et al. |
| 5,585,362 A | 12/1996 | Wilson et al. |
| 5,589,466 A | 12/1996 | Felgner et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,750,373 A | 5/1998 | Garrard et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |

(Continued)

FOREIGN PATENT DOCUMENTS

| | | |
|---|---|---|
| WO | WO-1997/02342 A1 | 1/1997 |
| WO | WO-1997/17852 A1 | 5/1997 |

(Continued)

OTHER PUBLICATIONS

Yun et al (Neoplasia, 2000, 2(5): 449-459).*
Torikai et al (Blood, 2012, 119(24): 5697-5705).*
Takihara et al (PNAS, 1988, 85: 6097-6101).*
Lefranc et al (PNAS, 1986, 83: 9596-9600).*
Ahuja, R. et al. (Sep. 10, 2014). "Human Oncogenic Viruses and Cancer," *Current Science* 107(5):768-785.
Anderson, W.F. (May 8, 1992). "Human Gene Therapy," *Science* 256(5058):808-813.

(Continued)

*Primary Examiner* — Sean E Aeder
(74) *Attorney, Agent, or Firm* — Morrison & Foerster LLP

(57) ABSTRACT

The present application provides antibody-TCR chimeric constructs comprising an antibody moiety that specifically binds to a target antigen fused to a TCRM capable of recruiting at least one TCR-associated signaling module. Also provided are methods of making and using these constructs.

46 Claims, 54 Drawing Sheets

Specification includes a Sequence Listing.

(56) References Cited

U.S. PATENT DOCUMENTS

| | | | |
|---|---|---|---|
| 7,172,869 | B2 | 2/2007 | June et al. |
| 7,175,843 | B2 | 2/2007 | June et al. |
| 7,232,566 | B2 | 6/2007 | June et al. |
| 7,741,465 | B1 | 6/2010 | Eshhar et al. |
| 10,011,658 | B2 | 7/2018 | Liu et al. |
| 2005/0079574 | A1 | 4/2005 | Bond |
| 2005/0119455 | A1 | 6/2005 | Fuh et al. |
| 2005/0266000 | A1 | 12/2005 | Bond et al. |
| 2006/0035320 | A1 | 2/2006 | Tissot et al. |
| 2006/0121005 | A1 | 6/2006 | Berenson et al. |
| 2007/0117126 | A1 | 5/2007 | Sidhu et al. |
| 2007/0160598 | A1 | 7/2007 | Dennis et al. |
| 2007/0237764 | A1 | 10/2007 | Birtalan et al. |
| 2007/0292936 | A1 | 12/2007 | Barthelemy et al. |
| 2008/0118512 | A1 | 3/2008 | Auf Der Maur et al. |
| 2008/0138336 | A1 | 6/2008 | Damschroder et al. |
| 2009/0002360 | A1 | 1/2009 | Chen et al. |
| 2009/0142349 | A1 | 6/2009 | Rao-Naik et al. |
| 2010/0005543 | A1 | 1/2010 | Sampson et al. |
| 2010/0153133 | A1 | 1/2010 | Igawa et al. |
| 2010/0183564 | A1 | 7/2010 | Boitano et al. |
| 2011/0286916 | A1 | 11/2011 | Aste-Amezaga et al. |
| 2011/0311517 | A1 | 12/2011 | Li et al. |
| 2012/0251579 | A1 | 10/2012 | Zender |
| 2014/0370022 | A1 | 12/2014 | Kim et al. |
| 2015/0118237 | A1 | 4/2015 | Kojoh et al. |
| 2015/0183877 | A1 | 7/2015 | Demarest et al. |
| 2015/0274828 | A1 | 10/2015 | Sun et al. |
| 2018/0134787 | A1 | 5/2018 | Liu et al. |

FOREIGN PATENT DOCUMENTS

| | | | |
|---|---|---|---|
| WO | WO-2001/29058 | A1 | 4/2001 |
| WO | WO-2001/96584 | A2 | 12/2001 |
| WO | WO-2003/068201 | A2 | 8/2003 |
| WO | WO-2003/068201 | A3 | 8/2003 |
| WO | WO-2003/070752 | A2 | 8/2003 |
| WO | WO-2003/070752 | A3 | 8/2003 |
| WO | WO-2005/116072 | A2 | 12/2005 |
| WO | WO-2005/116072 | A3 | 12/2005 |
| WO | WO-2006/106905 | A1 | 10/2006 |
| WO | WO-2007/131092 | A2 | 11/2007 |
| WO | WO-2014/093855 | A1 | 6/2014 |
| WO | WO-2015/063069 | A1 | 5/2015 |
| WO | WO-2016/161390 | A1 | 10/2016 |
| WO | WO-2016/199141 | A2 | 12/2016 |
| WO | WO-2016/199141 | A3 | 12/2016 |
| WO | WO-2017/004252 | A1 | 1/2017 |

OTHER PUBLICATIONS

Ashwood-Smith, M.J. (Jun. 24, 1961). "Preservation of Mouse Bone Marrow at -79° C. with Dimethyl Sulphoxide," *Nature* 190:1204-1205.

Barrett, D.M. et al. (2014; e-published on Nov. 20, 2013). "Chimeric Antigen Receptor Therapy for Cancer," *Annu. Rev. Med.* 65:333-347.

Bender, M.A. et al. (May 1, 1960). "Preservation of Viable Bone Marrow Cells by Freezing," *Journal of Applied Physiology* 15(3):520-524.

Berge, I.J.M. et al. (Dec. 1998). "Selective Expansion of a Peripheral Blood CD8+ Memory T Cell Subset Expressing Both Granzyme B and L-Selectin During Primary Viral Infection in Renal Allograft Recipients," *Transplant Proc.* 30(8)3975-3977.

Blattman, J.N. et al. (Jul. 9, 2004). "Cancer Immunotherapy: A Treatment for the Masses," *Science* 305(5681):200-205.

Boerner, P. et al. (Jul. 1, 1991). "Production of Antigen-Specific Human Monoclonal Antibodies From In Vitro-Primed Human Splenocytes," *The Journal of Immunology* 147(1): 86-95.

Brentjens, R.J. et al. (Nov. 3, 2011). "Safety and Persistence of Adoptively Transferred Autologous CD19-Targeted T Cells in Patients with Relapsed or Chemotherapy Refractory B-Cell Leukemias," *Blood* 118(18):4817-4828.

Broere, F. et al. (2011). "T Cell Subsets and T Cell-Mediated Immunity," in *Principles of Immunopharmacology*, 3$^{rd}$ Revised and extended Edition, Nijkamp, F.P. et al. (eds.), Springer, Basel, AG, pp. 15-27.

Brown, M. et al. (Jun. 5, 1987). "Lac Repressor Can Regulate Expression From a Hybrid SV40 Early Promoter Containing a Lac Operator in Animal Cells," *Cell* 49(5):603-612.

Brüggemann, M. et al. (1993). "Designer Mice: The Production of Human Antibody Repertoires in Transgenic Animals," *Year in Immunol.* 7:33-40.

Call, Me et al. (Dec. 27, 2002). "The Organizing Principle in the Formation of the T Cell Receptor-CD3 Complex," *Cell.* 111(7):967-979.

Carter P. (Feb. 1, 2001). "Bispecific Human IgG by Design," *J. Immunol Methods* 248(1-2):7-15.

Cheever, M.A. et al. (Sep. 1, 2009). "The Prioritization of Cancer Antigens: A National Cancer Institute Pilot Project for the Acceleration of Translational Research," *Clin. Cancer Res.* 15(17):5323-5337.

Chothia, C. et al. (1987). "Canonical Structures for the Hypervariable Regions of Immunoglobulins," *J. Mol. Biol.* 196:901-917.

Chowdhury, P.S. (2008). "Engineering Hot Spots for Affinity Enhancement of Antibodies," Chapter 11 in *Methods in Molecular Biology*, M. Welschof (eds.) et al., Humana Press Inc., Totowa, NJ, 207:179-196.

Clackson et al. (Aug. 15, 1991). "Making Antibody Fragments Using Phage Display Libraries," *Nature* 352:624-628.

Cole et al. (1985). "The EBV-Hybridoma Technique and Its Application to Human Lung Cancer," in *Monoclonal Antibodies and Cancer Therapy*, Ralph A. Reisfeld (ed.) et al., Alan R. Liss, Inc. p. 77-96.

Cunningham, B.C. et al. (Jun. 2, 1989). "High Resolution Epitope Mapping of hGH-Receptor Interactions by Alanine-Scanning Mutagenesis," *Science* 244:1081-1085.

Datta, R. et al. (Nov. 1, 1992). "Ionizing Radiation Activates Transcription of the EGR1 Gene Via CArG Elements," *Proc. Natl. Acad. Sci. USA* 89(21):10149-10153.

Davila, M.L. et al. (Dec. 1, 2012). "How do CARs work? Early Insight from Recent Clinical Studies Targeting CD19,"*Oncoimmunology* 1(9):1577-1583.

Davis, M.M. et al. (Apr. 1998). "Ligand Recognition by αβ T Cell Receptors," *Annual Review of Immunology* 16:523-544.

Davis, M.M. et al. (Aug. 4, 1988). "T-Cell Antigen Receptor Genes and T-Cell Recognition," *Nature* 334(6181):395-402.

Dillon, N. (May 1993). "Regulating Gene Expression in Gene Therapy," *TIBTECH* 11(5):167-173.

Dudley, M.E. et al. (Apr. 1, 2005). "Adoptive Cell Transfer Therapy Following Non-Myeloablative but Lymphodepleting Chemotherapy for the Treatment of Patients with Refractory Metastatic Melanoma," *J. Clin. Oncol.* 23(10):2346-2357.

Edgar, R.C. (2004; e-published on Mar. 19, 2004). "MUSCLE: Multiple Sequence Alignment With High Accuracy and High Throughput," *Nucleic Acids Research* 32(5):1792-1797.

Edgar, R.C. (Aug. 19, 2004). "MUSCLE: A Multiple Sequence Alignment Method With Reduced Time and Space Complexity," *BMC Bioinformatics* 5(1):113, pp. 1-19.

Fellouse, F.A. et al. (Aug. 24, 2004). "Synthetic Antibodies from a Four-Amino-Acid Code: A Dominant Role for Tyrosine in Antigen Recognition," *Proc. Natl. Acad. Sci. USA* 101(34):12467-12472.

Fishwild, D.M. et al. (Jul. 1996). "High-avidity Human IgG$_k$ Monoclonal Antibodies from a Novel Strain of Minilocus Transgenic Mice," *Nature Biotechnology* 14:845-851.

Friedmann-Morvinski, D. et al. (Apr. 15, 2005). "Redirected Primary T Cells Harboring a Chimeric Receptor Require Costimulation for their Antigen-Specific Activation," *Blood* 105(8):3087-3093.

Garland, R.J. et al. (Jul. 30, 1999). "The Use of Teflon Cell Culture Bags to Expand Functionally Active CD8+ Cytotoxic T Lymphocytes,"*Journal of Immunological Methods* 227(1-2):53-63.

Gingrich, J.R. et al. (1998). "Inducible Gene Expression in the Nervous System of Transgenic Mice," *Annual Rev. Neurosci.* 21:377-405.

Girardi, M. (2006). "Immunosurveillance and Immunoregulation by γδ T Cells" *J. Invest. Dermatol.* 126(1):25-31.

(56) References Cited

OTHER PUBLICATIONS

Goding, J.W. (1986). "Production of Monoclonal Antibodies," Chapter 3 in *Monoclonal Antibodies: Principles and Practice*, Academic Press, New York, pp. 56-103.
Griffiths, A.D. et al. (1993). "Human Anti-Self Antibodies with High Specificity from Phage Display Libraries," *The EMBO Journal* 12(2):725-734.
Gross, G et al. (1992). "Endowing T Cells with Antibody Specificity Using Chimeric T Cell Receptors," *FASEB J.* 6(15):3370-3378.
Gross, G. et al. (Dec. 1, 1989). "Expression of Immunoglobulin-T-Cell Receptor Chimeric Molecules as Functional Receptors With Antibody-Type Specificity," *Proc. Natl. Acad. Sci. USA.* 86(24):10024-10028.
Gunasekaran, K. et al. (Jun. 18, 2010; e-published on Apr. 16, 2010). "Enhancing Antibody Fc Heterodimer Formation Through Electrostatic Steering Effects: Applications to Bispecific Molecules and Monovalent IgG," *J Biol Chem.* 285(25):19637-19646.
Haanen, J. et al. (Nov. 1, 1999). "Selective Expansion of Cross-reactive $CD8^+$ Memory T Cells by Viral Variants," *J. Exp. Med.* 190(9):1319-1328.
Hayes, S.M. (Jun. 2002). "Distinct Structure and Signaling Potential of the γδTCR Complex," *Immunity* 16(6):827-838.
Hoet, R.M. et al. (Mar. 2005; e-published on Feb. 20, 2005). "Generation of High-Affinity Human Antibodies by Combining Donor-Derived and Synthetic Complementarity-Determining-Region Diversity," *Nature Biotechnology* 23(3):344-348.
Hoogenboom, H.R. (2001). "Overview of Antibody Phage-Display Technology and Its Applications," Chapter 1 in *Methods in Molecular Biology*, O'Brien (ed.) et al., Human Press, Totowa, NJ, 178:1-37.
Hoogenboom, H.R. et al. (1992). "By-Passing Immunization—Human Antibodies from Synthetic Repertoires of Germline $V_H$ Gene Segments Rearranged in Vitro," *J. Mol. Biol.* 227:381-388 (1992).
Hsu, P.D. et al. (Jun. 5, 2014). "Development and Applications of CRISPR-Cas9 for Genome Engineering," *Cell* 157(6):1262-1278.
Jakobovits, A. et al. (Mar. 18, 1993). "Germ-Line Transmission and Expression of a Human-Derived Yeast Artificial Chromosome," *Nature* 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *PNAS USA* 90:2551-2555.
Jiang, W. et al. (2015; e-published on Jul. 22, 2015). "CRISPR-Cas: New Tools for Genetic Manipulations from Bacterial Immunity Systems," *Annu. Rev. Microbiol.* 69:209-228.
Jones, P.T. et al. (May 29, 1986). "Replacing the Complementarity Determining Regions in a Human Antibody with those from a Mouse," *Nature* 321:522-525.
Kabat, E.A. et al. (1991). U.S. Department of Health and Human Services—Public Health Service National Institutes of health, in *Sequences of Proteins of Immunological Interest*, eighty five pages.
Kabat, E.A. et al. (Oct. 10, 1977). "Unusual Distributions of Amino Acids in Complementarity-Determining (Hypervariable) Segments of Heavy and Light Chains of Immunoglobulins and their Possible Roles in Specificity of Antibody-combining Sites," *The Journal of Biological Chemistry* 252(19):6609-6616.
Kam, N.W.S. et al. (Aug. 16, 2005). "Carbon Nanotubes as Multifunctional Biological Transporters and Near-Infrared Agents for Selective Cancer Cell Destruction," *Proc. Natl. Acad. Sci. USA* 102(33):11600-11605.
Kim, J.H. et al. (Apr. 2011). "High Cleavage Efficiency of a 2A Peptide Derived from Porcine Teschovirus-1 in Human Cell Lines, Zebrafish and Mice," *PloS One* 6(4):e18556, pp. 1-8.
Kobayashi, E. et al. (2014; e-published on Jan. 1, 2014). "A Novel System for Cloning Human TCRs," *Oncoimmunology* 3(1):e27258-1-e27258-2.
Kochenderfer, J.N. et al. (Nov. 18, 2010; e-published on Jul. 28, 2010). "Eradication of B-Lineage Cells and Regression of Lymphoma in a Patient Treated With Autologous T Cells Genetically Engineered to Recognize CD19," *Blood* 116(20):4099-4102.
Köhler G. et al. (Aug. 7, 1975). "Continuous Cultures of Fused Cells Secreting Antibody of Predefined Specificity," *Nature* 256:495-497.
Kozbor, D. et al. (Dec. 1984). "A Human Hybrid Myeloma for Production of Human Monoclonal Antibodies," *The Journal of Immunology* 133(6):3001-3005.
Kremer, E.J. et al. (Jan. 1995). "Adenovirus and Adeno-Associated Virus Mediated Gene Transfer," *British Medical Bulletin* 51(I):31-44.
Kuhns, M.S. (Jun. 25, 2012). "TCR Signaling Emerges from the Sum of Many Parts," *Front Immunol.* 3(Article 159):1-13.
Kunert, A. et al. (Nov. 8, 2013). "TCR-Engineered T Cells Meet New Challenges to Treat Solid Tumors: Choice of Antigen, T Cell Fitness, and Sensitization of Tumor Milieu," *Front. Immunol.* 4(Article 363):1-16.
Kuwana, Y. et al. (Dec. 31, 1987). "Expression of Chimeric Receptor Composed of Immunoglobulin-Derived V Regions and T-Cell Receptor-Derived C Regions," *Biochem. Biophys. Res. Commun.* 149(3):960-968.
Lee, C.V. et al. (2004). "Bivalent Antibody Phage Display Mimics Natural Immunoglobulin," *Journal of Immunological Methods* 284(1-2):119-132.
Lee, C.V. et al. (2004). "High-Affinity Human Antibodies from Phage-Displayed Synthetic Fab Libraries with a Single Framework Scaffold," *J. Mol. Biol.* 340(5):1073-1093.
Lewis, J.P. et al. (Jan.-Feb. 1967). "The Effect of Cooling Regimens on the Transplantation Potential of Marrow," *Transfusion* 7(1):17-32.
Linner, J.G. et al. (Sep. 1986). "A New Technique for Removal of Amorphous Phase Tissue Water Without Ice Crystal Damage: A Preparative Method for Ultrastructural Analysis and Immunoelectron Microscopy," *J. Histochem. Cytochem.* 34(9):1123-1135.
Livesey, S.A. et al. (May 21, 1987). "Cryofixation Taking on a New Look," *Nature* 327:255-256.
Lonberg, N. et al. (1995). "Human Antibodies from Transgenic Mice," *Intern. Rev. Immunol.*, 13:65-93.
Lonberg, N. et al. (Apr. 28, 1994). "Antigen-Specific Human Antibodies from Mice Comprising Four Distinct Genetic Modifications," *Nature* 368:856-859.
Louis, C.U. et al. (Dec. 1, 2011; e-published on Oct. 7, 2011). "Antitumor Activity and Long-Term Fate of Chimeric Antigen Receptor-Positive T Cells in Patients With Neuroblastoma,"*Blood* 118(23):6050-6056.
Lovelock, J.E. (Feb. 1, 1954). "The Protective Action of Neutral Solutes Against Haemolysis by Freezing and Thawing," *Biochem. J.* 56(2):265-270.
Lovelock, J.E. et al. (May 16, 1959). "Prevention of Freezing Damage to Living Cells by Dimethyl Sulphoxide," *Nature* 183(4672):1394-1395.
MacCallum, R.M. et al. (1996). "Antibody-Antigen Interactions: Contact Analysis and Binding Site Topography," *J. Mol. Biol.* 262:732-745.
Mader, S. et al. (Jun. 1993). "A Steroid-inducible Promoter for the Controlled Overexpression of Cloned Genes in Eukaryotic Cells," *Proc. Natl. Acad. Sci. USA* 90:5603-5607.
Manome, Y. et al. (1993). "Coinduction of C-Jun Gene Expression and Internucleosomal DNA Fragmentation by Ionizing Radiation," *Biochemistry* 32(40):10607-10613.
Marks, J.D. et al. (1991). "By-Passing Immunization—Human Antibodies from V-Gene Libraries Displayed on Phage," *J. Mol. Biol.* 222:581-597.
Marks, J.D. et al. (2004). "Selection of Human Antibodies from Phage Display Libraries," Chapter 8 in *Methods in Molecular Biology*, B.K.C. Lo, ed., Humana Press Inc., Totowa, N.J., 248:161-175.
Marks, J.D. et al. (Jul. 1992). "By-Passing Immunization: Building High Affinity Human Antibodies by Chain Shuffling," *Bio/Technology*, 10:779-783.
Martin, S.F. et al. (Mar. 19, 1998). "Application of $Alme_3$-Mediated Amidation Reactions to Solution Phase Peptide Synthesis," *Tetrahedron Letters* 39(12):1517-1520.

(56) References Cited

OTHER PUBLICATIONS

Maude, S.L. et al. (Oct. 16, 2014). "Chimeric Antigen Receptor T Cells for Sustained Remissions in Leukemia," *N. Engl .J. Med.* 371(16):1507-1517.
Mazur, P. (1977). "The Role of Intracellular Freezing in the Death of Cells Cooled at Supraoptimal Rates," *Cryobiology* 14(3):251-272.
Mazur, P. (May 22, 1970). "Cryobiology: The Freezing of Biological Systems," *Science* 168(3934):939-949.
McCafferty, J. et al. (Dec. 6, 1990). "Phage Antibodies: Filamentous Phage Displaying Antibody Variable Domains," *Nature* 348:552-554.
Miller, A.D. (Jun. 11, 1992). "Human Gene Therapy Comes of Age," *Nature* 357(6378):455-460.
Mitani, K. et al. (May 1993). "Delivering Therapeutic Genes—Matching Approach and Application," *Trends in Biotechnology (TIBTECH)* 11(5):162-166.
Morrison, S.L. (Apr. 28, 1994). "Success in Specification," *Nature* 368:812-813.
Morrison, S.L. et al. (Nov. 1984). "Chimeric Human Antibody Molecules: Mouse Antigen-Binding Domains with Human Constant Region Domains," *Proc. Natl. Acad. Sci. USA* 81:6851-6855.
Müller, K.M. et al. (1998). "The First Constant Domain ($C_H1$ and $C_L$) of an Antibody Used as Heterodimerization Domain for Bispecific Miniantibodies," *FEBS Letters* 422(2):259-264.
Munson, P.J. et al. (1980). "LIGAND: A Versatile Computerized Approach for Characterization of Ligand-Binding Systems," *Analytical Biochemistry* 107:220-239.
Murphy, K. (2012). Janeway's Immunobiology, pp. x-xix, 868 p, (TOC and Index only).
Nabel, G.J. et al. (May 1993). "Direct Gene Transfer for Immunotherapy and Immunization," *Trends in Biotechnology* 11(5):211-215.
Neuberger, M. (Jul. 1996). "Generating High-Avidity Human Mabs in Mice," *Nature Biotechnology* 14:826, one page.
O'Connell, M.R. et al. (Dec. 11, 2014; e-published on Sep. 28, 2014). "Programmable RNA Recognition and Cleavage by CRISPR/Cas9," *Nature* 516(7530):263-266.
Oren, R. et al. (2014). "Functional Comparison of Engineered T Cells Carrying a Native TCR Versus TCR-Like Antibody-Based Chimeric Antigen Receptors Indicates Affinity/Avidity Thresholds," *The Journal of Immunology* 193(11):5733-5743.
Phan, T.T. et al. (Sep. 1960). "Survival of Mouse Bone-Marrow Cells Frozen and Thawed in Solutions of Amino Acids," *Exp. Cell Res.* 20(3):651-654.
Presta, L.G. (1992). "Antibody Engineering," *Current Opinion in Structural Biology* 2:593-596.
Rapatz, G. et al. (Jul.-Aug. 1968). "Preservation of Erythrocytes in Blood Containing Various Cryoprotective Agents, Frozen at Various Rates and Brought to a Given Final Temperature," *Cryobiology* 5(1):18-25.
Ridgway, J.B.B. et al. (1996). "Knobs-into Holes' Engineering of Antibody $C_H3$ Domains for Heavy Chain Heterodimerization," *Protein Engineering* 9(7):617-621.
Riechmann, et al. (Mar. 24, 1988). "Reshaping Human Antibodies for Therapy," *Nature* 332:323-327.
Rinfret, A.P. (Apr. 1960). "Factors Affecting the Erythrocyte During Rapid Freezing and Thawing," *Annals of the New York Academy of Sciences* 85:576-594.
Robbins, P.F. et al. (Mar. 1, 2015; e-published on Dec. 23, 2014). "A Pilot Trial Using Lymphocytes Genetically Engineered With an NY-ESO-1-Reactive T-Cell Receptor: Long-Term Follow-Up and Correlates with Response," *Clin. Cancer Res.* 21(5):1019-1027.
Rosenberg, S.A. et al. (Apr. 2008). "Adoptive Cell Transfer: A Clinical Path to Effective Cancer Immunotherapy," *Nat. Rev. Cancer* 8(4):299-308.
Rosenberg, S.A. et al. (Apr. 3, 2015). "Adoptive Cell Transfer as Personalized Immunotherapy for Human Cancer," *Science* 348(6230):62-68.
Rowe, A.W. et al. (1962). "Controlled Rate Freezing of Bone Marrow," *Blood* 20:636-637.
Rowe, A.W. et al. (1962). "109-Cell, Tissue Culture," *Federation Proceedings* 21:157, three pages.
Rowe, A.W. et al. (Jul.-Aug. 1966). "Biochemical Aspects of Cryoprotective Agents in Freezing and Thawing," *Cryobiology* 3(1):12-18.
Scheinberg, D.A. et al. (May 2013). "Reaching Un-Drugable Intracellular Targets with the Long Arm of Antibodies," *Oncotarget* 4(5):647-648.
Sergeeva, A. et al. (Apr. 21, 2011). "An Anti-PR1/HLA-A2 T-Cell Receptor-Like Antibody Mediates Complement-Dependent Cytotoxicity Against Acute Myeloid Leukemia Progenitor Cells," *Blood* 117(16):4262-4272.
Sidhu, S.S. et al. (2004). "Phage-Displayed Antibody Libraries of Synthetic Heavy Chain Complementarity Determining Regions," *J. Mol. Biol.* 338(2): 299-310.
Simione, F.P., Jr. (Nov.-Dec. 1992). "Key Issues Relating to the Genetic Stability and Preservation of Cells and Cell Banks," *J. Parenter. Sci. Technol.* 46(6):226-232.
Singh, H. et al.(Dec. 1, 2001). "ProPred: Prediction of HLA-DR Binding Sites," *Bioinformatics* 17(12):1236-1237.
Sloviter, H.A. et al. (Dec. 1, 1962). "Recovery and Transfusion of Human Erythrocytes after freezing in Polyglycol Solutions," *Nature* 196(4857):899-900.
Spencer, D.M. (Nov. 12, 1993). "Controlling Signal Transduction with Synthetic Ligands," *Science* 262(5136):1019-1024.
Spitzer, G. et al. (Jun. 15, 1980). "High-Dose Combination Chemotherapy with Autologous Bone Marrow Transplantation in Adult Solid Tumors," *Cancer* 45:3075-3085.
Stiff, P.J. et al. (Feb. 1983). "Unfractionated Human Marrow Cell Cryopreservation Using Dimethylsulfoxide and Hydroxyethyl Starch," *Cryobiology* 20(1):17-24.
Ui-Tei, K. et al. (Aug. 18, 2000). "Sensitive Assay of RNA Interference in *Drosophila* and Chinese Hamster Cultured Cells Using Firefly Luciferase Gene as Target," *FEBS Letters* 479(3):79-82.
Van Brunt, J. (Oct. 1988). "Molecular Farming: Transgenic Animals as Bioreactors," *Biotechnology* 6(10):1149-1154.
Verhoeyen, M. et al. (1988). "Reshaping Human Antibodies: Grafting and Antilysozyme Activity," *Science* 239:1534-1536.
Vigne, E. et al. (Jun. 1995). "Third-generation Adenovectors for Gene Therapy," *Restorative Neurology and Neuroscience* 8(1-2):35-36.
Wang, J.-H. et al. (Nov. 2012). "The Structural Basis of $\alpha\beta$ T-Lineage Immune Recognition: TCR Docking Topologies, Mechanotransduction, and Co-Receptor Function," *Immunol Rev.* 250(1):102-119.
Winter, G. et al. (1994). "Making Antibodies by Phage Display Technology," *Ann. Rev. Immunol.*, 12:433-455.
Wucherpfennig, K.W. et al. (Apr. 2010). "Structural Biology of the T-Cell Receptor: Insights into Receptor Assembly, Ligand Recognition, and Initiation of Signaling," *Cold Spring Harb Perspect Biol.* 2(4):a005140, pp. 1-14.
Yu, M. et al. Jan. 1, 1994). "Progress Towards Gene Therapy for HIV Infection," *Gene Therapy* 1(1):13-26.
Invitation to Pay Additional Fees and, Where Applicable, Protest Fee, dated Dec. 22, 2016 for PCT Application No. PCT/US2016/58305 filed Oct. 21, 2016, two pages.
International Search Report and Written Opinion dated Mar. 16, 2017 for PCT Application No. PCT/US2016/58305 filed Oct. 21, 2016, seventeen pages.
Cohen, CJ. et al. (Sep.-Oct. 2003). "Recombinant Antibodies with MHC-Restricted, Peptide-Specific, T-Cell Receptor-Like Specificity: New Tools to Study Antigen Presentation and TCR-Peptide-MHC Interactions," *J. Mol. Recognit.* 16(5):324-332.
Engberg, J. et al. (Mar. 1999). "Recombinant Antibodies with the Antigen-Specific, MHC Restricted Specificity of T Cells: Novel Reagents for Basic and Clinical Investigations and Immunotherapy," *Immunotechnology* 4(3-4):273-278.
International Preliminary Report on Patentability dated May 3, 2018 for PCT Application No. PCT/US2016/058305 filed Oct. 21, 2016, nine pages.
U.S. Appl. No. 15/769,724, filed Apr. 19, 2018, by Lu et al.

(56) References Cited

OTHER PUBLICATIONS

Almåsbak, H. et al. (2018). "CAR T Cell Therapy: A Game Changer in Cancer Treatment," *Journal of Immunology Research* 2016(Article ID 5474602), ten pages.
Butterfield, L.H. et al. (Dec. 1, 2003). "T-Cell Responses to HLA-A*0201 Immunodominant Peptides Derived from α-Fetoprotein in Patients with Hepatocellular Cancer," *Clinical Cancer Research* 9(16 pt. 1):5902-5908.
Hammer, O. (Sep. 1 2012), "CD19 as an Attractive Target for Antibody-Based Therapy," *mAbs* 4(5):571-577.
Sela-Culang, I. et al. (Oct. 8, 2013). "The Structural Basis of Antibody-Antigen Recognition," *Frontiers in Immunology* 4(Article 302):1-13.
U.S. Appl. No. 15/563,912, filed Oct. 2, 2017, by Liu et al.

* cited by examiner

FIG. 1A

| abTCR-3 | abTCR-4 | abTCR-5 | abTCR-6 |
|---|---|---|---|
| $IgV_H$ — $IgV_L$ / $IgC_H1$ — $IgC_L$ / $TCR\alpha$ — $TCR\beta$ | $IgV_L$ — $IgV_H$ / $IgC_L$ — $IgC_H1$ / $TCR\alpha$ — $TCR\beta$ | $IgV_H$ — $IgV_L$ / $IgC_L$ — $IgC_H1$ / $TCR\delta$ — $TCR\gamma$ | $IgV_H$ — $IgV_L$ / $IgC_H1$ — $IgC_L$ / $TCR\delta$ — $TCR\gamma$ |

FIG. 1B

| Additional linker to extend, or deletion to reduce distance between TM and IgC | Additional intracellular effector domain(s) | Linker modification, or additional residues to extend distance between the Ig domains | Any combination or permutations of the variations |
|---|---|---|---|
| IgV — IgV / IgC — IgC / TCRα/δ — β/γ | IgV — IgV / IgC — IgC / TCRα/δ — β/γ | IgV — IgV / IgC — IgC / TCRα/δ — β/γ | IgV — IgV / IgC — IgC / TCRα/δ — β/γ |

FIG. 7A
FIG. 7B
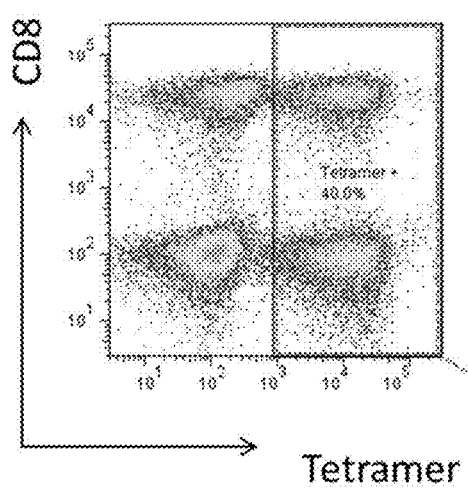
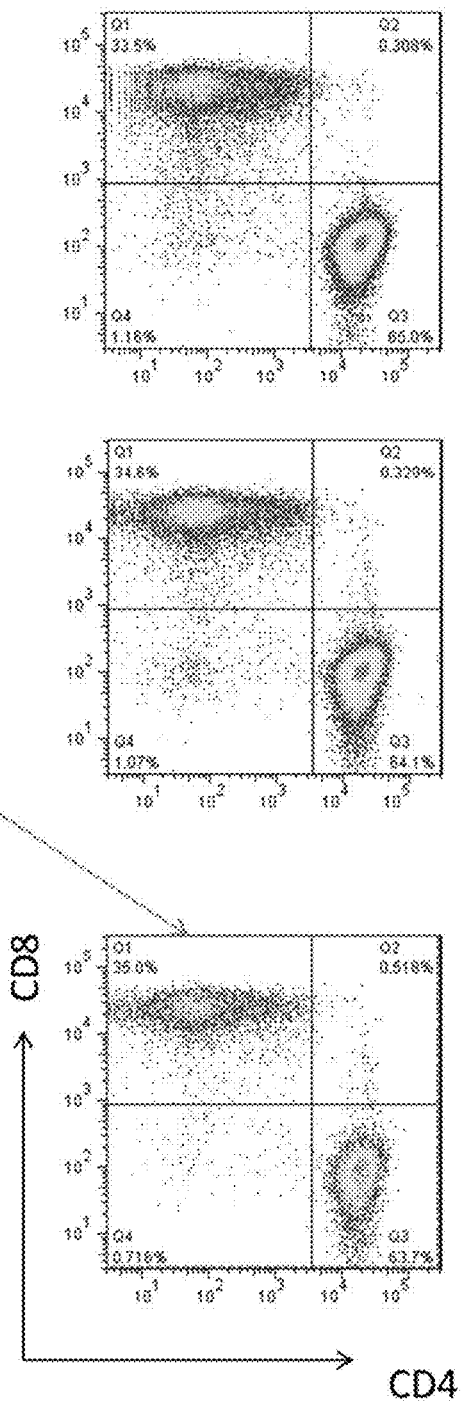

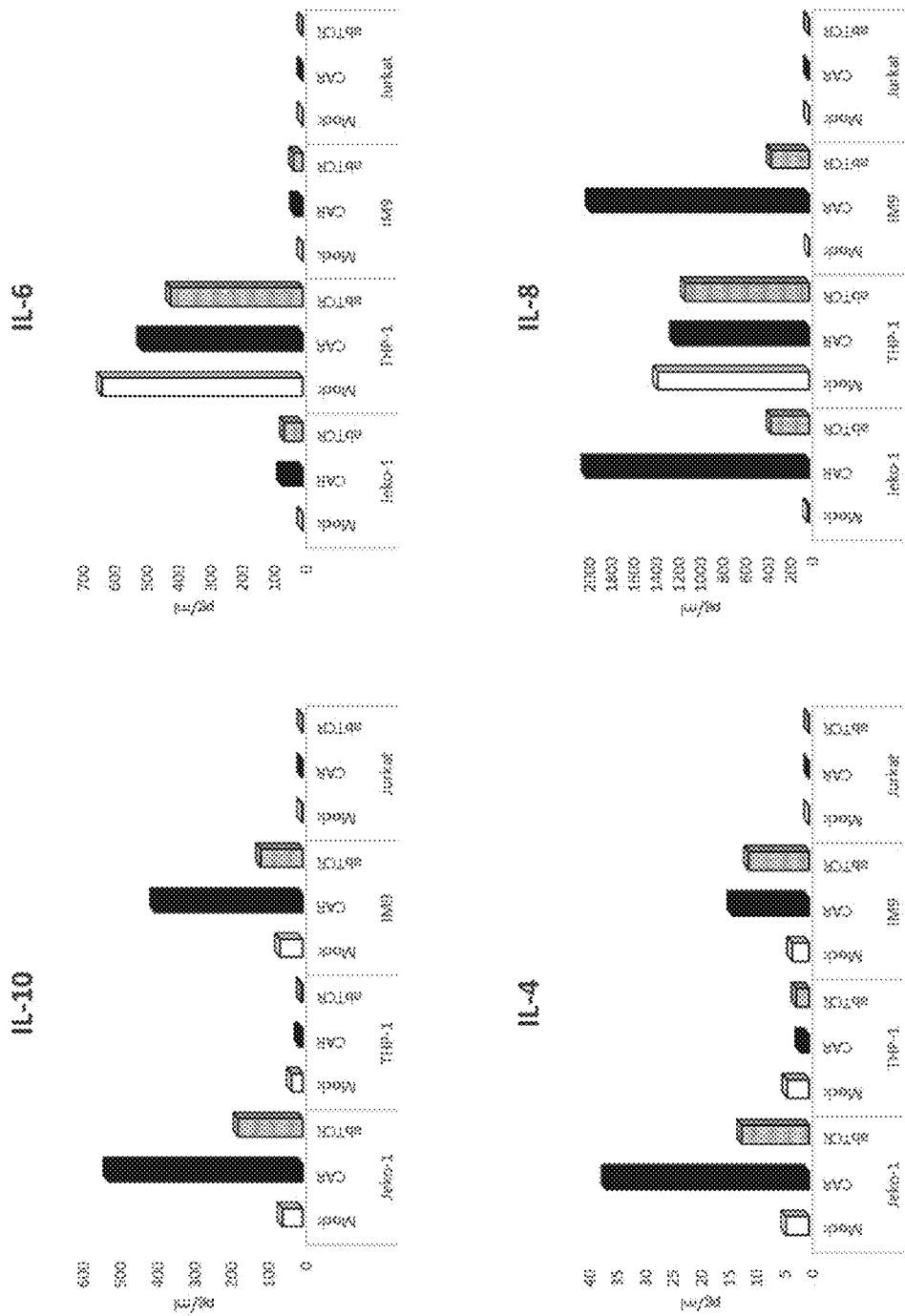

1: Mock + Raji
2: Mock + Raji-CD19ko
3: abTCR + Raji
4: abTCR + Raji-CD19ko
5: Mock alone
6: abTCR alone
7: Raji alone
8: Raji-CD19ko alone

ANTIBODY/T-CELL RECEPTOR CHIMERIC CONSTRUCTS AND USES THEREOF

CROSS-REFERENCE TO RELATED APPLICATIONS

This application is a continuation of International Application No. PCT/US2016/058305, filed on Oct. 21, 2016, which claims priority to U.S. Provisional Application No. 62/245,944, filed on Oct. 23, 2015, U.S. Provisional Application No. 62/304,918, filed on Mar. 7, 2016, U.S. Provisional Application No. 62/345,649, filed on Jun. 3, 2016, and U.S. Provisional Application No. 62/369,694, filed on Aug. 1, 2016, all of which are hereby incorporated by reference in their entireties.

FIELD OF THE INVENTION

This invention pertains to antibody/T cell receptor chimeric constructs and uses thereof including treating and diagnosing diseases.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750042000301SEQLIST.txt, date recorded: Nov. 28, 2017, size: 103 KB).

BACKGROUND OF THE INVENTION

T-cell mediated immunity is an adaptive process of developing antigen (Ag)-specific T lymphocytes to eliminate viruses, bacterial, parasitic infections or malignant cells. It can also involve aberrant recognition of self-antigen, leading to autoimmune inflammatory diseases. The Ag specificity of T lymphocytes is based on recognition through the T Cell Receptor (TCR) of unique antigenic peptides presented by Major Histocompatibility Complex (MHC) molecules on Ag-presenting cells (APC) (Broere, et al., *Principles of Immunopharmacology*, 2011). Each T lymphocyte expresses a unique TCR on the cell surface as the result of developmental selection upon maturation in the thymus. The TCR occurs in two forms as either an $\alpha\beta$ heterodimer or as a $\gamma\delta$ heterodimer. T cells express either the $\alpha\beta$ form or the $\gamma\delta$ form TCR on the cell surface. The four chains, $\alpha/\beta/\gamma/\delta$, all have a characteristic extracellular structure consisting of a highly polymorphic "immunoglobulin variable region"-like N-terminal domain and an "immunoglobulin constant region"-like second domain. Each of these domains has a characteristic intra-domain disulfide bridge. The constant region is proximal to the cell membrane, followed by a connecting peptide, a transmembrane region and a short cytoplasmic tail. The covalent linkage between the 2 chains of the heterodimeric TCR is formed by the cysteine residue located within the short connecting peptide sequence bridging the extracellular constant domain and the transmembrane region which forms a disulfide bond with the paired TCR chain cysteine residue at the corresponding position (The T cell Receptor Factsbook, 2001).

The $\alpha\beta$ and $\gamma\delta$ TCRs are associated with the non-polymorphic membrane-bound CD3 proteins to form the functional octameric TCR-CD3 complex, consisting of the TCR heterodimer and three dimeric signaling modules, CD3$\delta$/$\epsilon$, CD3$\gamma$/$\epsilon$ and CD3$\zeta$/$\zeta$ or $\zeta$/$\eta$. Ionizable residues in the transmembrane domain of each subunit form a polar network of interactions that hold the complex together. For T cell activation, the TCR N-terminal variable regions recognize the peptide/MHC complex presented on the surface of target cell, whereas the CD3 proteins participate in signal transduction (Call et al., *Cell*. 111(7):967-79, 2002; The T cell Receptor Factsbook, 2001).

$\alpha\beta$ TCR, also called conventional TCR, is expressed on most lymphocytes and consists of the glycosylated polymorphic $\alpha$ and $\beta$ chains. Different $\alpha\beta$ TCRs can discriminate among different peptides embedded in the surfaces of MHC II (mostly expressed on APC cell surfaces) and MHC I (expressed on all nucleated cells) molecules, whose dimensions and shapes are relatively constant. The $\gamma\delta$ TCR, though structurally similar to the $\alpha\beta$ TCR, recognizes carbohydrate-, nucleotide-, or phosphor-carrying antigens in a fashion independent of MHC presentation (The T cell Receptor Factsbook, 2001; Girardi et al., *J. Invest. Dermatol*. 126(1):25-31, 2006; Hayes et al., *Immunity*. 16(6):827-38, 2002).

Cell surface proteins constitute only a small fraction of the cellular proteins and most of these proteins are not tumor-specific. In contrast, mutated or oncogenic tumor-associated proteins are typically intracellularly located, nuclear, cytoplasmic or secretory. Most intracellular proteins are exposed on the cell surface as part of a normal process of protein catabolism and presentation by MHC molecules. Intracellular proteins are usually degraded by the proteasome or endo/lysosomes, and the resulting specific peptide fragments bind to MHC class I/II molecules. These peptide/MHC complexes are displayed at the cell surface where they provide targets for T cell recognition via peptide/MHC TCR interaction (Scheinberg et al., *Oncotarget*. 4(5):647-8, 2013; Cheever et al., *Clin. Cancer Res*. 15(17):5323-37, 2009).

In the past two decades, fundamental advances in immunology and tumor biology, combined with the identification of a large number of tumor antigens, have led to significant progress in the field of cell-based immunotherapy. T cell therapy occupies a large space in the field of cell-based immunotherapy, with the goal of treating cancer by transferring autologous and ex vivo expanded T cells to patients, and has resulted in some notable antitumor responses (Blattman et al., *Science*. 305(5681):200-5, 2004). For example, the administration of naturally occurring tumor infiltrating lymphocytes (TILs) expanded ex vivo mediated an objective response rate ranging from 50-70% in melanoma patients, including bulky invasive tumors at multiple sites involving liver, lung, soft tissue and brain (Rosenberg et al., *Nat. Rev. Cancer*. 8(4):299-308, 2008; Dudley M E et al., *J. Clin. Oncol*. 23(10):2346-57, 2005).

A major limitation to the widespread application of TIL therapy is the difficulty in generating human T cells with antitumor potential. As an alternative approach, exogenous high-affinity TCRs can be introduced into normal autologous T cells of the patients through T cell engineering. The adoptive transfer of these cells into lympho-depleted patients has been shown to mediate cancer regression in cancers such as melanoma, colorectal carcinoma, and synovial sarcoma (Kunert R et al., *Front. Immunol*. 4:363, 2013). A recent phase I clinical trial using anti NY-ESO-1 TCRs against synovial sarcoma reported an overall response rate of 66% and complete response was achieved in one of the patients receiving the T cell therapy (Robbins P F et al., *Clin. Cancer Res*. 21(5):1019-27, 2015).

One of the advantages of TCR-engineered T cell therapy is that it can target the entire array of potential intracellular tumor-specific proteins, which are processed and delivered to the cell surface through MHC presentation. Furthermore, the TCR is highly sensitive and can be activated by just a few antigenic peptide/MHC molecules, which in turn can trigger a cytolytic T cell response, including cytokine secretion, T cell proliferation and cytolysis of defined target cells. Therefore, compared with antibody or small molecule therapies, TCR-engineered T cells are particularly valuable for their ability to kill target cells with very few copies of target intracellular antigens (Kunert R et al., *Front. Immunol.* 4:363, 2013).

However, unlike therapeutic antibodies, which are mostly discovered through hybridoma or display technologies, identification of target-specific TCRs requires the establishment of target peptide/MHC specific TCR clones from patient T cells and screening for the right α-β chain combination that has the optimal target antigen-binding affinity. Very often, phage/yeast display is employed after cloning of the TCR from patient T cells to further enhance the target binding affinity of the TCR. The whole process requires expertise in many areas and is time-consuming (Kobayashi E et al., *Oncoimmunology.* 3(1):e27258, 2014). The difficulties in the TCR discovery process have largely impeded the widespread application of TCR-engineered T cell therapy. It has also been hampered by treatment-related toxicity, in particularly with TCRs against antigens that are over-expressed on tumor cells but also expressed on healthy cells, or with TCRs recognizing off-target peptide/MHC complexes (Rosenberg S A et al., *Science.* 348(6230):62-8, 2015).

A different approach has been developed in recent years to engage T cells for targeted cancer immunotherapy. This new approach is called Chimeric Antigen Receptor T cell Therapy (CAR-T). It merges the exquisite targeting specificity of monoclonal antibodies with the potent cytotoxicity and long-term persistence provided by cytotoxic T cells. A CAR is composed of an extracellular domain that recognizes a cell surface antigen, a transmembrane region, and an intracellular signaling domain. The extracellular domain consists of the antigen-binding variable regions from the heavy and light chains of a monoclonal antibody that are fused into a single-chain variable fragment (scFv). The intracellular signaling domain contains an immunoreceptor tyrosine-based activation motif (ITAM), such as those from CD3ζ or FcRγ, and one or more costimulatory signaling domains, such as those from CD28, 4-1BB or OX40 (Barrett D M et al., *Annu. Rev. Med.* 65:333-47, 2014; Davila M L et al., *Oncoimmunology.* 1(9):1577-1583, 2012). Binding of target antigens by CARs grafted onto a T cell surface can trigger T cell effector functions independent of TCR-peptide/MHC complex interaction. Thus, T cells equipped with CARs can be redirected to attack a broad variety of cells, including those that do not match the MHC type of the TCRs on the T cells but express the target cell-surface antigens. This approach overcomes the constraints of MHC-restricted TCR recognition and avoids tumor escape through impairments in antigen presentation or MHC molecule expression. Clinical trials have shown clinically significant antitumor activity of CAR-T therapy in neuroblastoma (Louis C U et al., *Blood.* 118(23):6050-6056, 2011), B-ALL (Maude, S L, et al., *New England Journal of Medicine* 371:16:1507-1517, 2014), CLL (Brentjens, R J, et al. *Blood* 118:18:4817-4828, 2011), and B cell lymphoma (Kochenderfer, J N, et al. *Blood* 116:20:4099-4102, 2010). In one study, a 90% complete remission rate in 30 patients with B-ALL treated with CD19-CAR T therapy was reported (Maude, S L, et al., supra).

Most, if not all, CARs studied so far have been directed to tumor antigens with high cell surface expression. To target low-copy number cell-surface tumor antigens and intracellular tumor antigens, which represent 95% of all known tumor-specific antigens, there is a need to develop more potent and effective engineered cell therapies (Cheever, et al., *Clin. Cancer Res.* 15(17):5323-37, 2009).

Several attempts have been made to engineer chimeric receptor molecules having antibody specificity with T cell receptor effector functions. See, for example, Kuwana, Y, et al., *Biochem. Biophys. Res. Commun.* 149(3):960-968, 1987; Gross, G, et al., *Proc. Natl. Acad. Sci. USA.* 86:10024-10028, 1989; Gross, G & Eshhar, Z, *FASEB J.* 6(15):3370-3378, 1992; U.S. Pat. No. 7,741,465. To this date, none of these chimeric receptors have been adopted for clinical use, and novel designs for antibody-TCR chimeric receptors with improved expression and functionality in human T cells are needed.

The disclosures of all publications, patents, patent applications and published patent applications referred to herein are hereby incorporated herein by reference in their entirety.

BRIEF SUMMARY OF THE INVENTION

The present application in one aspect provides a construct (such as an isolated construct) comprising an antibody moiety (such as a Fab-like antigen-binding module) fused to a T cell receptor module (said construct also referred to herein as an "antibody-TCR chimeric molecule," or "abTCR"). In some embodiments, the abTCR comprises a Fab-like antigen-binding module that specifically binds to a target antigen and a T cell receptor module (TCRM) capable of recruiting at least one TCR-associated signaling module. In some embodiments, the target antigen is a complex comprising a peptide and an MHC protein (such as an MHC class I protein or an MHC class II protein). In some embodiments, the target antigen is a cell-surface antigen.

In some embodiments, there is provided an abTCR (such as an isolated abTCR) that specifically binds to a target antigen, wherein the abTCR comprises: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form a Fab-like antigen-binding module that specifically binds to the target antigen, and wherein the first TCRD and the second TCRD form a T cell receptor module (TCRM) that is capable of recruiting at least one TCR-associated signaling module. In some embodiments, the first polypeptide chain and the second polypeptide chain are linked via one or more disulfide bonds. In some embodiments, the Fab-like antigen-binding module comprises a disulfide bond between a residue in the $C_H1$ domain in the first polypeptide chain and a residue in the $C_L$ domain in the second polypeptide chain. In some embodiments, the first polypeptide chain further comprises a first peptide linker between the first antigen-binding domain and the first TCRD. In some embodiments, the second polypeptide chain further comprises a second peptide linker between the second antigen-binding domain and the second TCRD. In some embodiments, the first peptide linker and/or the second peptide linker are, individually, from about 5 to about 50 amino acids in length. In some embodiments, the target antigen is a cell surface antigen. In some embodiments, the cell surface antigen is selected from the group consisting of protein, carbohydrate, and lipid. In some embodiments, the cell surface antigen is CD19, ROR1, ROR2, BCMA, GPRC5D, or FCRL5. In some embodiments, the target antigen is a complex comprising a peptide and a major histocompatibility complex (MHC) protein.

In some embodiments, there is provided an abTCR that specifically binds to a target antigen, comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to the target antigen, wherein the first TCRD and the second TCRD form a T cell receptor module (TCRM) that is capable of recruiting at least one TCR-associated signaling module, and wherein the target antigen is a complex comprising a peptide and an MHC protein. In some embodiments, the first polypeptide chain further comprises a first peptide linker between the first antigen-binding domain and the first TCRD and the second polypeptide chain further comprises a second peptide linker between the second antigen-binding domain and the second TCRD. In some embodiments, the first and/or second peptide linkers comprise, individually, a constant domain or fragment thereof from an immunoglobulin or T cell receptor subunit. In some embodiments, the first and/or second peptide linkers comprise, individually, a CH1, CH2, CH3, CH4 or CL antibody domain, or a fragment thereof. In some embodiments, the first and/or second peptide linkers comprise, individually, a Cα, Cβ, Cγ, or Cδ TCR domain, or a fragment thereof.

In some embodiments, according to any of the abTCRs (such as isolated abTCRs) described above, the first TCRD further comprises a first connecting peptide or fragment thereof of a TCR subunit N-terminal to the first transmembrane domain. the second TCRD further comprises a second connecting peptide or fragment thereof of a TCR subunit N-terminal to the second transmembrane domain. In some embodiments, the TCRM comprises a disulfide bond between a residue in the first connecting peptide and a residue in the second connecting peptide. In some embodiments, the first TCRD further comprises a first TCR intracellular domain comprising a TCR intracellular sequence C-terminal to the first transmembrane domain. In some embodiments, the second TCRD further comprises a second TCR intracellular domain comprising a TCR intracellular sequence C-terminal to the second transmembrane domain. In some embodiments, the abTCR binds to the target antigen with an equilibrium dissociation constant ($K_d$) from about 0.1 pM to about 500 nM. In some embodiments, the TCR-associated signaling module is selected from the group consisting of CD3δε, CD3γε, and ζζ.

In some embodiments, according to any of the abTCRs (such as isolated abTCRs) described above, the first polypeptide chain further comprises a first accessory intracellular domain comprising a co-stimulatory intracellular signaling sequence C-terminal to the first transmembrane domain. In some embodiments, the second polypeptide chain further comprises a second accessory intracellular domain comprising a co-stimulatory intracellular signaling sequence C-terminal to the second transmembrane domain. In some embodiments, the first polypeptide chain further comprises a first signaling peptide N-terminal to the first antigen-binding domain. In some embodiments, the second polypeptide chain further comprises a second signaling peptide N-terminal to the second antigen-binding domain.

In some embodiments, according to any of the abTCRs (such as isolated abTCRs) described above where the target antigen is a complex comprising a peptide and a major histocompatibility complex (MHC) protein, the peptide is derived from a protein selected from the group consisting of WT-1, AFP, HPV16-E7, NY-ESO-1, PRAME, EBV-LMP2A, HIV-1, and PSA.

In some embodiments, according to any of the abTCRs (such as isolated abTCRs) described above, a) the first TCR subunit is a TCR α chain, and the second TCR subunit is a TCR β chain; b) the first TCR subunit is a TCR β chain, and the second TCR subunit is a TCR α chain; c) the first TCR subunit is a TCR γ chain, and the second TCR subunit is a TCR δ chain; or d) the first TCR subunit is a TCR δ chain, and the second TCR subunit is a TCR γ chain.

In some embodiments, according to any of the abTCRs (such as isolated abTCRs) described above, there is provided a nucleic acid encoding the first and second polypeptide chains of the abTCR.

In some embodiments, according to any of the abTCRs (such as isolated abTCRs) described above, there is provided complex comprising the abTCR and at least one TCR-associated signaling module selected from the group consisting of CD3δε, CD3γε, and ζζ. In some embodiments, the complex is an octamer comprising the abTCR and CD3δε, CD3γε, and ζζ.

In some embodiments, according to any of the abTCRs (such as isolated abTCRs) described above, there is provided an effector cell presenting on its surface the abTCR. In some embodiments, the effector cell comprises a nucleic acid encoding the abTCR. In some embodiments, the effector cell does not express the first TCR subunit and/or the second TCR subunit. For example, in some embodiments, a) the first TCR subunit is TCRγ and the second TCR subunit is TCRδ; or b) the first TCR subunit is TCRδ and the second TCR subunit is TCRγ; and the effector cell is an αβ T cell. In some embodiments, a) the first TCR subunit is TCRγ and the second TCR subunit is TCRδ; or b) the first TCR subunit is TCRδ and the second TCR subunit is TCRγ; and the effector cell is an αβ T cell. In some embodiments, the effector cell is modified to block or decrease the expression of a first endogenous TCR subunit and/or a second endogenous TCR subunit. For example, in some embodiments, the first TCR subunit is TCRα and the second TCR subunit is TCRβ; or b) the first TCR subunit is TCRβ and the second TCR subunit is TCRα; and the effector cell is an αβ T cell modified to block or decrease the expression of TCRα and/or TCRβ. In some embodiments, a) the first TCR subunit is TCRγ and second TCR subunit is TCRδ; or b) the first TCR subunit is TCRδ and the second TCR subunit is TCRγ; and the effector cell is a γδ T cell modified to block or decrease the expression of TCRγ and/or TCRδ.

In some embodiments, according to any of the abTCRs (such as isolated abTCRs) described above, there is provided an effector cell presenting on its surface the abTCR, wherein the effector cell is a T cell. In some embodiments, the T cell is selected from the group consisting of a cytotoxic T cell, a helper T cell, a natural killer T cell, and a suppressor T cell.

In some embodiments, according to any of the abTCRs (such as isolated abTCRs) described above, there is provided an effector cell presenting on its surface the abTCR, wherein the effector cell comprises a) a first vector comprising a first nucleic acid sequence encoding the first polypeptide chain of the abTCR under the control of a first promoter and b) a second vector comprising a second nucleic acid sequence encoding the second polypeptide chain of the abTCR under the control of a second promoter.

In some embodiments, according to any of the abTCRs (such as isolated abTCRs) described above, there is provided an effector cell presenting on its surface the abTCR, wherein the effector cell comprises a vector comprising a) a first nucleic acid sequence encoding the first polypeptide chain of the abTCR under the control of a first promoter; and b) a second nucleic acid sequence encoding the second polypeptide chain of the abTCR under the control of a second promoter.

In some embodiments, according to any of the abTCRs (such as isolated abTCRs) described above, there is provided an effector cell presenting on its surface the abTCR, wherein the effector cell comprises a vector comprising a) a first nucleic acid sequence encoding the first polypeptide chain of the abTCR and a second nucleic acid sequence encoding the second polypeptide chain of the abTCR, wherein the first and second nucleic acid sequences are under the control of a single promoter.

In some embodiments, according to any of the abTCRs (such as isolated abTCRs) described above, there is provided an effector cell presenting on its surface the abTCR, wherein the expression of the first polypeptide chain of the abTCR is more than two-fold different than the expression of the second polypeptide chain of the abTCR.

In some embodiments, there is provided a method of killing a target cell presenting a target antigen, comprising contacting the target cell with an effector cell expressing an abTCR according to any of the abTCRs (such as isolated abTCRs) described above, wherein the abTCR specifically binds to the target antigen.

In some embodiments, there is provided a method of killing a target cell presenting a target antigen, comprising contacting the target cell with an effector αβ T cell comprising an abTCR that specifically binds to the target antigen comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to the target antigen, wherein the first TCRD and the second TCRD form a T cell receptor module (TCRM) that is capable of recruiting at least one TCR-associated signaling module, and wherein the first TCR subunit is TCRγ and the second TCR subunit is TCRδ, or the first TCR subunit is TCR and the second TCR subunit is TCRγ. In some embodiments, the first polypeptide chain further comprises a first peptide linker between the first antigen-binding domain and the first TCRD and the second polypeptide chain further comprises a second peptide linker between the second antigen-binding domain and the second TCRD. In some embodiments, the first and/or second peptide linkers comprise, individually, a constant domain or fragment thereof from an immunoglobulin or T cell receptor subunit. In some embodiments, the first and/or second peptide linkers comprise, individually, a CH1, CH2, CH3, CH4 or CL antibody domain, or a fragment thereof. In some embodiments, the first and/or second peptide linkers comprise, individually, a Cα, Cβ, Cγ, or Cδ TCR domain, or a fragment thereof.

In some embodiments, according to any of the methods of killing a target cell described above, the contacting is in vivo. In some embodiments, the contacting is in vitro.

In some embodiments, there is provided a pharmaceutical composition comprising an abTCR according to any of the abTCRs (such as isolated abTCRs) described above and a pharmaceutically acceptable carrier. In some embodiments, there is provided a pharmaceutical composition comprising a nucleic acid encoding an abTCR according to any of the embodiments described above and a pharmaceutically acceptable carrier. In some embodiments, there is provided a pharmaceutical composition comprising an effector cell expressing an abTCR according to any of the abTCRs (such as isolated abTCRs) described above and a pharmaceutically acceptable carrier.

In some embodiments, there is provided a method of treating a target antigen-associated disease in an individual in need thereof comprising administering to the individual an effective amount of a pharmaceutical composition comprising an effector cell expressing an abTCR according to any of the abTCRs (such as isolated abTCRs) described above.

In some embodiments, there is provided a method of treating a target antigen-associated disease in an individual in need thereof comprising administering to the individual an effective amount of a composition comprising an effector αβ T cell comprising an abTCR that specifically binds to the target antigen comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to the target antigen, wherein the first TCRD and the second TCRD form a T cell receptor module (TCRM) that is capable of recruiting at least one TCR-associated signaling module, and wherein the first TCR subunit is TCRγ and the second TCR subunit is TCRδ, or the first TCR subunit is TCR and the second TCR subunit is TCRγ. In some embodiments, the wherein the first polypeptide chain further comprises a first peptide linker between the first antigen-binding domain and the first TCRD and the second polypeptide chain further comprises a second peptide linker between the second antigen-binding domain and the second TCRD. In some embodiments, the first and/or second peptide linkers comprise, individually, a constant domain or fragment thereof from an immunoglobulin or T cell receptor subunit. In some embodiments, the first and/or second peptide linkers comprise, individually, a CH1, CH2, CH3, CH4 or CL antibody domain, or a fragment thereof. In some embodiments, the first and/or second peptide linkers comprise, individually, a Cα, Cβ, Cγ, or Cδ TCR domain, or a fragment thereof.

In some embodiments, according to any of the methods of treating a target antigen-associated disease described above, the target antigen-associated disease is cancer. In some embodiments, the cancer is selected from the group consisting of adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, lymphoma, leukemia, lung cancer, melanoma, mesothelioma, multiple myeloma, pancreatic cancer, pheochromocytoma, plasmacytoma, neuroblastoma, ovarian cancer, prostate cancer, sarcoma, stomach cancer, uterine cancer and thyroid cancer. In some embodiments, the target antigen-associated disease is viral infection. In some embodiments, the viral infection is caused by a virus selected from the group consisting of Cytomegalovirus (CMV), Epstein-Barr Virus (EBV), Hepatitis B Virus (HBV), Kaposi's Sarcoma associated herpesvirus (KSHV), Human papillomavirus (HPV), Molluscum contagiosum virus (MCV), Human T cell leukemia virus 1 (HTLV-1), HIV (Human immunodeficiency virus), and Hepatitis C Virus (HCV).

In some embodiments, there is provided a method of treating a target antigen-associated disease in an individual in need thereof comprising administering to the individual an effective amount of a pharmaceutical composition comprising a nucleic acid encoding an abTCR according to any of the abTCRs (such as isolated abTCRs) described above.

In some embodiments, there is provided a method of enriching a heterogeneous cell population for an effector cell expressing an abTCR according to any of the abTCRs (such as isolated abTCRs) described above, wherein the method comprises a) contacting the heterogeneous cell population with a ligand comprising the target antigen or one or more epitopes contained therein to form complexes of the effector cell bound to the ligand; and b) separating the complexes from the heterogeneous cell population, thereby generating a cell population enriched for the effector cell.

In some embodiments, there is provided a nucleic acid library comprising sequences encoding a plurality of abTCRs according to any of the abTCRs (such as isolated abTCRs) described above.

In some embodiments, there is provided a method of screening a nucleic acid library according to any of the embodiments described above for sequences encoding abTCRs specific for a target antigen, comprising: a) introducing the nucleic acid library into a plurality of cells, such that the abTCRs are expressed on the surface of the plurality of cells; b) incubating the plurality of cells with a ligand comprising the target antigen or one or more epitopes contained therein; c) collecting cells bound to the ligand; and d) isolating sequences encoding the abTCRs from cells collected in step c), thereby identifying abTCRs specific for the target antigen.

Also provided are methods of making any of the constructs described herein, articles of manufacture, and kits that are suitable for the methods described herein.

BRIEF DESCRIPTION OF THE DRAWINGS

FIG. 1A shows a schematic representation of the various abTCR construct designs (abTCR-3, abTCR-4, abTCR-5, and abTCR-6).

FIG. 1B shows contemplated variations of the abTCR construct designs.

FIG. 7A shows flow cytometry analysis of abTCR-transduced peripheral blood lymphocytes; cells were transduced with an abTCR-6MD construct having an anti-AFP158/HLA-A*02:01 binding moiety and co-stained with anti-CD4 antibody, anti-CD8 antibody and AFP158/HLA-A*02:01 tetramers. The dotted box indicates the tetramer⁺ population gate for the cells shown in the CD4/CD8 plot in FIG. 7B.

FIG. 7B shows flow cytometry analysis of CD4 and CD8 expression on peripheral blood lymphocytes that were either mock-transduced or transduced with an abTCR-6MD construct having an anti-AFP158/HLA-A*02:01 binding moiety and co-stained with anti-CD4 and anti-CD8 antibodies; CD4 and CD8 expression are shown for ungated cells (top 2 panels) or tetramer⁺ gated cells (bottom panel).

FIG. 16A shows cell growth of the transduced T cells. FIG. 16B shows Western blot analysis for expression of the abTCR-6MD and abTCR-7 in T cells using an anti-FLAG antibody to detect the FLAG-tagged constructs. Staining for CD3ζ was included as a loading control. FIG. 16C shows killing of SK-HEP-1 and SK-HEP-1-AFP-MG cells mediated by T cells transduced with either the abTCR-6MD or abTCR-7.

FIGS. 18A and 18B show the level of secretion of a panel of cytokines by mock-transduced T cells or T cells transduced with either a CAR or an abTCR-6MD, both having the same anti-CD19 binding moiety variable domains, co-cultured with JeKo-1, IM9, THP-1 or Jurkat cell lines.

FIG. 23A shows cell growth of the abTCR and cTCR T cells. FIG. 23B shows killing of CD19-positive cancer cell line Nalm-6 mediated by mock-transduced T cells or T cells transduced with either the abTCR or cTCR.

DETAILED DESCRIPTION OF THE INVENTION

Figure 2:
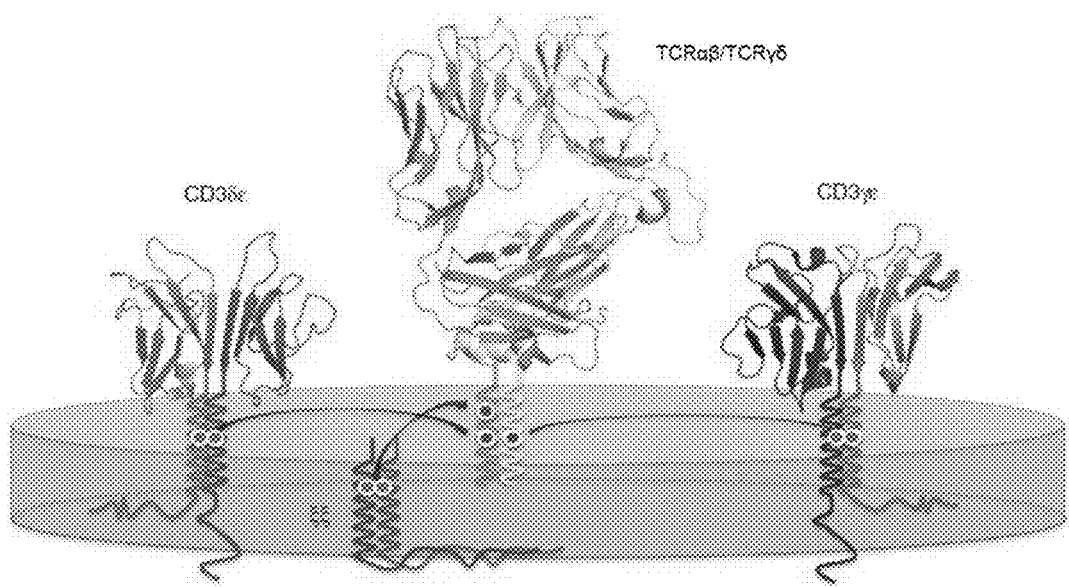
FIG. 2 shows a conventional model for the assembly of the TCR-CD3 complex.

The present application provides an isolated chimeric antibody/T cell receptor construct (referred to herein as "abTCR") that comprises a) an antibody moiety, such as a Fab or Fv fragment, that specifically binds to a target antigen; and b) a T cell receptor module (TCRM) capable of recruiting at least one TCR-associated signaling module.

We have developed a series of novel and synthetic chimeric antibody/TCR constructs that combine the binding specificity and affinity of our TCR-like mAbs, as well as conventional mAbs, with the target-specific cytotoxic potency and controlled activation afforded by TCRs. Primary T cells transduced to express abTCRs showed efficient surface expression and formation of stable TCR-like signaling complexes in association with endogenous CD3 molecules. When engineered into T cells, the abTCRs endowed the T cells with potent cytotoxicity against target-bearing tumor cells both in vitro and in vivo, in both MHC-dependent (peptide/MHC antigen) and MHC-independent (cell-surface antigen) configurations. Target-specific activation was observed for multiple different T cell subsets transduced to express an abTCR, including CD4+ T cells, CD8+ T cells, natural killer T (NKT) cells, and regulatory T (Treg) cells. In addition, abTCRs including intracellular co-stimulatory sequences were found to perform as well as, and in some cases better than, corresponding abTCRs without any co-stimulatory sequences.

Despite the remarkable curative potential demonstrated with CAR T cell therapy, clinical trials continue to trigger severe adverse events that are associated with excessive cytokine release and uncontrolled T-cell proliferation. Without being bound by theory, it is believed that abTCRs can be regulated by the naturally occurring machinery that controls TCR activation, requiring assembly with an endogenous CD3 complex to activate T-cell-mediated killing, and can thus avoid being constitutively activated. We have found that T cells transduced with abTCR constructs express lower levels of cytokines (e.g., IL-2) and T cell exhaustion markers (e.g., PD-1, TIM3, and LAG1) than T cells transduced with corresponding chimeric antigen receptors (CARs) bearing the same antibody variable regions, while having equivalent potency in cancer cell killing. This strategy thus provides a significant technical advantage over using CARs, yielding T cells whose cytotoxic signaling responds to endogenous T-cell regulatory mechanisms and which have the potential to functionally persist longer in vivo. By combining the exquisitely optimized binding of monoclonal antibodies to specific antigens, such as cell surface antigens or peptide/MHC complexes, with the ability of the T cell receptor to engage endogenous signaling complexes to activate immune cells, the invention allows for highly specific and potent targeting of low-copy number cell surface antigens, as well as intracellular or secreted antigens via peptide/MHC complexes.

The present application thus provides an abTCR (such as an isolated abTCR) comprising an antibody moiety that specifically binds to a target antigen and a TCRM capable of recruiting at least one TCR-associated signaling module. The abTCR may be a heterodimer comprising a first polypeptide chain and a second polypeptide chain. The antibody moiety may comprise a heavy chain variable antibody domain ($V_H$) and a light chain variable antibody domain ($V_L$). In some embodiments, the antibody moiety further comprises one or more antibody heavy chain constant domains, such as a heavy chain constant 1 antibody domain ($C_H1$) and/or a light chain constant antibody domain ($C_L$). The TCRM comprises a first T cell receptor domain (TCRD) comprising a transmembrane domain of a first TCR subunit and a second TCRD comprising a transmembrane domain of a second TCR subunit. The first polypeptide chain and the second polypeptide chain of the abTCR may be linked via one or more disulfide bonds. See FIG. 1A for exemplary abTCR construct designs.

In another aspect, there is provided one or more nucleic acids encoding an abTCR.

In yet another aspect, there is provided a complex (referred to herein as an "abTCR-CD3 complex") comprising an abTCR and at least one TCR-associated signaling module. The complex may be an octamer comprising the four dimers abTCR, CD3δε, CD3γε, and ζζ. Also provided is an effector cell, such as a T cell, expressing or associated with an abTCR or abTCR-CD3 complex.

In yet another aspect, there is provided a composition comprising an abTCR. The composition can be a pharmaceutical composition comprising an abTCR or an effector cell expressing or associated with the abTCR (for example a T cell expressing an abTCR).

Also provided are methods of making and using an abTCR (or cells expressing or associated with an abTCR) for treatment purposes, as well as kits and articles of manufacture useful for such methods. Further provided are methods of treating a disease using an abTCR (or cells expressing or associated with an abTCR).

Definitions

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of the disease (such as, for example, tumor volume in cancer). The methods of the invention contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

"Activation", as used herein in relation to T cells, refers to the state of a T cell that has been sufficiently stimulated to induce detectable cellular proliferation. Activation can also be associated with induced cytokine production, and detectable effector functions.

The term "antibody" or "antibody moiety" includes full-length antibodies and antigen-binding fragments thereof. A full-length antibody comprises two heavy chains and two light chains. The variable regions of the light and heavy chains are responsible for antigen-binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

A "Fab-like antigen-binding module" refers to an antibody moiety that comprises a first polypeptide chain and a second polypeptide chain, wherein the first and second polypeptide chains comprise a $V_L$ antibody domain, a $C_L$ antibody domain, a $V_H$ antibody domain, and a $C_H1$ antibody domain. The $V_L$ and $C_L$ antibody domains may be on one chain with the $V_H$ and $C_H1$ antibody domains on the other chain, or the $V_L$ and $C_H1$ antibody domains may be on one chain with the $V_H$ and $C_L$ antibody domains on the other chain. In some embodiments, the first and second polypeptide chains are linked by a disulfide bond.

As used herein, a first antibody moiety "competes" for binding to a target antigen with a second antibody moiety when the first antibody moiety inhibits target antigen-binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds" or "is specific for" refers to measurable and reproducible interactions, such as binding between a target and an antibody or antibody moiety, that is determinative of the presence of the target in the presence of a heterogeneous population of molecules, including biological molecules. For example, an antibody moiety that specifically binds to a target (which can be an epitope) is an antibody moiety that binds the target with greater affinity, avidity, more readily, and/or with greater duration than its bindings to other targets. In some embodiments, an antibody moiety that specifically binds to an antigen reacts with one or more antigenic determinants of the antigen (for example a cell surface antigen or a peptide/ MHC protein complex) with a binding affinity that is at least about 10 times its binding affinity for other targets.

The term "T cell receptor," or "TCR," refers to a heterodimeric receptor composed of αβ or γδ chains that pair on the surface of a T cell. Each α, β, γ, and δ chain is composed of two Ig-like domains: a variable domain (V) that confers antigen recognition through the complementarity determining regions (CDR), followed by a constant domain (C) that is anchored to cell membrane by a connecting peptide and a transmembrane (TM) region. The TM region associates with the invariant subunits of the CD3 signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

The term "TCR-associated signaling module" refers to a molecule having a cytoplasmic immunoreceptor tyrosine-based activation motif (ITAM) that is part of the TCR-CD3 complex. TCR-associated signaling modules include CD3γε, CD3δε, and ζζ.

The term "module" when referring to a protein or portion of a protein means the protein or portion of the protein comprises a plurality of polypeptide chains (e.g., a dimeric protein or portion of a dimeric protein). The plurality of polypeptide chains may be linked, such as by a linker (e.g., a peptide linker) or chemical linkage (e.g., a peptide linkage). A "module" is meant to include structurally and/or functionally related portions of one or more polypeptides which make up the protein. For example, a transmembrane module of a dimeric receptor may refer to the portions of each polypeptide chain of the receptor that span the membrane. A module may also refer to related portions of a single polypeptide chain. For example, a transmembrane module of a monomeric receptor may refer to portions of the single polypeptide chain of the receptor that span the membrane.

The term "T cell receptor module," or "TCRM," refers to a heterodimer comprising sequences derived from a T cell receptor. The TCRM comprises T cell receptor transmembrane domains, and may further comprise all or a portion of T cell receptor connecting peptides and/or intracellular domains.

An "isolated" construct (such as an abTCR) as used herein refers to a construct that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR DEFINITIONS

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA*, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

The term "fully synthetic" in reference to an antibody or antibody moiety means that the antibody or antibody moiety has fixed, mostly or all naturally occurring $V_H/V_L$ framework pairings, but non-naturally occurring (i.e., synthetic) sequences of all 6 CDRs of both heavy and light chains. Non-naturally occurring CDRs include those comprising modified human CDR sequences, such as CDR sequences modified by conservative amino acid substitutions or introduced cysteine residues.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Homology" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are "homologous" at that position. The "percent of homology" or "percent sequence identity" between two sequences is a function of the number of matching or homologous positions shared by the two sequences divided by the number of positions compared times 100, considering any conservative substitutions as part of the sequence identity. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5): 1792-1797, 2004; Edgar, R. C., *BMC Bioinformatics* 5(1): 113, 2004).

The "$C_H1$ domain" of a human IgG (also referred to as "C1" of "H1" domain) usually extends from about amino acid 118 to about amino acid 215 (EU numbering system).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "inducible promoter" refers to a promoter whose activity can be regulated by adding or removing one or more specific signals. For example, an inducible promoter may activate transcription of an operably linked nucleic acid under a specific set of conditions, e.g., in the presence of an inducing agent that activates the promoter and/or relieves repression of the promoter.

An "effective amount" of an abTCR or composition comprising an abTCR as disclosed herein is an amount sufficient to carry out a specifically stated purpose. An "effective amount" can be determined empirically and by known methods relating to the stated purpose.

The term "therapeutically effective amount" refers to an amount of an abTCR or composition comprising an abTCR as disclosed herein, effective to "treat" a disease or disorder in an individual. In the case of cancer, the therapeutically effective amount of an abTCR or composition comprising an abTCR as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent an abTCR or composition comprising an abTCR as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that improves progression free survival of a patient. In the case of infectious disease, such as viral infection, the therapeutically effective amount of an abTCR or composition comprising an abTCR as disclosed herein can reduce the number of cells infected by the pathogen; reduce the production or release of pathogen-derived antigens; inhibit (i.e., slow to some extent and preferably stop) spread of the pathogen to uninfected cells; and/or relieve to some extent one or more symptoms associated with the infection. In some embodiments, the therapeutically effective amount is an amount that extends the survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of X.

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

Chimeric Antibody/T Cell Receptor Constructs

In one aspect, the present invention provides a target antigen-specific chimeric antibody/T cell receptor (abTCR) that specifically binds to a target antigen (such as a cell surface antigen or a peptide/MHC complex) and is capable of recruiting at least one TCR-associated signaling module (such as CD3δε, CD3γε, or ζ. In some embodiments, the abTCR comprises a first polypeptide chain and a second polypeptide chain. In some embodiments, the first and second polypeptide chains are linked, such as by a covalent linkage (e.g., peptide or other chemical linkage) or non-covalent linkage. In some embodiments, the abTCR is a heterodimer comprising a first polypeptide chain and a second polypeptide chain. In some embodiments, the first polypeptide chain and the second polypeptide chain are linked by at least one disulfide bond. The specificity of the abTCR derives from an antibody moiety that confers binding specificity to the target antigen. In some embodiments, the antibody moiety is a Fab-like antigen-binding module comprising $V_H$, $C_H1$, $V_L$, and $C_L$ antibody domains. In some embodiments, the antibody moiety is an Fv-like antigen-binding module comprising $V_H$ and $V_L$ antibody domains. The capability of the abTCR to recruit a TCR-associated signaling module derives from a T cell receptor module (TCRM). In some embodiments, the TCRM comprises the transmembrane module of a TCR (such as an αβTCR or a γδTCR). In some embodiments, the TCRM further comprises one or both of the connecting peptides or fragments thereof of a TCR. In some embodiments, the transmembrane module and the connecting peptides or fragments thereof are derived from the same TCR type (αβ or γδ). In some embodiments, the transmembrane module is derived from an αβ TCR and the connecting peptides or fragments thereof are derived from a γδ TCR, or the transmembrane module is derived from a γδ TCR and the connecting peptides or fragments thereof are derived from an αβ TCR. In some embodiments, the abTCR further comprises at least one intracellular domain. In some embodiments, one or more of the at least one intracellular domain of the abTCR comprises a sequence from the intracellular domain of a TCR. In some embodiments, one or more of the at least one intracellular domain of the abTCR comprises a T cell costimulatory signaling sequence. The costimulatory signaling sequence can be a portion of the intracellular domain of a costimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the antibody moiety is contained in an extracellular domain of the abTCR. In some embodiments, the abTCR further comprises one or more peptide linkers between the antibody moiety and the TCRM to optimize the length of the extracellular domain. In some embodiments, reference to an antigen-binding module (such as a Fab-like or Fv-like antigen-binding module) that specifically binds to a target antigen means that the antigen-binding module binds to the target antigen with a) an affinity that is at least about 10 (including for example at least about any of 10, 20, 30, 40, 50, 75, 100, 200, 300, 400, 500, 750, 1000 or more) times its binding affinity for other molecules; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to other molecules. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

Contemplated abTCR constructs include, for example, abTCRs that specifically bind to cell surface antigens and abTCRs that specifically bind to cell surface-presented peptide/MHC complexes.

In some embodiments, the abTCR comprises a Fab-like antigen-binding module comprising a) a first polypeptide chain comprising a first antigen-binding domain comprising a $V_H$ antibody domain and a $C_H1$ antibody domain and b) a second polypeptide chain comprising a second antigen-binding domain comprising a $V_L$ antibody domain and a $C_L$ antibody domain. In some embodiments, the first antigen-binding domain comprises the $V_H$ antibody domain amino-terminal to the $C_H1$ antibody domain and/or the second antigen-binding domain comprises the $V_L$ antibody domain amino-terminal to the $C_L$ antibody domain. In some embodiments, there is a peptide linker between the $V_L$ and $C_L$ antibody domains and/or a peptide linker between the $V_H$ and $C_H1$ antibody domains. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the $V_L$ antibody domain comprises antibody CDRs derived from a $V_H$ antibody domain and/or the $V_H$ antibody domain comprises antibody CDRs derived from a $V_L$ antibody domain. In some embodiments, the $V_L$ antibody domain comprises framework regions derived from one antibody and one or more CDRs derived from another antibody and/or the $V_H$ antibody domain comprises framework regions derived from one antibody and one or more CDRs derived from another antibody. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second antigen-binding domains are linked by a disulfide bond between a residue in the $C_H1$ domain and a residue in the $C_L$ domain. In some embodiments, the $C_H1$ domain is derived from an IgG (e.g, IgG1, IgG2, IgG3, or IgG4), IgA (e.g., IgA1 or IgA2), IgD, IgM, or IgE heavy chain, optionally human. In some embodiments, the $C_H1$ domain comprises (such as consists of) the amino acid sequence of any one of SEQ ID NOs: 39 and 60-69). In some embodiments, the $C_H1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain comprises (such as consists of) the amino acid sequence of SEQ ID NO: 41. In some embodiments, the $C_L$ domain is a variant comprising one or more modifications (e.g., amino acid substitutions, insertions, and/or deletions) compared to the sequence from which it is derived. In some embodiments, the $C_H1$ and/or $C_L$ domains comprise one or more modifications that do not substantially alter their binding affinities for one another. In some embodiments, the $C_H1$ and/or $C_L$ domains comprise one or more modifications that increase their binding affinities for one another and/or introduce a non-naturally occurring disulfide bond. In some embodiments, the $C_H1$ and $C_L$ domains comprise a knob-into-hole modification (see, for example, Carter P. *J Immunol Methods.* 248:7-15, 2001). In some embodiments, the $C_H1$ and $C_L$ domains are modified by electrostatic steering to enhance their association with one another (see, for example, WO2006106905 and Gunasekaran K, et al. *J Biol Chem.* 285:19637-46, 2010). In some embodiments, the Fab-like antigen-binding module is human, humanized, chimeric, semi-synthetic, or fully synthetic.

In some embodiments, the abTCR comprises a Fab-like antigen-binding module comprising a) a first polypeptide chain comprising a first antigen-binding domain comprising a $V_L$ antibody domain and a $C_H1$ antibody domain and b) a second polypeptide chain comprising a second antigen-binding domain comprising a $V_H$ antibody domain and a $C_L$ antibody domain. In some embodiments, the first antigen-binding domain comprises the $V_L$ antibody domain amino-terminal to the $C_H1$ antibody domain and/or the second antigen-binding domain comprises the $V_H$ antibody domain amino-terminal to the $C_L$ antibody domain. In some embodiments, there is a peptide linker between the $V_H$ and $C_L$ antibody domains and/or a peptide linker between the $V_L$ and $C_H1$ antibody domains. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the $V_L$ antibody domain comprises antibody CDRs derived from a $V_H$ antibody domain and/or the $V_H$ antibody domain comprises antibody CDRs derived from a $V_L$ antibody domain. In some embodiments, the $V_L$ antibody domain comprises framework regions derived from one antibody and one or more CDRs derived from another antibody and/or the $V_H$ antibody domain comprises framework regions derived from one antibody and one or more CDRs derived from another antibody. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second antigen-binding domains are linked by a disulfide bond between a residue in the $C_H1$ domain and a residue in the $C_L$ domain. In some embodiments, the $C_H1$ domain is derived from an IgG (e.g, IgG1, IgG2, IgG3, or IgG4), IgA (e.g., IgA1 or IgA2), IgD, IgM, or IgE heavy chain, optionally human. In some embodiments, the $C_H1$ domain comprises (such as consists of) the amino acid sequence of any one of SEQ ID NOs: 39 and 60-69). In some embodiments, the $C_H1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain comprises (such as consists of) the amino acid sequence of SEQ ID NO: 41. In some embodiments, the $C_L$ domain is a variant comprising one or more modifications (e.g., amino acid substitutions, insertions, and/or deletions) compared to the sequence from which it is derived. In some embodiments, the $C_H1$ and/or $C_L$ domains comprise one or more modifications that do not substantially alter their binding affinities for one another. In some embodiments, the $C_H1$ and/or $C_L$ domains comprise one or more modifications that increase their binding affinities for one another and/or introduce a non-naturally occurring disulfide bond. In some embodiments, the $C_H1$ and $C_L$ domains comprise a knob-into-hole modification (see, for example, Carter P. *J Immunol Methods.* 248:7-15, 2001). In some embodiments, the $C_H1$ and $C_L$ domains are modified by electrostatic steering to enhance their association with one another (see, for example, WO2006106905 and Gunasekaran K, et al. *J Biol Chem.* 285:19637-46, 2010). In some embodiments, the Fab-like antigen-binding module is human, humanized, chimeric, semi-synthetic, or fully synthetic.

In some embodiments, the abTCR comprises an Fv-like antigen-binding module comprising a) a first polypeptide chain comprising a first antigen-binding domain comprising a $V_H$ antibody domain and b) a second polypeptide chain comprising a second antigen-binding domain comprising a $V_L$ antibody domain. In some embodiments, there is a first peptide linker fused to the C-terminus of the $V_L$ antibody domain and/or a second peptide linker fused to the C-terminus of the $V_H$ antibody domain. In some embodiments, the first and second peptide linkers are capable of binding to one another. In some embodiments, the first and/or second peptide linkers are derived from immunoglobulin heavy and/or light chain constant regions. In some embodiments, the first and/or second peptide linkers comprise a CH3 antibody domain or a variant thereof. In some embodiments, immunoglobulin heavy chain constant domains (e.g., $C_H1$ or CH3) contained in the peptide linkers are derived from an IgG (e.g, IgG1, IgG2, IgG3, or IgG4), IgA (e.g., IgA1 or IgA2), IgD, IgM, or IgE heavy chain, optionally human. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the $V_L$ antibody domain comprises antibody CDRs derived from a $V_H$ antibody domain and/or the $V_H$ antibody domain comprises antibody CDRs derived from a $V_L$ antibody domain. In some embodiments, the $V_L$ antibody domain comprises framework regions derived from one antibody and one or more CDRs derived from another antibody and/or the $V_H$ antibody domain comprises framework regions derived from one antibody and one or more CDRs derived from another antibody. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second peptide linkers are linked by a disulfide bond. In some embodiments, the first and/or second peptide linker is a variant comprising one or more modifications (e.g., amino acid substitutions, insertions, and/or deletions) compared to the sequence from which it is derived. In some embodiments, the first and/or second peptide linkers comprise one or more modifications that do not substantially alter their binding affinity for one another. In some embodiments, the first and/or second peptide linkers comprise one or more modifications that increase their binding affinity for one another and/or introduce a non-naturally occurring disulfide bond. In some embodiments, the first and second peptide linkers comprise a knob-into-hole modification (see, for example, Carter P. *J Immunol Methods*. 248:7-15, 2001). In some embodiments, the first and second peptide linkers are modified by electrostatic steering to enhance their association with one another (see, for example, WO2006106905 and Gunasekaran K, et al. *J Biol Chem*. 285:19637-46, 2010). In some embodiments, the Fv-like antigen-binding module is human, humanized, chimeric, semi-synthetic, or fully synthetic.

In some embodiments, the antibody moiety (e.g., Fab-like antigen-binding module or Fv-like antigen-binding module) is semi-synthetic, comprising fully human sequences and one or more synthetic regions. In some embodiments, the antibody moiety is semi-synthetic, comprising a fully human $V_L$ and a semi-synthetic $V_H$ comprising fully human FR1, HC-CDR1, FR2, HC-CDR2, FR3, and FR4 regions and a synthetic HC-CDR3. In some embodiments, the semi-synthetic $V_H$ comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic $V_H$ or the synthetic HC-CDR3 is obtained from a semi-synthetic library (such as a semi-synthetic human library) comprising fully synthetic HC-CDR3 regions having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is randomly selected from the standard human amino acids, minus cysteine. In some embodiments, the synthetic HC-CDR3 is from about 10 to about 19 (such as about any of 10, 11, 12, 13, 14, 15, 16, 17, 18 or 19) amino acids in length. In some embodiments, the antibody moiety is semi-synthetic, comprising a semi-synthetic $V_L$ and a semi-synthetic $V_H$. In some embodiments, the antibody moiety is fully-synthetic, comprising antibodies with fixed human $V_H/V_L$ framework pairings, but randomized and synthetic sequences for all 6 CDRs of both heavy and light chains.

The antibody moiety (e.g., Fab-like antigen-binding module or Fv-like antigen-binding module) in some embodiments comprises specific CDR sequences derived from one or more antibody moieties (such as a monoclonal antibody) or certain variants of such sequences comprising one or more amino acid substitutions. In some embodiments, the amino acid substitutions in the variant sequences do not substantially reduce the ability of the antibody moiety to bind the target antigen. Alterations that substantially improve target antigen binding affinity or affect some other property, such as specificity and/or cross-reactivity with related variants of the target antigen, are also contemplated.

The TCRM comprises a) a first polypeptide chain comprising a first T cell receptor domain (TCRD) comprising a first transmembrane domain and b) a second polypeptide chain comprising a second TCRD comprising a second transmembrane domain. In some embodiments, the first transmembrane domain is the transmembrane domain of a first TCR subunit and/or the second transmembrane domain is the transmembrane domain of a second TCR subunit. In some embodiments, the first TCR subunit is a TCR α chain (e.g., GenBank Accession No: CCI73895), and the second TCR subunit is a TCR β chain (e.g., GenBank Accession No: CCI73893). In some embodiments, the first TCR subunit is a TCR β chain, and the second TCR subunit is a TCR α chain. In some embodiments, the first TCR subunit is a TCR γ chain (e.g., GenBank Accession No: AGE91788), and the second TCR subunit is a TCR δ chain (e.g., GenBank Accession No: AAQ57272). In some embodiments, the first TCR subunit is a TCR δ chain, and the second TCR subunit is a TCR γ chain. In some embodiments, the first and/or second transmembrane domains comprise (such as consist of), individually, a transmembrane domain contained in one of the amino acid sequences of SEQ ID NOs: 77-80. In some embodiments, the first and/or second transmembrane domains comprise (such as consist of), individually, any one of the amino acid sequences of SEQ ID NOs: 1-4. In some embodiments, the first TCRD further comprises a first connecting peptide amino-terminal to the transmembrane domain and/or the second TCRD further comprises a second connecting peptide amino-terminal to the transmembrane domain. In some embodiments, the first connecting peptide comprises all or a portion of the connecting peptide of the first TCR subunit and/or the second connecting peptide comprises all or a portion of the connecting peptide of the second TCR subunit. In some embodiments, the first transmembrane domain and the first connecting peptide are derived from different TCR subunits and/or the second transmembrane domain and the second connecting peptide are derived from different TCR subunits. In some embodiments, the first and/or second connecting peptides comprise (such as consist of), individually, a connecting peptide or fragment thereof contained in one of the amino acid sequences of SEQ ID NOs: 77-80. In some embodiments, the first and/or second connecting peptides comprise (such as consist of), individually, any one of the amino acid sequences of SEQ ID NOs: 5-12. In some embodiments, the first TCRD further comprises a first TCR intracellular domain carboxy-terminal to the first transmembrane domain and/or the second TCRD further comprises a second TCR intracellular domain carboxy-terminal to the second transmembrane domain. In some embodiments, the first TCR intracellular domain comprises all or a portion of the intracellular domain of the first TCR subunit and/or the second TCR intracellular domain comprises all or a portion of the intracellular domain of the second TCR subunit. In some embodiments, the first and/or second TCR intracellular domains comprise, individually, all or a portion of an intracellular domain contained in any one of the amino acid sequences of SEQ ID NOs: 77-80. In some embodiments, the first and/or second TCR intracellular domains comprise, individually, any one of the amino acid sequences of SEQ ID NOs: 13-14. In some embodiments, the first TCRD is a fragment of the first TCR subunit and/or the second TCRD is a fragment of the second TCR chain. In some embodiments, the first and second polypeptide chains are linked, such as by a covalent linkage (e.g., peptide or other chemical linkage) or non-covalent linkage. In some embodiments, the first and second TCRDs are linked by a disulfide bond. In some embodiments, the first and second TCRDs are linked by a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM is capable of recruiting each of CD3δε, CD3γε, and ζζ to form an octameric abTCR-CD3 complex (i.e., promotes abTCR-CD3 complex formation).

In some embodiments, the abTCR is a molecule comprising a fusion of the first polypeptide chain of the antibody moiety (e.g., Fab-like antigen-binding module or Fv-like antigen-binding module) amino-terminal to the first polypeptide chain of the TCRM, thereby forming a first polypeptide chain of the abTCR, and a fusion of the second polypeptide chain of the antibody moiety amino-terminal to the second polypeptide chain of the TCRM, thereby forming a second polypeptide chain of the abTCR. In some embodiments, the abTCR further comprises a first peptide linker between the first polypeptide chain of the antibody moiety and the first polypeptide chain of the TCRM and/or a second peptide linker between the second polypeptide chain of the antibody moiety and the second polypeptide chain of the TCRM. In some embodiments, the first and/or second peptide linker is between about 5 to about 70 (such as about any of 5, 10, 15, 20, 25, 30, 35, 40, 45, 50, 55, 60, 65, or 70, including any ranges between these values) amino acids in length. In some embodiments, the first polypeptide chain of the abTCR further comprises a first signal peptide amino-terminal to the first antigen-binding domain and/or the second polypeptide chain of the abTCR further comprises a second signal peptide amino-terminal to the second antigen-binding domain. In some embodiments, the first and/or second signal peptides comprise (such as consist of) the amino acid sequence of SEQ ID NO: 49. In some embodiments, the first polypeptide chain of the abTCR further comprises a first accessory intracellular domain carboxy-terminal to the first transmembrane domain and/or the second polypeptide chain of the abTCR further comprises a second accessory intracellular domain carboxy-terminal to the second transmembrane domain. In some embodiments, the first and/or second accessory intracellular domains comprise a TCR costimulatory domain. In some embodiments, the TCR costimulatory domain comprises all or a portion of the amino acid sequence of SEQ ID NO: 70 or 71. In some embodiments, the first and/or second accessory intracellular domains comprise an epitope tag. In some embodiments, the epitope tag comprises any one of the amino acid sequences of SEQ ID NOs: 50-52. In some embodiments, the first and second polypeptide chains of the abTCR are linked, such as by a covalent linkage (e.g., peptide or other chemical linkage) or non-covalent linkage. In some embodiments, the abTCR is a heterodimer.

In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen expressed in a diseased cell. In some embodiments, the target antigen is a complex comprising a peptide and an MHC protein. Peptide/MHC complexes include, for example, a surface-presented complex comprising a peptide derived from a disease-associated antigen expressed in a diseased cell and an MHC protein. In some embodiments, the full-length disease-associated antigen is not normally expressed on the surface of the diseased cell (e.g., the disease-associated antigen is an intracellular or secreted protein). In some embodiments, the disease is cancer and the disease-associated antigen is a tumor-associated antigen expressed in a cancer cell. In some embodiments, the tumor-associated antigen is an oncoprotein. In some embodiments, the oncoprotein is the result of a mutation in a proto-oncogene, and the oncoprotein comprises a neoepitope comprising the mutation. For example, in some embodiments, the target antigen is a cell surface tumor-associated antigen (e.g., an oncoprotein comprising a neoepitope). In some embodiments, the target antigen is a complex comprising a peptide derived from a tumor-associated antigen (e.g., an oncoprotein comprising a neoepitope) not normally expressed on the surface of a cancer cell (e.g., an intracellular or secreted tumor-associated antigen) and an MHC protein. In some embodiments, the disease is viral infection and the disease-associated antigen is a virus-associated antigen expressed in an infected cell. For example, in some embodiments, the target antigen is a cell surface virus-associated antigen. In some embodiments, the target antigen is a complex comprising a peptide derived from a virus-associated antigen not normally expressed on the surface of a virus-infected cell (e.g., an intracellular or secreted virus-associated antigen) and an MHC protein. In some embodiments, the abTCR construct binds the target antigen with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values).

In some embodiments, the abTCR comprises an antibody moiety (e.g., Fab-like antigen-binding module or Fv-like antigen-binding module) that specifically binds to a cell surface antigen, wherein the cell surface antigen is CD19, ROR1, ROR2, BCMA, GPRC5D, or FCRL5. Specific binding to a full antigen, e.g., a cell surface antigen, is sometimes referred to as "non-MHC-restricted binding".

In some embodiments, the abTCR comprises an antibody moiety (e.g., Fab-like antigen-binding module or Fv-like antigen-binding module) that specifically binds to a complex comprising a peptide and an MHC protein, wherein the peptide is derived from a protein selected from the group consisting of WT-1, AFP, HPV16-E7, NY-ESO-1, PRAME, EBV-LMP2A, HIV-1, and PSA. Specific binding to a complex comprising a peptide and an MHC protein is sometimes referred to as "MHC-restricted binding".

In some embodiments, the abTCR comprises an antibody moiety (e.g., Fab-like antigen-binding module or Fv-like antigen-binding module) that specifically binds to a complex comprising a peptide derived from a disease-associated antigen (such as a tumor-associated or virally-encoded antigen) and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01.

In some embodiments, the abTCR comprises an antibody moiety (e.g., Fab-like antigen-binding module or Fv-like antigen-binding module) that specifically binds to a complex comprising a peptide derived from a disease-associated antigen (such as a tumor-associated or virally-encoded antigen) and an MHC class II protein, wherein the MHC class II protein is HLA-DP, HLA-DQ, or HLA-DR. In some embodiments, the MHC class II protein is HLA-DP. In some embodiments, the MHC class II protein is HLA-DQ. In some embodiments, the MHC class II protein is HLA-DR.

For example, in some embodiments, there is provided an abTCR (such as an isolated abTCR) comprising a) a Fab-like antigen-binding module that specifically binds to a target antigen, and b) a TCRM capable of recruiting at least one TCR-associated signaling module. In some embodiments, the Fab-like antigen-binding module comprises a $V_H$ antibody domain, a $C_H1$ antibody domain, a $V_L$ antibody domain, and a $C_L$ antibody domain. In some embodiments, the $C_H1$ domain is derived from an IgG (e.g, IgG1, IgG2, IgG3, or IgG4) heavy chain, optionally human. In some embodiments, the $C_H1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain is a variant comprising one or more modifications (e.g., amino acid substitutions, insertions, and/or deletions) compared to the sequence from which it is derived. In some embodiments, the Fab-like antigen-binding module is human, humanized, chimeric, semi-synthetic, or fully synthetic. In some embodiments, the TCRM comprises the transmembrane domains of a TCR, such as an αβTCR or a γδTCR. In some embodiments, the TCRM further comprises the connecting peptides or fragments thereof of a TCR, such as an αβTCR or a γδTCR. In some embodiments, the transmembrane domains and the connecting peptides are derived from an αβTCR or a γδTCR. In some embodiments, the transmembrane domains are derived from an αβTCR and the connecting peptides are derived from a γδTCR, or the transmembrane domains are derived from a γδTCR and the connecting peptides are derived from an αβTCR. In some embodiments, the TCRM further comprises at least one portion of an extracellular domain of the TCR. In some embodiments, the TCRM further comprises at least one TCR intracellular domain comprising a sequence from an intracellular domain of the TCR. In some embodiments, the TCRM comprises fragments of the TCR subunits. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the abTCR further comprises at least one disulfide bond. In some embodiments, the Fab-like antigen binding module comprises a disulfide bond and/or the TCRM comprises a disulfide bond. In some embodiments, the Fab-like antigen binding module comprises a disulfide bond between a residue in the $C_H1$ domain and a residue in the $C_L$ domain and/or the TCRM comprises a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a peptide linker between the Fab-like antigen-binding module and the TCRM. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR (such as an isolated abTCR) comprising a) an Fv-like antigen-binding module that specifically binds to a target antigen, and b) a TCRM capable of recruiting at least one TCR-associated signaling module, wherein the target antigen is a peptide/MHC complex. In some embodiments, the Fv-like antigen-binding module comprises a $V_H$ antibody domain and a $V_L$ antibody domain. In some embodiments, there is a first peptide linker fused to the C-terminus of the $V_L$ antibody domain and/or a second peptide linker fused to the C-terminus of the $V_H$ antibody domain. In some embodiments, the first and second peptide linkers are capable of binding to one another. In some embodiments, the first and/or second peptide linkers are derived from immunoglobulin heavy and/or light chain constant regions. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, the Fv-like antigen-binding module is human, humanized, chimeric, semi-synthetic, or fully synthetic. In some embodiments, the TCRM comprises the transmembrane domains of a TCR, such as an αβTCR or a γδTCR. In some embodiments, the TCRM further comprises the connecting peptides or fragments thereof of a TCR, such as an αβTCR or a γδTCR. In some embodiments, the transmembrane domains and the connecting peptides are derived from an αβTCR or a γδTCR. In some embodiments, the transmembrane domains are derived from an αβTCR and the connecting peptides are derived from a γδTCR, or the transmembrane domains are derived from a γδTCR and the connecting peptides are derived from an αβTCR. In some embodiments, the TCRM further comprises at least one portion of an extracellular domain of the TCR. In some embodiments, the TCRM further comprises at least one TCR intracellular domain comprising a sequence from an intracellular domain of the TCR. In some embodiments, the TCRM comprises fragments of the TCR subunits. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the abTCR further comprises at least one disulfide bond. In some embodiments, the first and/or second peptide linkers comprise a disulfide bond and/or the TCRM comprises a disulfide bond. In some embodiments, the TCRM comprises a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the target antigen peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H1$ antibody domains and a first TCRD comprising the transmembrane domain of a first TCR subunit; and b) a second polypeptide chain comprising a second antigen-binding domain comprising $V_L$ and $C_L$ antibody domains and a second TCRD comprising the transmembrane domain of a second TCR subunit, wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCR subunit is a TCR α chain, and the second TCR subunit is a TCR β chain. In some embodiments, the first TCR subunit is a TCR β chain, and the second TCR subunit is a TCR α chain. In some embodiments, the first TCR subunit is a TCR γ chain, and the second TCR subunit is a TCR δ chain. In some embodiments, the first TCR subunit is a TCR δ chain, and the second TCR subunit is a TCR γ chain. In some embodiments, the first TCRD further comprises the connecting peptide or a fragment thereof of the first TCR subunit and/or the second TCRD further comprises the connecting peptide or a fragment thereof of the second TCR subunit. In some embodiments, the first TCRD further comprises a portion of the extracellular domain of the first TCR subunit and/or the second TCRD further comprises a portion of the extracellular domain of the second TCR subunit. In some embodiments, the first TCRD further comprises a first TCR intracellular domain and/or the second TCRD further comprises a second TCR intracellular domain. In some embodiments, the first TCR intracellular domain comprises a sequence from the intracellular domain of the first TCR subunit and/or the second TCR intracellular domain comprises a sequence from the intracellular domain of the second TCR subunit. In some embodiments, the first TCRD is a fragment of the first TCR subunit and/or the second TCRD is a fragment of the second TCR chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the $C_H1$ domain is derived from an IgG (e.g, IgG1, IgG2, IgG3, or IgG4) heavy chain, optionally human. In some embodiments, the $C_H1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain is a variant comprising one or more modifications (e.g., amino acid substitutions, insertions, and/or deletions) compared to the sequence from which it is derived. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising a $V_H$ antibody domain and a first TCRD comprising the transmembrane domain of a first TCR subunit; and b) a second polypeptide chain comprising a second antigen-binding domain comprising a $V_L$ antibody domain and a second TCRD comprising the transmembrane domain of a second TCR subunit, wherein the $V_H$ domain of the first antigen-binding domain and the $V_L$ domain of the second antigen-binding domain form an Fv-like antigen-binding module that specifically binds the target antigen, wherein the first TCRD and the second TCRD form a TCRM that is capable of recruiting at least one TCR-associated signaling module, and wherein the target antigen is a peptide/MHC complex. In some embodiments, the Fv-like antigen-binding module is human, humanized, chimeric, semi-synthetic, or fully synthetic. In some embodiments, the first TCR subunit is a TCR α chain, and the second TCR subunit is a TCR β chain. In some embodiments, the first TCR subunit is a TCR β chain, and the second TCR subunit is a TCR α chain. In some embodiments, the first TCR subunit is a TCR γ chain, and the second TCR subunit is a TCR δ chain. In some embodiments, the first TCR subunit is a TCR δ chain, and the second TCR subunit is a TCR γ chain. In some embodiments, the first TCRD further comprises the connecting peptide or a fragment thereof of the first TCR subunit and/or the second TCRD further comprises the connecting peptide or a fragment thereof of the second TCR subunit. In some embodiments, the first TCRD further comprises a portion of the extracellular domain of the first TCR subunit and/or the second TCRD further comprises a portion of the extracellular domain of the second TCR subunit. In some embodiments, the first TCRD further comprises a first TCR intracellular domain and/or the second TCRD further comprises a second TCR intracellular domain. In some embodiments, the first TCR intracellular domain comprises a sequence from the intracellular domain of the first TCR subunit and/or the second TCR intracellular domain comprises a sequence from the intracellular domain of the second TCR subunit. In some embodiments, the first TCRD is a fragment of the first TCR subunit and/or the second TCRD is a fragment of the second TCR chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and/or second peptide linkers are derived from immunoglobulin heavy and/or light chain constant regions. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the first peptide linker and a residue in the second peptide linker. In some embodiments, the first and/or second peptide linker is a variant comprising one or more modifications (e.g., amino acid substitutions, insertions, and/or deletions) compared to the sequence from which it is derived. In some embodiments, the first and/or second peptide linkers comprise one or more modifications that do not substantially alter their binding affinities for one another. In some embodiments, the first and/or second peptide linkers comprise one or more modifications that increase their binding affinities for one another and/or introduce a non-naturally occurring disulfide bond. In some embodiments, the target antigen peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H1$ antibody domains and a first TCRD comprising the transmembrane domain of a TCR α chain;

and b) a second polypeptide chain comprising a second antigen-binding domain comprising $V_L$ and $C_L$ antibody domains and a second TCRD comprising the transmembrane domain of a TCR β chain, wherein the $V_H$ and $C_H 1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR α chain and/or the second TCRD further comprises the connecting peptide or a fragment thereof of the TCR β chain. In some embodiments, the first TCRD further comprises a portion of the extracellular domain of the TCR α chain and/or the second TCRD further comprises a portion of the extracellular domain of the TCR β chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR α chain and/or the second TCR intracellular domain comprises a sequence from the intracellular domain of the TCR β chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H 1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H 1$ antibody domains and a first TCRD comprising the transmembrane domain of a TCR β chain; and b) a second polypeptide chain comprising a second antigen-binding domain comprising $V_L$ and $C_L$ antibody domains and a second TCRD comprising the transmembrane domain of a TCR α chain, wherein the $V_H$ and $C_H 1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR β chain and/or the second TCRD further comprises the connecting peptide or a fragment thereof of the TCR α chain. In some embodiments, the first TCRD further comprises a portion of the extracellular domain of the TCR β chain and/or the second TCRD further comprises a portion of the extracellular domain of the TCR α chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR β chain and/or the second TCR intracellular domain comprises a sequence from the intracellular domain of the TCR α chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H 1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H1$ antibody domains and a first TCRD comprising the transmembrane domain of a TCR γ chain; and b) a second polypeptide chain comprising a second antigen-binding domain comprising $V_L$ and $C_L$ antibody domains and a second TCRD comprising the transmembrane domain of a TCR δ chain, wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR γ chain and/or the second TCRD further comprises the connecting peptide or a fragment thereof of the TCR δ chain. In some embodiments, the first TCRD further comprises a portion of the extracellular domain of the TCR γ chain and/or the second TCRD further comprises a portion of the extracellular domain of the TCR δ chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR γ chain and/or the second TCR intracellular domain comprises a sequence from the intracellular domain of the TCR δ chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3ε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD.

In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H1$ antibody domains and a first TCRD comprising the transmembrane domain of a TCR δ chain; and b) a second polypeptide chain comprising a second antigen-binding domain comprising $V_L$ and $C_L$ antibody domains and a second TCRD comprising the transmembrane domain of a TCR γ chain, wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR δ chain and/or the second TCRD further comprises the connecting peptide or a fragment thereof of the TCR γ chain. In some embodiments, the first TCRD further comprises a portion of the extracellular domain of the TCR δ chain and/or the second TCRD further comprises a portion of the extracellular domain of the TCR γ chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR δ chain and/or the second TCR intracellular domain comprises a sequence from the intracellular domain of the TCR γ chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising $V_H$ and $C_H1$ antibody domains and a first TCRD comprising a transmembrane domain comprising (such as consisting of) the amino acid sequence of any one of SEQ ID NOs: 1-4; and b) a second polypeptide chain comprising a second antigen-binding domain comprising $V_L$ and $C_L$ antibody domains and a second TCRD comprising a transmembrane domain comprising (such as consisting of) the amino acid sequence of any one of SEQ ID NOs: 1-4, wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises a first connecting peptide or fragment thereof of a first TCR subunit and/or the second TCRD further comprises a second connecting peptide or fragment thereof of a second TCR subunit, wherein the first and/or second connecting peptides comprise (such as consist of) the amino acid sequence of any one of SEQ ID NOs: 5-12. In some embodiments, the first TCRD further comprises a first TCR intracellular domain and/or the second TCRD further comprises a second TCR intracellular domain, wherein the first and/or second TCR intracellular domains comprise (such as consist of) the amino sequence of any one of SEQ ID NOs: 13-14. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising a first antigen-binding domain comprising a $V_H$ antibody domain and a first TCRD comprising a transmembrane domain comprising (such as consisting of) the amino acid sequence of any one of SEQ ID NOs: 1-4; and b) a second polypeptide chain comprising a second antigen-binding domain comprising a $V_L$ antibody domain and a second TCRD comprising a transmembrane domain comprising (such as consisting of) the amino acid sequence of any one of SEQ ID NOs: 1-4, wherein the $V_H$ domain of the first antigen-binding domain and the $V_L$ domain of the second antigen-binding domain form an Fv-like antigen-binding module that specifically binds the target antigen, wherein the first TCRD and the second TCRD form a TCRM that is capable of recruiting at least one TCR-associated signaling module, and wherein the target antigen is a peptide/MHC complex. In some embodiments, the Fv-like antigen-binding module is human, humanized, chimeric, semi-synthetic, or fully synthetic. In some embodiments, the first TCRD further comprises a first connecting peptide or fragment thereof of a first TCR subunit and/or the second TCRD further comprises a second connecting peptide or fragment thereof of a second TCR subunit, wherein the first and/or second connecting peptides comprise (such as consist of) the amino acid sequence of any one of SEQ ID NOs: 5-12. In some embodiments, the first TCRD further comprises a first TCR intracellular domain and/or the second TCRD further comprises a second TCR intracellular domain, wherein the first and/or second TCR intracellular domains comprise (such as consist of) the amino sequence of any one of SEQ ID NOs: 13-14. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second peptide linkers are capable of binding to one another. In some embodiments, the first and/or second peptide linkers are derived from immunoglobulin heavy and/or light chain constant regions. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the first peptide linker and a residue in the second peptide linker. In some embodiments, the first and/or second peptide linker is a variant comprising one or more modifications (e.g., amino acid substitutions, insertions, and/or deletions) compared to the sequence from which it is derived. In some embodiments, the first and/or second peptide linkers comprise one or more modifications that do not substantially alter their binding affinities for one another. In some embodiments, the first and/or second peptide linkers comprise one or more modifications that increase their binding affinities for one another and/or introduce a non-naturally occurring disulfide bond. In some embodiments, the target antigen peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain comprising $V_H$ and $C_H1$ antibody domains, and a first TCRD comprising a connecting peptide comprising (such as consisting of) the amino acid sequence of any one of SEQ ID NOs: 5-12 and a transmembrane domain comprising (such as consisting of) the amino acid sequence of any one of SEQ ID NOs: 1-4; and b) a second polypeptide chain comprising, in order from amino terminus to carboxy terminus, a second antigen-binding domain comprising $V_L$ and $C_L$ antibody domains and a second TCRD comprising a connecting peptide comprising (such as consisting of) the amino acid sequence of any one of SEQ ID NOs: 5-12 and a transmembrane domain comprising (such as consisting of) the amino acid sequence of any one of SEQ ID NOs: 1-4; wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises a first TCR intracellular domain and/or the second TCRD further comprises a second TCR intracellular domain, wherein the first and/or second TCR intracellular domains comprise (such as consist of) the amino sequence of any one of SEQ ID NOs: 13-14. In some embodiments, the abTCR further comprises at least one accessory intracellular domain comprising at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain comprising a $V_H$ antibody domain, and a first TCRD comprising a connecting peptide comprising (such as consisting of) the amino acid sequence of any one of SEQ ID NOs: 5-12 and a transmembrane domain comprising (such as consisting of) the amino acid sequence of any one of SEQ ID NOs: 1-4; and b) a second polypeptide chain comprising, in order from amino terminus to carboxy terminus, a second antigen-binding domain comprising a $V_L$ antibody domain, and a second TCRD comprising a connecting peptide comprising (such as consisting of) the amino acid sequence of any one of SEQ ID NOs: 5-12 and a transmembrane domain comprising (such as consisting of) the amino acid sequence of any one of SEQ ID NOs: 1-4, wherein the $V_H$ domain of the first antigen-binding domain and the $V_L$ domain of the second antigen-binding domain form an Fv-like antigen-binding module that specifically binds the target antigen, wherein the first TCRD and the second TCRD form a TCRM that is capable of recruiting at least one TCR-associated signaling module, and wherein the target antigen is a peptide/MHC complex. In some embodiments, the Fv-like antigen-binding module is human, humanized, chimeric, semi-synthetic, or fully synthetic. In some embodiments, the first TCRD further comprises a first connecting peptide or fragment thereof of a first TCR subunit and/or the second TCRD further comprises a second connecting peptide or fragment thereof of a second TCR subunit, wherein the first and/or second connecting peptides comprise (such as consist of) the amino acid sequence of any one of SEQ ID NOs: 5-12. In some embodiments, the first TCRD further comprises a first TCR intracellular domain and/or the second TCRD further comprises a second TCR intracellular domain, wherein the first and/or second TCR intracellular domains comprise (such as consist of) the amino sequence of any one of SEQ ID NOs: 13-14. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second peptide linkers are capable of binding to one another. In some embodiments, the first and/or second peptide linkers are derived from immunoglobulin heavy and/or light chain constant regions. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the first peptide linker and a residue in the second peptide linker. In some embodiments, the first and/or second peptide linker is a variant comprising one or more modifications (e.g., amino acid substitutions, insertions, and/or deletions) compared to the sequence from which it is derived. In some embodiments, the first and/or second peptide linkers comprise one or more modifications that do not substantially alter their binding affinities for one another. In some embodiments, the first and/or second peptide linkers comprise one or more modifications that increase their binding affinities for one another and/or introduce a non-naturally occurring disulfide bond. In some embodiments, the target antigen peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain and a first TCRD comprising the amino acid sequence of SEQ ID NO: 15; and b) a second polypeptide chain comprising, in order from amino terminus to carboxy terminus, a second antigen-binding domain and a second TCRD comprising the amino acid sequence of SEQ ID NO: 16; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain and a first TCRD comprising the amino acid sequence of SEQ ID NO: 17; and b) a second polypeptide chain comprising, in order from amino terminus to carboxy terminus, a second antigen-binding domain and a second TCRD comprising the amino acid sequence of SEQ ID NO: 18; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain and a first TCRD comprising the amino acid sequence of SEQ ID NO: 19; and b) a second polypeptide chain comprising, in order from amino terminus to carboxy terminus, a second antigen-binding domain and a second TCRD comprising the amino acid sequence of SEQ ID NO: 20; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a target antigen comprising a) a first polypeptide chain comprising, in order from amino terminus to carboxy terminus, a first antigen-binding domain and a first TCRD comprising the amino acid sequence of SEQ ID NO: 21; and b) a second polypeptide chain comprising, in order from amino terminus to carboxy terminus, a second antigen-binding domain and a second TCRD comprising the amino acid sequence of SEQ ID NO: 22; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 23; and b) a second polypeptide chain comprising a second abTCR domain comprising the amino acid sequence of SEQ ID NO: 24. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 25; and b) a second polypeptide chain comprising a second abTCR domain comprising the amino acid sequence of SEQ ID NO: 26. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 27; and b) a second polypeptide chain comprising a second abTCR domain comprising the amino acid sequence of SEQ ID NO: 28. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 29; and b) a second polypeptide chain comprising a second abTCR domain comprising the amino acid sequence of SEQ ID NO: 30. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 31; and b) a second polypeptide chain comprising a second abTCR domain comprising the amino acid sequence of SEQ ID NO: 32. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 33; and b) a second polypeptide chain comprising a second abTCR domain comprising the amino acid sequence of SEQ ID NO: 34. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein comprising a) a first polypeptide chain comprising a first abTCR domain comprising the amino acid sequence of SEQ ID NO: 35; and b) a second polypeptide chain comprising a second abTCR domain comprising the amino acid sequence of SEQ ID NO: 36. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes a complex comprising an AFP peptide and an MHC I protein, comprising an antigen-binding module comprising a $V_H$ antibody domain comprising (and in some embodiments consisting of) the amino acid sequence of SEQ ID NO: 38, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 40, or a variant thereof having at least about 95% (for example at least about any of 96%, 97%, 98%, or 99%) sequence identity.

Thus, in some embodiments, there is provided an abTCR that specifically recognizes a complex comprising an AFP peptide and an MHC I protein according to any of the abTCRs described above, wherein the $V_H$ antibody domain of the Fab-like antigen-binding module is replaced with a sequence comprising (and in some embodiments consisting of) the amino acid sequence of SEQ ID NO: 38, or a variant thereof having at least about 95% (for example at least about any of 96%, 97%, 98%, or 99%) sequence identity, and wherein the $V_L$ antibody domain of the Fab-like antigen-binding module is replaced with a sequence comprising (and in some embodiments consisting of) the amino acid sequence of SEQ ID NO: 40, or a variant thereof having at least about 95% (for example at least about any of 96%, 97%, 98%, or 99%) sequence identity.

In some embodiments, there is provided an abTCR that specifically recognizes CD19 comprising a) a first polypeptide chain comprising a first abTCR domain comprising the amino acid sequence of SEQ ID NO: 42; and b) a second polypeptide chain comprising a second abTCR domain comprising the amino acid sequence of SEQ ID NO: 43. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes CD19 comprising a) a first polypeptide chain comprising a first abTCR domain comprising the amino acid sequence of SEQ ID NO: 42; and b) a second polypeptide chain comprising a second abTCR domain comprising the amino acid sequence of SEQ ID NO: 54. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes CD19 comprising a) a first polypeptide chain comprising a first abTCR domain comprising the amino acid sequence of SEQ ID NO: 55; and b) a second polypeptide chain comprising a second abTCR domain comprising the amino acid sequence of SEQ ID NO: 54. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR that specifically recognizes CD19 comprising a) a first polypeptide chain comprising a first abTCR domain comprising the amino acid sequence of SEQ ID NO: 56; and b) a second polypeptide chain comprising a second abTCR domain comprising the amino acid sequence of SEQ ID NO: 54. In some embodiments, the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49.

In some embodiments, there is provided an abTCR according to any of the embodiments described herein that specifically recognizes CD19 comprising an antigen-binding module comprising a $V_H$ antibody domain comprising (and in some embodiments consisting of) the amino acid sequence of SEQ ID NO: 45, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 46, or a variant thereof having at least about 95% (for example at least about any of 96%, 97%, 98%, or 99%) sequence identity.

In some embodiments, there is provided an abTCR according to any of the embodiments described herein that specifically recognizes CD19 comprising an antigen-binding module comprising a $V_H$ antibody domain comprising (and in some embodiments consisting of) the amino acid sequence of SEQ ID NO: 45, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 57, or a variant thereof having at least about 95% (for example at least about any of 96%, 97%, 98%, or 99%) sequence identity.

In some embodiments, there is provided an abTCR according to any of the embodiments described herein that specifically recognizes CD19 comprising an antigen-binding module comprising a $V_H$ antibody domain comprising (and in some embodiments consisting of) the amino acid sequence of SEQ ID NO: 58, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 57, or a variant thereof having at least about 95% (for example at least about any of 96%, 97%, 98%, or 99%) sequence identity.

In some embodiments, there is provided an abTCR according to any of the embodiments described herein that specifically recognizes CD19 comprising an antigen-binding module comprising a $V_H$ antibody domain comprising (and in some embodiments consisting of) the amino acid sequence of SEQ ID NO: 59, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 57, or a variant thereof having at least about 95% (for example at least about any of 96%, 97%, 98%, or 99%) sequence identity.

In some embodiments, there is provided an abTCR according to any of the embodiments described herein that specifically recognizes a complex comprising an NY-ESO-1 157-165 peptide and an MHC I protein comprising an antigen-binding module comprising a $V_H$ antibody domain comprising (and in some embodiments consisting of) the amino acid sequence of SEQ ID NO: 72, or a variant thereof having at least about 95% (for example at least about any of 96%, 97%, 98%, or 99%) sequence identity, and a $V_L$ antibody domain comprising (and in some embodiments consisting of) the amino acid sequence of SEQ ID NO: 73, or a variant thereof having at least about 95% (for example at least about any of 96%, 97%, 98%, or 99%) sequence identity.

In some embodiments, there is provided an abTCR comprising a first antigen-binding module that competes for binding to a target antigen with a second antigen-binding module according to any of the abTCRs described herein. In some embodiments, the first antigen-binding module binds to the same, or substantially the same, epitope as the second antigen-binding module. In some embodiments, binding of the first antigen-binding module to the target antigen inhibits binding of the second antigen-binding module to the target antigen by at least about 70% (such as by at least about any of 75%, 80%, 85%, 90%, 95%, 98% or 99%), or vice versa. In some embodiments, the first antigen-binding module and the second antigen-binding module cross-compete for binding to the target antigen, i.e., each of the first and second antigen-binding modules competes with the other for binding to the target antigen.

In some embodiments, there is provided an abTCR according to any of the abTCRs described herein, wherein the $V_L$ and $V_H$ domains are interchanged, such that the first antigen-binding domain comprises $V_L$ and $C_H1$ antibody domains and the second antigen-binding domain comprises $V_H$ and $C_L$ antibody domains.

In some embodiments, there is provided a complex comprising an abTCR according to any of the abTCRs described herein and at least one signaling module selected from the group consisting of CD3δε, CD3γε, and ζζ. In some embodiments, the complex comprises each of CD3δε, CD3γε, and ζζ. Thus, in some embodiments, there is provided a complex comprising the abTCR, CD3δε, CD3γε, and ζζ.

The different aspects are discussed in various sections below in further detail.

Nucleic Acids

Nucleic acid molecules encoding the abTCRs are also contemplated. In some embodiments, according to any of the abTCRs described herein, there is provided a nucleic acid (or a set of nucleic acids) encoding the abTCR.

The present invention also provides vectors in which a nucleic acid of the present invention is inserted.

In brief summary, the expression of an abTCR by a nucleic acid encoding the abTCR can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to, a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405.

An exemplary inducible promoter system for use in the present invention is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from E. coli. (See, Brown et al., Cell 49:603-612 (1987). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding an abTCR according to any of the abTCRs described herein. In some embodiments, the nucleic acid encoding the abTCR comprises a first nucleic acid sequence encoding the first polypeptide chain of the abTCR and a second nucleic acid sequence encoding the second polypeptide chain of the abTCR. In some embodiments, the first nucleic acid sequence is located on a first vector and the second nucleic acid sequence is located on a second vector. In some embodiments, the first and second nucleic acid sequences are located on the same vector. Vectors may be selected, for example, from the group consisting of mammalian expression vectors and viral vectors (such as those derived from retroviruses, adenoviruses, adeno-associated viruses, herpes viruses, and lentiviruses). In some embodiments, the first nucleic acid sequence is under the control of a first promoter and the second nucleic acid sequence is under the control of a second promoter. In some embodiments, the first and second promoters have the same sequence. In some embodiments, the first and second promoters have different sequences. In some embodiments, the first and second nucleic acid sequences are expressed as a single transcript under the control of a single promoter in a multicistronic (such as a bicistronic) vector. See for example Kim, J H, et al., *PLoS One* 6(4):e18556, 2011. In some embodiments, the first, second, and/or single promoters are inducible. In some embodiments, the first nucleic acid sequence has an expression level in a host cell (such as a T cell) that is about the same as the expression level of the second nucleic acid sequence in the host cell. In some embodiments, the first nucleic acid sequence has an expression level in a host cell (such as a T cell) that is at least about two (such as at least about any of 2, 3, 4, 5, or more) times the expression level of the second nucleic acid sequence in the host cell. In some embodiments, the first nucleic acid sequence has an expression level in a host cell (such as a T cell) that is no more than about ½ (such as no more than about any of ½, ⅓, ¼, ⅕ or less) times the expression level of the second nucleic acid sequence in the host cell. Expression can be determined at the mRNA or protein level. The level of mRNA expression can be determined by measuring the amount of mRNA transcribed from the nucleic acid using various well-known methods, including Northern blotting, quantitative RT-PCR, microarray analysis and the like. The level of protein expression can be measured by known methods including immunocytochemical staining, enzyme-linked immunosorbent assay (ELISA), western blot analysis, luminescent assays, mass spectrometry, high performance liquid chromatography, high-pressure liquid chromatography-tandem mass spectrometry, and the like.

Thus, in some embodiments, there is provided nucleic acid encoding an abTCR according to any of the abTCRs described herein comprising a) a first nucleic acid sequence encoding the first polypeptide chain of the abTCR, and b) a second nucleic acid sequence encoding the second polypeptide chain of the abTCR, wherein the first nucleic acid sequence is located on a first vector (such as a lentiviral vector) and operably linked to a first promoter and the second nucleic acid sequence is located on a second vector (such as a lentiviral vector) and operably linked to a second promoter. In some embodiments, the first and second promoters have the same sequence. In some embodiments, the first and second promoters have different sequences. In some embodiments, the first and/or second promoters are inducible. In some embodiments, the first nucleic acid sequence has an expression level in a host cell (such as a T cell) that is about the same as the expression level of the second nucleic acid sequence in the host cell. In some embodiments, the first nucleic acid sequence has an expression level in a host cell (such as a T cell) that is at least about two (such as at least about any of 2, 3, 4, 5, or more) times the expression level of the second nucleic acid sequence in the host cell. In some embodiments, the first nucleic acid sequence has an expression level in a host cell (such as a T cell) that is no more than about ½ (such as no more than about any of ½, ⅓, ¼, ⅕ or less) times the expression level of the second nucleic acid sequence in the host cell. In some embodiments, the first and/or second vectors are viral vectors (such as lentiviral vectors).

In some embodiments, there is provided a vector (such as a lentiviral vector) comprising nucleic acid encoding an abTCR according to any of the abTCRs described herein comprising a) a first promoter operably linked to a first nucleic acid sequence encoding the first polypeptide chain of the abTCR; and b) a second promoter operably linked to a second nucleic acid sequence encoding the second polypeptide chain of the abTCR. In some embodiments, the first and second promoters have the same sequence. In some embodiments, the first and second promoters have different sequences. In some embodiments, the first and/or second promoters are inducible. In some embodiments, the first nucleic acid sequence has an expression level in a host cell (such as a T cell) that is about the same as the expression level of the second nucleic acid sequence in the host cell. In some embodiments, the first nucleic acid sequence has an expression level in a host cell (such as a T cell) that is at least about two (such as at least about any of 2, 3, 4, 5, or more) times the expression level of the second nucleic acid sequence in the host cell. In some embodiments, the first nucleic acid sequence has an expression level in a host cell (such as a T cell) that is no more than about ½ (such as no more than about any of ½, ⅓, ¼, ⅕ or less) times the expression level of the second nucleic acid sequence in the host cell. In some embodiments, the vector is a viral vector (such as a lentiviral vector).

In some embodiments, there is provided a vector (such as a lentiviral vector) comprising nucleic acid encoding an abTCR according to any of the abTCRs described herein comprising a) a first nucleic acid sequence encoding the first polypeptide chain of the abTCR; and b) a second nucleic acid sequence encoding the second polypeptide chain of the abTCR; wherein the first and second nucleic acid sequences are under the control of a single promoter. In some embodiments, the promoter is operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, the promoter is operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the vector is a viral vector (such as a lentiviral vector).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human, cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

abTCR Effector Cells

In some embodiments, there is provided an effector cell (such as a T cell) presenting on its surface an abTCR according to any of the abTCRs described herein. In some embodiments, the effector cell comprises a nucleic acid encoding the abTCR, wherein the abTCR is expressed from the nucleic acid and localized to the effector cell surface. In some embodiments, the abTCR is exogenously expressed and combined with the effector cell. In some embodiments, the effector cell is a T cell. In some embodiments, the effector cell is selected from the group consisting of a cytotoxic T cell, a helper T cell, a natural killer T cell, and a suppressor T cell. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the T cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. Modifications of cells to disrupt gene expression include any such techniques known in the art, including for example RNA interference (e.g., siRNA, shRNA, miRNA), gene editing (e.g., CRISPR- or TALEN-based gene knockout), and the like. For example, in some embodiments, there is provided an effector cell (such as a T cell) comprising a nucleic acid encoding an abTCR according to any of the abTCRs described herein, wherein the abTCR is expressed from the nucleic acid and localized to the effector cell surface. In some embodiments, the nucleic acid encoding the abTCR comprises a first nucleic acid sequence encoding the first polypeptide chain of the abTCR and a second nucleic acid sequence encoding the second polypeptide chain of the abTCR. In some embodiments, the first nucleic acid sequence is located on a first vector and the second nucleic acid sequence is located on a second vector. In some embodiments, the first and second nucleic acid sequences are located on the same vector. Vectors may be selected, for example, from the group consisting of mammalian expression vectors and viral vectors (such as those derived from retroviruses, adenoviruses, adeno-associated viruses, herpes viruses, and lentiviruses). In some embodiments, one or more of the vectors is integrated into the host genome of the effector cell. In some embodiments, the first nucleic acid sequence is under the control of a first promoter and the second nucleic acid sequence is under the control of a second promoter. In some embodiments, the first and second promoters have the same sequence. In some embodiments, the first and second promoters have different sequences. In some embodiments, the first and second nucleic acids are under the control of a single promoter. In some embodiments, the first, second, and/or single promoters are inducible. In some embodiments, the expression of the first polypeptide chain is about the same as the expression of the second polypeptide chain. In some embodiments, the expression of the first polypeptide chain is at least about two (such as at least about any of 2, 3, 4, 5, or more) times the expression of the second polypeptide chain. In some embodiments, the expression of the first polypeptide chain is no more than about ½ (such as no more than about any of ½, ⅓, ¼, ⅕ or less) times the expression of the second polypeptide chain. Expression can be determined at the mRNA or protein level. The level of mRNA expression can be determined by measuring the amount of mRNA transcribed from the nucleic acid using various well-known methods, including Northern blotting, quantitative RT-PCR, microarray analysis and the like. The level of protein expression can be measured by known methods including immunocytochemical staining, enzyme-linked immunosorbent assay (ELISA), western blot analysis, luminescent assays, mass spectrometry, high performance liquid chromatography, high-pressure liquid chromatography-tandem mass spectrometry, and the like. In some embodiments, the effector cell is selected from the group consisting of a cytotoxic T cell, a helper T cell, a natural killer T cell, and a suppressor T cell.

Thus, in some embodiments, there is provided an abTCR effector cell (such as a T cell) expressing on its surface an abTCR according to any of the abTCRs described herein, wherein the abTCR effector cell comprises a) a first nucleic acid comprising a first promoter operably linked to a nucleic acid sequence encoding the first polypeptide chain of the abTCR and b) a second nucleic acid comprising a second promoter operably linked to a nucleic acid sequence encoding the second polypeptide chain of the abTCR, wherein the first polypeptide chain is expressed from the first nucleic acid and the second polypeptide chain is expressed from the second nucleic acid to form the abTCR, and wherein the abTCR localizes to the surface of the effector cell. In some embodiments, the first and second promoters have the same sequence. In some embodiments, the first and second promoters have different sequences. In some embodiments, the first and/or second promoters are inducible. In some embodiments, the expression of the first polypeptide chain is about the same as the expression of the second polypeptide chain. In some embodiments, the expression of the first polypeptide chain is at least about two (such as at least about any of 2, 3, 4, 5, or more) times the expression of the second polypeptide chain. In some embodiments, the expression of the first polypeptide chain is no more than about ½ (such as no more than about any of ½, ⅓, ¼, ⅕ or less) times the expression of the second polypeptide chain. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is selected from the group consisting of a cytotoxic T cell, a helper T cell, a natural killer T cell, and a suppressor T cell. In some embodiments, the vector is a viral vector (such as a lentiviral vector) integrated into the host genome of the effector cell.

In some embodiments, there is provided an abTCR effector cell (such as a T cell) expressing on its surface an abTCR according to any of the abTCRs described herein, wherein the abTCR effector cell comprises a) a first vector comprising a first promoter operably linked to a first nucleic acid sequence encoding the first polypeptide chain of the abTCR and b) a second vector comprising a second promoter operably linked to a second nucleic acid sequence encoding the second polypeptide chain of the abTCR, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, the first and second promoters have the same sequence. In some embodiments, the first and second promoters have different sequences. In some embodiments, the first and/or second promoters are inducible. In some embodiments, the expression of the first polypeptide chain is about the same as the expression of the second polypeptide chain. In some embodiments, the expression of the first polypeptide chain is at least about two (such as at least about any of 2, 3, 4, 5, or more) times the expression of the second polypeptide chain. In some embodiments, the expression of the first polypeptide chain is no more than about ½ (such as no more than about any of ½, ⅓, ¼, ⅕ or less) times the expression of the second polypeptide chain. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is selected from the group consisting of a cytotoxic T cell, a helper T cell, a natural killer T cell, and a suppressor T cell. In some embodiments, the first and second vectors are viral vectors (such as lentiviral vectors) integrated into the host genome of the effector cell.

In some embodiments, there is provided an abTCR effector cell (such as a T cell) expressing on its surface an abTCR according to any of the abTCRs described herein, wherein the abTCR effector cell comprises a vector comprising a) a first promoter operably linked to a first nucleic acid sequence encoding the first polypeptide chain of the abTCR and b) a second promoter operably linked to a second nucleic acid sequence encoding the second polypeptide chain of the abTCR, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, the first and second promoters have the same sequence. In some embodiments, the first and second promoters have different sequences. In some embodiments, the first and/or second promoters are inducible. In some embodiments, the expression of the first polypeptide chain is about the same as the expression of the second polypeptide chain. In some embodiments, the expression of the first polypeptide chain is at least about two (such as at least about any of 2, 3, 4, 5, or more) times the expression of the second polypeptide chain. In some embodiments, the expression of the first polypeptide chain is no more than about ½ (such as no more than about any of ½, ⅓, ¼, ⅕ or less) times the expression of the second polypeptide chain. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is selected from the group consisting of a cytotoxic T cell, a helper T cell, a natural killer T cell, and a suppressor T cell. In some embodiments, the first and second vectors are viral vectors (such as lentiviral vectors) integrated into the host genome of the effector cell.

In some embodiments, there is provided an abTCR effector cell (such as a T cell) expressing on its surface an abTCR according to any of the abTCRs described herein, wherein the abTCR effector cell comprises a host genome-integrated lentiviral vector comprising a) a first promoter operably linked to a first nucleic acid sequence encoding the first polypeptide chain of the abTCR and b) a second promoter operably linked to a second nucleic acid sequence encoding the second polypeptide chain of the abTCR, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, the first and second promoters have the same sequence. In some embodiments, the first and second promoters have different sequences. In some embodiments, the first and/or second promoters are inducible. In some embodiments, the expression of the first polypeptide chain is about the same as the expression of the second polypeptide chain. In some embodiments, the expression of the first polypeptide chain is at least about two (such as at least about any of 2, 3, 4, 5, or more) times the expression of the second polypeptide chain. In some embodiments, the expression of the first polypeptide chain is no more than about ½ (such as no more than about any of ½, ⅓, ¼, ⅕ or less) times the expression of the second polypeptide chain. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is modified to block or decrease the expression of one or both of the endogenous TCR chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR according to any of the abTCRs described herein, wherein the abTCR effector cell comprises a vector comprising a) a first nucleic acid sequence encoding the first polypeptide chain of the abTCR and b) a second nucleic acid sequence encoding the second polypeptide chain of the abTCR, wherein the first and second nucleic acid sequences are under the control of a single promoter, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, the promoter is operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, the promoter is operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is selected from the group consisting of a cytotoxic T cell, a helper T cell, a natural killer T cell, and a suppressor T cell. In some embodiments, the vector is a viral vector (such as a lentiviral vector) integrated into the host genome of the effector cell.

In some embodiments, there is provided an abTCR effector cell (such as a T cell) expressing on its surface an abTCR according to any of the abTCRs described herein, wherein the abTCR effector cell comprises a host genome-integrated lentiviral vector comprising a) a first nucleic acid sequence encoding the first polypeptide chain of the abTCR and b) a second nucleic acid sequence encoding the second polypeptide chain of the abTCR, wherein the first and second nucleic acid sequences are under the control of a single promoter, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the effector cell does not express the TCR subunits from which the TCRDs of the abTCR are derived. For example, in some embodiments, the effector cell is an αβ T cell and the TCRDs of the introduced abTCR comprise sequences derived from TCR δ and γ chains, or the effector cell is a γδ T cell and the TCRDs of the introduced abTCR comprise sequences derived from TCR α and β chains. In some embodiments, the effector cell is modified to block or decrease the expression of one or both of the endogenous TCR subunits from which the TCRDs of the abTCR are derived. For example, in some embodiments, the effector cell is an αβ T cell modified to block or decrease the expression of the TCR α and/or β chains and the TCRDs of the introduced abTCR comprise sequences derived from TCR α and β chains, or the effector cell is a γδ T cell modified to block or decrease the expression of the TCR γ and/or δ chains and the TCRDs of the introduced abTCR comprise sequences derived from TCR γ and δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain comprising, in order from amino terminus to carboxy terminus, a first antigen-binding domain and a first TCRD comprising the amino acid sequence of SEQ ID NO: 15; and b) a second nucleic acid sequence encoding a second polypeptide chain comprising, in order from amino terminus to carboxy terminus, a second antigen-binding domain and a second TCRD comprising the amino acid sequence of SEQ ID NO: 16; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain comprising, in order from amino terminus to carboxy terminus, a first antigen-binding domain and a first TCRD comprising the amino acid sequence of SEQ ID NO: 17; and b) a second nucleic acid sequence encoding a second polypeptide chain comprising, in order from amino terminus to carboxy terminus, a second antigen-binding domain and a second TCRD comprising the amino acid sequence of SEQ ID NO: 18; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain comprising, in order from amino terminus to carboxy terminus, a first antigen-binding domain and a first TCRD comprising the amino acid sequence of SEQ ID NO: 19; and b) a second nucleic acid sequence encoding a second polypeptide chain comprising, in order from amino terminus to carboxy terminus, a second antigen-binding domain and a second TCRD comprising the amino acid sequence of SEQ ID NO: 20; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain comprising, in order from amino terminus to carboxy terminus, a first antigen-binding domain and a first TCRD comprising the amino acid sequence of SEQ ID NO: 21; and b) a second nucleic acid sequence encoding a second polypeptide chain comprising, in order from amino terminus to carboxy terminus, a second antigen-binding domain and a second TCRD comprising the amino acid sequence of SEQ ID NO: 22; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 23 and b) a second nucleic acid sequence encoding a second polypeptide chain of the abTCR comprising a second abTCR domain comprising the amino acid sequence of SEQ ID NO: 24, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 25 and b) a second nucleic acid sequence encoding a second polypeptide chain of the abTCR comprising a second abTCR domain comprising the amino acid sequence of SEQ ID NO: 26, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 27 and b) a second nucleic acid sequence encoding a second polypeptide chain of the abTCR comprising a second abTCR domain comprising the amino acid sequence of SEQ ID NO: 28, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 29 and b) a second nucleic acid sequence encoding a second polypeptide chain of the abTCR comprising a second abTCR domain comprising the amino acid sequence of SEQ ID NO: 30, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 31 and b) a second nucleic acid sequence encoding a second polypeptide chain of the abTCR comprising a second abTCR domain comprising the amino acid sequence of SEQ ID NO: 32, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 33 and b) a second nucleic acid sequence encoding a second polypeptide chain of the abTCR comprising a second abTCR domain comprising the amino acid sequence of SEQ ID NO: 34, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 35 and b) a second nucleic acid sequence encoding a second polypeptide chain of the abTCR comprising a second abTCR domain comprising the amino acid sequence of SEQ ID NO: 36, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 42 and b) a second nucleic acid sequence encoding a second polypeptide chain of the abTCR comprising a second abTCR domain comprising the amino acid sequence of SEQ ID NO: 43, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 42 and b) a second nucleic acid sequence encoding a second polypeptide chain of the abTCR comprising a second abTCR domain comprising the amino acid sequence of SEQ ID NO: 54, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 55 and b) a second nucleic acid sequence encoding a second polypeptide chain of the abTCR comprising a second abTCR domain comprising the amino acid sequence of SEQ ID NO: 54, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided an abTCR effector cell (such as a T cell) expressing on its surface an abTCR comprising a) a first nucleic acid sequence encoding a first polypeptide chain of the abTCR comprising a first abTCR domain comprising the amino acid sequence of SEQ ID NO: 56 and b) a second nucleic acid sequence encoding a second polypeptide chain of the abTCR comprising a second abTCR domain comprising the amino acid sequence of SEQ ID NO: 54, wherein the first polypeptide chain is expressed from the first nucleic acid sequence and the second polypeptide chain is expressed from the second nucleic acid sequence to form the abTCR, and wherein the abTCR localizes to the surface of the effector cell. In some embodiments, there is a promoter operably linked to the 5' end of the first nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first nucleic acid sequence to the 5' end of the second nucleic acid sequence, wherein the first nucleic acid sequence and the second nucleic acid sequence are transcribed as a single RNA under the control of the promoter. In some embodiments, there is a promoter operably linked to the 5' end of the second nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second nucleic acid sequence to the 5' end of the first nucleic acid sequence, wherein the first nucleic acid sequence and the second nucleic acid sequence are transcribed as a single RNA under the control of the promoter. In some embodiments, the promoter is inducible. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an $\alpha\beta$ T cell. In some embodiments, the effector cell is a $\gamma\delta$ T cell modified to block or decrease the expression of the TCR $\gamma$ and/or $\delta$ chains. In some embodiments, the effector cell is selected from the group consisting of a cytotoxic T cell, a helper T cell, a natural killer T cell, and a suppressor T cell.

In any of some such embodiments described herein, the abTCR effector cell has a lower rate of chimeric receptor internalization compared to a corresponding CAR effector cell (such as an effector cell presenting on its surface a CAR comprising the antibody moiety of the abTCR, e.g., a CAR comprising an scFv comprising the antibody variable domains of the abTCR) when compared under similar conditions. For example, in some embodiments, the abTCR effector cell has a lower rate of chimeric receptor internalization compared to the corresponding CAR effector cell following target antigen-dependent stimulation of the chimeric receptor effector cells under similar conditions. In some embodiments, the abTCR effector cell has less than about 50% (such as less than about any of 45, 40, 35, 30, 25, 20, 15, 10, or 5%, including any ranges between these values) abTCR internalization about 90 minutes following stimulation with the target antigen of the abTCR. In some embodiments, the abTCR effector cell is an abTCR T cell.

In any of some such embodiments described herein, an abTCR effector cell has a lower rate and/or incidence of exhaustion compared to a corresponding CAR effector cell (such as an effector cell presenting on its surface a CAR comprising the antibody moiety of the abTCR) when compared under similar conditions. Effector cell exhaustion can be determined by any means known in the art, such as by measuring the expression level of exhaustion markers, including, without limitation, PD-1, TIM-3 and LAG-3. For example, in some embodiments, the abTCR effector cell has a lower expression level of one or more exhaustion markers (such as PD-1, TIM-3 or LAG-3) compared to the corresponding CAR effector cell following target antigen-dependent stimulation of the chimeric receptor effector cells under similar conditions. In some embodiments, the abTCR effector cell has a lower incidence rate of being positive for one or more exhaustion markers (such as PD-1, TIM-3 or LAG-3) compared to the corresponding CAR effector cell following target antigen-dependent stimulation of the chimeric receptor effector cells under similar conditions. In some embodiments, the abTCR effector cell has an incidence rate of less than about 50% (such as less than about any of 45, 40, 35, 30, 25, 20, 15, 10, 5, 4, 3, 2, 1%, including any ranges between these values) for being positive for one or more exhaustion markers (such as PD-1, TIM-3 or LAG-3) following stimulation with the target antigen of the abTCR. In some embodiments, the abTCR effector cell is an abTCR T cell. Incidence rate can be calculated by any means known in the art, for example, by quantifying the percentage of chimeric receptor effector cells positive for an exhaustion marker in a population of chimeric receptor effector cells, wherein the percentage of cells positive for the exhaustion marker is the incidence rate.

In any of some such embodiments described herein, the abTCR effector cell has a lower rate and/or incidence of terminal differentiation compared to a corresponding CAR effector cell (such as an effector cell presenting on its surface a CAR comprising the antibody moiety of the abTCR) when compared under similar conditions. Terminal differentiation can be determined by any means known in the art, such as by measuring the expression level of differentiation markers, including, without limitation, CD28, CCR7 and granzyme B. For example, in some embodiments, the abTCR effector cell has a lower expression level of one or more terminal differentiation markers (such as granzyme B) and/or a greater expression of one or more non-terminal differentiation markers (such as CD28 or CCR7) compared to the corresponding CAR effector cell under similar conditions. In some embodiments, the abTCR effector cell has a lower incidence rate of being positive for one or more terminal differentiation markers (such as granzyme B) and/or a greater incidence rate of being positive for one or more non-terminal differentiation markers (such as CD28 or CCR7) compared to the corresponding CAR effector cell under similar conditions. In some embodiments, the abTCR effector cell has an incidence rate of less than about 50% (such as less than about any of 45, 40, 35, 30, 25, 20, 15, 10, 5, 4, 3, 2, 1%, including any ranges between these values) for being positive for one or more terminal differentiation markers (such as granzyme B) and/or an incidence rate of more than about 10% (such as more than about any of 15, 20, 25, 30, 35, 40, 45, 50, 55, 60, 65, 70, 75, 80, 85, 90, or 95%, including any ranges between these values) for being positive for one or more non-terminal differentiation markers (such as CD28 or CCR7) following stimulation with the target antigen of the abTCR. In some embodiments, the abTCR effector cell is an abTCR T cell. Incidence rate can be calculated by any means known in the art, for example, by quantifying the percentage of chimeric receptor effector cells positive for a terminal differentiation marker in a population of chimeric receptor effector cells, wherein the percentage of cells positive for the terminal differentiation marker is the incidence rate.

In any of some such embodiments described herein, the abTCR effector cell has a greater rate of proliferation compared to a corresponding CAR effector cell (such as an effector cell presenting on its surface a CAR comprising the antibody moiety of the abTCR) when compared under similar conditions. Proliferation can be determined by any means known in the art, such as by measuring dye dilution. In some embodiments, the abTCR effector cell is an abTCR T cell.

Preparation of abTCR

In some embodiments, according to any of the abTCRs described herein, the antibody moiety is a Fab-like antigen-binding module comprising sequences from a monoclonal antibody. In some embodiments, the Fab-like antigen-binding module comprises $V_H$, $C_H1$, $V_L$, and $C_L$ domains from the monoclonal antibody. Monoclonal antibodies can be prepared, e.g., using hybridoma methods, such as those described by Kohler and Milstein, *Nature*, 256:495 (1975) and Sergeeva et al., *Blood*, 117(16):4262-4272.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules, such as a complex comprising a peptide and an MHC protein. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103 Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al. Monoclonal Antibody Production Techniques and Applications (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub-cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub-clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the abTCRs described herein, the antibody moiety is a Fab-like antigen-binding module comprising sequences from a clone selected from an antibody moiety library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The Fab-like antigen-binding module can be prepared using phage display to screen libraries for antibodies specific to the target antigen (such as a peptide/MHC class I/II complex or a cell surface antigen). The library can be a human scFv phage display library having a diversity of at least one×$10^9$ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat.*

Biotechnol. 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target antigen with high affinity can be selected by iterative binding of phage to the target antigen, which is bound to a solid support (such as, for example, beads for solution panning or mammalian cells for cell panning), followed by removal of non-bound phage and by elution of specifically bound phage. In an example of solution panning, the target antigen can be biotinylated for immobilization to a solid support. The biotinylated target antigen is mixed with the phage library and a solid support, such as streptavidin-conjugated Dynabeads M-280, and then target antigen-phage-bead complexes are isolated. The bound phage clones are then eluted and used to infect an appropriate host cell, such as E. coli XL1-Blue, for expression and purification. In an example of cell panning, T2 cells (a TAP-deficient, HLA-A*02:01$^+$ lymphoblast cell line) loaded with an AFP peptide are mixed with the phage library, after which the cells are collected and the bound clones are eluted and used to infect an appropriate host cell for expression and purification. The panning can be performed for multiple (such as about any of 2, 3, 4, 5, 6 or more) rounds with either solution panning, cell panning, or a combination of both, to enrich for phage clones binding specifically to the target antigen. Enriched phage clones can be tested for specific binding to the target antigen by any methods known in the art, including for example ELISA and FACS.

Human and Humanized Antibody Moieties

The abTCR antibody moieties can be human or humanized. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody moiety nor in the imported CDR or framework sequences. In general, the humanized antibody moiety can comprise substantially all of at least one, and typically two, variable domains, in which all or substantially all of the CDR regions correspond to those of a non-human immunoglobulin, and all or substantially all of the FR regions are those of a human immunoglobulin consensus sequence. See, e.g., Jones et al., *Nature,* 321: 522-525 (1986); Riechmann et al., *Nature,* 332: 323-329 (1988); Presta, *Curr. Op. Struct. Biol.,* 2:593-596 (1992).

Generally, a humanized antibody moiety has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody moiety. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Variants

In some embodiments, amino acid sequence variants of the antibody moieties provided herein are contemplated. For example, it may be desirable to improve the binding affinity and/or other biological properties of the antibody moiety Amino acid sequence variants of an antibody moiety may be prepared by introducing appropriate modifications into the nucleotide sequence encoding the antibody moiety, or by peptide synthesis. Such modifications include, for example, deletions from, and/or insertions into and/or substitutions of residues within the amino acid sequences of the antibody moiety. Any combination of deletion, insertion, and substitution can be made to arrive at the final construct, provided that the final construct possesses the desired characteristics, e.g., antigen-binding.

In some embodiments, antibody moiety variants having one or more amino acid substitutions are provided. Sites of interest for substitutional mutagenesis include the HVRs and FRs Amino acid substitutions may be introduced into an antibody moiety of interest and the products screened for a desired activity, e.g., retained/improved antigen binding or decreased immunogenicity.

Conservative substitutions are shown in Table 1 below.

TABLE 1

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
  a. hydrophobic: Norleucine, Met, Ala, Val, Leu, Ile;
  b. neutral hydrophilic: Cys, Ser, Thr, Asn, Gln;
  c. acidic: Asp, Glu;
  d. basic: His, Lys, Arg;
  e. residues that influence chain orientation: Gly, Pro;
  f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody moiety that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody moiety with antigen is affected. Further substitutions may be introduced at the amino acid locations demonstrating functional sensitivity to the initial substitutions. Alternatively, or additionally, a crystal structure of an antigen-antibody moiety complex can be determined to identify contact points between the antibody moiety and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody moiety with an N-terminal methionyl residue. Other insertional variants of the antibody moiety include the fusion to the N- or C-terminus of the antibody moiety to an enzyme (e.g., for ADEPT) or a polypeptide which increases the serum half-life of the antibody moiety.

Derivatives

In some embodiments, an abTCR according to any of the abTCRs described herein may be further modified to contain additional nonproteinaceous moieties that are known in the art and readily available. The moieties suitable for derivatization of the abTCR include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the abTCR may vary, and if more than one polymer are attached, they can be the same or different molecules. In general, the number and/or type of polymers used for derivatization can be determined based on considerations including, but not limited to, the particular properties or functions of the abTCR to be improved, whether the abTCR derivative will be used in a therapy under defined conditions, etc.

In some embodiments, conjugates of an abTCR and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the abTCR-nonproteinaceous moiety are killed.

Preparation of abTCR Effector Cells

The present invention in one aspect provides effector cells (such as lymphocytes, for example T cells) expressing an abTCR. Exemplary methods of preparing effector cells (such as T cells) expressing the abTCRs (abTCR effector cells, such as abTCR T cells) are provided herein.

In some embodiments, an abTCR effector cell (such as an abTCR T cell) can be generated by introducing one or more nucleic acids (including for example a lentiviral vector) encoding an abTCR (such as any of the abTCRs described herein) that specifically binds to a target antigen (such as a disease-associated antigen) into the effector cell. The introduction of the one or more nucleic acids into the effector cell can be accomplished using techniques known in the art, such as those described herein for Nucleic Acids. In some embodiments, the abTCR effector cells (such as abTCR T cells) of the invention are able to replicate in vivo, resulting in long-term persistence that can lead to sustained control of a disease associated with expression of the target antigen (such as cancer or viral infection).

In some embodiments, the invention relates to administering a genetically modified T cell expressing an abTCR that specifically binds to a target antigen according to any of the abTCRs described herein for the treatment of a patient having or at risk of developing a disease and/or disorder associated with expression of the target antigen (also referred to herein as a "target antigen-positive" or "TA-positive" disease or disorder), including, for example, cancer or viral infection, using lymphocyte infusion. In some embodiments, autologous lymphocyte infusion is used in the treatment. Autologous PBMCs are collected from a patient in need of treatment and T cells are activated and expanded using the methods described herein and known in the art and then infused back into the patient.

In some embodiments, there is provided a T cell expressing an abTCR that specifically binds to a target antigen according to any of the abTCRs described herein (also referred to herein as an "abTCR T cell"). The abTCR T cells of the invention can undergo robust in vivo T cell expansion and can establish target antigen-specific memory cells that persist at high levels for an extended amount of time in blood and bone marrow. In some embodiments, the abTCR T cells of the invention infused into a patient can eliminate target antigen-presenting cells, such as target antigen-presenting cancer or virally-infected cells, in vivo in patients having a target antigen-associated disease. In some embodiments, the abTCR T cells of the invention infused into a patient can eliminate target antigen-presenting cells, such as target antigen-presenting cancer or virally-infected cells, in vivo in patients having a target antigen-associated disease that is refractory to at least one conventional treatment.

Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable abTCR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a costimulatory molecule on the surface of the T cells. In particular, T cell populations may be stimulated, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

In some of any such embodiments described herein, preparation of abTCR effector cells results in minimal or substantially no exhaustion of the abTCR effector cells. For example, in some embodiments, preparation results in fewer than about 50% (such as fewer than about any of 45, 40, 35, 30, 25, 20, 15, 10, or 5%) of the abTCR effector cells becoming exhausted. Effector cell exhaustion can be determined by any means known in the art, including any means described herein.

In some of any such embodiments described herein, preparation of abTCR effector cells results in minimal or substantially no terminal differentiation of the abTCR effector cells. For example, in some embodiments, preparation results in fewer than about 50% (such as fewer than about any of 45, 40, 35, 30, 25, 20, 15, 10, or 5%) of the abTCR effector cells becoming terminally differentiated. Effector cell differentiation can be determined by any means known in the art, including any means described herein.

In some of any such embodiments described herein, preparation of abTCR effector cells results in minimal or substantially no internalization of abTCRs on the abTCR effector cells. For example, in some embodiments, preparation results in less than about 50% (such as less than about any of 45, 40, 35, 30, 25, 20, 15, 10, or 5%) of abTCRs on the abTCR effector cells becoming internalized. Internalization of abTCRs on abTCR effector cells can be determined by any means known in the art, including any means described herein.

Genetic Modification

In some embodiments, the abTCR effector cells (such as abTCR T cells) of the invention are generated by transducing effector cells (such as T cells prepared by the methods described herein) with a viral vector encoding an abTCR as described herein. Viral vector delivery systems include DNA and RNA viruses, which have either episomal or integrated genomes after delivery to the effector cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11: 167-175 (1993); Miller, Nature 357:455-460 (1992); Van Brunt, Biotechnology 6(10): 1149-1 154 (1988); Vigne, Restorative Neurology and Neuroscience 8:35-36 (1995); Kremer & Perricaudet, British Medical Bulletin 51(1):31-44 (1995); and Yu et al., Gene Therapy 1:13-26 (1994). In some embodiments, the viral vector is a lentiviral vector, and the abTCR effector cell comprises the lentiviral vector integrated into the abTCR effector cell genome. In some embodiments, the abTCR effector cell is an abTCR T cell comprising the lentiviral vector integrated into its genome.

In some embodiments, the abTCR effector cell is a T cell modified to block or decrease the expression of one or both of the endogenous TCR chains. For example, in some embodiments, the abTCR effector cell is an αβ T cell modified to block or decrease the expression of the TCR α and/or β chains, or the abTCR effector cell is a γδ T cell modified to block or decrease the expression of the TCR γ and/or δ chains. Modifications of cells to disrupt gene expression include any such techniques known in the art, including for example RNA interference (e.g., siRNA, shRNA, miRNA), gene editing (e.g., CRISPR- or TALEN-based gene knockout), and the like.

In some embodiments, abTCR T cells with reduced expression of one or both of the endogenous TCR chains of the T cell are generated using the CRISPR/Cas system. For a review of the CRISPR/Cas system of gene editing, see for example Jian W & Marraffini L A, *Annu. Rev. Microbiol.* 69, 2015; Hsu P D et al., *Cell,* 157(6):1262-1278, 2014; and O'Connell M R et al., *Nature* 516:263-266, 2014. In some embodiments, abTCR T cells with reduced expression of one or both of the endogenous TCR chains of the T cell are generated using TALEN-based genome editing.

Enrichment

In some embodiments, there is provided a method of enriching a heterogeneous cell population for an abTCR effector cell according to any of the abTCR effector cells described herein.

A specific subpopulation of abTCR effector cells (such as abTCR T cells) that specifically bind to a target antigen can be enriched for by positive selection techniques. For example, in some embodiments, abTCR effector cells (such as abTCR T cells) are enriched for by incubation with target antigen-conjugated beads for a time period sufficient for positive selection of the desired abTCR effector cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of abTCR effector cells present at low levels in the heterogeneous cell population, use of longer incubation times, such as 24 hours, can increase cell yield. Longer incubation times may be used to isolate abTCR effector cells in any situation where there are few abTCR effector cells as compared to other cell types. The skilled artisan would recognize that multiple rounds of selection can also be used in the context of this invention.

For isolation of a desired population of abTCR effector cells by positive selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of abTCR effector cells that may weakly express the abTCR.

In some of any such embodiments described herein, enrichment results in minimal or substantially no exhaustion of the abTCR effector cells. For example, in some embodiments, enrichment results in fewer than about 50% (such as fewer than about any of 45, 40, 35, 30, 25, 20, 15, 10, or 5%) of the abTCR effector cells becoming exhausted. Effector cell exhaustion can be determined by any means known in the art, including any means described herein.

In some of any such embodiments described herein, enrichment results in minimal or substantially no terminal differentiation of the abTCR effector cells. For example, in some embodiments, enrichment results in fewer than about 50% (such as fewer than about any of 45, 40, 35, 30, 25, 20, 15, 10, or 5%) of the abTCR effector cells becoming terminally differentiated. Effector cell differentiation can be determined by any means known in the art, including any means described herein.

In some of any such embodiments described herein, enrichment results in minimal or substantially no internalization of abTCRs on the abTCR effector cells. For example, in some embodiments, enrichment results in less than about 50% (such as less than about any of 45, 40, 35, 30, 25, 20, 15, 10, or 5%) of abTCRs on the abTCR effector cells becoming internalized. Internalization of abTCRs on abTCR effector cells can be determined by any means known in the art, including any means described herein.

In some of any such embodiments described herein, enrichment results in increased proliferation of the abTCR effector cells. For example, in some embodiments, enrichment results in an increase of at least about 10% (such as at least about any of 20, 30, 40, 50, 60, 70, 80, 90, 100, 200, 300, 400, 500, 1000% or more) in the number of abTCR effector cells following enrichment.

Thus, in some embodiments, there is provided a method of enriching a heterogeneous cell population for abTCR effector cells expressing an abTCR that specifically binds to a target antigen comprising: a) contacting the heterogeneous cell population with a ligand comprising the target antigen or one or more epitopes contained therein to form complexes comprising the abTCR effector cell bound to the ligand; and b) separating the complexes from the heterogeneous cell population, thereby generating a cell population enriched for the abTCR effector cells. In some embodiments, the ligand is immobilized to a solid support. In some embodiments, the solid support is particulate (such as beads). In some embodiments, the solid support is a surface (such as the bottom of a well). In some embodiments, the ligand is labelled with a tag. In some embodiments, the tag is a fluorescent molecule, an affinity tag, or a magnetic tag. In some embodiments, the method further comprises eluting the abTCR effector cells from the ligand and recovering the eluate.

Library Screening

To isolate candidate abTCR constructs specific for a target antigen, an abTCR library, for example cells expressing a library of nucleic acids encoding a plurality of abTCRs, may be exposed to a ligand comprising the target antigen or one or more epitopes contained therein, followed by isolation of affinity members of the library that specifically bind the ligand. In some embodiments, the ligand is immobilized on a solid support. In some embodiments, the support may be the surfaces of beads, microtitre plates, immunotubes, or any material known in the art useful for such purposes. In some embodiments, the interaction takes place in solution on tagged ligand targets (e.g. biotinylated ligand). In some embodiments, the procedure involves one or more washing steps to remove unspecific and non-reactive library members (panning). In some embodiments, to purify complexes in solution, they are captured by either immobilization or by centrifugation. In some embodiments, affinity members are captured on a soluble biotinylated ligand, followed by immobilization of the affinity complex (affinity member and ligand) on streptavidin beads. In some embodiments, the solid support is a bead. In some embodiments, the beads include, for example, magnetic beads (e.g. from Bangs Laboratories, Polysciences inc., Dynal Biotech, Miltenyi Biotech or Quantum Magnetic), nonmagnetic beads (e.g. Pierce and Upstate technology), monodisperse beads (e.g. Dynal Biotech and Microparticle Gmbh), and polydisperse beads (e.g. Chemagen). The use of magnetic beads has been described exhaustingly in literature (Uhlen, M, et al (1994) in Advances in Biomagnetic Separation, BioTechniques press, Westborough, Mass.). In some embodiments, the affinity members are purified by positive selection. In some embodiments, the affinity members are purified by negative selection to remove unwanted library members. In some embodiments, the affinity members are purified by both positive and negative selection steps.

Generally, the techniques used to prepare the library constructs will be based on known genetic engineering techniques. In this regard, nucleic acid sequences encoding the abTCRs to be expressed in the library are incorporated into expression vectors appropriate for the type of expression system to be used. Appropriate expression vectors for use in display in cells, such as CD3+ cells, are well known and described in the art. For example, in some embodiments, the expression vector is a viral vector, such as a lentiviral vector.

In some embodiments, there is provided a nucleic acid library comprising sequences encoding a plurality of abTCRs according to any one of the embodiments described herein. In some embodiments, the nucleic acid library comprises viral vectors encoding the plurality of abTCRs. In some embodiments, the viral vectors are lentiviral vectors.

In some embodiments, there is provided a method of screening a nucleic acid library according to any of the embodiments described herein for sequences encoding abTCRs specific for a target antigen, comprising: a) introducing the nucleic acid library into a plurality of cells, such that the abTCRs are expressed on the surface of the plurality of cells; b) incubating the plurality of cells with a ligand comprising the target antigen or one or more epitopes contained therein; c) collecting cells bound to the ligand; and d) isolating sequences encoding the abTCRs from cells collected in step c), thereby identifying abTCRs specific for the target antigen. In some embodiments, the method further comprises one or more wash steps. In some embodiments, the one or more wash steps are carried out between steps b) and c). In some embodiments, the plurality of cells is a plurality of CD3+ cells. In some embodiments, the ligand is immobilized on a solid support. In some embodiments, the solid support is a bead. In some embodiments, collecting cells bound to the ligand comprises eluting cells from the ligand bound to the solid support and collecting the eluate. In some embodiments, the ligand is labelled with a tag. In some embodiments, the tag is a fluorescent molecule, an affinity tag, or a magnetic tag. In some embodiments, collecting cells bound to the ligand comprises isolating complexes comprising the cells and the labelled ligand. In some embodiments, the cells are dissociated from the complexes.

MHC Proteins

MHC class I proteins are one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign or mutated proteins will be attacked by the immune system. Because MHC class I proteins present peptides derived from cytosolic proteins, the pathway of MHC class I presentation is often called the cytosolic or endogenous pathway. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation.

MHC class I proteins consist of two polypeptide chains, α and β2-microglobulin (β2M). The two chains are linked noncovalently via interaction of β2M and the α3 domain. Only the α chain is polymorphic and encoded by a HLA gene, while the β2M subunit is not polymorphic and encoded by the β-2 microglobulin gene. The α3 domain is plasma membrane-spanning and interacts with the CD8 co-receptor of T-cells. The α3-CD8 interaction holds the MHC I molecule in place while the T cell receptor (TCR) on the surface of the cytotoxic T cell binds its α1-α2 heterodimer ligand, and checks the coupled peptide for antigenicity. The α1 and α2 domains fold to make up a groove for peptides to bind. MHC class I proteins bind peptides that are 8-10 amino acid in length.

MHC class II molecules are a family of molecules normally found only on antigen-presenting cells such as dendritic cells, mononuclear phagocytes, some endothelial cells, thymic epithelial cells, and B cells. The antigens presented by class II peptides are derived from extracellular proteins (not cytosolic as in class I); hence, the MHC class II-dependent pathway of antigen presentation is called the endocytic or exogenous pathway. Loading of an MHC class II molecule occurs by phagocytosis; extracellular proteins are endocytosed, digested in lysosomes, and the resulting epitopic peptide fragments are loaded onto MHC class II molecules prior to their migration to the cell surface.

Like MHC class I molecules, class II molecules are also heterodimers, but in this case consist of two homogenous peptides, an α and β chain. The subdesignation α1, α2, etc.

refers to separate domains within the HLA gene; each domain is usually encoded by a different exon within the gene, and some genes have further domains that encode leader sequences, transmembrane sequences, etc. Because the antigen-binding groove of MHC class II molecules is open at both ends while the corresponding groove on class I molecules is closed at each end, the antigens presented by MHC class II molecules are longer, generally between 15 and 24 amino acid residues long.

The human leukocyte antigen (HLA) genes are the human versions of the MHC genes. The three major MHC class I proteins in humans are HLA-A, HLA-B, and HLA-C, while the 3 minor ones are HLA-E, HLA-F, and HLA-G. The three major MHC class II proteins involved in antigen presentation in humans are HLA-DP, HLDA-DQ, and HLA-DR, while the other MHC class II proteins, HLA-DM and HLA-DO, are involved in the internal processing and loading of antigens. HLA-A is ranked among the genes in humans with the fastest-evolving coding sequence. As of December 2013, there were 2432 known HLA-A alleles coding for 1740 active proteins and 117 null proteins. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface, enhancing the likelihood that a subset of the population will be resistant to any given foreign invader. This decreases the likelihood that a single pathogen has the capability to wipe out the entire human population. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, a person can only express either one or two of the 2432 known HLA-A alleles.

All alleles receive at least a four digit classification, e.g., HLA-A*02:12. The A signifies which HLA gene the allele belongs to. There are many HLA-A alleles, so that classification by serotype simplifies categorization. The next pair of digits indicates this assignment. For example, HLA-A*02:02, HLA-A*02:04, and HLA-A*02:324 are all members of the A2 serotype (designated by the *02 prefix). This group is the primary factor responsible for HLA compatibility. All numbers after this cannot be determined by serotyping and are designated through gene sequencing. The second set of digits indicates what HLA protein is produced. These are assigned in order of discovery and as of December 2013 there are 456 different HLA-A02 proteins known (assigned names HLA-A*02:01 to HLA-A*02:456). The shortest possible HLA name includes both of these details. Each extension beyond that signifies a nucleotide change that may or may not change the protein.

In some embodiments, the Fab-like antigen-binding module specifically binds to a complex comprising a peptide derived from a disease-associated antigen (such as a tumor-associated or virally-encoded antigen) and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01. HLA-A*02:01 is expressed in 39-46% of all Caucasians, and therefore represents a suitable choice of MHC class I protein for use in the present invention.

In some embodiments, the Fab-like antigen-binding module specifically binds to a complex comprising a peptide derived from a disease-associated antigen (such as a tumor-associated or virally-encoded antigen) and an MHC class II protein, wherein the MHC class II protein is HLA-DP, HLA-DQ, or HLA-DR. In some embodiments, the MHC class II protein is HLA-DP. In some embodiments, the MHC class II protein is HLA-DQ. In some embodiments, the MHC class II protein is HLA-DR.

Peptides suitable for use in generating Fab-like antigen-binding modules can be determined, for example, based on the presence of HLA (such as HLA-A*02:01) binding motifs and cleavage sites for proteasomes and immune-proteasomes using computer prediction models known to those of skill in the art. For predicting MHC binding sites, such models include, but are not limited to, ProPred1 (described in more detail in Singh and Raghava, *ProPred: prediction of HLA-DR binding sites. BIOINFORMATICS* 17(12):1236-1237, 2001), and SYFPEITHI (see Schuler et al. *SYFPEITHI, Database for Searching and T-Cell Epitope Prediction. in Immunoinformatics Methods in Molecular Biology*, vol 409(1): 75-93, 2007).

Once appropriate peptides have been identified, peptide synthesis may be done in accordance with protocols well known to those of skill in the art. Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention (See for example, Solid Phase Peptide Synthesis by John Morrow Stewart and Martin et al. *Application of Almez-mediated Amidation Reactions to Solution Phase Peptide Synthesis*, Tetrahedron Letters Vol. 39, pages 1517-1520, 1998).

Pharmaceutical Compositions

Also provided herein are compositions (such as pharmaceutical compositions, also referred to herein as formulations) comprising an abTCR according to any of the embodiments described herein, a nucleic acid encoding an abTCR according to any of the embodiments described herein, or an abTCR effector cell according to any of the embodiments described herein. In some embodiments, the composition is an abTCR effector cell composition (such as a pharmaceutical composition) comprising an effector cell (such as a T cell) presenting on its surface an abTCR according to any of the abTCRs described herein. In some embodiments, the abTCR effector cell composition is a pharmaceutical composition.

The composition may comprise a homogenous cell population comprising abTCR effector cells of the same cell type and expressing the same abTCR, or a heterogeneous cell population comprising a plurality of abTCR effector cell populations comprising abTCR effector cells of different cell types and/or expressing different abTCRs. The composition may further comprise cells that are not abTCR effector cells.

Thus, in some embodiments, there is provided an abTCR effector cell composition comprising a homogeneous cell population of abTCR effector cells (such as abTCR T cells) of the same cell type and expressing the same abTCR. In some embodiments, the abTCR effector cell is a T cell. In some embodiments, the abTCR effector cell is selected from the group consisting of a cytotoxic T cell, a helper T cell, a natural killer T cell, and a suppressor T cell. In some embodiments, the abTCR effector cell composition is a pharmaceutical composition.

In some embodiments, there is provided an abTCR effector cell composition comprising a heterogeneous cell population comprising a plurality of abTCR effector cell populations comprising abTCR effector cells of different cell types and/or expressing different abTCRs. In some embodiments, the abTCR effector cells are T cells. In some embodiments, each population of abTCR effector cells is of a cell type selected from the group consisting of cytotoxic T cells, helper T cells, natural killer T cells, and suppressor T cells. In some embodiments, all of the abTCR effector cells in the composition are of the same cell type (e.g., all of the abTCR effector cells are cytotoxic T cells). In some embodiments, at least one population of abTCR effector cells is of a different cell type than the others (e.g., one population of abTCR effector cells consists of cytotoxic T cells and the other populations of abTCR effector cells consist of natural killer T cells). In some embodiments, each population of abTCR effector cells expresses the same abTCR. In some embodiments, at least one population of abTCR effector cells expresses a different abTCR than the others. In some embodiments, each population of abTCR effector cells expresses a different abTCR than the others. In some embodiments, each population of abTCR effector cells expresses an abTCR that specifically binds to the same target antigen. In some embodiments, at least one population of abTCR effector cells expresses an abTCR that specifically binds to a different target antigen than the others (e.g., one population of abTCR effector cells specifically binds to a pMHC complex and the other populations of abTCR effector cells specifically bind to a cell surface receptor). In some embodiments, where at least one population of abTCR effector cells expresses an abTCR that specifically binds to a different target antigen, each population of abTCR effector cells expresses an abTCR that specifically binds to a target antigen associated with the same disease or disorder (e.g., each of the target antigens are associated with a cancer, such as breast cancer). In some embodiments, the abTCR effector cell composition is a pharmaceutical composition.

Thus, in some embodiments, there is provided an abTCR effector cell composition comprising a plurality of abTCR effector cell populations according to any of the embodiments described herein, wherein all of the abTCR effector cells in the composition are of the same cell type (e.g., all of the abTCR effector cells are cytotoxic T cells), and wherein each population of abTCR effector cells expresses a different abTCR than the others. In some embodiments, the abTCR effector cells are T cells. In some embodiments, the abTCR effector cells are selected from the group consisting of cytotoxic T cells, helper T cells, natural killer T cells, and suppressor T cells. In some embodiments, each population of abTCR effector cells expresses an abTCR that specifically binds to the same target antigen. In some embodiments, at least one population of abTCR effector cells expresses an abTCR that specifically binds to a different target antigen than the others (e.g., one population of abTCR effector cells specifically binds to a pMHC complex and the other populations of abTCR effector cells specifically bind to a cell surface receptor). In some embodiments, where at least one population of abTCR effector cells expresses an abTCR that specifically binds to a different target antigen, each population of abTCR effector cells expresses an abTCR that specifically binds to a target antigen associated with the same disease or disorder (e.g., each of the target antigens are associated with a cancer, such as breast cancer). In some embodiments, the abTCR effector cell composition is a pharmaceutical composition.

In some embodiments, there is provided a composition comprising a plurality of abTCR effector cell populations according to any of the embodiments described herein, wherein at least one population of abTCR effector cells is of a different cell type than the others. In some embodiments, all of the populations of abTCR effector cells are of different cell types. In some embodiments, the abTCR effector cells are T cells. In some embodiments, each population of abTCR effector cells is of a cell type selected from the group consisting of cytotoxic T cells, helper T cells, natural killer T cells, and suppressor T cells. In some embodiments, each population of abTCR effector cells expresses the same abTCR. In some embodiments, at least one population of abTCR effector cells expresses a different abTCR than the others. In some embodiments, each population of abTCR effector cells expresses a different abTCR than the others. In some embodiments, each population of abTCR effector cells expresses an abTCR that specifically binds to the same target antigen. In some embodiments, at least one population of abTCR effector cells expresses an abTCR that specifically binds to a different target antigen than the others (e.g., one population of abTCR effector cells specifically binds to a pMHC complex and the other populations of abTCR effector cells specifically bind to a cell surface receptor). In some embodiments, where at least one population of abTCR effector cells expresses an abTCR that specifically binds to a different target antigen, each population of abTCR effector cells expresses an abTCR that specifically binds to a target antigen associated with the same disease or disorder (e.g., each of the target antigens are associated with a cancer, such as breast cancer). In some embodiments, the abTCR effector cell composition is a pharmaceutical composition.

At various points during preparation of a composition, it can be necessary or beneficial to cryopreserve a cell. The terms "frozen/freezing" and "cryopreserved/cryopreserving" can be used interchangeably. Freezing includes freeze drying.

As is understood by one of ordinary skill in the art, the freezing of cells can be destructive (see Mazur, P., 1977, Cryobiology 14:251-272) but there are numerous procedures available to prevent such damage. For example, damage can be avoided by (a) use of a cryoprotective agent, (b) control of the freezing rate, and/or (c) storage at a temperature sufficiently low to minimize degradative reactions. Exemplary cryoprotective agents include dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad.

Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, llbery ed., Butterworth, London, p. 59). In particular embodiments, DMSO can be used. Addition of plasma (e.g., to a concentration of 20-25%) can augment the protective effects of DMSO. After addition of DMSO, cells can be kept at 0° C. until freezing, because DMSO concentrations of 1% can be toxic at temperatures above 4° C.

In the cryopreservation of cells, slow controlled cooling rates can be critical and different cryoprotective agents (Rapatz et al., 1968, Cryobiology 5(1): 18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1): 17-32; and Mazur, 1970, Science 168:939-949 for effects of cooling velocity on survival of stem cells and on their transplantation potential). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling.

In particular embodiments, DMSO-treated cells can be pre-cooled on ice and transferred to a tray containing chilled methanol which is placed, in turn, in a mechanical refrigerator (e.g., Harris or Revco) at −80° C. Thermocouple measurements of the methanol bath and the samples indicate a cooling rate of 1° to 3° C./minute can be preferred. After at least two hours, the specimens can have reached a temperature of −80° C. and can be placed directly into liquid nitrogen (−196° C.).

After thorough freezing, the cells can be rapidly transferred to a long-term cryogenic storage vessel. In a preferred embodiment, samples can be cryogenically stored in liquid nitrogen (−196° C.) or vapor (−1° C.). Such storage is facilitated by the availability of highly efficient liquid nitrogen refrigerators.

Further considerations and procedures for the manipulation, cryopreservation, and long-term storage of cells, can be found in the following exemplary references: U.S. Pat. Nos. 4,199,022; 3,753,357; and 4,559,298; Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186; Livesey and Linner, 1987, Nature 327:255; Linner et al., 1986, J. Histochem. Cytochem. 34(9):1 123-1 135; Simione, 1992, J. Parenter. Sci. Technol. 46(6):226-32).

Following cryopreservation, frozen cells can be thawed for use in accordance with methods known to those of ordinary skill in the art. Frozen cells are preferably thawed quickly and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed on ice.

In particular embodiments, methods can be used to prevent cellular clumping during thawing. Exemplary methods include: the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc. [0162] As is understood by one of ordinary skill in the art, if a cryoprotective agent that is toxic to humans is used, it should be removed prior to therapeutic use. DMSO has no serious toxicity.

Exemplary carriers and modes of administration of cells are described at pages 14-15 of U.S. Patent Publication No. 2010/0183564. Additional pharmaceutical carriers are described in Remington: The Science and Practice of Pharmacy, 21 st Edition, David B. Troy, ed., Lippicott Williams & Wilkins (2005).

In particular embodiments, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

In compositions and formulations disclosed herein, cells are generally in a volume of a liter or less, 500 ml or less, 250 ml or less or 100 ml or less. Hence the density of administered cells is typically greater than $10^4$ cells/ml, $10^7$ cells/ml or $10^8$ cells/ml.

Also provided herein are abTCR nucleic acid compositions (such as pharmaceutical compositions, also referred to herein as formulations) comprising any of the nucleic acids encoding an abTCR described herein. In some embodiments, the abTCR nucleic acid composition is a pharmaceutical composition. In some embodiments, the abTCR nucleic acid composition further comprises any of an isotonizing agent, an excipient, a diluent, a thickener, a stabilizer, a buffer, and/or a preservative; and/or an aqueous vehicle, such as purified water, an aqueous sugar solution, a buffer solution, physiological saline, an aqueous polymer solution, or RNase free water. Tsubunit ishe amounts of such additives and aqueous vehicles to be added can be suitably selected according to the form of use of the abTCR nucleic acid composition.

The compositions and formulations disclosed herein can be prepared for administration by, for example, injection, infusion, perfusion, or lavage. The compositions and formulations can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

The formulations to be used for in vivo administration must be sterile. This is readily accomplished by, e.g., filtration through sterile filtration membranes.

Methods of Treatment Using abTCRs

The abTCRs and/or compositions of the invention can be administered to individuals (e.g., mammals such as humans) to treat a disease and/or disorder associated with target antigen (TA) expression (also referred to herein as a "target-antigen positive" or "TA-positive" disease or disorder), including, for example, cancer and infectious disease (such as viral infection). The present application thus in some embodiments provides a method for treating a target antigen-positive disease (such as cancer or viral infection) in an individual comprising administering to the individual an effective amount of a composition (such as a pharmaceutical composition) comprising an abTCR comprising an antibody moiety, such as any one of the abTCRs described herein. In some embodiments, the composition further comprises a cell (such as an effector cell) associated with the abTCR. In some embodiments, the cancer is selected, for example, from the group consisting of adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, lung cancer, melanoma, mesothelioma, multiple myeloma, pancreatic cancer, pheochromocytoma, plasmacytoma, neuroblastoma, ovarian cancer, prostate cancer, sarcoma, stomach cancer, uterine cancer and thyroid cancer. In some embodiments, the viral infection is caused by a virus selected, for example, from the group consisting of Cytomegalovirus (CMV), Epstein-Barr Virus (EBV), Hepatitis B Virus (HBV), Kaposi's Sarcoma associated herpesvirus (KSHV), Human papillomavirus (HPV), Molluscum contagiosum virus (MCV), Human T cell leukemia virus 1 (HTLV-1), HIV (Human immunodeficiency virus), and Hepatitis C Virus (HCV).

For example, in some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR (such as an isolated abTCR) comprising a) a Fab-like antigen-binding module that specifically binds to the target antigen, and b) a TCRM capable of recruiting at least one TCR-associated signaling module. In some embodiments, the Fab-like antigen-binding module comprises a $V_H$ antibody domain, a $C_H1$ antibody domain, a $V_L$ antibody domain, and a $C_L$ antibody domain. In some embodiments, the Fab-like antigen-binding module is human, humanized, chimeric, semi-synthetic, or fully synthetic. In some embodiments, the TCRM comprises the transmembrane domains of a TCR, such as an αβTCR or a γδTCR. In some embodiments, the TCRM further comprises the connecting peptides or fragments thereof of the TCR. In some embodiments, the TCRM further comprises at least one portion of an extracellular domain of the TCR. In some embodiments, the abTCR further comprises at least one intracellular domain. In some embodiments, the at least one intracellular domain comprises any of a sequence from an intracellular domain of the TCR, a co-stimulatory intracellular signaling sequence, an epitope tag, or a combination thereof. In some embodiments, the abTCR further comprises at least one disulfide bond. In some embodiments, the Fab-like antigen binding module comprises a disulfide bond and/or the TCRM comprises a disulfide bond. In some embodiments, the Fab-like antigen binding module comprises a disulfide bond between a residue in the $C_H1$ domain and a residue in the $C_L$ domain and/or the TCRM comprises a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a peptide linker between the Fab-like antigen-binding module and the TCRM. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the method results in minimal or substantially no exhaustion of the abTCR effector cells. In some embodiments, the method results in minimal or substantially no terminal differentiation of the abTCR effector cells. In some embodiments, the method results in minimal or substantially no internalization of abTCRs on the abTCR effector cells. In some embodiments, the method results in increased proliferation of the abTCR effector cells.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR (such as an isolated abTCR) comprising a) an Fv-like antigen-binding module that specifically binds to a target antigen, and b) a TCRM capable of recruiting at least one TCR-associated signaling module, wherein the target antigen is a peptide/MHC complex. In some embodiments, the Fv-like antigen-binding module comprises a $V_H$ antibody domain and a $V_L$ antibody domain. In some embodiments, there is a first peptide linker fused to the C-terminus of the $V_L$ antibody domain and/or a second peptide linker fused to the C-terminus of the $V_H$ antibody domain. In some embodiments, the first and second peptide linkers are capable of binding to one another. In some embodiments, the first and/or second peptide linkers are derived from immunoglobulin heavy and/or light chain constant regions. In some embodiments, the first and/or second peptide linkers are derived from TCR subunit constant regions. For example, in some embodiments, the first and/or second peptide linkers are derived from a) TCR α and β subunit constant domains; or b) TCR γ and δ subunit constant domains. In some embodiments, the first and/or second peptide linkers are synthetic. In some embodiments, the Fv-like antigen-binding module is human, humanized, chimeric, semi-synthetic, or fully synthetic. In some embodiments, the TCRM comprises the transmembrane domains of a TCR, such as an αβTCR or a γδTCR. In some embodiments, the TCRM further comprises the connecting peptides or fragments thereof of a TCR, such as an αβTCR or a γδTCR. In some embodiments, the transmembrane domains and the connecting peptides are derived from an αβTCR or a γδTCR. In some embodiments, the transmembrane domains are derived from an αβTCR and the connecting peptides are derived from a γδTCR, or the transmembrane domains are derived from a γδTCR and the connecting peptides are derived from an αβTCR. In some embodiments, the TCRM further comprises at least one portion of an extracellular domain of the TCR. In some embodiments, the TCRM further comprises at least one TCR intracellular domain comprising a sequence from an intracellular domain of the TCR. In some embodiments, the TCRM comprises fragments of the TCR subunits. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the abTCR further comprises at least one disulfide bond. In some embodiments, the first and/or second peptide linkers comprise a disulfide bond and/or the TCRM comprises a disulfide bond. In some embodiments, the TCRM comprises a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the target antigen peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the method results in minimal or substantially no exhaustion of the abTCR effector cells. In some embodiments, the method results in minimal or substantially no terminal differentiation of the abTCR effector cells. In some embodiments, the method results in minimal or substantially no internalization of abTCRs on the abTCR effector cells. In some embodiments, the method results in increased proliferation of the abTCR effector cells.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising a first antigen-binding domain comprising $V_H$ and $C_H1$ antibody domains and a first TCRD comprising the transmembrane domain of a first TCR subunit; and b) a second polypeptide chain comprising a second antigen-binding domain comprising $V_L$ and $C_L$ antibody domains and a second TCRD comprising the transmembrane domain of a second TCR subunit, wherein the $V_H$ and $C_H1$ domains of the first antigen-binding domain and the $V_L$ and $C_L$ domains of the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCR subunit is a TCR α chain, and the second TCR subunit is a TCR β chain. In some embodiments, the first TCR subunit is a TCR β chain, and the second TCR subunit is a TCR α chain. In some embodiments, the first TCR subunit is a TCR γ chain, and the second TCR subunit is a TCR δ chain. In some embodiments, the first TCR subunit is a TCR δ chain, and the second TCR subunit is a TCR γ chain. In some embodiments, the first TCRD further comprises the connecting peptide or a fragment thereof of the first TCR subunit and/or the second TCRD further comprises the connecting peptide or a fragment thereof of the second TCR subunit. In some embodiments, the first TCRD further comprises a portion of the extracellular domain of the first TCR subunit and/or the second TCRD further comprises a portion of the extracellular domain of the second TCR subunit. In some embodiments, the first TCRD further comprises a first TCR intracellular domain and/or the second TCRD further comprises a second TCR intracellular domain. In some embodiments, the first TCR intracellular domain comprises a sequence from the intracellular domain of the first TCR subunit and/or the second TCR intracellular domain comprises a sequence from the intracellular domain of the second TCR subunit. In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising a first antigen-binding domain comprising $V_H$ and $C_H1$ antibody domains and a first TCRD comprising the transmembrane domain of a TCR α chain; and b) a second polypeptide chain comprising a second antigen-binding domain comprising $V_L$ and $C_L$ antibody domains and a second TCRD comprising the transmembrane domain of a TCR β chain, wherein the $V_H$ and $C_H1$ domains of the first antigen-binding domain and the $V_L$ and $C_L$ domains of the second antigen-binding domain form a Fab-like antigen-binding module that specifically binds to the cell surface antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR α chain and/or the second TCRD further comprises the connecting peptide or a fragment thereof of the TCR β chain. In some embodiments, the first TCRD further comprises a portion of the extracellular domain of the TCR α chain and/or the second TCRD further comprises a portion of the extracellular domain of the TCR β chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR α chain and/or the second TCR intracellular domain comprises a sequence from the intracellular domain of the TCR β chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising a first antigen-binding domain comprising $V_H$ and $C_H1$ antibody domains and a first TCRD comprising the transmembrane domain of a TCR β chain; and b) a second polypeptide chain comprising a second antigen-binding domain comprising $V_L$ and $C_L$ antibody domains and a second TCRD comprising the transmembrane domain of a TCR α chain, wherein the $V_H$ and $C_H1$ domains of the first antigen-binding domain and the $V_L$ and $C_L$ domains of the second antigen-binding domain form a Fab-like antigen-binding module that specifically binds to the cell surface antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR β chain and/or the second TCRD further comprises the connecting peptide or a fragment thereof of the TCR α chain. In some embodiments, the first TCRD further comprises a portion of the extracellular domain of the TCR β chain and/or the second TCRD further comprises a portion of the extracellular domain of the TCR α chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR β chain and/or the second TCR intracellular domain comprises a sequence from the intracellular domain of the TCR α chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising a first antigen-binding domain comprising $V_H$ and $C_H1$ antibody domains and a first TCRD comprising the transmembrane domain of a TCR γ chain; and b) a second polypeptide chain comprising a second antigen-binding domain comprising $V_L$ and $C_L$ antibody domains and a second TCRD comprising the transmembrane domain of a TCR δ chain, wherein the $V_H$ and $C_H1$ domains of the first antigen-binding domain and the $V_L$ and $C_L$ domains of the second antigen-binding domain form a Fab-like antigen-binding module that specifically binds to the cell surface antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR γ chain and/or the second TCRD further comprises the connecting peptide or a fragment thereof of the TCR δ chain. In some embodiments, the first TCRD further comprises a portion of the extracellular domain of the TCR γ chain and/or the second TCRD further comprises a portion of the extracellular domain of the TCR δ chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR γ chain and/or the second TCR intracellular domain comprises a sequence from the intracellular domain of the TCR δ chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD;

and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising a first antigen-binding domain comprising $V_H$ and $C_H1$ antibody domains and a first TCRD comprising the transmembrane domain of a TCR δ chain; and b) a second polypeptide chain comprising a second antigen-binding domain comprising $V_L$ and $C_L$ antibody domains and a second TCRD comprising the transmembrane domain of a TCR γ chain, wherein the $V_H$ and $C_H1$ domains of the first antigen-binding domain and the $V_L$ and $C_L$ domains of the second antigen-binding domain form a Fab-like antigen-binding module that specifically binds to the cell surface antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the first TCRD further comprises the connecting peptide or a fragment thereof of the TCR δ chain and/or the second TCRD further comprises the connecting peptide or a fragment thereof of the TCR γ chain. In some embodiments, the first TCRD further comprises a portion of the extracellular domain of the TCR δ chain and/or the second TCRD further comprises a portion of the extracellular domain of the TCR γ chain. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR δ chain and/or the second TCR intracellular domain comprises a sequence from the intracellular domain of the TCR γ chain. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the abTCR further comprises a first signal peptide amino-terminal to the first antigen-binding domain and/or a second signal peptide amino-terminal to the second antigen-binding domain. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, there is a first peptide linker between the first antigen-binding domain and the first TCRD and/or a second peptide linker between the second antigen-binding domain and the second TCRD. In some embodiments, the first and second polypeptide chains are linked, such as by a covalent linkage (e.g., peptide or other chemical linkage) or non-covalent linkage. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between a residue in the $C_H1$ antibody domain in the first antigen-binding domain and a residue in the $C_L$ antibody domain in the second antigen-binding domain. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising, in order from amino terminus to carboxy terminus, a first antigen-binding domain and a first TCRD comprising the amino acid sequence of SEQ ID NO: 15; and b) a second polypeptide chain comprising, in order from amino terminus to carboxy terminus, a second antigen-binding domain and a second TCRD comprising the amino acid sequence of SEQ ID NO: 16;

wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising, in order from amino terminus to carboxy terminus, a first antigen-binding domain and a first TCRD comprising the amino acid sequence of SEQ ID NO: 17; and b) a second polypeptide chain comprising, in order from amino terminus to carboxy terminus, a second antigen-binding domain and a second TCRD comprising the amino acid sequence of SEQ ID NO: 18; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising, in order from amino terminus to carboxy terminus, a first antigen-binding domain and a first TCRD comprising the amino acid sequence of SEQ ID NO: 19; and b) a second polypeptide chain comprising, in order from amino terminus to carboxy terminus, a second antigen-binding domain and a second TCRD comprising the amino acid sequence of SEQ ID NO: 20; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising effector cells (such as T cells or natural killer cells) presenting on their surface an abTCR that specifically recognizes the target antigen comprising a) a first polypeptide chain comprising, in order from amino terminus to carboxy terminus, a first antigen-binding domain and a first TCRD comprising the amino acid sequence of SEQ ID NO: 21; and b) a second polypeptide chain comprising, in order from amino terminus to carboxy terminus, a second antigen-binding domain and a second TCRD comprising the amino acid sequence of SEQ ID NO: 22; wherein the first antigen-binding domain and the second antigen-binding domain form a Fab-like antigen-binding module that specifically binds the target antigen, wherein the first TCRD and the second TCRD form a TCRM that is capable of recruiting at least one TCR-associated signaling module. In some embodiments, the Fab-like antigen-binding module is human, humanized, chimeric, semi-synthetic, or fully synthetic. In some embodiments, the abTCR further comprises at least one accessory intracellular domain comprising a) at least one T cell costimulatory signaling sequence comprising (such as consisting of) the amino acid sequence of SEQ ID NO: 70 or 71; and/or b) an epitope tag comprising (such as consisting of) the amino acid sequence of any one of SEQ ID NOs: 50-52. In some embodiments, the abTCR further comprises a first signal peptide amino-terminal to the first antigen-binding domain and/or a second signal peptide amino-terminal to the second antigen-binding domain, wherein the first and/or second signal peptides comprise the amino acid sequence of SEQ ID NO: 49. In some embodiments, the TCRM is capable of recruiting at least one TCR-associated signaling module selected from the group consisting of CD3δε, CD3γε, and ζζ. In some embodiments, the TCRM promotes abTCR-CD3 complex formation. In some embodiments, the first polypeptide chain and the second polypeptide chain are linked via a) a disulfide bond between a residue in the connecting peptide of the first TCRD and a residue in the connecting peptide of the second TCRD; and/or b) a disulfide bond between residues in the $C_H1$ and $C_L$ antibody domains in the Fab-like antigen-binding module. In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, HIV-1, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 23; and b) a second polypeptide chain comprising a second abTCR domain comprising the amino acid sequence of SEQ ID NO: 24, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 25; and b) a second polypeptide chain comprising a second abTCR domain comprising the amino acid sequence of SEQ ID NO: 26, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 27; and b) a second polypeptide chain comprising a second abTCR domain comprising the amino acid sequence of SEQ ID NO: 28, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is a γδ T cell. In some embodiments, the effector cell is an αβ T cell modified to block or decrease the expression of the TCR α and/or β chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 29; and b) a second polypeptide chain comprising a second abTCR domain comprising the amino acid sequence of SEQ ID NO: 30, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 31; and b) a second polypeptide chain comprising a second abTCR domain comprising the amino acid sequence of SEQ ID NO: 32, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 33; and b) a second polypeptide chain comprising a second abTCR domain comprising the amino acid sequence of SEQ ID NO: 34, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating an AFP-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 35; and b) a second polypeptide chain comprising a second abTCR domain comprising the amino acid sequence of SEQ ID NO: 36, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a CD19-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 42; and b) a second polypeptide chain comprising a second abTCR domain comprising the amino acid sequence of SEQ ID NO: 43, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a CD19-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 42; and b) a second polypeptide chain comprising a second abTCR domain comprising the amino acid sequence of SEQ ID NO: 54, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a CD19-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 55; and b) a second polypeptide chain comprising a second abTCR domain comprising the amino acid sequence of SEQ ID NO: 54, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

In some embodiments, there is provided a method of treating a CD19-associated disease in an individual in need thereof comprising administering to the individual an effective amount of a composition comprising effector cells (such as T cells or natural killer cells) presenting on their surface an abTCR comprising a) a first polypeptide chain comprising a first abTCR domain comprising the amino acid sequence of SEQ ID NO: 56; and b) a second polypeptide chain comprising a second abTCR domain comprising the amino acid sequence of SEQ ID NO: 54, wherein the first polypeptide chain and the second polypeptide chain are linked via one or more disulfide bonds. In some embodiments, the abTCR further comprises at least one accessory intracellular domain comprising a T cell costimulatory signaling sequence (such as from CD27, CD28, 4-1BB (CD137), OX40, CD30, or CD40) and/or an epitope tag (such as HA, FLAG, or myc). In some embodiments, the epitope tag comprises any one of the amino acid sequences of SEQ ID NOs: 50-52. In some embodiments, the first polypeptide chain further comprises a first signal peptide amino terminal to the first abTCR domain and/or the second polypeptide chain further comprises a second signal peptide amino terminal to the second abTCR domain. In some embodiments, the first and/or second signal peptides comprise (such as consist of) the amino acid sequence of SEQ ID NO: 49. In some embodiments, the effector cell is an αβ T cell. In some embodiments, the effector cell is a γδ T cell modified to block or decrease the expression of the TCR γ and/or δ chains. In some embodiments, the effector cell is selected from the group consisting of a cytotoxic T cell, a helper T cell, a natural killer T cell, and a suppressor T cell.

Also contemplated are methods of treating a target antigen-associated disease in an individual in need thereof comprising administering to the individual a composition comprising a plurality of effector cells expressing different abTCRs. Thus, in some embodiments, according to any of the methods for treating a target antigen-associated disease in an individual described herein, the composition is a heterogeneous abTCR effector cell composition as described herein.

For example, in some embodiments, there is provided a method of treating a target antigen-associated disease (such as cancer or viral infection) in an individual in need thereof comprising administering to the individual an effective amount of a heterogeneous abTCR effector cell composition comprising a plurality of abTCR effector cell populations according to any of the embodiments described herein, wherein all of the abTCR effector cells in the composition are of the same cell type (e.g., all of the abTCR effector cells are cytotoxic T cells), wherein each population of abTCR effector cells expresses a different abTCR than the others, and wherein at least one population of abTCR effector cells expresses an abTCR that specifically binds to the target antigen. In some embodiments, the abTCR effector cells are T cells. In some embodiments, the abTCR effector cells are selected from the group consisting of cytotoxic T cells, helper T cells, natural killer T cells, and suppressor T cells. In some embodiments, each population of abTCR effector cells expresses an abTCR that specifically binds to the target antigen. In some embodiments, at least one population of abTCR effector cells expresses an abTCR that specifically binds to a different target antigen. In some embodiments, where at least one population of abTCR effector cells expresses an abTCR that specifically binds to a different target antigen, each of the different target antigens is associated with the target antigen-associated disease.

In some embodiments, there is provided a method of treating a target antigen-associated disease (such as cancer or viral infection) in an individual in need thereof comprising administering to the individual an effective amount of a heterogeneous abTCR effector cell composition comprising a plurality of abTCR effector cell populations according to any of the embodiments described herein, wherein at least one population of abTCR effector cells is of a different cell type than the others, and wherein at least one population of abTCR effector cells expresses an abTCR that specifically binds to the target antigen. In some embodiments, all of the populations of abTCR effector cells are of different cell types. In some embodiments, the abTCR effector cells are T cells. In some embodiments, each population of abTCR effector cells is of a cell type selected from the group consisting of cytotoxic T cells, helper T cells, natural killer T cells, and suppressor T cells. In some embodiments, each population of abTCR effector cells expresses the same abTCR. In some embodiments, at least one population of abTCR effector cells expresses a different abTCR than the others. In some embodiments, each population of abTCR effector cells expresses a different abTCR than the others. In some embodiments, each population of abTCR effector cells expresses an abTCR that specifically binds to the target antigen. In some embodiments, at least one population of abTCR effector cells expresses an abTCR that specifically binds to a different target antigen. In some embodiments, where at least one population of abTCR effector cells expresses an abTCR that specifically binds to a different target antigen, each of the different target antigens is associated with the target antigen-associated disease.

In some embodiments, there is provided a method of treating a disease associated with a plurality of target antigens in an individual in need thereof comprising administering to the individual an effective amount of a heterogeneous abTCR effector cell composition comprising a plurality of abTCR effector cell populations according to any of the embodiments described herein, wherein all of the abTCR effector cells in the composition are of the same cell type (e.g., all of the abTCR effector cells are cytotoxic T cells), wherein each population of abTCR effector cells expresses a different abTCR than the others, and wherein for each target antigen of the plurality of target antigens, at least one population of abTCR effector cells expresses an abTCR that specifically binds to the target antigen. In some embodiments, the abTCR effector cells are T cells. In some embodiments, the abTCR effector cells are selected from the group consisting of cytotoxic T cells, helper T cells, natural killer T cells, and suppressor T cells.

In some embodiments, there is provided a method of treating a disease associate with a plurality of target antigens in an individual in need thereof comprising administering to the individual an effective amount of a heterogeneous abTCR effector cell composition comprising a plurality of abTCR effector cell populations according to any of the embodiments described herein, wherein at least one population of abTCR effector cells is of a different cell type than the others, and wherein for each target antigen of the plurality of target antigens, at least one population of abTCR effector cells expresses an abTCR that specifically binds to the target antigen. In some embodiments, all of the populations of abTCR effector cells are of different cell types. In some embodiments, the abTCR effector cells are T cells. In some embodiments, each population of abTCR effector cells is of a cell type selected from the group consisting of cytotoxic T cells, helper T cells, natural killer T cells, and suppressor T cells. In some embodiments, each population of abTCR effector cells expresses a different abTCR than the others.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or environmentally or genetically prone to one or more of the diseases or disorders described herein (such as cancer or viral infection). In some embodiments, the individual has one or more risk factors associated with one or more diseases or disorders described herein.

In some embodiments, the abTCR effector cell compositions of the invention are administered in combination with a second, third, or fourth agent (including, e.g., an antineoplastic agent, a growth inhibitory agent, a cytotoxic agent, or a chemotherapeutic agent) to treat diseases or disorders involving target antigen expression. In some embodiments, the abTCR effector cell composition is administered in combination with a cytokine (such as IL-2). In some embodiments, the abTCR is administered in combination with an agent that increases the expression of MHC proteins and/or enhances the surface presentation of peptides by MHC proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

In some embodiments, there is provided a method of treating a target antigen-positive disease in an individual in need thereof comprising administering to the individual an abTCR effector cell composition according to any of the embodiments described herein in combination with a cytokine (such as IL-2). In some embodiments, the abTCR effector cell composition and the cytokine are administered simultaneously. In some embodiments, the abTCR effector cell composition and the cytokine are administered sequentially.

In some embodiments, there is provided a method of treating a target antigen-positive disease in an individual in need thereof, wherein the cells expressing the target antigen do not normally present, or present at relatively low levels, a complex comprising the target antigen and an MHC class I protein on their surface, the method comprising administering to the individual an abTCR effector cell compositions according to any of the embodiments described herein in combination with an agent that increases the expression of MHC class I proteins and/or enhances the surface presentation of target antigens by MHC class I proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine. In some embodiments, the abTCR effector cell composition and the agent are administered simultaneously. In some embodiments, the abTCR effector cell composition and the agent are administered sequentially.

In some embodiments, there is provided a method of treating a target antigen-associated disease (such as cancer or viral infection) in an individual in need thereof comprising administering to the individual an effective amount of a composition comprising nucleic acid encoding an abTCR according to any of the embodiments described herein. Methods for gene delivery are known in the art. See, e.g., U.S. Pat. Nos. 5,399,346, 5,580,859, 5,589,466, incorporated by reference herein in their entireties.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation 100−(T/C×100), where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%.

Viral infection treatments can be evaluated, for example, by viral load, duration of survival, quality of life, protein expression and/or activity.

Diseases

The abTCR effector cells in some embodiments can be useful for treating cancers associated with a target antigen. Cancers that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the abTCR effector cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

The abTCR effector cells in other embodiments can be useful for treating infectious diseases by targeting pathogen-associated (such as virally-encoded) antigens. The infection to be prevented or treated, for example, may be caused by a virus, bacteria, protozoa, or parasite. The target antigen may be a pathogenic protein, polypeptide or peptide that is responsible for a disease caused by the pathogen, or is capable of inducing an immunological response in a host infected by the pathogen. Pathogenic antigens which can be targeted by abTCR effector cells include, but are not limited to, antigens derived from *Acinetobacter baumannii, Anaplasma* genus, *Anaplasma phagocytophilum, Ancylostoma braziliense, Ancylostoma duodenale, Arcanobacterium haemolyticum, Ascaris lumbricoides, Aspergillus* genus, *Astroviridae, Babesia* genus, *Bacillus anthracis, Bacillus cereus, Bartonella henselae,* BK virus, *Blastocystis hominis, Blastomyces dermatitidis, Bordetella pertussis, Borrelia burgdorferi, Borrelia* genus, *Borrelia* spp, *Brucella* genus, *Brugia malayi,* Bunyaviridae family, *Burkholderia cepacia* and other *Burkholderia* species, *Burkholderia mallei, Burkholderia pseudomallei,* Caliciviridae family, *Campylobacter* genus, *Candida albicans, Candida* spp, *Chlamydia trachomatis, Chlamydophila pneumoniae, Chlamydophila psittaci,* CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii,* Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis,* Ebolavirus (EBOV), *Echinococcus* genus, *Ehrlichia chaffeensis, Ehrlichia ewingii, Ehrlichia* genus, *Entamoeba histolytica, Enterococcus* genus, *Enterovirus* genus, Enteroviruses, mainly Coxsackie A virus and *Enterovirus* 71 (EV71), *Epidermophyton* spp, Epstein-Barr Virus (EBV), *Escheri-* chia coli O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae, Klebsiella granulomatis*, Kuru prion, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis*.

In some embodiments, the abTCR effector cells are used for treating oncogenic infectious diseases, such as infection by oncogenic viruses. Oncogenic viruses include, but are not limited to, CMV, EBV, HBV, KSHV, HPV, MCV, HTLV-1, HIV-1, and HCV. The target antigen of the abTCR can be a viral oncoprotein including, but not limited to, Tax, E7, E6/E7, E6, HBx, EBNA proteins (e.g., EBNA3 A, EBNA3 C, and EBNA 2), v-cyclin, LANA1, LANA2, LMP-1, k-bZIP, RTA, KSHV K8, and fragments thereof. See Ahuja, Richa, et al., *Curr. Sci.*, 2014.

Articles of Manufacture and Kits

In some embodiments of the invention, there is provided an article of manufacture containing materials useful for the treatment of a target antigen-positive disease such as cancer (for example adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, lung cancer, melanoma, mesothelioma, multiple myeloma, pancreatic cancer, pheochromocytoma, plasmacytoma, neuroblastoma, ovarian cancer, prostate cancer, sarcoma, stomach cancer, uterine cancer or thyroid cancer) or viral infection (for example infection by CMV, EBV, HBV, KSHV, HPV, MCV, HTLV-1, HIV-1, or HCV). The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an effector cell presenting on its surface an abTCR of the invention. The label or package insert indicates that the composition is used for treating the particular condition. The label or package insert will further comprise instructions for administering the abTCR effector cell composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a target antigen-positive cancer (such as adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, lung cancer, melanoma, mesothelioma, multiple myeloma, pancreatic cancer, pheochromocytoma, plasmacytoma, neuroblastoma, ovarian cancer, prostate cancer, sarcoma, stomach cancer, uterine cancer or thyroid cancer). In other embodiments, the package insert indicates that the composition is used for treating a target antigen-positive viral infection (for example infection by CMV, EBV, HBV, KSHV, HPV, MCV, HTLV-1, HIV-1, or HCV).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a target antigen-positive disease or disorder described herein, optionally in combination with the articles of manufacture. Kits of the invention include one or more containers comprising an abTCR effector cell composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an effector cell presenting on its surface an abTCR. In some embodiments, the kit comprises a) a composition comprising an effector cell presenting on its surface an abTCR, and b) an effective amount of at least one other agent, wherein the other agent increases the expression of MHC proteins and/or enhances the surface presentation of peptides by MHC proteins (e.g., IFNγ, IFNβ, IFNα, or Hsp90 inhibitor). In some embodiments, the kit comprises a) a composition comprising an effector cell presenting on its surface an abTCR, and b) instructions for administering the abTCR effector cell composition to an individual for treatment of a target antigen-positive disease (such as cancer or viral infection). In some embodiments, the kit comprises a) a composition comprising an effector cell presenting on its surface an abTCR, b) an effective amount of at least one other agent, wherein the other agent increases the expression of MHC proteins and/or enhances the surface presentation of peptides by MHC proteins (e.g., IFNγ, IFNβ, IFNα, or Hsp90 inhibitor), and c) instructions for administering the abTCR effector cell composition and the other agent(s) to an individual for treatment of a target antigen-positive disease (such as cancer or viral infection). The abTCR effector cell composition and the other agent(s) can be present in separate containers or in a single container. For example, the kit may comprise one distinct composition or two or more compositions wherein one composition comprises the abTCR effector cell and another composition comprises the other agent.

In some embodiments, the kit comprises a) a composition comprising an abTCR, and b) instructions for combining the abTCR with effector cells (such as effector cells, e.g., T cells or natural killer cells, derived from an individual) to form a composition comprising the effector cells presenting on their surface the abTCR and administering the abTCR effector cell composition to the individual for treatment of a target antigen-positive disease (such as cancer or viral infection). In some embodiments, the kit comprises a) a composition comprising an abTCR, and b) an effector cell (such as a cytotoxic cell). In some embodiments, the kit comprises a) a composition comprising an abTCR, b) an effector cell (such as a cytotoxic cell), and c) instructions for combining the abTCR with the effector cell to form a composition comprising the effector cell presenting on its surface the abTCR and administering the abTCR effector cell composition to an individual for the treatment of a target antigen-positive disease (such as cancer or viral infection).

In some embodiments, the kit comprises a nucleic acid (or set of nucleic acids) encoding an abTCR. In some embodiments, the kit comprises a) a nucleic acid (or set of nucleic acids) encoding an abTCR, and b) a host cell (such as an effector cell) for expressing the nucleic acid (or set of nucleic acids). In some embodiments, the kit comprises a) a nucleic acid (or set of nucleic acids) encoding an abTCR, and b) instructions for i) expressing the abTCR in a host cell (such as an effector cell, e.g., a T cell), ii) preparing a composition comprising the host cell expressing the abTCR, and iii) administering the composition comprising the host cell expressing the abTCR to an individual for the treatment of a target antigen-positive disease (such as cancer or viral infection). In some embodiments, the host cell is derived from the individual. In some embodiments, the kit comprises a) a nucleic acid (or set of nucleic acids) encoding an abTCR, b) a host cell (such as an effector cell) for expressing the nucleic acid (or set of nucleic acids), and c) instructions for i) expressing the abTCR in the host cell, ii) preparing a composition comprising the host cell expressing the abTCR, and iii) administering the composition comprising the host cell expressing the abTCR to an individual for the treatment of a target antigen-positive disease (such as cancer or viral infection).

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the abTCR effector cell compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an abTCR effector cell composition as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the abTCR and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXEMPLARY EMBODIMENTS

Embodiment 1

An antibody-T cell receptor (TCR) chimeric molecule (abTCR) that specifically binds to a target antigen, comprising:

a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to the target antigen, and wherein the first TCRD and the second TCRD form a T cell receptor module (TCRM) that is capable of recruiting at least one TCR-associated signaling module.

Embodiment 2

The abTCR of embodiment 1, wherein the antigen-binding module comprises a disulfide bond between a residue in the $C_H1$ domain and a residue in the $C_L$ domain.

Embodiment 3

The abTCR of embodiment 1 or 2, wherein the first polypeptide chain further comprises a first peptide linker between the first antigen-binding domain and the first TCRD.

Embodiment 4

The abTCR of any one of embodiments 1-3, wherein the second polypeptide chain further comprises a second peptide linker between the second antigen-binding domain and the second TCRD.

Embodiment 5

The abTCR of embodiment 3 or 4, wherein the first peptide linker and/or the second peptide linker are, individually, from about 5 to about 50 amino acids in length.

Embodiment 6

The abTCR of any one of embodiments 1-5, wherein the target antigen is a cell surface antigen.

Embodiment 7

The abTCR of embodiment 6, wherein the cell surface antigen is selected from the group consisting of protein, carbohydrate, and lipid.

Embodiment 8

The abTCR of embodiment 7, wherein the cell surface antigen is CD19, ROR1, ROR2, BCMA, GPRC5D, or FCRL5.

Embodiment 9

The abTCR of any one of embodiments 1-5, wherein the target antigen is a complex comprising a peptide and a major histocompatibility complex (MHC) protein.

Embodiment 10

An abTCR that specifically binds to a target antigen, comprising:
a) a first polypeptide chain comprising a first antigen-binding domain comprising a $V_H$ antibody domain and a first TCRD comprising a first transmembrane domain of a first TCR subunit; and
b) a second polypeptide chain comprising a second antigen-binding domain comprising a $V_L$ antibody domains and a second TCRD comprising a second transmembrane domain of a second TCR subunit,
wherein the $V_H$ domain of the first antigen-binding domain and the $V_L$ domain of the second antigen-binding domain form an antigen-binding module that specifically binds to the target antigen, wherein the first TCRD and the second TCRD form a T cell receptor module (TCRM) that is capable of recruiting at least one TCR-associated signaling module, and wherein the target antigen is a complex comprising a peptide and an MHC protein.

Embodiment 11

The abTCR of embodiment 10, wherein the first polypeptide chain further comprises a first peptide linker between the first antigen-binding domain and the first TCRD and the second polypeptide chain further comprises a second peptide linker between the second antigen-binding domain and the second TCRD.

Embodiment 12

The abTCR of embodiment 11, wherein the first and/or second peptide linkers comprise, individually, a constant domain or fragment thereof from an immunoglobulin or T cell receptor subunit.

Embodiment 13

The abTCR of embodiment 12, wherein the first and/or second peptide linkers comprise, individually, a CH1, CH2, CH3, CH4 or CL antibody domain, or a fragment thereof.

Embodiment 14

The abTCR of embodiment 12, wherein the first and/or second peptide linkers comprise, individually, a Cα, Cβ, Cγ, or Cδ TCR domain, or a fragment thereof.

Embodiment 15

The abTCR of any one of embodiments 1-14, wherein the first TCRD further comprises a first connecting peptide or fragment thereof of a TCR subunit N-terminal to the first transmembrane domain.

Embodiment 16

The abTCR of any one of embodiments 1-15, wherein the second TCRD further comprises a second connecting peptide or fragment thereof of a TCR subunit N-terminal to the second transmembrane domain.

Embodiment 17

The abTCR of embodiment 15 or 16, wherein the TCRM comprises a disulfide bond between a residue in the first connecting peptide and a residue in the second connecting peptide.

Embodiment 18

The abTCR of any one of embodiments 1-17, wherein the first TCRD further comprises a first TCR intracellular domain comprising a TCR intracellular sequence C-terminal to the first transmembrane domain.

Embodiment 19

The abTCR of any one of embodiments 1-18, wherein the second TCRD further comprises a second TCR intracellular domain comprising a TCR intracellular sequence C-terminal to the second transmembrane domain.

Embodiment 20

The abTCR of any one of embodiments 1-19, wherein the first polypeptide chain further comprises a first accessory intracellular domain comprising a co-stimulatory intracellular signaling sequence C-terminal to the first transmembrane domain.

Embodiment 21

The abTCR of any one of embodiments 1-20, wherein the second polypeptide chain further comprises a second accessory intracellular domain comprising a co-stimulatory intracellular signaling sequence C-terminal to the second transmembrane domain.

Embodiment 22

The abTCR of any one of embodiments 1-21, wherein the first polypeptide chain further comprises a first signaling peptide N-terminal to the first antigen-binding domain.

Embodiment 23

The abTCR of any one of embodiments 1-22, wherein the second polypeptide chain further comprises a second signaling peptide N-terminal to the second antigen-binding domain.

Embodiment 24

The abTCR of any one of embodiments 9-23, wherein the peptide in the target antigen complex is derived from a protein selected from the group consisting of WT-1, AFP, HPV16-E7, NY-ESO-1, PRAME, EBV-LMP2A, HIV-1, and PSA.

Embodiment 25

The abTCR of any one of embodiments 1-24, wherein the molecule binds to the target antigen with an equilibrium dissociation constant ($K_d$) from about 0.1 pM to about 500 nM.

Embodiment 26

The abTCR of any one of embodiments 1-25, wherein the TCR-associated signaling module is selected from the group consisting of CD3δε, CD3γε, and ζζ.

Embodiment 27

The abTCR of any one of embodiments 1-26, wherein the first TCR subunit is a TCR α chain, and the second TCR subunit is a TCR β chain.

Embodiment 28

The abTCR of any one of embodiments 1-26, wherein the first TCR subunit is a TCR β chain, and the second TCR subunit is a TCR α chain.

Embodiment 29

The abTCR of any one of embodiments 1-26, wherein the first TCR subunit is a TCR γ chain, and the second TCR subunit is a TCR δ chain.

Embodiment 30

The abTCR of any one of embodiments 1-26, wherein the first TCR subunit is a TCR δ chain, and the second TCR subunit is a TCR γ chain.

Embodiment 31

Nucleic acid(s) encoding the first and second polypeptide chains of the abTCR of any one of embodiments 1-30.

Embodiment 32

A complex comprising the abTCR of any one of embodiments 1-30 and at least one TCR-associated signaling module selected from the group consisting of CD3δε, CD3γε, and ζζ.

Embodiment 33

The complex of embodiment 32, wherein the complex is an octamer comprising the abTCR and CD3δε, CD3γε, and ζζ.

Embodiment 34

An effector cell presenting on its surface the abTCR of any one of embodiments 1-30 or the complex of embodiment 32 or 33.

Embodiment 35

An effector cell comprising the nucleic acid(s) of embodiment 31.

Embodiment 36

The effector cell of embodiment 34 or 35, wherein the effector cell does not express the first TCR subunit and/or the second TCR subunit.

Embodiment 37

The effector cell of embodiment 36, wherein
a) the first TCR subunit is TCRα and the second TCR subunit is TCRβ; or
b) the first TCR subunit is TCRβ and the second TCR subunit is TCRα; and
wherein the effector cell is a γδ T cell.

Embodiment 38

The effector cell of embodiment 36, wherein
a) the first TCR subunit is TCRγ and the second TCR subunit is TCRδ; or
b) the first TCR subunit is TCRδ and the second TCR subunit is TCRγ; and
wherein the effector cell is an αβ T cell.

Embodiment 39

The effector cell of any one of embodiments 34-36, wherein the effector cell is modified to block or decrease the expression of a first endogenous TCR subunit and/or a second endogenous TCR subunit.

Embodiment 40

The effector cell of embodiment 39, wherein
a) the first TCR subunit is TCRα and second TCR subunit is TCRβ; or
b) the first TCR subunit it TCRβ and the second TCR subunit is TCRα; and
wherein the effector cell is an αβ T cell modified to block or decrease the expression of TCRα and/or TCRβ.

Embodiment 41

The effector cell of embodiment 39, wherein
a) the first TCR subunit is TCRγ and second TCR subunit is TCRδ; or
b) the first TCR subunit is TCR and the second TCR subunit is TCRγ; and
wherein the effector cell is a γδ T cell modified to block or decrease the expression of TCRγ and/or TCRδ.

Embodiment 42

The effector cell of any one of embodiments 34-41, wherein the effector cell is a CD3$^+$ cell.

Embodiment 43

The effector cell of embodiment 42, wherein the CD3$^+$ cell is selected from the group consisting of a cytotoxic T cell, a helper T cell, a natural killer T cell, and a suppressor T cell.

Embodiment 44

The effector cell of any one of embodiments 34-43, comprising a) a first vector comprising a first nucleic acid sequence encoding the first polypeptide chain of the abTCR under the control of a first promoter and b) a second vector comprising a second nucleic acid sequence encoding the second polypeptide chain of the abTCR under the control of a second promoter.

Embodiment 45

The effector cell of any one of embodiments 34-43, comprising a vector comprising a) a first nucleic acid sequence encoding the first polypeptide chain of the abTCR under the control of a first promoter; and b) a second nucleic acid sequence encoding the second polypeptide chain of the abTCR under the control of a second promoter.

Embodiment 46

The effector cell of any one of embodiments 34-43, comprising a vector comprising a) a first nucleic acid sequence encoding the first polypeptide chain of the abTCR and a second nucleic acid sequence encoding the second polypeptide chain of the abTCR, wherein the first and second nucleic acid sequences are under the control of a single promoter.

Embodiment 47

The effector cell of any one of embodiments 34-45, wherein the expression of the first polypeptide chain of the abTCR is more than two-fold different than the expression of the second polypeptide chain of the abTCR.

Embodiment 48

A method of killing a target cell presenting a target antigen, comprising contacting the target cell with the effector cell of any one of embodiments 34-47, wherein the abTCR specifically binds to the target antigen.

Embodiment 49

A method of killing a target cell presenting a target antigen, comprising contacting the target cell with an effector αβ T cell comprising an abTCR that specifically binds to the target antigen comprising:
a) a first polypeptide chain comprising a first antigen-binding domain comprising a $V_H$ antibody domain and a first TCRD comprising a first transmembrane domain of a first TCR subunit; and
b) a second polypeptide chain comprising a second antigen-binding domain comprising a $V_L$ antibody domains and a second TCRD comprising a second transmembrane domain of a second TCR subunit,
wherein the $V_H$ domain of the first antigen-binding domain and the $V_L$ domain of the second antigen-binding domain form an antigen-binding module that specifically binds to the target antigen,
wherein the first TCRD and the second TCRD form a T cell receptor module (TCRM) that is capable of recruiting at least one TCR-associated signaling module, and
wherein the first TCR subunit is TCRγ and the second TCR subunit is TCRδ, or the first TCR subunit is TCR and the second TCR subunit is TCRγ.

Embodiment 50

The method of embodiment 49, wherein the first polypeptide chain further comprises a first peptide linker between the first antigen-binding domain and the first TCRD and the second polypeptide chain further comprises a second peptide linker between the second antigen-binding domain and the second TCRD.

Embodiment 51

The method of embodiment 50, wherein the first and/or second peptide linkers comprise, individually, a constant domain or fragment thereof from an immunoglobulin or T cell receptor subunit.

Embodiment 52

The method of embodiment 51, wherein the first and/or second peptide linkers comprise, individually, a CH1, CH2, CH3, CH4 or CL antibody domain, or a fragment thereof.

Embodiment 53

The method of embodiment 51, wherein the first and/or second peptide linkers comprise, individually, a Cα, Cβ, Cγ, or Cδ TCR domain, or a fragment thereof.

Embodiment 54

The method of any one of embodiments 48-53, wherein the contacting is in vivo.

Embodiment 55

The method of any one of embodiments 48-53, wherein the contacting is in vitro.

Embodiment 56

A pharmaceutical composition comprising the abTCR of any one of embodiments 1-30, the nucleic acid(s) of embodiment 31, or the effector cell of any one of embodiments 34-47, and a pharmaceutically acceptable carrier.

Embodiment 57

A method of treating a target antigen-associated disease in an individual in need thereof comprising administering to the individual an effective amount of the pharmaceutical composition of embodiment 51.

Embodiment 58

A method of treating a target antigen-associated disease in an individual in need thereof comprising administering to the individual an effective amount of a composition comprising an effector αβ T cell comprising an abTCR that specifically binds to the target antigen comprising:
a) a first polypeptide chain comprising a first antigen-binding domain comprising a $V_H$ antibody domain and a first TCRD comprising a first transmembrane domain of a first TCR subunit; and
b) a second polypeptide chain comprising a second antigen-binding domain comprising a $V_L$ antibody domains and a second TCRD comprising a second transmembrane domain of a second TCR subunit,
wherein the $V_H$ domain of the first antigen-binding domain and the $V_L$ domain of the second antigen-binding domain form an antigen-binding module that specifically binds to the target antigen,
wherein the first TCRD and the second TCRD form a T cell receptor module (TCRM) that is capable of recruiting at least one TCR-associated signaling module, and
wherein the first TCR subunit is TCRγ and the second TCR subunit is TCRδ, or the first TCR subunit is TCRδ and the second TCR subunit is TCRγ.

Embodiment 59

The method of embodiment 58, wherein the wherein the first polypeptide chain further comprises a first peptide linker between the first antigen-binding domain and the first TCRD and the second polypeptide chain further comprises a second peptide linker between the second antigen-binding domain and the second TCRD.

Embodiment 60

The method of embodiment 59, wherein the first and/or second peptide linkers comprise, individually, a constant domain or fragment thereof from an immunoglobulin or T cell receptor subunit.

Embodiment 61

The method of embodiment 60, wherein the first and/or second peptide linkers comprise, individually, a CH1, CH2, CH3, CH4 or CL antibody domain, or a fragment thereof.

Embodiment 62

The method of embodiment 60, wherein the first and/or second peptide linkers comprise, individually, a Cα, Cβ, Cγ, or Cδ TCR domain, or a fragment thereof.

Embodiment 63

The method of any one of embodiments 57-62, wherein the target antigen-associated disease is cancer.

Embodiment 64

The method of embodiment 63, wherein the cancer is selected from the group consisting of adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lymphoma, lung cancer, melanoma, mesothelioma, multiple myeloma, pancreatic cancer, pheochromocytoma, plasmacytoma, neuroblastoma, ovarian cancer, prostate cancer, sarcoma, stomach cancer, uterine cancer and thyroid cancer.

Embodiment 65

The method of any one of embodiments 57-62, wherein the target antigen-associated disease is viral infection.

Embodiment 66

The method of embodiment 65, wherein the viral infection is caused by a virus selected from the group consisting of Cytomegalovirus (CMV), Epstein-Barr Virus (EBV), Hepatitis B Virus (HBV), Kaposi's Sarcoma associated herpesvirus (KSHV), Human papillomavirus (HPV), Molluscum contagiosum virus (MCV), Human T cell leukemia virus 1 (HTLV-1), HIV (Human immunodeficiency virus), and Hepatitis C Virus (HCV).

Embodiment 67

A method of enriching a heterogeneous cell population for the effector cell of any one of embodiments 34-47, comprising:
a) contacting the heterogeneous cell population with the target antigen immobilized to a solid support to form complexes of the effector cell bound to the target antigen on the solid support; and
b) separating the complexes from the heterogeneous cell population, thereby generating a cell population enriched for the effector cell.

Embodiment 68

A nucleic acid library comprising sequences encoding a plurality of abTCRs according to any one of embodiments 1-30.

Embodiment 69

A method of screening the nucleic acid library of embodiment 68 for sequences encoding abTCRs specific for a target antigen, comprising:
a) introducing the nucleic acid library into a plurality of CD3$^+$ cells, such that the abTCRs are expressed on the surface of the plurality of CD3$^+$ cells;

b) incubating the plurality of CD3+ cells with labelled target antigen;
c) collecting CD3+ cells bound with the labelled target antigen; and
d) isolating sequences encoding the abTCRs from cells collected in step c), thereby identifying abTCRs specific for the target antigen.

EXAMPLES

Materials and Methods
Cell Samples, Cell Lines, and Antibodies

The cell lines HepG2 (ATCC HB-8065; HLA-A2+, AFP+), SK-HEP-1 (ATCC HTB-52; HLA-A2+, AFP−), Raji (ATCC CCL-86; CD19+), CA46 (ATCC CRL-1648; CD19+), Jurkat (ATCC CRL-2899, CD19−), J.RT3-T3.5 (ATCC TIB-153), Jeko-1 (ATCC CRL-3006; CD19+), THP-1 (ATCC TIB-202, CD19−), Daudi (ATCC CCL-213; CD19+), HeLa (ATCC CCL-2), MDA-MB-231 (ATCC HTB-26) and MCF-7 (ATCC HTB-22) were obtained from the American Type Culture Collection. Jurkat is a human T lymphocyte cell line derived from T cell leukemia. J.RT3-T3.5 is a mutant line derived from Jurkat cells that lacks the T cell receptor β chain. Raji is a Burkitt lymphoma cell line that expresses CD19. Raji-CD19 knockout (Raji-CD19KO) line was generated by CRISPR technology. Three different guide sequences were designed to target CD19 in Raji cells. CRISPR-Cas9 vector was purchased from Origene and each guide was cloned separately into the pCas-Guide vector. Three days after electroporation, efficiency of knock-out by each guide was evaluated by flow cytometry and the best CD19-knock-out pool was chosen for clonal selection by limiting dilution. The selected clone was confirmed as a complete CD19 knock-out by sequencing. Another control cell line, SK-HEP-1-AFP-MG was generated by transducing SK-HEP-1 cell line with a minigene cassette expressing an AFP peptide AFP158 (SEQ ID NO: 53), which results in a high level of cell surface expression of AFP158/HLA-A*02:01 complex. All cell lines were cultured in RPMI 1640 or DMEM supplemented with 10% FBS and 2 mM glutamine at 37° C./5% $CO_2$.

Monoclonal Ab against human HLA-A02 (clone BB7.2) conjugated to FITC or APC, and its isotype control mouse IgG 2b conjugated to FITC or APC, antibodies against human or mouse CD3, human T cell receptor various subunit, 3×Flag tag, HA tag, goat F(ab)2 anti-human IgG conjugated with PE or FITC, and fluorescence-conjugated goat F(ab')2 anti-mouse Ig's (Invitrogen) were purchased. The anti-idiotypic antibody against an AFP158/HLA-A*02:01-specific antibody was developed and produced in house at Eureka Therapeutics. Flow cytometry data were collected using BD FACSCanto II and analyzed using FlowJo software package.

All peptides were purchased and synthesized by Elim Biopharma. Peptides were >90% pure. The peptides were dissolved in DMSO or diluted in saline at 10 mg/mL and frozen at −80° C. Biotinylated single chain AFP158/HLA-A*02:01 and control peptides/HLA-A*02:01 complex monomers were generated by refolding the peptides with recombinant HLA-A*02:01 and beta-2 microglobulin (β2M). The monomers were biotinylated via the BSP peptide linked to the C-terminal end of HLA-A*02:01 extracellular domain (ECD) by the BirA enzyme. Fluorescence-labelled streptavidin was mixed with biotinylated peptide/HLA-A*02:01 complex monomer to form fluorescence-labelled peptide/HLA-A*02:01 tetramer.

Lentiviruses containing human CD19-specific or AFP158/HLA-A*02:01-specific CAR or abTCRs were produced, for example, by transfection of 293T cells with vectors encoding the chimeric constructs. Primary human T-cells were used for transduction after one-day stimulation with CD3/CD28 beads (Dynabeads®, Invitrogen) in the presence of interleukin-2 (IL-2) at 100 U/ml. Concentrated lentiviruses were applied to T-cells in Retronectin- (Takara) coated 6-well plates for 96 hours. Transduction efficiencies of the anti-AFP and anti-CD19 chimeric constructs were assessed by flow cytometry, using biotinylated AFP158/HLA-A*02:01 tetramer ("AFP158 tetramer") with PE-conjugated streptavidin or anti-myc antibody respectively. Repeat flow cytometry analyses were done on day 5 and every 3-4 days thereafter.

Cell lines were transduced with either one or two vectors that encode the two subunits of abTCR construct. Five days post-transduction, cell lysates were generated for western blot using anti-HA (Anti-HA tag antibody—ChIP Grade, Abcam) or anti-Flag antibody (Anti-Flag Antibody Produced in Rabbit, Sigma).

Tumor cytotoxicities were assayed by Cytox 96 Non-radioactive LDH Cytotoxicity Assay (Promega). CD3+ T cells were prepared from PBMC-enriched whole blood using EasySep Human T Cell Isolation Kit (StemCell Technologies) which negatively depletes CD14, CD16, CD19, CD20, CD36, CD56, CD66b, CD123, glycophorin A expressing cells. Human T cells were activated and expanded with, for example, CD3/CD28 Dynabeads (Invitrogen) according to manufacturer's protocol. Activated T cells (ATC) were cultured and maintained in RPMI1640 medium with 10% FBS plus 100 U/ml IL-2, and used at day 7-14. Activated T cells (effector cells) and target cells were co-cultured at various effector-to-target ratios (e.g., 2.5:1 or 5:1) for 16 hours and assayed for cytotoxicities.

Example 1. Antibody-T Cell Receptor (abTCR) Chimera Designs

Four different antibody-T cell receptor chimeric construct (abTCRs) designs (abTCR-3, abTCR-4, abTCR-5, and abTCR-6), including contemplated variations, are shown in FIGS. 1A and 1B. In these designs, the heavy ($IgV_H$-$IgC_H1$) and light ($IgV_L$-$IgC_L$) chain domains of an antibody Fab fragment are fused to the amino terminus of T cell receptor α/β chain or γ/δ chain fragments lacking variable and constant domains and including all or part of their connecting peptide (region after the constant domain) to form chimeric antibody-TCR heterodimers which can be expressed on the surface of T cells. The $IgV_H$ and $IgV_L$ domains in each of the abTCR designs determine the antigen-binding specificity, and together with the $IgC_H1$ and $IgC_L$, form a structure that resembles a Fab fragment. In a native TCR, the Vα/Vβ or Vδ/Vγ domains form the antigen-binding domain of the TCR. These designs replace the Vα-Cα/Vβ-Cβ or Vδ-Cδ/Vγ-Cγ regions with $IgV_H$-$IgC_H1$ or $IgV_L$-$IgC_L$, thus conferring an antibody's binding specificity to the construct, while maintaining the ability of the construct to be associated with the accessory molecules in a native TCR complex, such as CD3δε, CD3γε and CD3ζζ. These designs are distinct from the cTCR designs described by Gross and Eshhar (Endowing T cells with antibody specificity using chimeric T cell receptors, FASEB J. 1992 (15):3370), where the variable domains of antibodies are linked to TCR constant regions, replacing only the Vα/Vβ regions with $IgV_H$/$IgV_L$.

In other abTCR designs, the heavy (IgV$_H$) and light (IgV$_L$) chain domains of an antibody Fv fragment that is specific for a complex comprising a peptide and an MHC protein (an MHC-restricted antibody moiety) are fused to the amino terminus of T cell receptor α/β chain or γ/δ chain fragments lacking variable domains and including all or part of their connecting peptides (region after the constant domain). In some of these abTCR designs, the T cell receptor α/β chain or γ/δ chain fragments include all or part of the TCR constant domains. In one such design, abTCR-7, the IgV$_H$ is fused to a TCR fragment including the constant domain and the IgV$_L$ is fused to a TCRγ fragment including the constant domain. These designs are distinct from the cTCR designs described by Gross and Eshhar (supra), where the antibody variable domains are for non-MHC-restricted binding.

In the abTCR-3 (IgV$_H$-IgC$_H$1-TCRα/IgV$_L$-IgC$_L$-TCRβ) design, the variable domain and the first constant domain (IgV$_H$-IgC$_H$1) of an antibody heavy chain replaces the amino terminal portion of the TCRα chain up to a position bordering or within the connecting peptide in the extracellular domain after the Vα-Cα region. The variable domain and the constant domain (IgV$_L$-IgC$_L$) of the corresponding antibody light chain replaces the amino terminal portion of the TCRβ chain up to a position bordering or within the connecting peptide in the extracellular domain after the Vβ-Cβ region. In the abTCR-4 (IgV$_H$-IgC$_H$1-TCRβ/IgV$_L$-IgC$_L$-TCRα) design, the variable domain and the first constant domain (IgV$_H$-IgC$_H$1) of an antibody heavy chain replaces the amino terminal portion of the TCRβ chain up to a position bordering or within the connecting peptide in the extracellular domain after the Vβ-Cβ region. The variable domain and the constant domain (IgV$_L$-IgC$_L$) of the corresponding antibody light chain replaces the amino terminal portion of the TCRα chain up to a position bordering or within the connecting peptide in the extracellular domain after the Vα-Cα region. The chimeric α and β chains are dimerized through two disulfide bonds, one between the IgC$_L$ and the IgC$_H$1 domains, and one between the connecting peptides in the TCRα and β chains. A 3×-Flag tag is optionally fused to the C-terminus of the TCRα chain cytoplasmic region, and an HA tag is optionally fused to the C-terminus of the TCRβ chain cytoplasmic region.

In one abTCR-3 embodiment, one chain includes the sequence of SEQ ID NO: 23 (anti-AFP158/HLA-A*02:01-abTCR-3), where the IgV$_H$ domain of an anti-AFP158/HLA-A*02:01 antibody (SEQ ID NO: 38) is fused to an IgC$_H$1 domain (SEQ ID NO: 39) fused to SEQ ID NO: 15, a portion of the TCRα chain including part of the connecting peptide in the extracellular domain of the TCRα chain after the Vα-Cα region, and the other chain includes the sequence of SEQ ID NO: 24, where the IgV$_L$ domain of the anti-AFP158/HLA-A*02:01 antibody (SEQ ID NO: 40) is fused to an IgC$_L$ domain (SEQ ID NO: 41) fused to SEQ ID NO: 16, a carboxy portion of the TCRβ chain including part of the connecting peptide in the extracellular domain of the TCRβ chain after the Vβ-Cβ region. In one abTCR-4 embodiment, one chain includes the sequence of SEQ ID NO: 25 (anti-AFP158/HLA-A*02:01-abTCR-4), where the IgV$_L$ domain of an anti-AFP158/HLA-A*02:01 antibody (SEQ ID NO: 40) is fused to an IgC$_L$ domain (SEQ ID NO: 41) fused to SEQ ID NO: 15, a portion of the TCRα chain including part of the connecting peptide in the extracellular domain of the TCRα chain after the Vα-Cα region, and the other chain includes the sequence of SEQ ID NO: 26, where the IgV$_H$ domain of the anti-AFP158/HLA-A*02:01 antibody (SEQ ID NO: 38) is fused to an IgC$_H$1 domain (SEQ ID NO: 39) fused to SEQ ID NO: 16, a carboxy portion of the TCRβ chain including part of the connecting peptide in the extracellular domain of the TCRβ chain after the Vβ-Cβ region.

In the abTCR-5 (IgV$_H$-IgC$_H$1-TCRγ/IgV$_L$-IgC$_L$-TCRδ) design, the variable domain and the first constant domain (IgV$_H$-IgC$_H$1) of an antibody heavy chain replaces the amino terminal portion of the TCRγ chain up to a position bordering or within the connecting peptide in the extracellular domain of the TCRγ chain after the Vγ-Cγ region. The variable domain and the constant domain (IgV$_L$-IgC$_L$) of the corresponding antibody light chain replaces the amino terminal portion of the TCRδ chain up to a position bordering or within the connecting peptide in the extracellular domain of the TCRδ chain after the Vδ-Cδ region. In the abTCR-6 (IgV$_H$-IgC$_H$1-TCRδ/IgV$_L$-IgC$_L$-TCRγ) design, the variable domain and the first constant domain (IgV$_H$-IgC$_H$1) of an antibody heavy chain replaces the amino terminal portion of the TCRδ chain up to a position bordering or within the connecting peptide in the extracellular domain of the TCRδ chain after the Vδ-Cδ region. The variable domain and the constant domain (IgV$_L$-IgC$_L$) of the corresponding antibody light chain replaces the amino terminal portion of the TCRγ chain up to a position bordering or within the connecting peptide in the extracellular domain of the TCRγ chain after the Vγ-Cγ region. The chimeric γ and δ chains are dimerized through two disulfide bonds, one between the IgC$_L$ and the IgC$_H$1 domains, and one between the connecting peptides in the TCRγ and δ chains. A 3×flag tag is optionally fused to the C-terminus of the TCRγ chain cytoplasmic region, and an HA tag is optionally fused to the C-terminus of the TCRδ chain cytoplasmic region.

In one abTCR-5 embodiment, one chain includes the sequence of SEQ ID NO: 30 (anti-AFP158/HLA-A*02:01-abTCR-5), where the IgV$_H$ domain of an anti-AFP158/HLA-A*02:01 antibody (SEQ ID NO: 38) is fused to an IgC$_H$1 domain (SEQ ID NO: 39) fused to SEQ ID NO: 20, a portion of the TCRγ chain including part of the connecting peptide in the extracellular domain of the TCRγ chain after the Vγ-Cγ region, and the other chain includes the sequence of SEQ ID NO: 29, where the IgV$_L$ domain of the anti-AFP158/HLA-A*02:01 antibody (SEQ ID NO: 40) is fused to an IgC$_L$ domain (SEQ ID NO: 41) and then to SEQ ID NO: 19, a carboxy portion of the TCRδ chain including part of the connecting peptide in the extracellular domain of the TCRδ chain after the Vδ-Cδ region. In one abTCR-6 embodiment, one chain includes the sequence of SEQ ID NO: 34 (anti-AFP158/HLA-A*02:01-abTCR-6) where the IgV$_L$ domain of an anti-AFP158/HLA-A*02:01 antibody (SEQ ID NO: 40) is fused to an IgC$_L$ domain (SEQ ID NO: 41) fused to SEQ ID NO: 20, a portion of the TCRγ chain including part of the connecting peptide in the extracellular domain of the TCRγ chain after the Vγ-Cγ region, and the other chain includes the sequence of SEQ ID NO: 33, where the IgV$_H$ domain of the anti-AFP158/HLA-A*02:01 antibody (SEQ ID NO: 38) is fused to an IgC$_H$1 domain (SEQ ID NO: 39) fused to SEQ ID NO: 19, a carboxy terminal portion of the TCRδ chain including part of the connecting peptide in the extracellular domain of the TCRδ chain after the Vδ-Cδ region.

As illustrated in FIG. 1B, variations of each of the four abTCR designs are also contemplated. Such variations may include varying the length of the extracellular domain, such as (i) lengthening by adding residues at the junction formed by the IgC and TCR fusion or (ii) shortening by deleting residues at the N-terminal of the TCR connecting peptides. An embodiment of such a variation of abTCR-6 is abTCR- 6MD, where one chain includes the sequence of SEQ ID NO: 36 (anti-AFP158/HLA-A*02:01-abTCR-6MD), where the IgV$_L$ domain of an anti-AFP158/HLA-A*02:01 antibody (SEQ ID NO: 40) is fused to an IgC$_L$ domain (SEQ ID NO: 41) fused to SEQ ID NO: 22, a carboxy terminal portion of the TCRγ chain including a longer (compared to abTCR-6) portion of the connecting peptide after the Vγ-Cγ region in the TCRγ chain, and the other chain includes the sequence of SEQ ID NO: 35, where the IgV$_H$ domain of the anti-AFP158/HLA-A*02:01 antibody (SEQ ID NO: 38) is fused to an IgC$_H$1 domain (SEQ ID NO: 39) fused to SEQ ID NO: 21, a carboxy terminal portion of the TCRδ chain including a longer (compared to abTCR-6) portion of the connecting peptide after the Vδ-Cδ region of the TCRδ chain. An embodiment of such a variation of abTCR-5 is abTCR-5MD, where one chain includes the sequence of SEQ ID NO: 31 (anti-AFP158/HLA-A*02:01-abTCR-5MD) where the IgV$_L$ domain of the anti-AFP158/HLA-A*02:01 antibody (SEQ ID NO: 40) is fused to an IgC$_L$ domain (SEQ ID NO: 41) fused to SEQ ID NO: 21, a carboxy terminal portion of the TCR chain including a longer (compared to abTCR-5) portion of the connecting peptide after the Vδ-Cδ region of the TCR chain, and the other chain includes the sequence of SEQ ID NO: 32, where the IgV$_H$ domain of an anti-AFP158/HLA-A*02:01 antibody (SEQ ID NO: 38) is fused to an IgC$_H$1 domain (SEQ ID NO: 39) fused to SEQ ID NO: 22, a carboxy terminal portion of the TCRγ chain including a longer (compared to abTCR-5) portion of the connecting peptide after the Vγ-Cγ region in the TCRγ chain. An embodiment of such a variation of abTCR-4 is abTCR-4MD, where one chain includes the sequence of SEQ ID NO: 27 (anti-AFP158/HLA-A*02:01-abTCR-4MD) where the IgV$_L$ domain of an anti-AFP158/HLA-A*02:01 antibody (SEQ ID NO: 40) is fused to an IgC$_L$ domain (SEQ ID NO: 41) fused to SEQ ID NO: 17, a carboxy terminal portion of the TCRα chain including a longer (compared to abTCR-4) portion of the connecting peptide after the Vα-Cα region, and the other chain includes the sequence of SEQ ID NO: 28, where the IgV$_H$ domain of the anti-AFP158/HLA-A*02:01 antibody (SEQ ID NO: 38) is fused to an IgC$_H$1 domain (SEQ ID NO: 39) fused to SEQ ID NO: 18, a carboxy terminal portion of the TCRβ chain including a longer (compared to abTCR-4) portion of the connecting peptide after the Vβ-Cβ region.

Additional variations may include fusing additional effector domains (e.g., intracellular domain of CD28) to the C-terminal end of any of the TCRα/β/δ/γ chains. Another variation may include varying the linker region between the IgV and IgC domains.

Example 2: Expression of abTCRs in T Cell Lines

In mature T cells, the TCR-CD3 complex is composed of four dimeric modules: TCRαβ (or TCRγδ), CD3δε, CD3γε and CD3ζζ, which is thought to associate through intramembrane and extramembrane contacts to form the intact complex, as shown in FIG. 2 (from Wucherpfennig K W, et al., *Structural biology of the T-cell receptor: insights into receptor assembly, ligand recognition, and initiation of signaling.* Cold Spring Harb Perspect Biol. 2010 April; 2(4):a005140). Complex assembly occurs in the endoplasmic reticulum (ER). Only complete TCR-CD3 complexes are transferred into the Golgi apparatus where they go through the glycosylation process and get transported to the plasma membrane of T cells. Incomplete TCRs are directed from the Golgi to the lysosomes, where they are degraded.

To test abTCR expression in T cells and to examine whether abTCRs can function like endogenous TCRs in recruiting CD3 molecules and enabling the expression of the abTCR-CD3 complex on T cell surface, abTCR constructs were introduced into a mutant Jurkat T cell line, J.RT3-T3.5. Unlike Jurkat, an αβ TCR-positive leukemia T cell line, J.RT3-T3.5 is a Jurkat mutant line which lacks TCR β subunit expression. Since the assembly of TCR-CD3 complex is impaired without the TCR β subunit, neither TCR nor CD3 can be transported to the plasma membrane in J.RT3-T3.5 cells.

Detection of abTCR Expression by Western Blot

Figure 3:
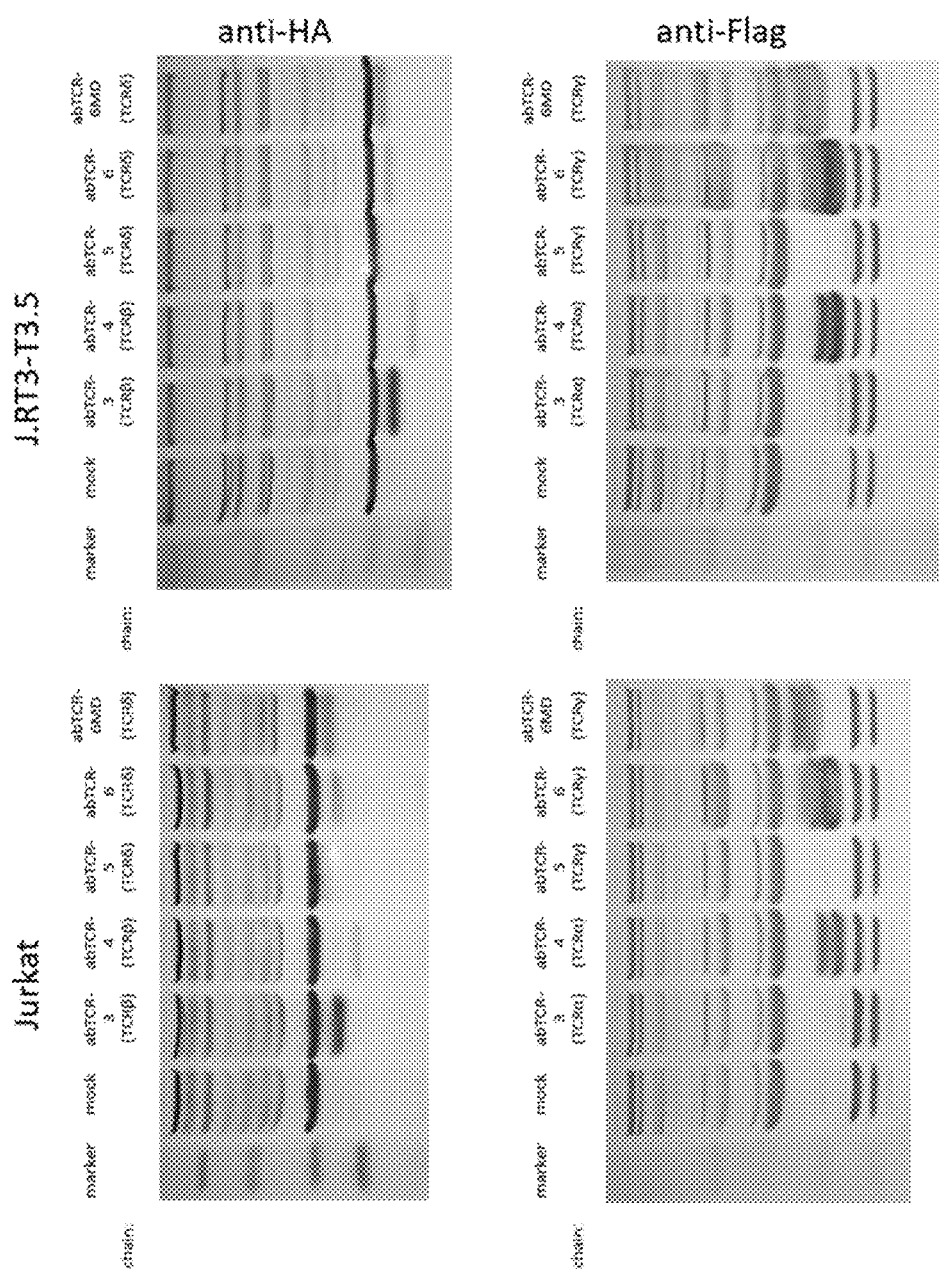
FIG. 3 shows Western blot analysis of lysates from J.RT3-T3.5 or Jurkat cells individually transduced with abTCR-3, -4, -5, -6, or -6MD constructs having an anti-AFP158/HLA*02:01 binding moiety, stained with anti-FLAG (TCRα- and TCRγ-derived chimeric subunits) or anti-HA antibodies (TCRβ- and TCRδ-derived chimeric subunits).

Five sets of abTCR constructs (abTCR-3, -4, -5, -6, -6MD) were generated with the IgV$_H$ and IgV$_L$ regions of an anti-AFP158/HLA-A*02:01 antibody. J.RT3-T3.5 and Jurkat cells were transduced with abTCR-3 (SEQ ID NOs: 23 and 24), abTCR-4 (SEQ ID NOs: 25 and 26), abTCR-5 (SEQ ID NOs: 29 and 30), abTCR-6 (SEQ ID NOs: 33 and 34), or abTCR-6MD (SEQ ID NOs: 35 and 36) constructs and expression of individual subunits of abTCRs was detected in western blots using anti-Flag or anti-HA antibodies (FIG. 3). For each construct, the two subunits were subcloned into two separate lentiviral vectors. To express the complete abTCR heterodimer, T cells were transduced with both vectors. TCRβ and TCRδ chimeras were tagged with HA while TCRα and TCRγ chimeras were tagged with 3×Flag attached at the C-termini of the abTCR subunits. The TCR chains bearing HA- or 3×Flag-tags are indicated in parenthesis in FIG. 3, under the label for each abTCR design.

Among the HA-tagged chimeras in both J.RT3-T3.5 and Jurkat (FIG. 3, anti-HA panels), the IgV$_L$-IgC$_L$-TCRβ subunit in abTCR-3 exhibited the highest expression, followed by the IgV$_H$-IgC$_H$1-TCRδ subunit in abTCR-6 and abTCR-6MD and the IgV$_H$-IgC$_H$1-TCRβ subunit in abTCR-4. Among the 3×Flag-tagged chimeras (FIG. 3, anti-flag panels), the highest expression was observed for IgV$_L$-IgC$_L$-TCRγ in abTCR-6 and abTCR-6MD, followed by IgV$_L$-IgC$_L$-TCRα in ab-TCR-4. Both chains for abTCR-5 (IgV$_H$-IgC$_H$1-TCRγ/IgV$_L$-IgC$_L$-TCRδ) exhibited the lowest expression among the 5 sets of constructs tested. The TCRδ chain for abTCR-6MD was expressed at a similar level as abTCR6, while the TCRγ chain for abTCR-6MD was expressed at a lower level than observed for abTCR6. Both the percentage of cells transduced and the level of expression within the transduced cells contribute to the signals detected in western blots. Therefore, flow cytometry was next performed to determine the level of abTCR expression on the cell surface.

Detection of abTCR Cell-Surface Expression and TCR-CD3 Complex Formation by Flow Cytometry The 5 pairs of chimeric abTCR chains described above (abTCR-3, -4, -5, -6, -6MD) were individually transduced into J.RT3-T3.5 (FIGS. 4A-4C) and Jurkat (FIGS. 5A-5C) cells. The cells transduced with abTCR constructs were assessed by the following: (i) anti-CD3ε antibody to assess the rescue of CD3ε expression on J.RT3-T3.5 cells (FIG. 4A), (ii) anti-TCRαβ antibody to assess the impact of abTCR constructs on endogenous expression of TCRαβ in Jurkat cells (FIG. 5A), (iii) PE-labelled AFP158/HLA-A*02:01 tetramer to assess antigen binding by the transduced abTCR constructs (FIGS. 4B and 5B) and (iv) anti-idiotype antibody against the anti-AFP158/HLA-A*02:01 antibody used in the abTCR chimeras (FIGS. 4C and 5C) to assess the surface expression of the chimeric constructs.

Figure 4A:
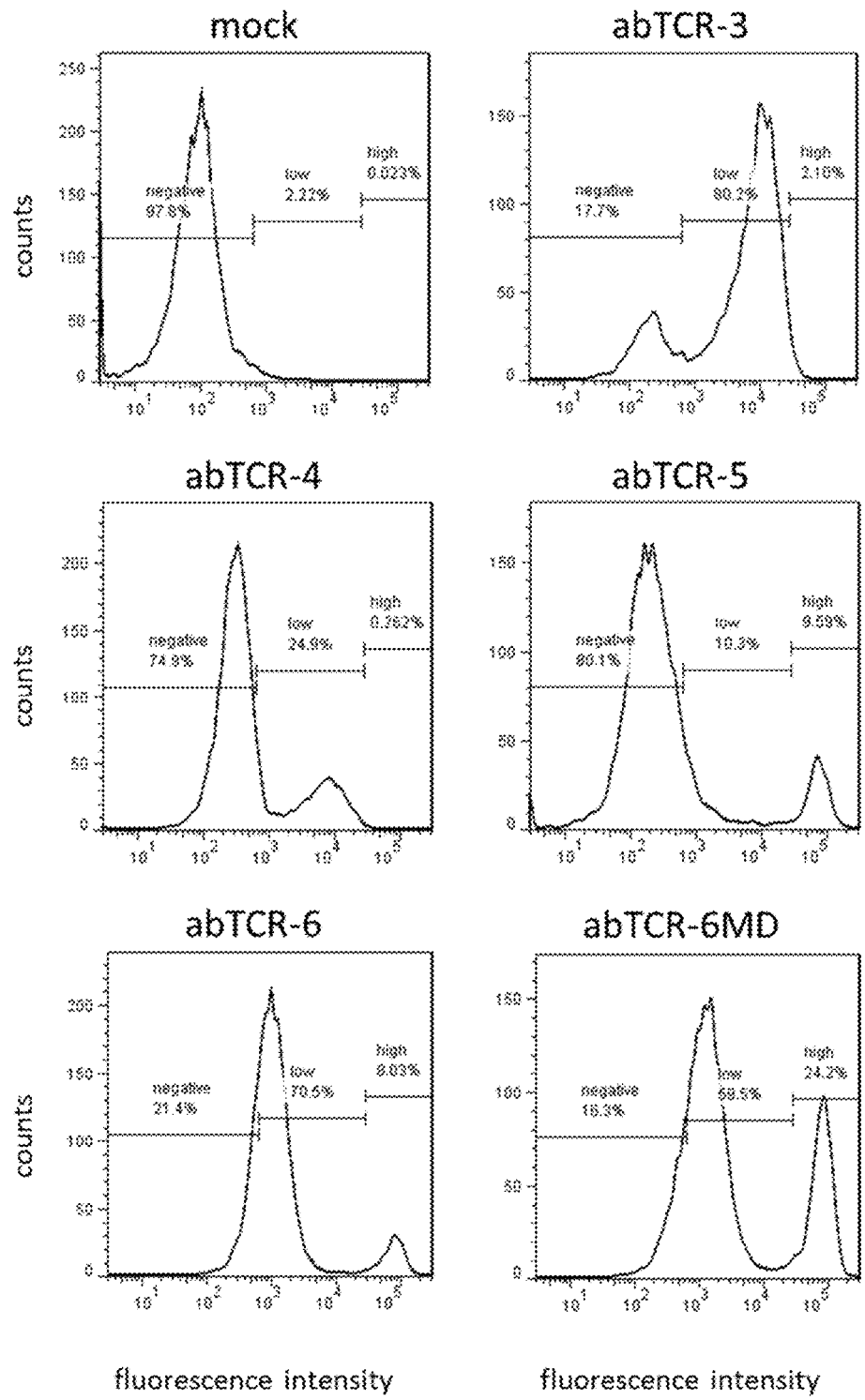
FIG. 4A shows flow cytometry analysis of surface CD3ε expression in J.RT3-T3.5 cells individually transduced with abTCR-3, -4, -5, -6, or -6MD constructs having an anti-AFP158/HLA-A*02:01 binding moiety; cells were stained with anti-CD3ε antibody.
Figure 4B:
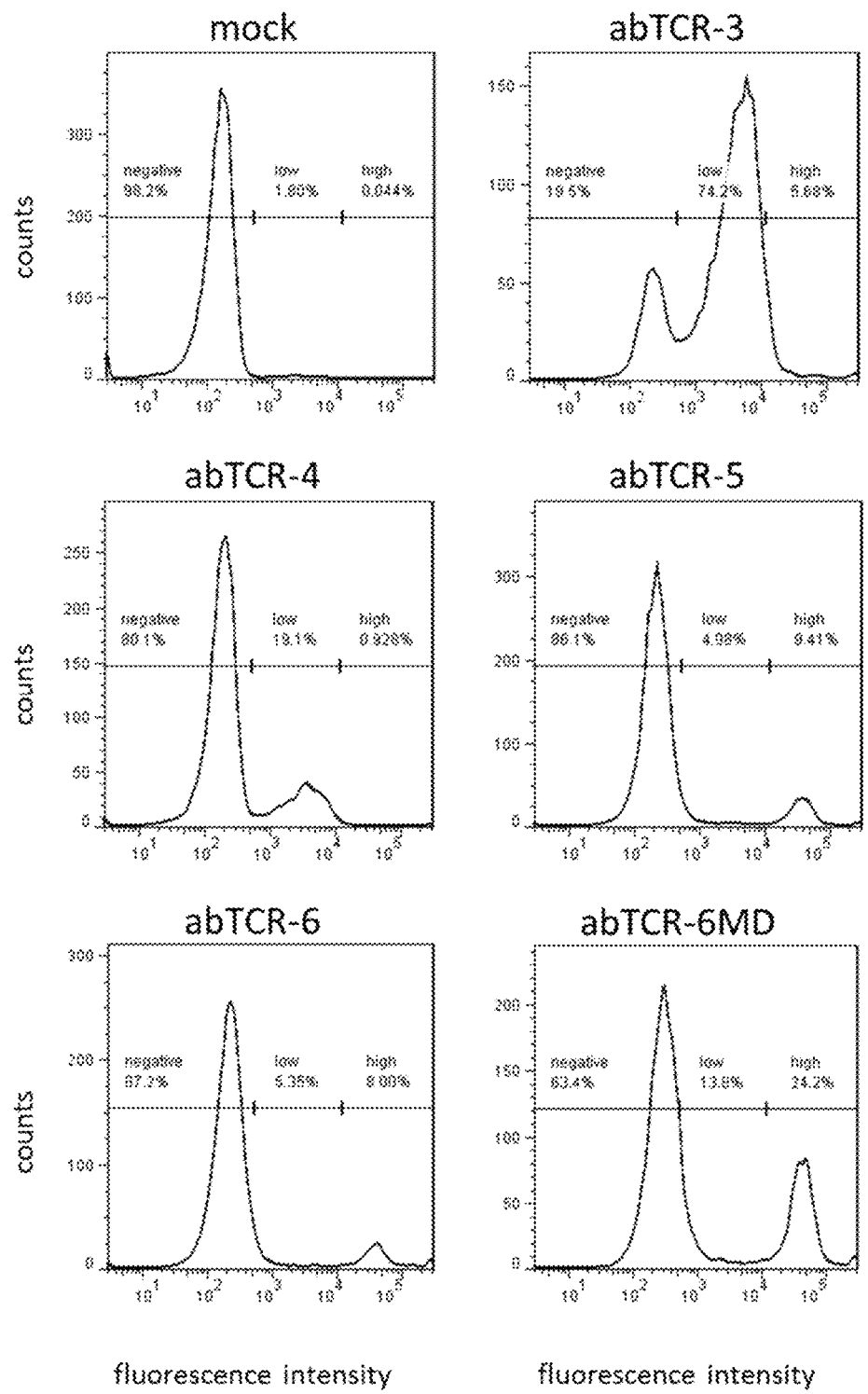
FIG. 4B shows flow cytometry analysis of surface AFP158/HLA-A*02:01 tetramer binding in J.RT3-T3.5 cells individually transduced with abTCR-3, -4, -5, -6, or -6MD constructs having an anti-AFP158/HLA-A*02:01 binding moiety; cells were stained with phycoerythrin (PE)-labeled AFP158/HLA-A*02:01 tetramers.
Figure 4C:
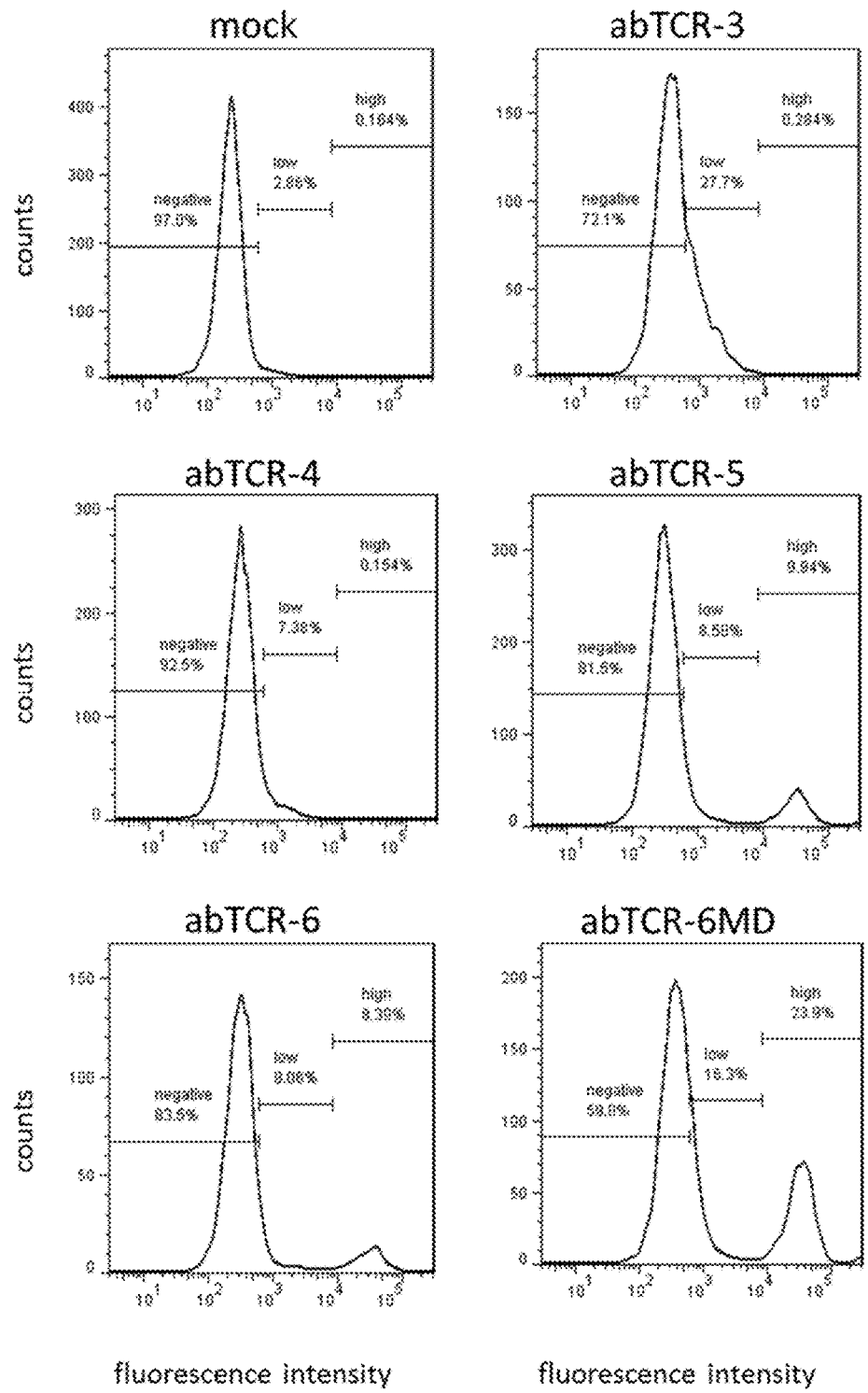
FIG. 4C shows flow cytometry analysis of surface anti-idiotype antibody binding in J.RT3-T3.5 cells individually transduced with abTCR-3, -4, -5, -6, or -6MD constructs having an anti-AFP158/HLA-A*02:01 binding moiety recognized by the antibody; cells were stained with anti-idiotype antibody against the anti-AFP158/HLA-A*02:01 binding moiety of the abTCR constructs.
Figure 6:
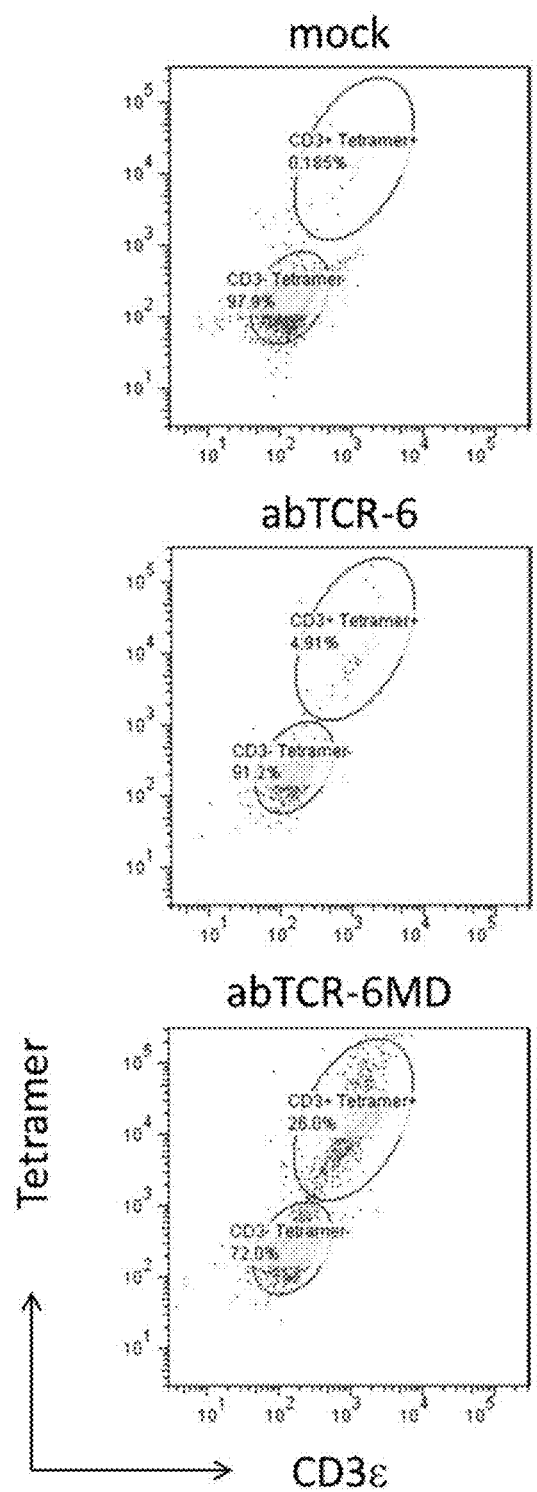
FIG. 6 shows flow cytometry analysis of the co-expression of CD3ε with abTCR chimeras in J.RT3-T3.5 cells individually transduced with abTCR-6 or abTCR-6MD constructs having an anti-AFP158/HLA-A*02:01 binding moiety; cells were co-stained with anti-CD3ε antibody and AFP158/HLA-A*02:01 tetramers.

For J.RT3-T3.5 cells, mock transduction did not confer binding to AFP158/HLA-A*02:01 tetramers and anti-idiotype antibody and did not result in CD3ε expression on the cell surface (FIGS. 4A-4C). Anti-idiotype antibody detected a shoulder extending from the abTCR-negative peak in J.RT3-T3.5 cells transduced with abTCR-3 and abTCR-4. In contrast, cells transduced with abTCR-5, -6 and -6MD displayed distinct peaks at high fluorescence intensities when stained with the anti-idiotype antibody (FIG. 4C). The abTCR constructs are functional in being able to bind target antigen AFP158 tetramer (FIG. 4B). A larger population of cells expressed abTCR-6MD constructs compared to abTCR-6, as evident by a higher AFP158 tetramer-positive peak in abTCR-6MD. However, the abTCR-6MD transduced cells appear to express a similar copy number per cell as abTCR-6 transduced cells, since the AFP158 tetramer-positive peaks have similar mean fluorescence intensity (MFI). Additionally, expression of abTCR constructs rescued cell surface expression of CD3ε in J.RT3-T3.5 cells (FIG. 4A). This is unexpected since the constant domains of the TCR have been attributed to the interaction with the CD3 chains (reviewed by Kuhns and Davis, TCR Signaling Emerges from the Sum of Many Parts, Front Immunol. 2012; 3: 159, Wang and Reinherz, The structural basis of αβ T-lineage immune recognition: TCR docking topologies, mechanotransduction, and co-receptor function, Immunol Rev. 2012, 250:102). Since the chimeras replaced the TCR constant domains with IgC, we demonstrated that the TCR constant domain is not necessary for CD3 assembly with the TCR complex. When the abTCR-6 and abTCR-6MD transduced cells were co-stained with anti-CD3ε and AFP158/HLA-A*02:01 tetramers and analyzed by flow cytometry, we confirmed that the CD3ε+ J.RT3-T3.5 cells are also AFP158 tetramer-positive (FIG. 6). This indicates that the exogenous abTCR chimeras form functional receptors that can bind their cognate antigens, and rescue the cell surface expression of CD3 complex on J.RT3-T3.5 cells.

Figure 5A:
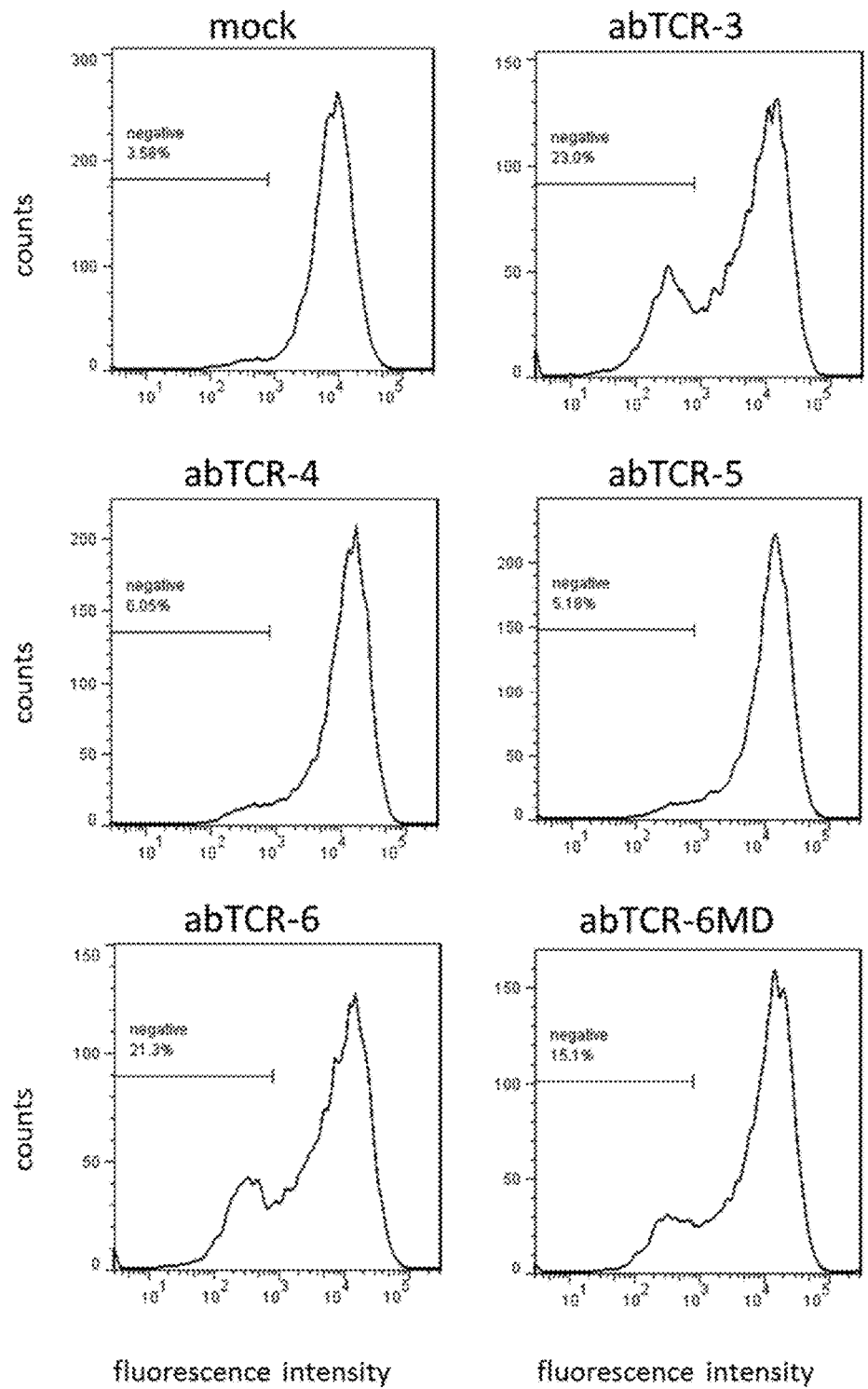
FIG. 5A shows flow cytometry analysis of surface anti-TCRα/β antibody binding in Jurkat cells individually transduced with abTCR-3, -4, -5, -6, or -6MD constructs having an anti-AFP158/HLA-A*02:01 binding moiety; cells were stained with anti-TCRα/β antibody.
Figure 5B:
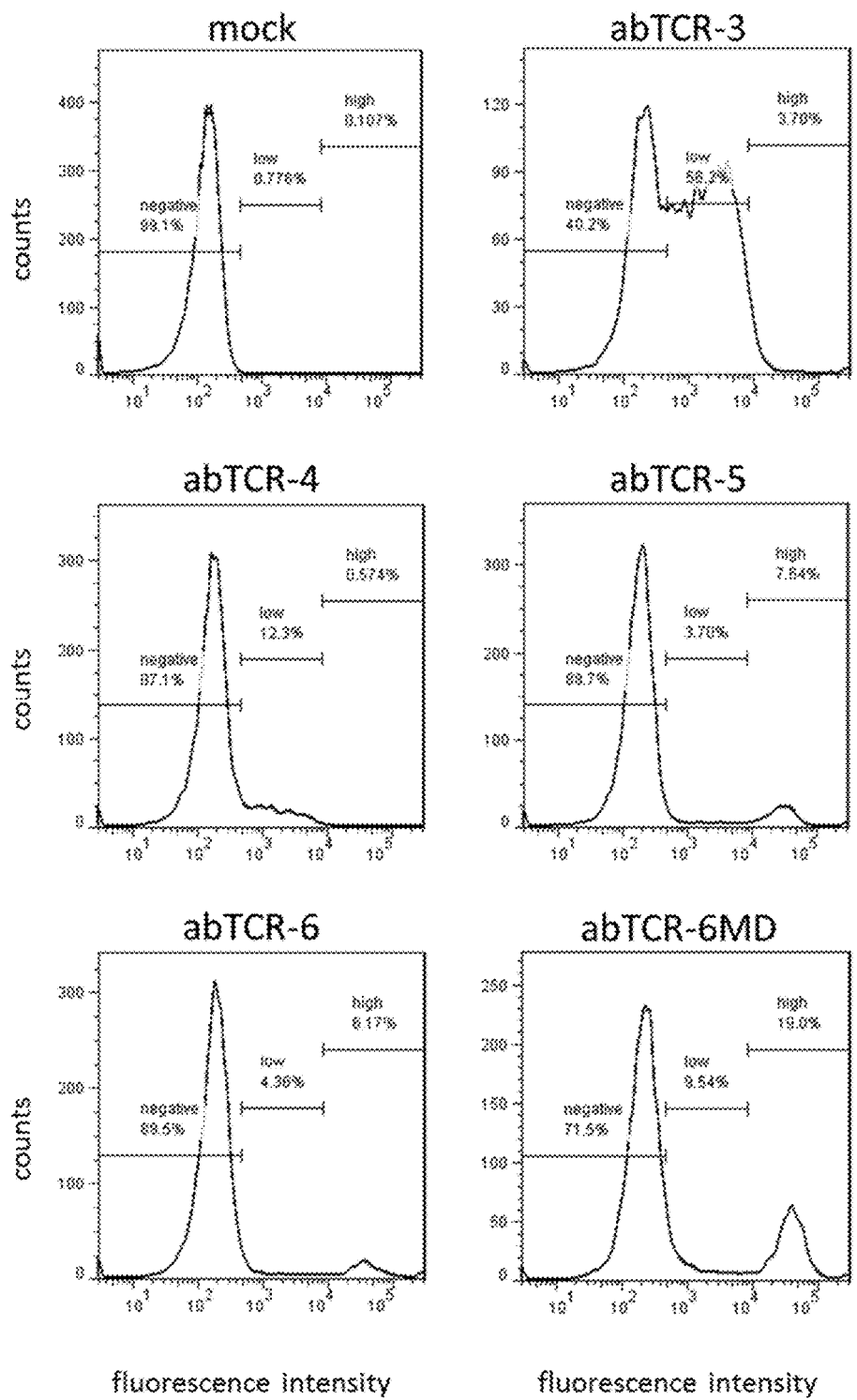
FIG. 5B shows flow cytometry analysis of surface AFP158/HLA-A*02:01 tetramer binding in Jurkat cells individually transduced with abTCR-3, -4, -5, -6, or -6MD constructs having an anti-AFP158/HLA-A*02:01 binding moiety; cells were stained with PE-labeled AFP158/HLA-A*02:01 tetramers.
Figure 5C:
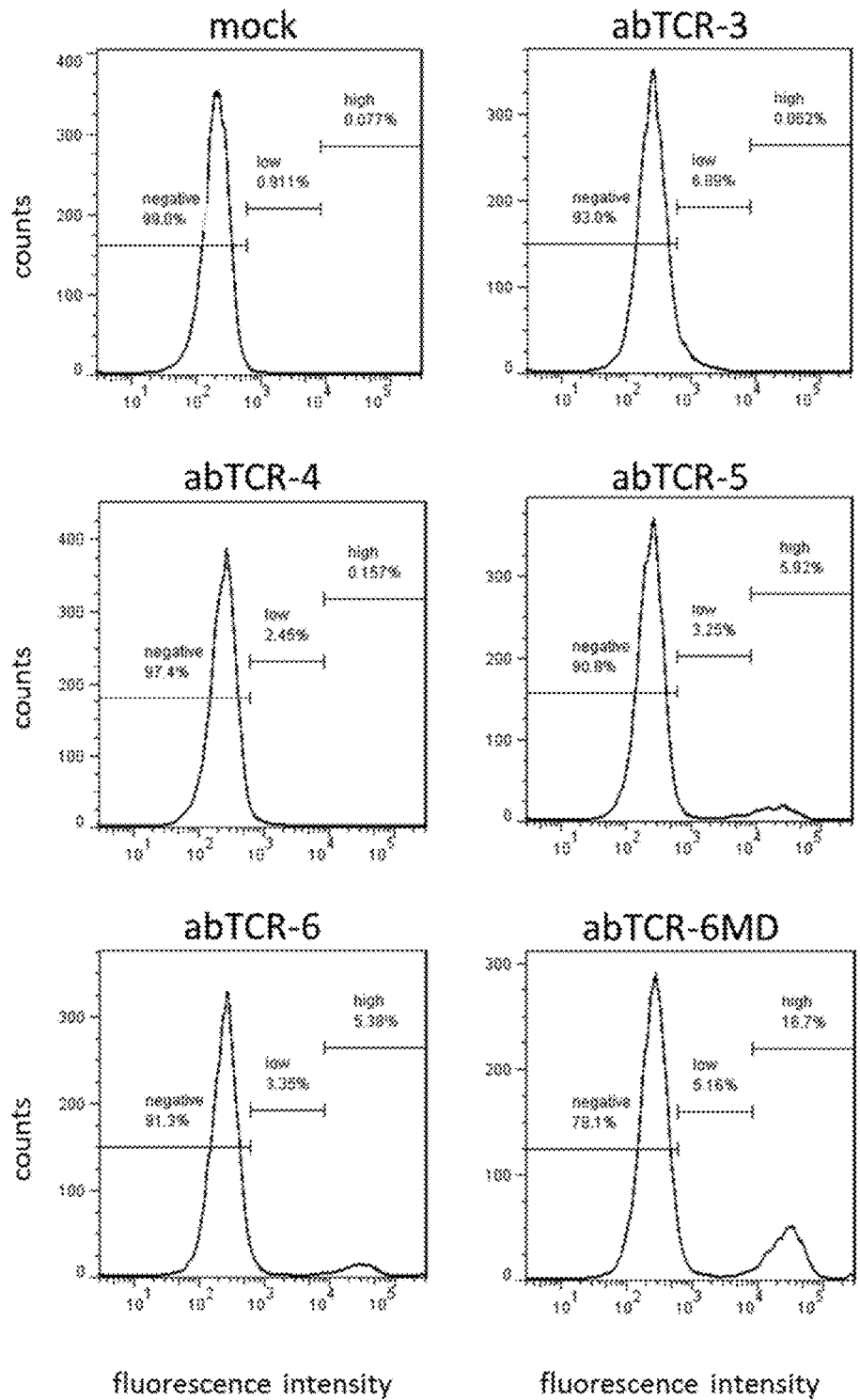
FIG. 5C shows flow cytometry analysis of surface anti-idiotype antibody binding in Jurkat cells individually transduced with abTCR-3, -4, -5, -6, or -6MD constructs having an anti-AFP158/HLA-A*02:01 binding moiety recognized by the antibody; cells were stained with anti-idiotype antibody against the anti-AFP158/HLA-A*02:01 binding moiety of the abTCR constructs.

The same set of experiments were also conducted in Jurkat cells (an αβ TCR positive T cell line), using the abTCR-3, -4, -5, -6 and -6MD constructs with the anti-AFP158/HLA-A*02:01 antibody (FIG. 5A-5C). The results are consistent with that observed in J.RT3-T3.5 cells in terms of AFP158 tetramer staining (FIG. 5B) and anti-idiotypic antibody binding (FIG. 5C). The transduced cells were also stained with an anti-TCRα/β antibody to determine the impact of the abTCR constructs on the expression of endogenous TCRα/β chains. While mock-transduced Jurkat cells expressed a high level of TCRα/β, a TCRα/β negative population was detected in each of abTCR-transduced cells as a shoulder on the left of the TCRα/β peak (FIG. 5A). These data suggest that expression of the abTCR chimeras competes for the CD3 chains, resulting in a reduction in the surface expression of endogenous TCRα/β.

Combining the observations from the western blots and flow cytometry experiments, we postulate that in abTCR-3 and -4 transduced cells, some of the endogenous TCRα subunit may pair with the exogenous β chains of the abTCR chimera, to form TCR-CD3 complexes that can be transported to the cell surface. Alternatively, abTCR-3 and -4 may have different conformation which limited the exposure of the epitope for the anti-idiotype antibody. In abTCR-3-transduced J.RT3-T3.5 and Jurkat cells, the high level expression of the IgV$_L$-IgC$_L$-TCRβ chain (per western blot, FIG. 3) resulted in a large percentage of J.RT3-T3.5 cells that express CD3ε on the cell surface (FIG. 4A) and a reduction in endogenous TCRα/β expression in a subset of the Jurkat cells transduced with abTCR-3. In abTCR-4 transduced cells, the IgV$_H$-IgC$_H$1-TCRβ chain also resulted in CD3ε expression in J.RT3-T3.5 cells and reduction in endogenous TCRα/β expression in Jurkat cells, but to a much lesser extent since the chimeric abTCR β chain expression is much lower in abTCR-4 compared to abTCR-3 (per western blot, FIG. 3).

For abTCR-3 and -4 transduced cells, the pairing of exogenous TCRβ chimera with the endogenous TCRα chains in TCRαβ+ T cells is expected to reduce the pool of TCRβ chimera chains available for correct pairing with exogenous TCRα chimera chains. This will not be an issue in TCRαβ+ T cells when expressing abTCR-5, -6 or -6MD constructs, where the chimeras are generated with the TCRδ and TCRγ chains. The high MFI in the abTCR positive peaks are consistent with a high number of correctly-paired chimeras in both J.RT3-T3.5 and Jurkat cells that express the abTCR-5, -6 or -6MD constructs. Conversely, usage of abTCR-3 and -4 constructs, where the chimeras are generated with the TCRα and TCRβ chains, for expression in TCRδγ+ T cells would be preferred to avoid the pairing of the exogenous chimeric chains with the endogenous TCRδ and TCRγ chains.

Example 3. Expression of abTCR in Primary T Cells

Having demonstrated that the abTCR constructs can be successfully transduced into T cell lines and expressed on the cell surface along with CD3 complex as functional antigen-binding receptors, we next tested the expression of abTCR in primary T cells.

abTCR Expressed in CD4+ and CD8+ Primary T Cells

Peripheral blood lymphocytes were isolated from healthy donors and transduced with an abTCR-6MD construct encoding an anti-AFP158/HLA-A*02:01 binding moiety (SEQ ID NOs: 35 and 36). The abTCRγ and δ subunits were subcloned into the same lentiviral vector to transduce primary human T cells. After 5 days of transduction, abTCR-T cells and mock-transduced cells were co-stained with AFP158 tetramer, and CD4 and CD8 antibodies and analyzed by flow cytometry. FIG. 7A shows a scatter plot of CD8 vs antigen (AFP158 tetramer) binding, while FIG. 7B shows scatter plots of CD8 vs CD4. In the mock-transduced T cells, the CD4:CD8 ratio is about 2:1 (FIG. 7B top panel). The same CD4:CD8 ratio was observed in cells transduced with the abTCR-6MD construct (FIG. 7B middle panel). We found that CD4:CD8 ratio is also about 2:1 among the AFP158 tetramer+ population in the abTCR-6MD transduced cells (see FIG. 7B bottom panel and gating in FIG. 7A). This indicates that the abTCR chimera can be expressed in both CD4+ and CD8+ primary T cells.

Exogenous abTCR Chains are Physically Associated with the CD3 Complex

Figure 8:
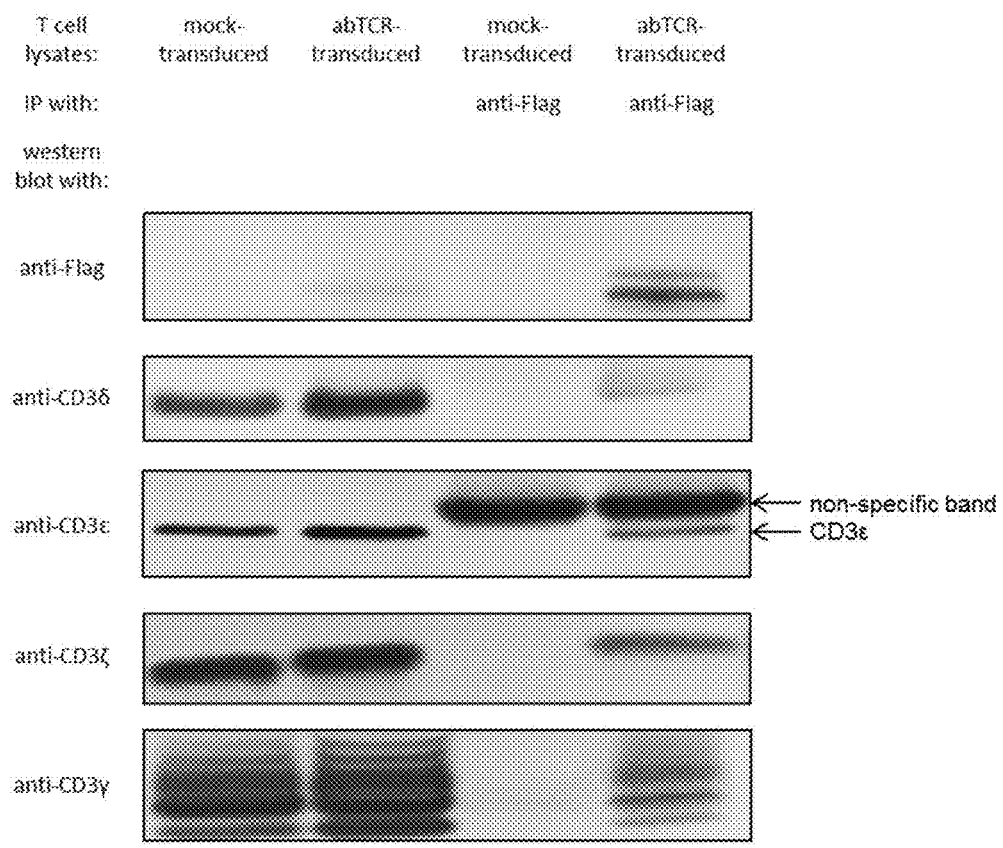
FIG. 8 shows Western blot analysis of the association of exogenous abTCR chains with the CD3 complex; Digitonin lysates were made from primary T cells that were either mock-transduced or transduced with abTCR-6MD having an anti-AFP158/HLA-A*02:01 binding moiety; lysates or anti-FLAG immunoprecipitates were blotted with anti-FLAG, anti-CD3δ, anti-CD3ε, anti-CD3γ or anti-CD3ζ antibodies.

Given that abTCR expression in T cell lines was able to rescue surface expression of CD3ε in J.RT3-T3.5 cells, we tested if abTCR constructs expressed in primary T cell are physically associated with individual chains in the CD3 complex by co-immunoprecipitation (co-ip). Primary T cells were stimulated using anti-CD3 and anti-CD28 and then mock-transduced or transduced with abTCR-6MD constructs encoding an anti-AFP158/HLA-A*02:01 binding moiety (SEQ ID NOs: 35 and 36). Twelve days after transduction, abTCR-T cells were co-cultured with SK-HEP-1-AFP-MG for another 12 days to enrich for AFP158 tetramer+ cells. The cells were then lysed with digitonin (0.1%) lysis buffer and an anti-Flag antibody was used to i.p. the TCRγ chain via the 3×Flag tag. As shown in FIG. 8, the CD3δ, CD3ε, CD3γ and CD3ζ chains were co-immunoprecipitated with abTCRγ chimera, demonstrating that the transduced abTCR chimeras were physically associated with the endogenous CD3 complex. The band with a higher MW than CD3ε, observed in the mock-transduced sample with anti-Flag immunoprecipitation, is a non-specific band.

Similar co-immunoprecipitation experiments are done in JRT3-T3.5 and Jurkat cell lines. JRT3-T3.5 and Jurkat cell lines are transduced with abTCR-6MD constructs encoding an anti-AFP158/HLA-A*02:01 binding moiety (SEQ ID NOs: 35 and 36). 5 days post-transduction, CELLection biotin binder kit is used to purify AFP158 tetramer+ populations from JRT3-T3.5 and Jurkat cell lines. Jurkat and JRT3-T3.5 cells transduced with abTCR-6MD and purified with AFP158 tetramer are named as Jurkat-abTCR-pure and JRT3-T3.5-abTCR-pure, respectively. JRT3-T3.5, JRT3-T3.5-abTCR-pure, Jurkat and Jurkat-abTCR-pure cells are expanded and lysed in 0.1% digitonin lysis buffer. Co-immunoprecipitation is performed using anti-Flag antibody (Sigma) and Dynabeads Protein G for immunoprecipitation (Life Technologies) following standard protocol.

Figure 9A:
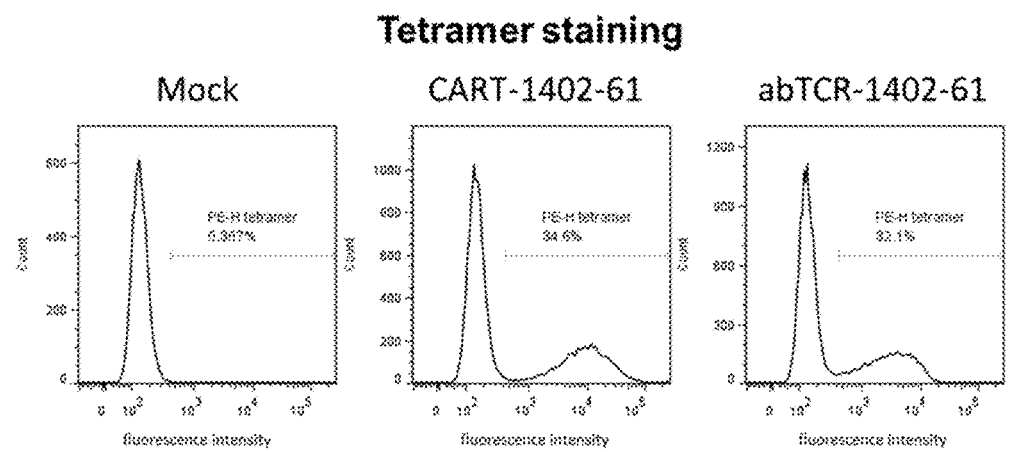
FIG. 9A shows transduction efficiency in primary T cells after they were transduced with a CAR or an abTCR-6MD, both having the same anti-AFP158/HLA-A*02:01 binding moiety variable domains; cells were stained with PE-labeled AFP158/HLA-A*02:01 tetramers.
Figure 9B:
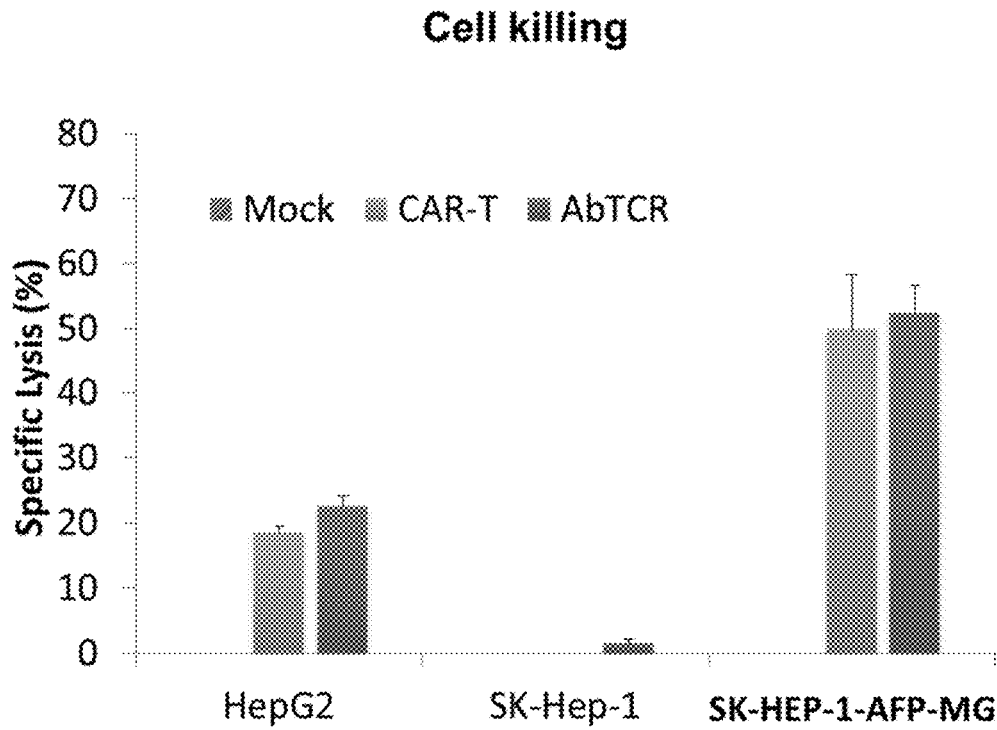
FIG. 9B shows killing of cancer cell lines HepG2, SK-HEP-1 and SK-HEP-1-AFP-MG, mediated by T cells transduced with either a CAR or an abTCR-6MD construct, both having the same anti-AFP158/HLA-A*02:01 binding moiety variable domains.

Example 4. Characterizing Biological Activities of T Cells Transduced with abTCR-6MD and CAR Constructs Containing the Same Anti-AFP158/HLA-A*02:01 Variable Domains abTCR-Transduced T Cells can Specifically Kill Antigen-Positive Cancer Cells Primary T cells were mock-transduced or transduced with lentiviral vectors encoding a CAR containing an anti-AFP158/HLA-A*02:01 scFv (SEQ ID NO: 37) or an abTCR-6MD containing the same anti-AFP158/HLA-A*02:01 variable domains (SEQ ID NOs: 35 and 36). The transduction efficiency was determined by staining with PE-labeled AFP158/HLA-A*02:01 tetramers (FIG. 9A). T cell populations with similar transduction rates (32% for CART and 34% for abTCR) were used to test their abilities to kill cancer cell lines. Three cell lines were used: HepG2 (AFP+/HLA-A2+), SK-HEP-1 (AFP-/HLA-A2+) and SK-HEP-1-AFP-MG (SK-HEP-1 transduced with an AFP minigene) at an effector-to-target ratio of 2.5:1. Specific lysis was measured after 16 hr incubation using the Cytox 96 Non-radioactive Cytotoxicity Assay (Promega). As shown in FIG. 9B, T cells transduced with both CAR and abTCR-6MD bearing an anti-AFP158/HLA-A*02:01 binding moiety directed killing of antigen-positive cell lines HepG2 and SK-HEP-1-AFP-MG, but did not lead to killing of antigen-negative cell line SK-HEP-1. The level of specific lysis observed in abTCR-transduced cells is equivalent to that for CAR-T cells.

abTCR-Transduced T Cells Degranulate Upon Antigen Stimulation

Figure 10:
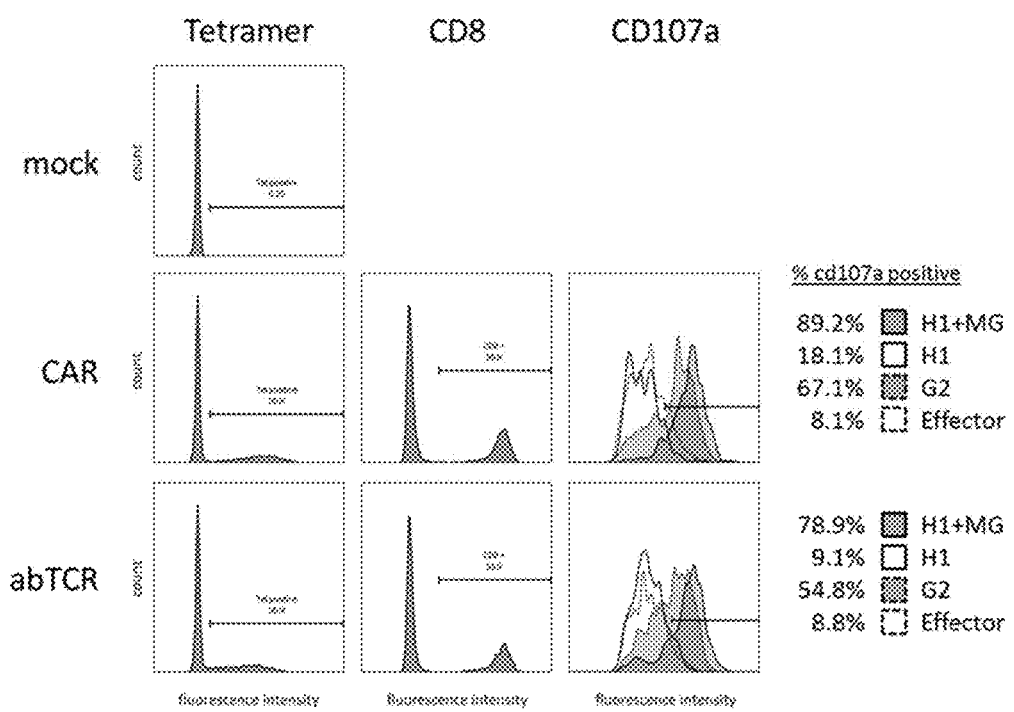
FIG. 10 shows flow cytometry analysis of the degranulation of abTCR-transduced T cells after co-culturing with target cells; T cells were transduced with either a CAR or an abTCR-6MD, both having the same anti-AFP158/HLA-A*02:01 binding moiety variable domains. Staining of the transduced cells with AFP158/HLA-A*02:01 tetramers, anti-CD8 antibody or anti-CD107a antibody after co-culturing with target cells HepG2, SK-HEP-1 and SK-HEP-1-AFP-MG are shown.

To further characterize the biological activities in abTCR- vs CAR-transduced T cells, we used a flow cytometry assay to detect CD107a surface expression as a measurement of degranulation activity. abTCR- and CAR-transduced T cells with an anti-AFP158/HLA*02:01 binding moiety were generated as above and were co-incubated with HepG2, SK-HEP-1 and SK-HEP-1-AFP-MG cells for 4 hours in the presence of a 1:200 dilution of anti-CD107a antibody and protein transport inhibitor cocktail (eBioscience). After co-incubation with target cells, transduced T cells were stained with AFP158/HLA tetramers and anti-CD8. Degranulation in tetramer-positive, CD8-positive T cells is shown in FIG. 10, right panel. The highest level of degranulation, as measured by CD107a expression, was observed upon co-incubation with SK-HEP-1-AFP-MG (solid line, gray-filled), followed by HepG2 (dotted line, gray-filled), while no degranulation was observed with the parental antigen-negative SK-HEP-1 (solid line, white-filled) with both abTCR and CAR-transduced T cells. The level of degranulation was similar between abTCR- and CAR-transduced cells when the same target cells were used. This is consistent with the T-cell mediated cell lysis data above. Taken together, we demonstrated that abTCR-transduced T cells are equally as responsive as CAR-transduced cells to anti-gen-positive cancer cells in degranulation (FIG. 10) and mediating cell killing (FIG. 9).

Cytokine Production and Secretion by abTCR and CAR T Cells in Tumor Cell Killing T cells transduced with either abTCR or CAR and having similar transduction rates were generated and co-incubated with target cells as above. Release of IL-2, IL-4, IL-6, IL-8, IL-10, GM-CSF, IFN-γ and TNF-α into the media after the in vitro killing assay shown in FIG. 9B was measured using the Magpix multiplex system (Luminex) with the Bio-plex Pro Human Cytokine 8-plex Assay (BioRad). To reach the detection limits of the assay supernatants from SK-HEP-1-AFP-MG target reactions were diluted 25-fold, while all other samples were undiluted. Cytokine concentrations were determined with a known standard curve, after subtracting cytokine release from media, target alone and effecter alone.

Figure 11A:
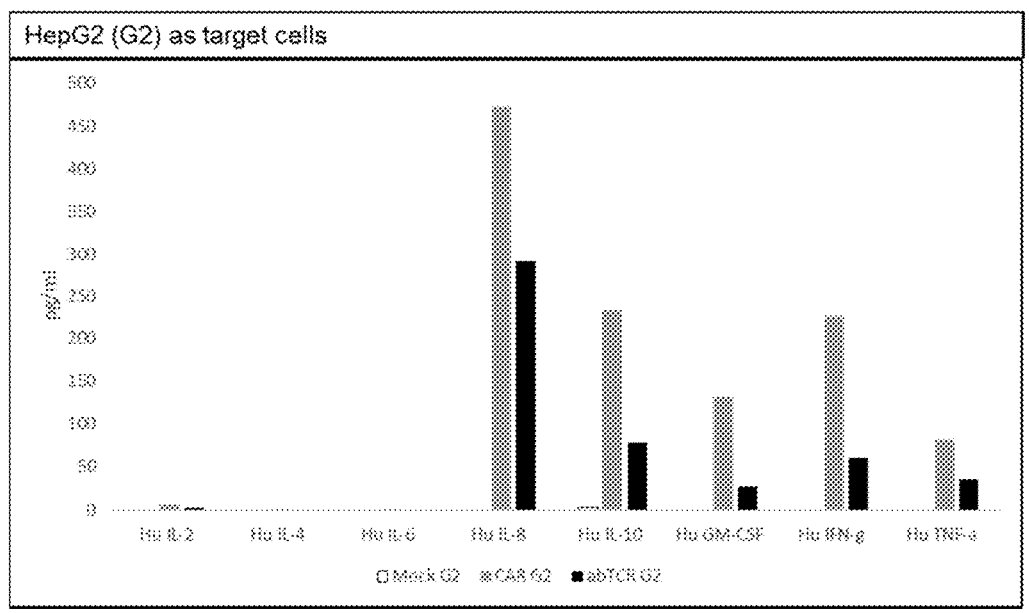
FIG. 11A shows the level of secretion of a panel of cytokines by mock-transduced T cells or T cells transduced with either a CAR or an abTCR-6MD, both having the same anti-AFP158/HLA-A*02:01 binding moiety variable domains, after co-culture with HepG2 cells.
Figure 11B:
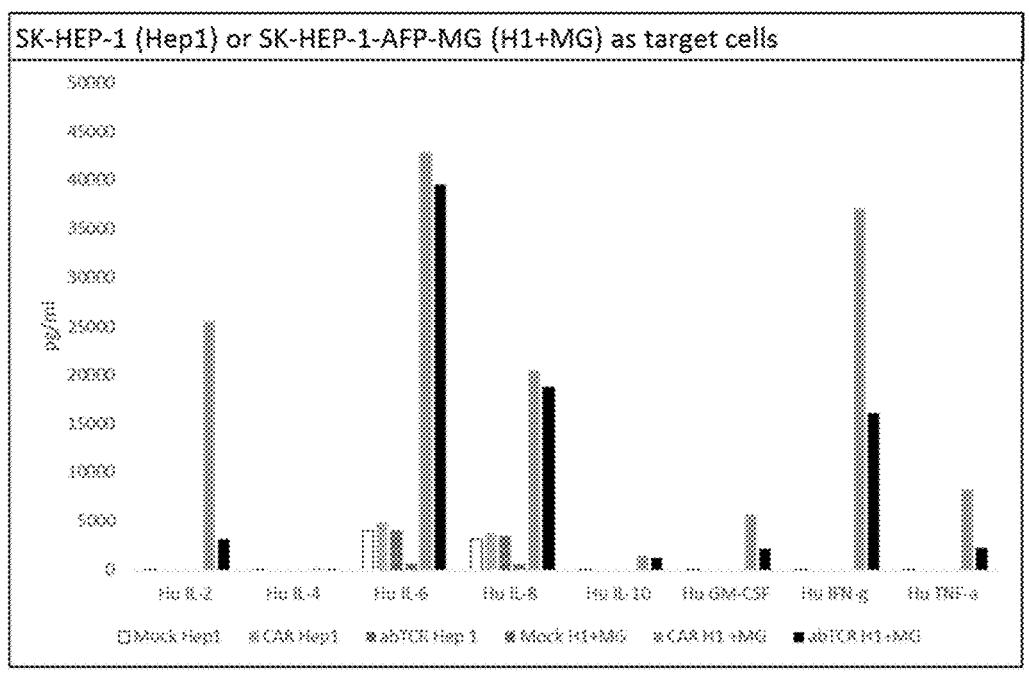
FIG. 11B shows the level of secretion of a panel of cytokines by mock-transduced T cells or T cells transduced with either a CAR or an abTCR-6MD, both having the same anti-AFP158/HLA-A*02:01 binding moiety variable domains, co-cultured with either SK-HEP-1 or SK-HEP-1-AFP-MG cells.
Figure 12A:
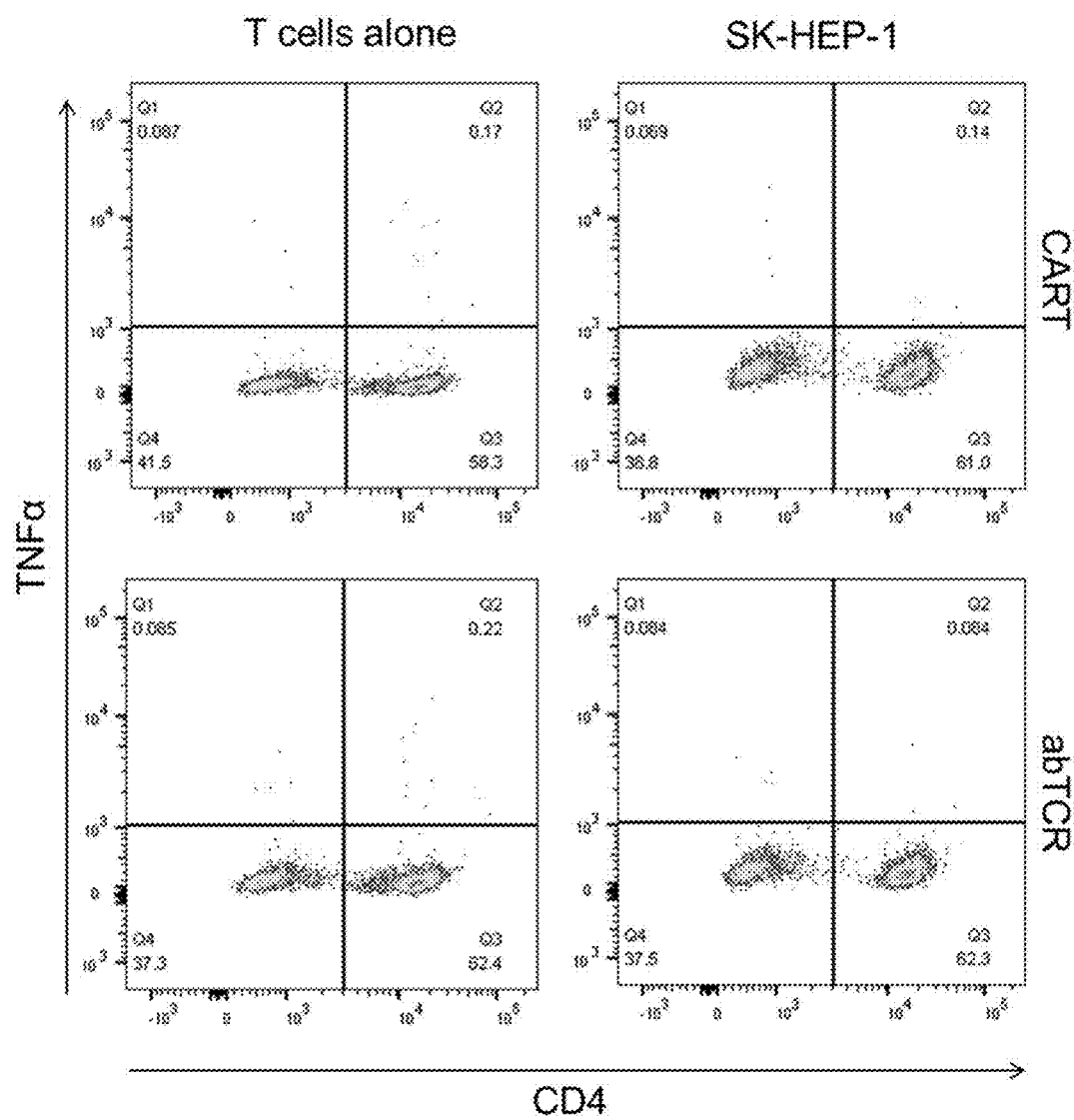
FIGS. 12A-12H show flow cytometry analysis of transduced T cells for cytokine production with or without the presence of target cancer cells; T cells were transduced with either a CAR or an abTCR-6MD, both having the same anti-AFP158/HLA-A*02:01 binding moiety variable domains, co-cultured with either SK-HEP-1, SK-HEP-1-AFP-MG, or HepG2 cells; cells were subsequently co-stained with PE-labeled AFP158/HLA-A*02:01 tetramers, anti-CD4 antibody and one of anti-TNF-α antibody (12A and 12B), anti-IFNγ antibody (12C and 12D), anti-IL-2 antibody (12E and 12F), or anti-IL-6 antibody (12G and 12H). Populations shown were gated on AFP158/HLA-A*02:01 tetramer$^+$ cells.
Figure 12B:
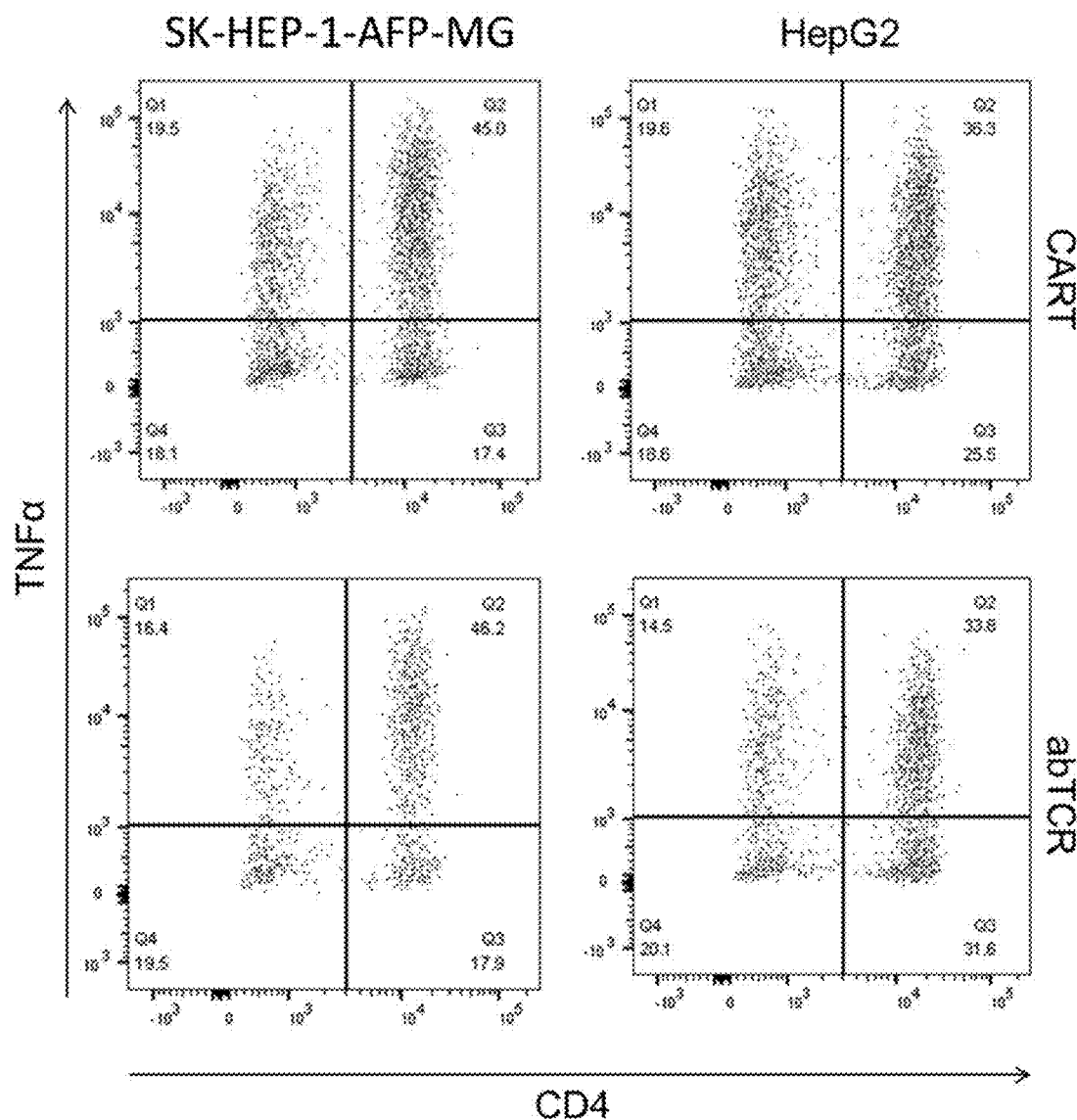
Figure 12C:
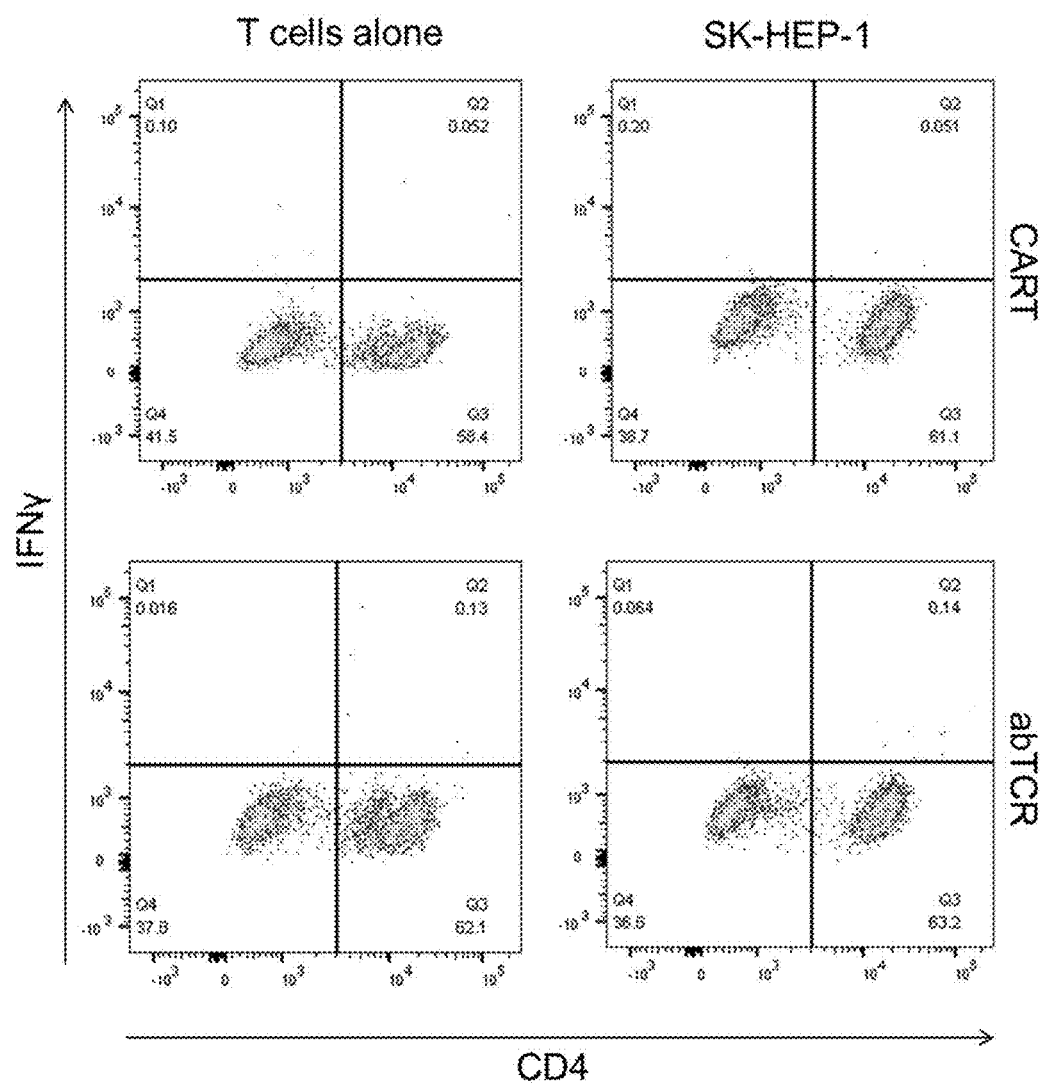
Figure 12D:
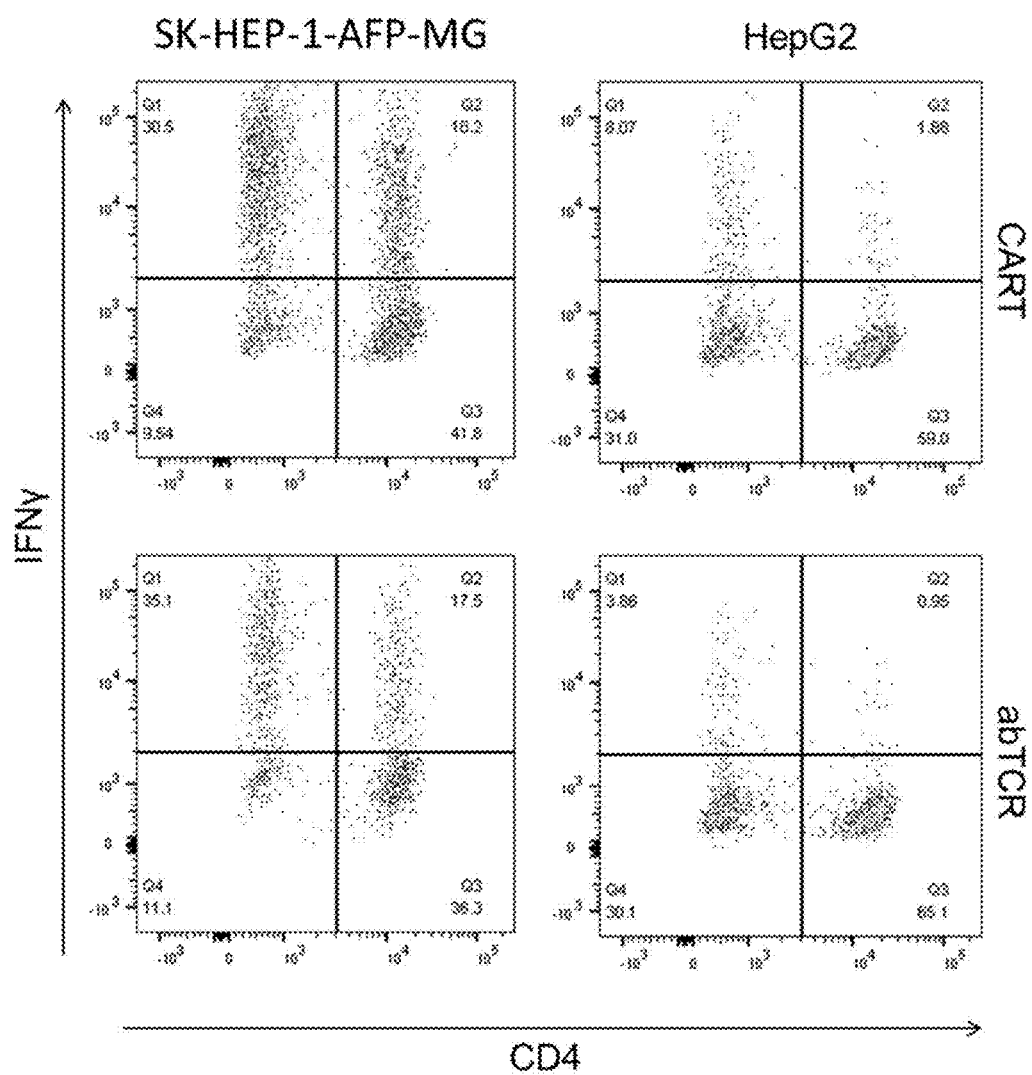
Figure 12E:
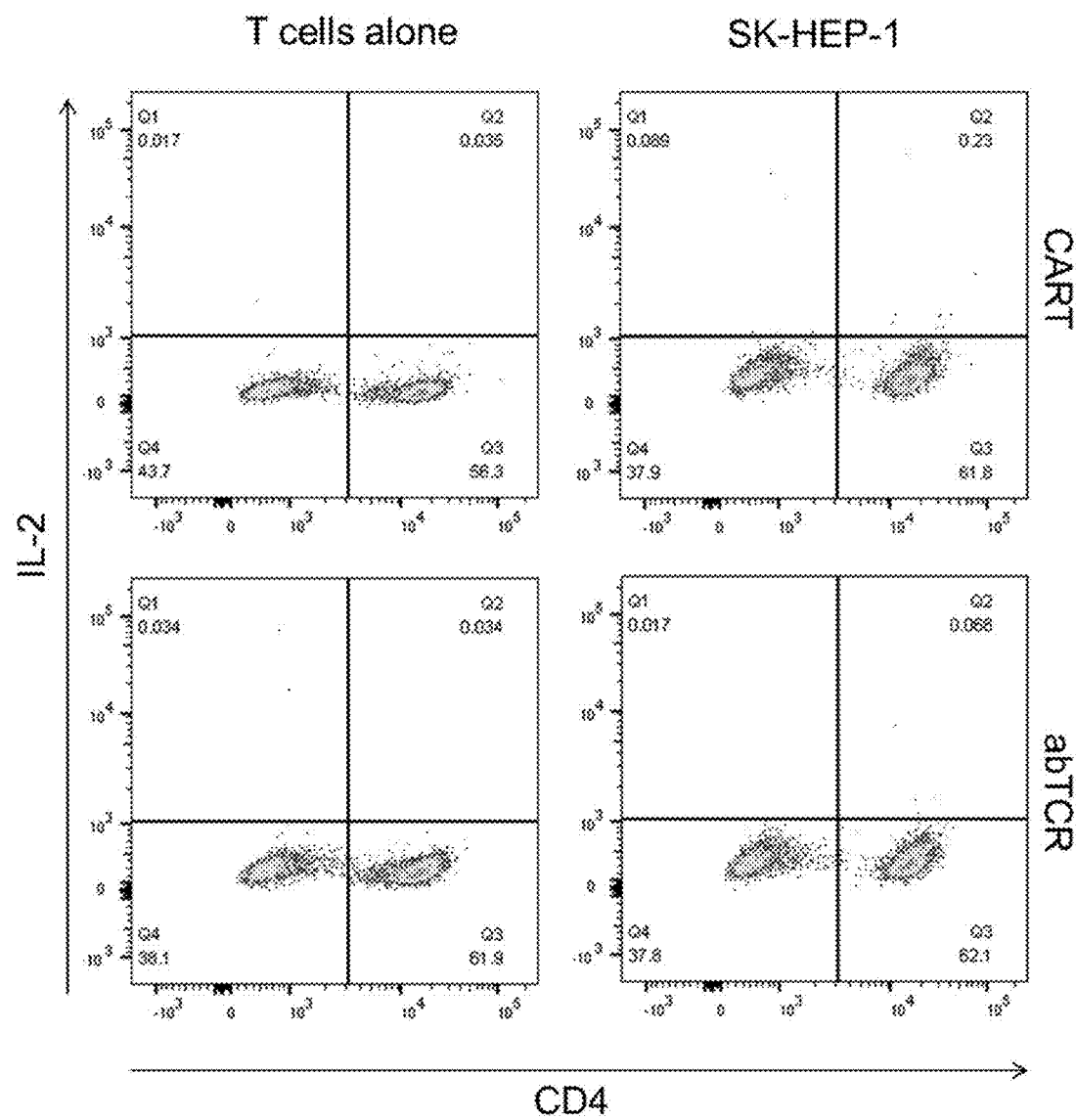
Figure 12F:
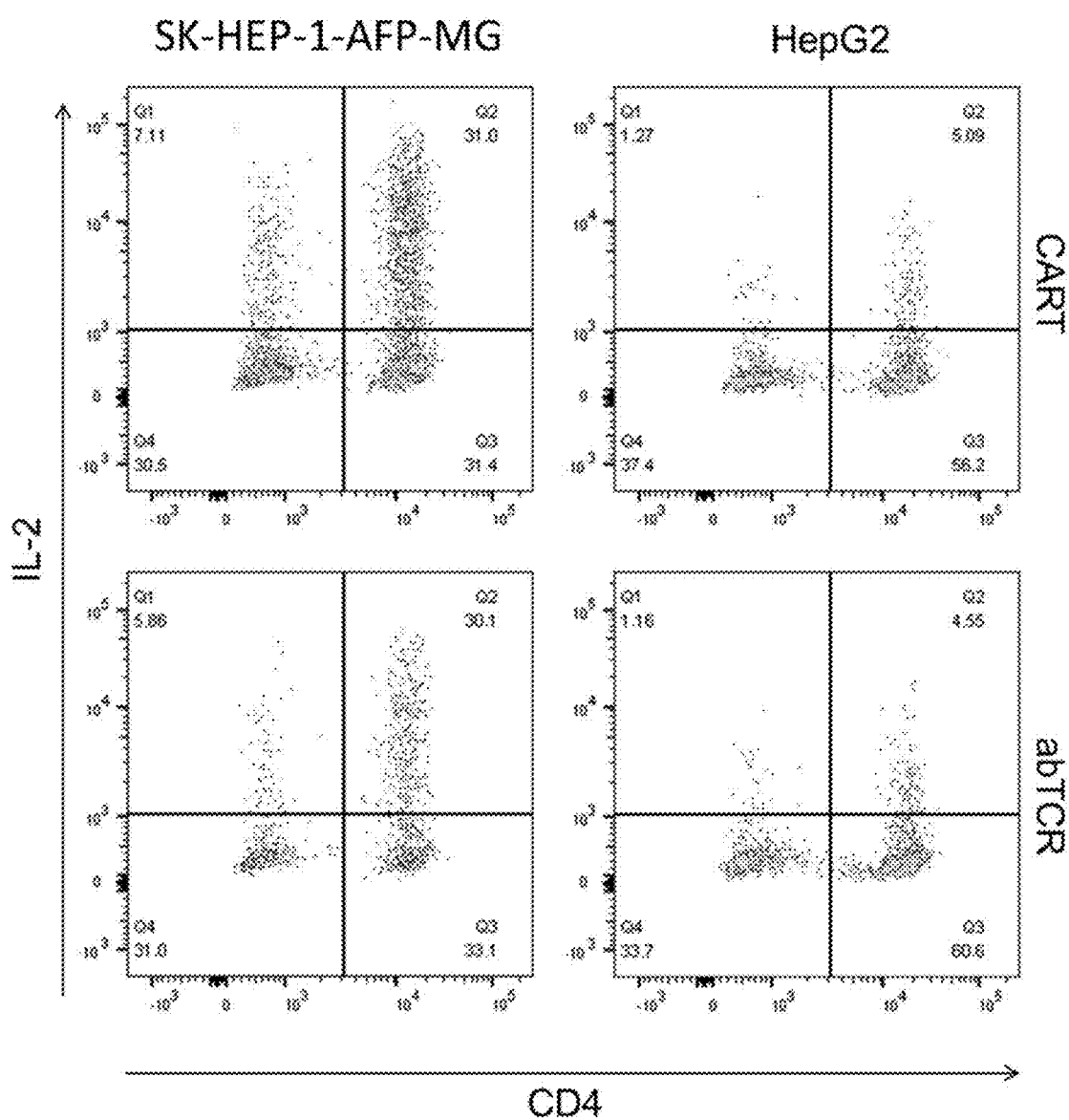
Figure 12G:
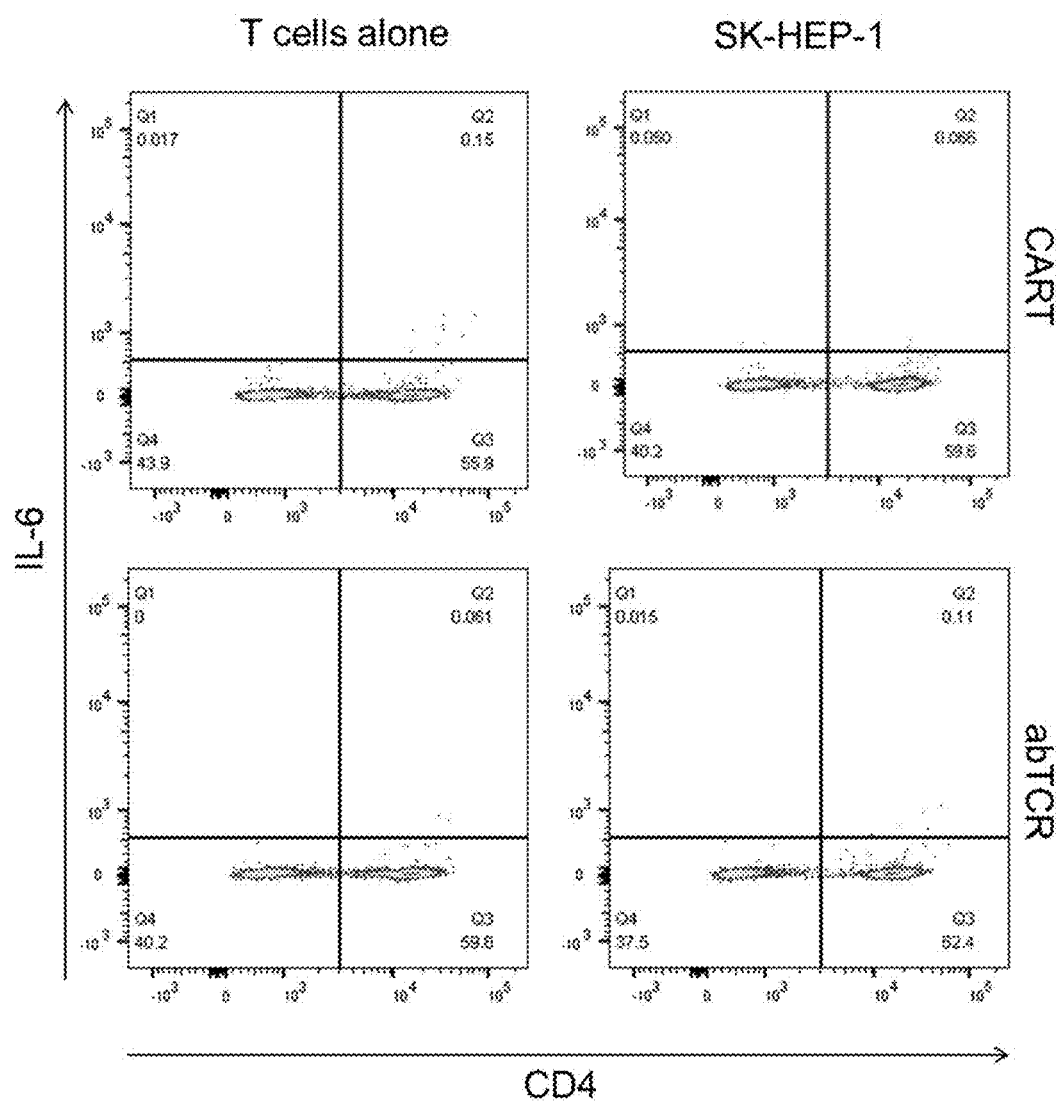
Figure 12H:
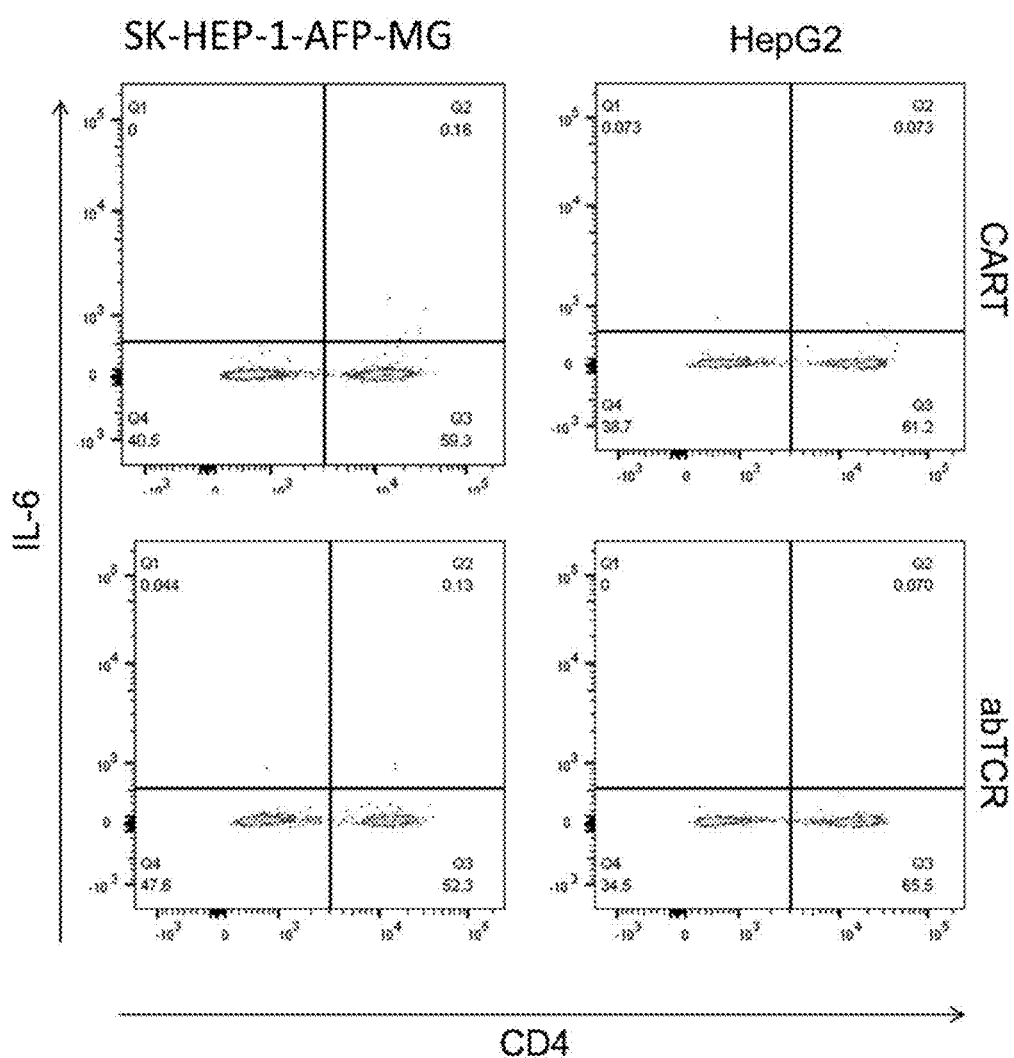

We estimated the number of AFP158/HLA-A*02:01 complexes on the surface of HepG2 to be ~100 per cell, using high resolution microscopy (data not shown). At such a low copy number of peptide/HLA complex, flow cytometry using the anti-AFP158/HLA-A*02:01 antibody was unable to detect a significant MFI shift. In contrast, expression of an AFP minigene in the SK-HEP-1-AFP-MG cells resulted in one log shift in MFI by flow cytometry, indicating that the level of AFP158/HLA-A*02:01 complex on SK-HEP-1-AFP-MG cells was significantly higher than that in HepG2. When HepG2 was used as target cells and a panel of eight human cytokines (IL-2, IL-4, IL-6, IL-8, IL-10, GM-CSF, IFN-γ, TNF-α) was measured after 16 hours of co-incubation with abTCR- or CAR-transduced T cells, IL-8, IL-10, GM-CSF, IFN-γ, TNF-α was detectable in the media (FIG. 11A). The cytokine release was consistently lower in the abTCR-transduced samples when compared to the CAR-transduced samples. When the same assay was done with SK-HEP-1-AFP-MG, secretion of 7 out of the 8 cytokines that we tested were detected upon co-incubation with abTCR- or CAR-transduced primary T cells (FIG. 11B). In the case of each cytokine tested, the level of cytokine detected in the media was either similar or lower in samples containing abTCR-transduced T cells compared with the CAR-T samples, some by more than two fold (e.g., IL-2, IFN-γ, TNF-α. SK-HEP-1 cells alone also exhibited a detectable level (~3000 pg/ml above background) of IL-6 and IL-8 in the absence of T cells.

To determine the contribution of the transduced T cells as the source of the cytokines detected in the media, abTCR- and CAR-transduced T cells with similar transduction efficiencies (34%) were co-cultured with target cells at a ratio of 2.5:1 with a protein transport inhibitor cocktail (eBioscience Cat#00498003) to prevent cytokine secretion. After 4 hours of treatment, T cells were stained with AFP158/HLA-A*02:01 tetramer and anti-CD4 antibody along with anti-TNF-α, anti-IFN-γ, anti-IL-2 or anti-IL-6 antibodies. Using flow cytometry, gating on AFP158 tetramer+ cells (FIGS. 12A-12H), we demonstrated that intracellular TNF-α, IFN-γ and IL-2, but not IL-6, were expressed in both abTCR- and CAR-transduced T cells when they are co-cultured with antigen-positive target cells. For each cytokine examined, the level of intracellular cytokine was consistently higher in SK-HEP-1-AFP-MG than HepG2, correlating with the level of antigen expression on the target cells. For each target cell population, there was no significant difference in intracellular cytokines between abTCR- vs CAR-transduced cells, for each cytokine tested. This suggests that the difference seen in the cytokine release assay may be due to cytokine feedback. The absence of intracellular IL-6 in the transduced T cells suggests that the source of the IL-6 detected in the media in FIG. 11B is from the SK-HEP-1 cells and not the T cells.

Figure 13:
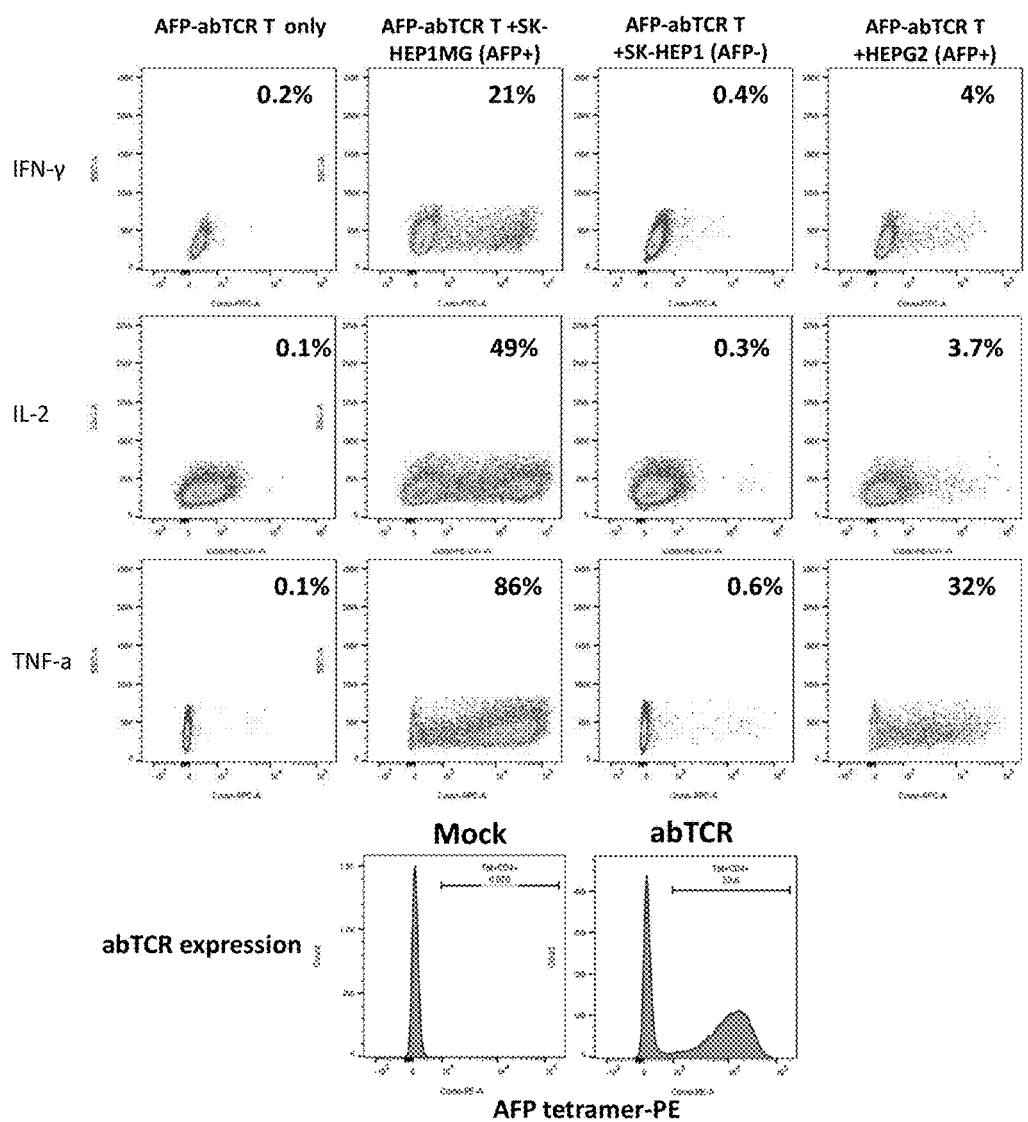
FIG. 13 shows target-specific activation of cytokine expression in CD4+ T cells transduced with an anti-AFP158 abTCR and incubated with cancer cell lines positive or negative for AFP expression.

To determine if the activation of abTCRs in CD4+ T cells could lead to specific biological responses, we investigated the intracellular cytokine expression in CD4+, anti-AFP158 abTCR-expressing T cells following stimulation with cancer cell lines expressing AFP. CD3+ T cells were transduced with the anti-AFP158 abTCR as described above and incubated with cancer cell line SK-HEP1-MG (AFP+), SK-HEP1 (AFP−), or HEPG2 (AFP+) for 4 hours in the presence of protein transporter inhibitor. As a negative control, abTCR-transduced T cells were incubated in the absence of any cancer cell line. After the incubation, the T cells were stained with anti-IFNγ, anti-IL2, or anti-TNFα antibodies, and co-stained with AFP-tetramer-PE and anti-CD4. Cells gated for abTCR expression were analyzed by flow cytometry for granularity and cytokine expression (FIG. 13, Y-axis is side scattering, X-axis is cytokine staining). The expression of IFNγ, IL2, and TNFα was induced following incubation of the anti-AFP158 abTCR-transduced T cells with AFP+ cancer cell lines SK-HEP1-MG and HEPG2, but not when incubated with AFP− cell line SK-HEP1 or in the absence of any cancer cell line, indicating the antigen-specific activation of the abTCR in CD4+ T cells.

Expression of T Cell Exhaustion Markers in abTCR and CAR T Cells after Co-Culture with Target Cells To examine the level of exhaustion markers expressed on abTCR- and CAR-transduced cells upon antigen stimulation, CD3+ T cells were prepared from PBMC-enriched whole blood using EasySep Human T Cell Isolation Kit (StemCell Technologies) and activated with CD3/CD28 Dynabeads as above. The activated and expanded cell population was >99% CD3+ by flow cytometry. These cells were then transduced with lentiviral vectors encoding a CAR containing an anti-AFP158/HLA-A*02:01 scFv (SEQ ID NO: 37) or an abTCR-6MD containing the same anti-AFP158/HLA-A*02:01 variable domains (SEQ ID NOs: 35 and 36) for 7-9 days. The transduced cells were co-cultured with target cells for 16 hours at an effector-to-target ratio of 2.5:1 and co-stained with AFP158 tetramer and anti-CD8 antibody, along with antibodies to exhaustion markers PD-1, TIM-3 or LAG-3. The level of exhaustion markers on the transduced T cells were analyzed by flow cytometry by gating on the tetramer+ (i.e., transduced) T cells. In an independent flow cytometry experiment, we determined that tetramer+ T cells that were CD8− were CD4+ (data not shown).

Figure 14:
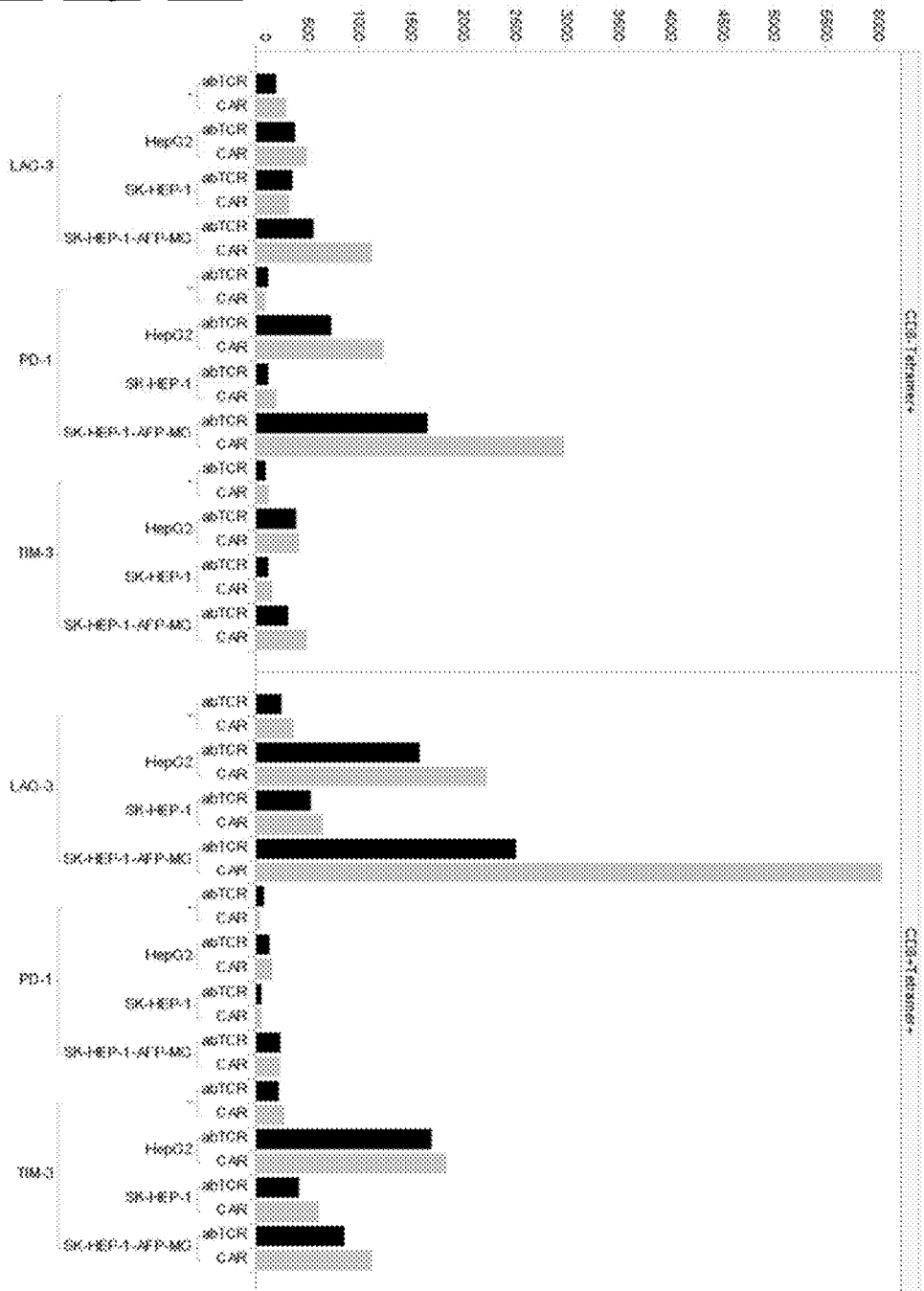
FIG. 14 shows the flow cytometry analysis of T cell exhaustion markers PD-1, LAG-3 and TIM-3 on CAR- or abTCR-transduced T cells, both having the same anti-AFP158/HLA-A*02:01 binding moiety variable domains, upon exposure to antigen-positive or -negative target cells.

Upregulation of PD-1 was observed among CD8−tetramer+ T cells, while upregulation of LAG-1 and TIM-3 were observed among CD8+tetramer+ T cells, after exposure to target cells that express AFP (HepG2 and SK-HEP-1-AFP-MG) (FIG. 14). In all cases, the level of exhaustion marker upregulation observed on CAR-transduced T cells were equal or higher than that observed on abTCR-transduced T cells. This suggests that abTCR transduced T cells may cause lower level of T cell exhaustion, resulting in longer T cell persistances in vivo. The percent of cells positive for each of the exhaustion markers in the tested conditions was determined and is shown in Table 2.

TABLE 2

| Target cell lines | T cell subset | PD1 (%) CAR | PD1 (%) abTCR | TIM3 (%) CAR | TIM3 (%) abTCR | LAG3 (%) CAR | LAG3 (%) abTCR |
|---|---|---|---|---|---|---|---|
| HEPG2 | CD8 | 11 | 5.0 | 33 | 15 | 21 | 7.7 |
|  | CD4 | 41 | 22 | 22 | 6.8 | 2.0 | 0.8 |
| SK-HEP1 | CD8 | 3.2 | 2.0 | 7.3 | 2.2 | 4.9 | 2.8 |
|  | CD4 | 27 | 14 | 8.1 | 2.0 | 1.0 | 0.5 |
| SK-HEP1-AFP MG | CD8 | 42 | 35 | 45 | 34 | 88 | 81 |
|  | CD4 | 87 | 81 | 46 | 34 | 32 | 24 |
| T cell only | CD8 | 1.7 | 1.1 | 1.1 | 0.5 | 1.4 | 1.0 |
|  | CD4 | 15 | 7.4 | 2.2 | 0.4 | 0.4 | 0.2 |

Expression of T Cell Differentiation Markers in abTCR and CAR T Cells

Figure 15:
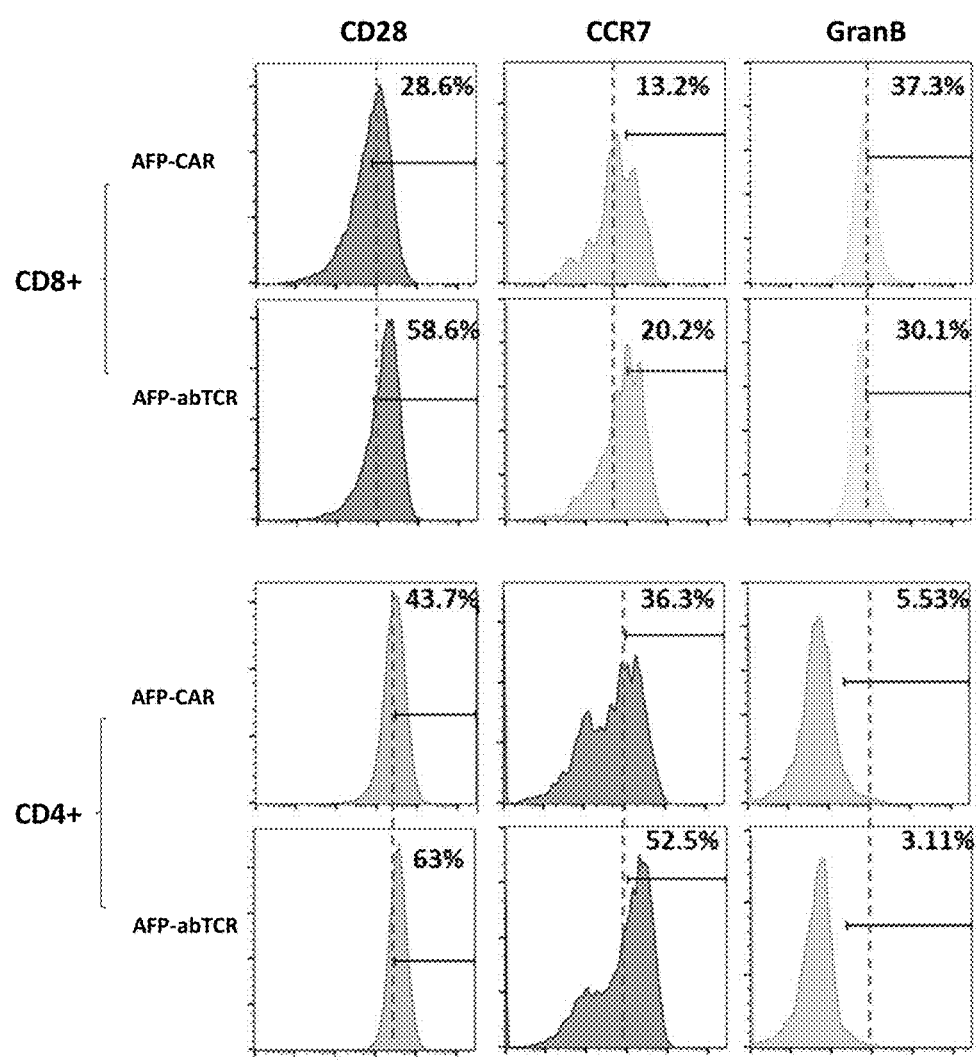
FIG. 15 shows flow cytometry analysis of T cell differentiation markers CD28, CCR7 and granzyme B on CAR- or abTCR-transduced T cells, both having the same anti-AFP158/HLA-A*02:01 binding moiety variable domains, upon exposure to antigen-positive or -negative target cells.

To determine if anti-AFP158 abTCRs can delay the differentiation of T cells during in vitro expansion, we measured the cell surface expression of three T cell differentiation markers, memory T cell markers CCR7 and CD28, and terminal differentiation marker Granzyme B. T cells were transduced with lentiviral vectors encoding a CAR containing an anti-AFP158/HLA-A*02:01 scFv (SEQ ID NO: 37) or an abTCR-6MD containing the same anti-AFP158/HLA-A*02:01 variable domains (SEQ ID NOs: 35 and 36), stained with antibodies against these markers, and analyzed by flow cytometry at day 10-12 after viral transduction (FIG. 15). The results show that for both CD4+ and CD8+ T cells, abTCR T cells expressed more CCR7 and CD28, but less Granzyme B, than CAR T cells, suggesting that the anti-AFP158 abTCR T cells were less differentiated than the anti-AFP158 CAR T cells after T cell expansion in vitro.

Comparison of Anti-AFP abTCR-6MD and abTCR-7 Constructs

Figure 16A:
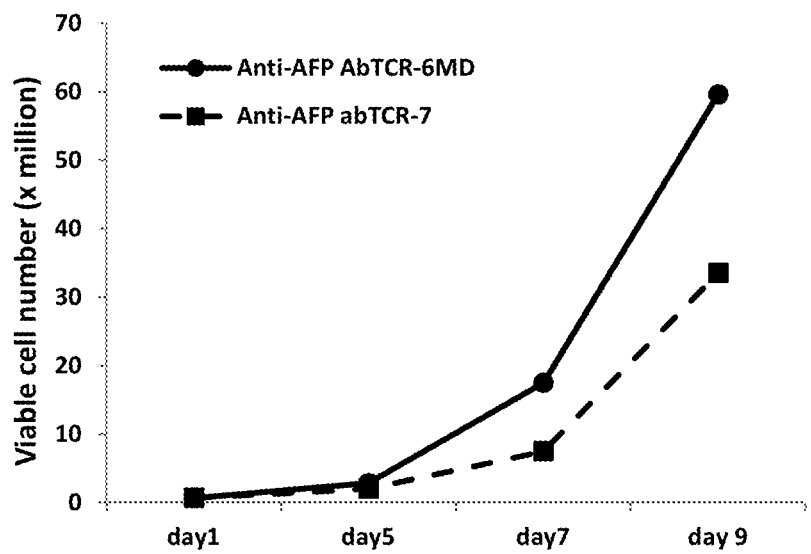
FIGS. 16A-16C show the characterization of T cells transduced with either an anti-AFP158/HLA-A*02:01 abTCR-6MD or an anti-AFP158/HLA-A*02:01 abTCR-7, both having the same anti-AFP158/HLA-A*02:01 binding moiety variable domains.
Figure 16B:
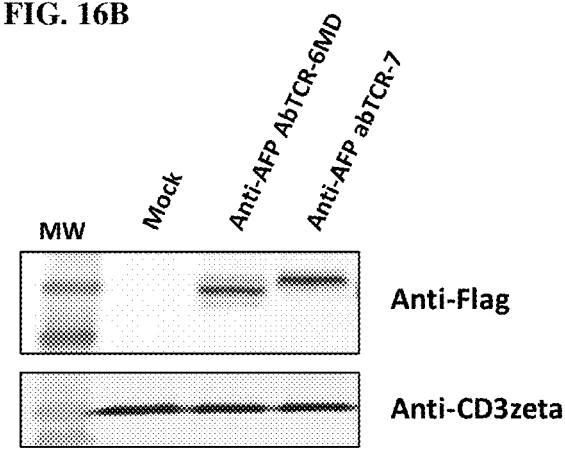

The cell growth of primary T cells transduced to express an anti-AFP158/HLA-A*02:01 abTCR-6MD was compared with that of T cells transduced with an anti-AFP158/HLA-A*02:01 abTCR-7 having the same antibody variable domains. $6.7 \times 10^5$ T cells were activated by αCD3/αCD28 beads (1:1 ratio) in the presence of 100 U/ml IL-2 on day 0. Activated T cells were transduced with either a lentiviral vector encoding the anti-AFP158/HLA-A*02:01 abTCR-6MD (TCRδ chimera subunit having the amino acid sequence of SEQ ID NO: 35 and TCRγ chimera subunit having the amino acid sequence of SEQ ID NO: 36) or a lentiviral vector encoding the anti-AFP158/HLA-A*02:01 abTCR-7 (TCRδ chimera subunit having the amino acid sequence of SEQ ID NO: 81 and TCRγ chimera subunit having the amino acid sequence of SEQ ID NO: 82) at MOI 4 on day 1. Transduced T cells were then cultured and expanded in the presence of IL-2 for 9-10 days. Cell numbers were counted on day 1, day 5, day 7, and day 9. As shown in FIG. 16A, the abTCR-6-MD transduced T cells grew faster than the abTCR-7-transduced T cells, with almost twice as many viable cells by day 9. Expression of the abTCR-6MD and abTCR-7 constructs in the transduced T cells at day 9 was assessed by Western blot analysis for the FLAG-tagged constructs. Briefly, 5 million transduced T cells were lysed in 100 μl lysis buffer and 13 μl of lysate was separated on a 4-12% polyacrylamide gel using the NuPage system. Mouse anti-FLAG antibody (1 μg/ml) was used to detect abTCR gamma chains and mouse anti-CD3zeta (1 μg/ml) was used to detect endogenous CD3. As shown in FIG. 16B, the abTCR-7 construct was expressed at higher levels than the abTCR-6MD construct. The intensities of the anti-FLAG bands for the lysates, normalized to the corresponding anti-CD3ζ bands, were quantified using ImageJ software and showed a relative increase of 20% for the expression of the abTCR-7 compared to the abTCR-6MD.

Figure 16C:
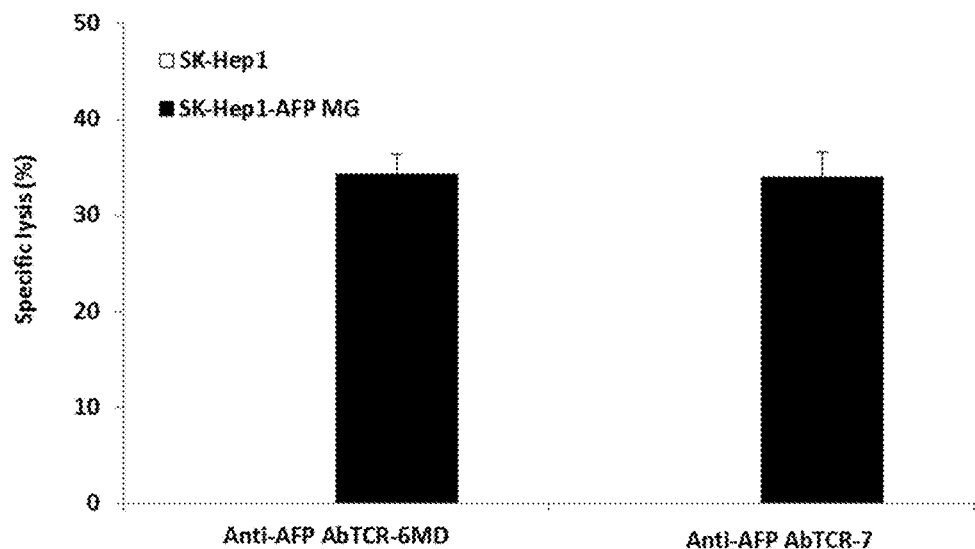

The target-cell killing activity of the anti-AFP158/HLA-A*02:01 abTCR-6MD T cells was compared with that of the anti-AFP158/HLA-A*02:01 abTCR-7 T cells. Primary T cells were mock-transduced or transduced with lentiviral vectors encoding either the anti-AFP158/HLA-A*02:01 abTCR-6MD or anti-AFP158/HLA-A*02:01 abTCR-7 constructs described above. T cells transduced with the abTCR-6MD or abTCR-7 were tested for their ability to kill SK-HEP-1 (AFP-/HLA-A2+) and SK-HEP-1-AFP-MG (SK-HEP-1 transduced with an AFP minigene) cells at an effector-to-target ratio of 5:1. The level of specific killing was measured at 16 hours as described above. As shown in FIG. 16C, the abTCR-6MD construct with the anti-AFP158/HLA-A*02:01 binding moiety directed similar specific lysis of AFP-positive SK-HEP-1-AFP-MG cells as compared to the abTCR-7 with the same antibody variable domains.

Example 5. Characterizing Biological Activities of T Cells Transduced with abTCR-6MD and CAR Constructs Having the Same Anti-Human CD19 Variable Domains In example 4, the antibody moiety used was a TCR-mimic, which binds a peptide/MHC complex as antigen. To demonstrate that abTCR designs also work with traditional antibody targets (cell surface antigens), a similar set of experiments was carried out using constructs based on an antibody against human CD19.

CD19 abTCR-Transduced T Cells can Kill CD19-Positive Cancer Cells

Figure 17:
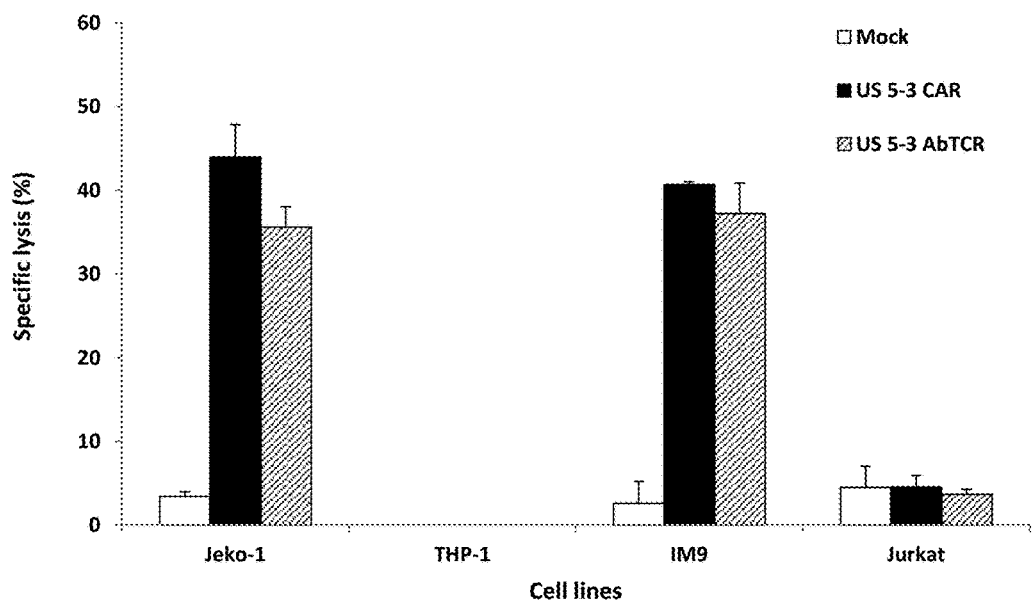
FIG. 17 shows killing of cancer cell lines JeKo-1, IM9, THP-1 and Jurkat, mediated by mock-transduced T cells or T cells transduced with either a CAR or an abTCR-6MD, both having the same anti-CD19 binding moiety variable domains.

Primary T cells were mock-transduced or transduced with lentiviral vectors encoding a CAR containing an anti-CD19 binding domain (SEQ ID NO: 44, comprising a scFv with an IgV$_H$ domain, SEQ ID NO: 45, and an IgV$_L$ domain, SEQ ID NO: 46, from an exemplary anti-CD19 antibody) or an abTCR-6MD containing the same anti-CD19 variable domains (SEQ ID NOs: 42 and 43). T cells transduced with CAR or abTCR (both at 25% transduction rate) were used to test their abilities to kill B cell lines JeKo-1 (CD19$^+$), IM9 (CD19$^+$), Jurkat (CD19$^-$), and THP-1 (CD19$^-$), at an effector-to-target ratio of 5:1. The level of specific killing was measured at 16 hours using the same method as described for FIG. 9B. As shown in FIG. 17, both CAR and abTCR-6MD with an anti-CD19 binding moiety directed killing of CD19-positive JeKo-1 and IM9 cells at similar levels, but did not kill Jurkat and THP-1, which are CD19-negative.

Cytokine Secretion by abTCR and CAR T Cells in Tumor Cell Killing

Figure 18A:
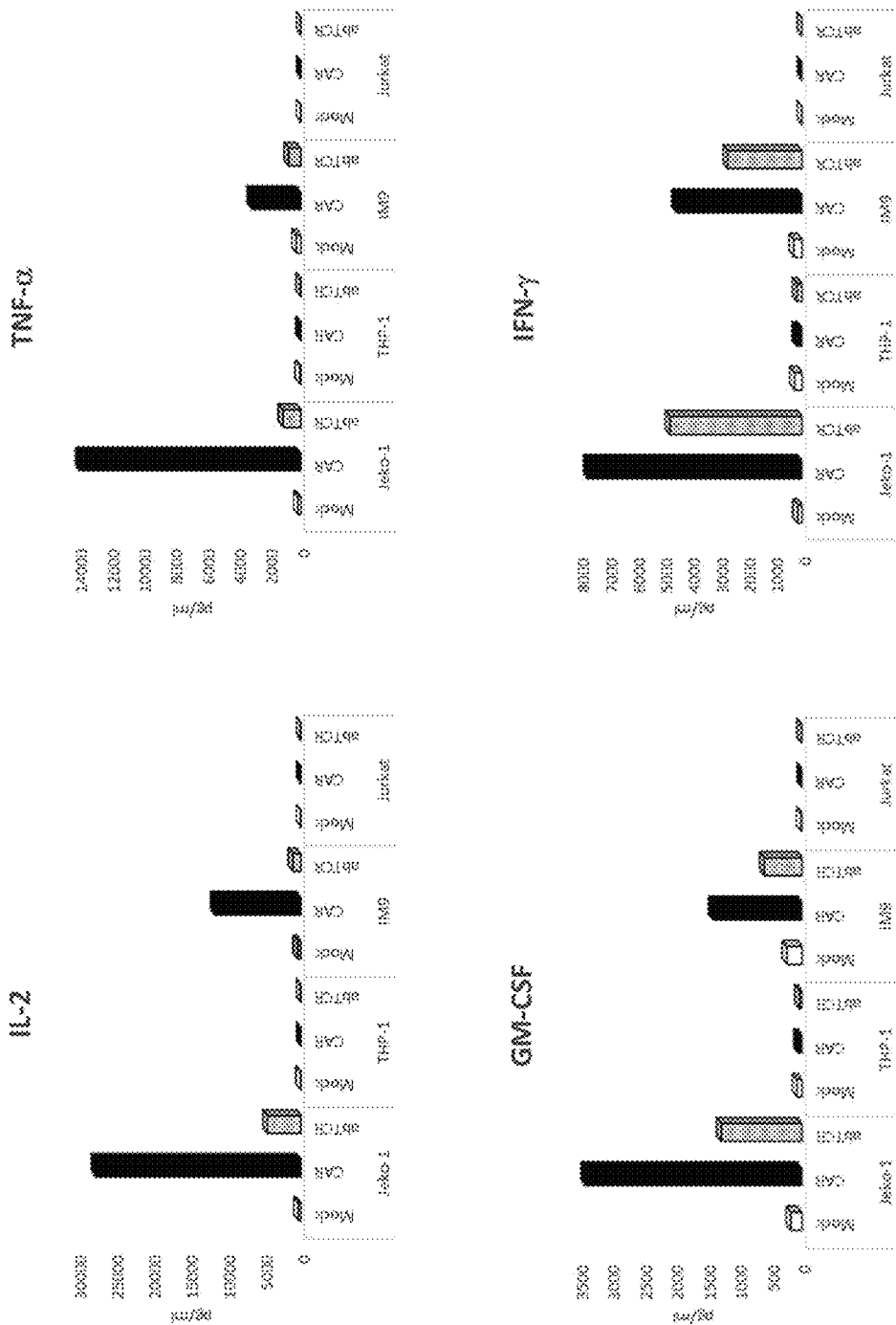

The same transduced T cell populations as used in the cancer killing experiment above were used in a cytokine release assay by co-incubating them with JeKo-1, IM9, THP-1 and Jurkat as target cells. A panel of eight human cytokines (IL-2, IL-4, IL-6, IL-8, IL-10, GM-CSF, IFN-γ, TNF-α) was measured after 16 hours. All cytokines tested were detected in the media of CAR-transduced T cells upon co-incubation with CD19$^+$ target cells, but not CD19$^-$ cells (FIGS. 18A and 18B). In samples co-incubated with abTCR-transduced T cells, the release for all cytokines tested, with the exception of IL-10, was lower in the abTCR samples with CD19$^+$ cells. These findings with the anti-CD19 antibody constructs are similar to those of the anti-AFP158/HLA-A*02:01 antibody constructs: while similar cancer cell killing was observed for CAR-T and abTCR-transduced cells, the level of cytokine release was lower when abTCR-transduced T cells were used. This could be an advantage for using abTCRs in settings where high levels of cytokine release cause undesirable physiological effects.

Figure 19:
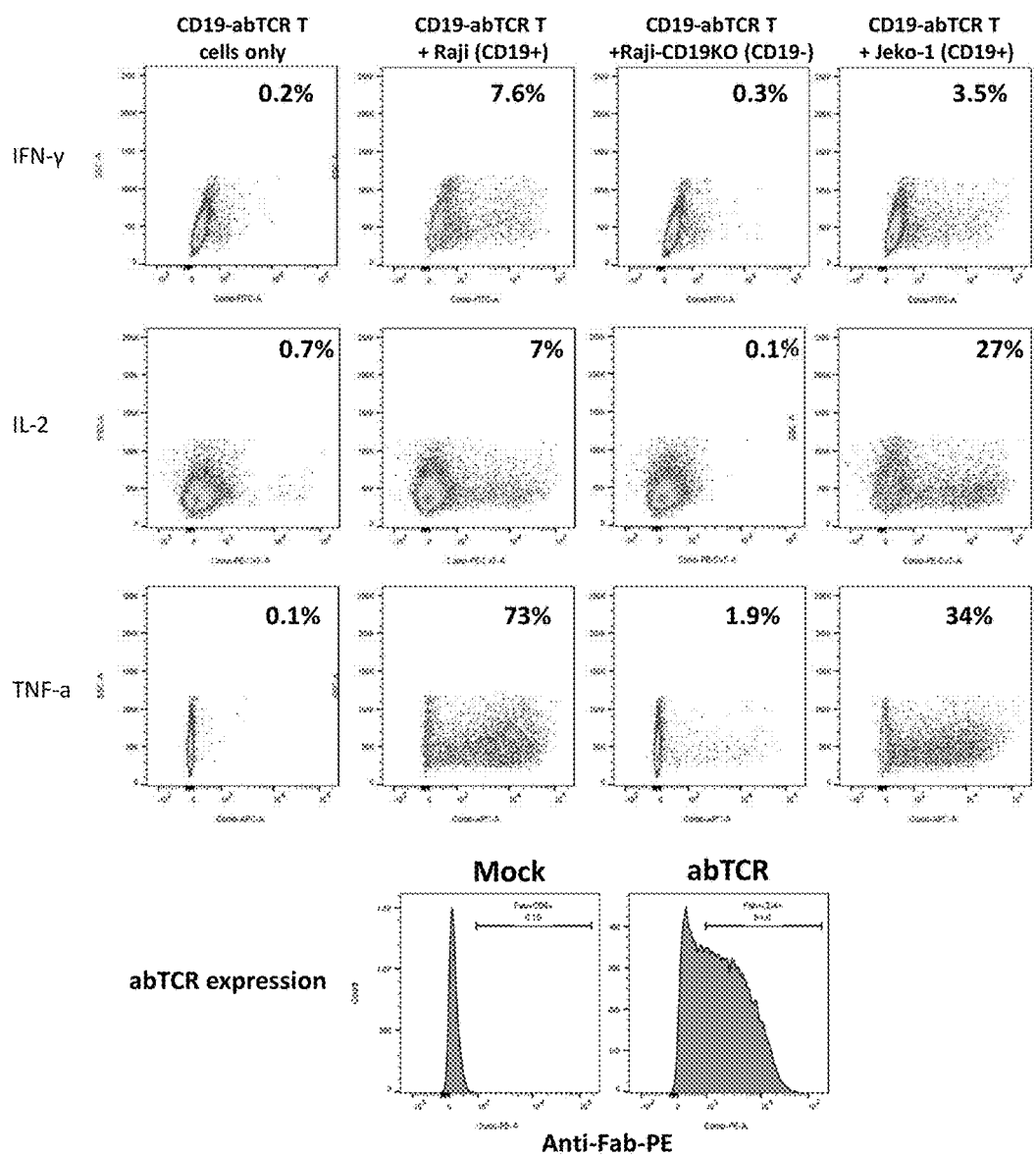
FIG. 19 shows target-specific activation of cytokine expression in CD4+ T cells transduced with an anti-CD19 abTCR and incubated with cancer cell lines positive or negative for CD19 expression.

To determine if the activation of abTCRs in CD4+ T cells could lead to specific biological responses, we investigated the intracellular cytokine expression in CD4$^+$, anti-CD19 abTCR-expressing T cells following stimulation with cancer cell lines expressing CD19. CD3+ T cells were transduced with Clone 5-13 abTCR-6MD (abTCR-6MD having anti-CD19 clone 5-13 binding moiety which comprises amino acid sequences of SEQ ID NOs: 56 and 54) and incubated with cancer cell line Raji (CD19$^+$), Raji-CD19KO (CD19$^-$), or Jeko-1 (CD19$^+$) for 4 hours in the presence of protein transporter inhibitor. As a negative control, abTCR-transduced T cells were incubated in the absence of any cancer cell line. After the incubation, the T cells were stained with anti-IFNγ, anti-IL2, or anti-TNFα antibodies, and co-stained with anti-human Fab (CD19) and anti-CD4. Cells gated for abTCR expression were analyzed by flow cytometry for granularity and cytokine expression (FIG. 19, Y-axis is side scattering, X-axis is cytokine staining). The expression of IFNγ, IL2, and TNFα was induced following incubation of the anti-CD19 abTCR-transduced T cells with CD19$^+$ cancer cell lines Raji and Jeko-1, but not when incubated with CD19$^-$ cell line Raji-CD19KO or in the absence of any cancer cell line, indicating the antigen-specific activation of the abTCR in CD4+ T cells.

Expression of T Cell Exhaustion Markers in abTCR and CAR T Cells after Co-Culture with Target Cells The level of exhaustion markers expressed on anti-CD19 abTCR- and CAR-transduced cells upon antigen stimulation was determined as described above for anti-AFP158 chimeric receptors. The cells were transduced with Clone 5-13 abTCR-6MD or a CAR containing the same anti-CD19 variable domains. Target cell lines included Raji (CD19+), Raji-CD19KO (CD19−), and Jeko-1 (CD19+). The percent of cells positive for each of the exhaustion markers in the tested conditions was determined and is shown in Table 3.

TABLE 3

| Target cell lines | T cell subset | PD1 (%) CAR | PD1 (%) abTCR | TIM3 (%) CAR | TIM3 (%) abTCR | LAG3 (%) CAR | LAG3 (%) abTCR |
|---|---|---|---|---|---|---|---|
| Raji | CD8 | 14 | 4.0 | 47 | 37 | 95 | 93 |
|  | CD4 | 74 | 41 | 29 | 24 | 65 | 47 |
| Raji-CD19 KO | CD8 | 2.9 | 0.3 | 54 | 35 | 40 | 29 |
|  | CD4 | 27 | 7.0 | 12 | 13 | 5.3 | 4.1 |
| Jeko-1 | CD8 | 14 | 4.7 | 48 | 40 | 92 | 76 |
|  | CD4 | 70 | 33 | 36 | 30 | 58 | 31 |
| T cell only | CD8 | 1.7 | 0.2 | 5.1 | 9.8 | 9.4 | 5.6 |
|  | CD4 | 15 | 2.2 | 0.3 | 1.0 | 1.1 | 1.0 |

Expression of T Cell Differentiation Markers in abTCR and CAR T Cells

Figure 20:
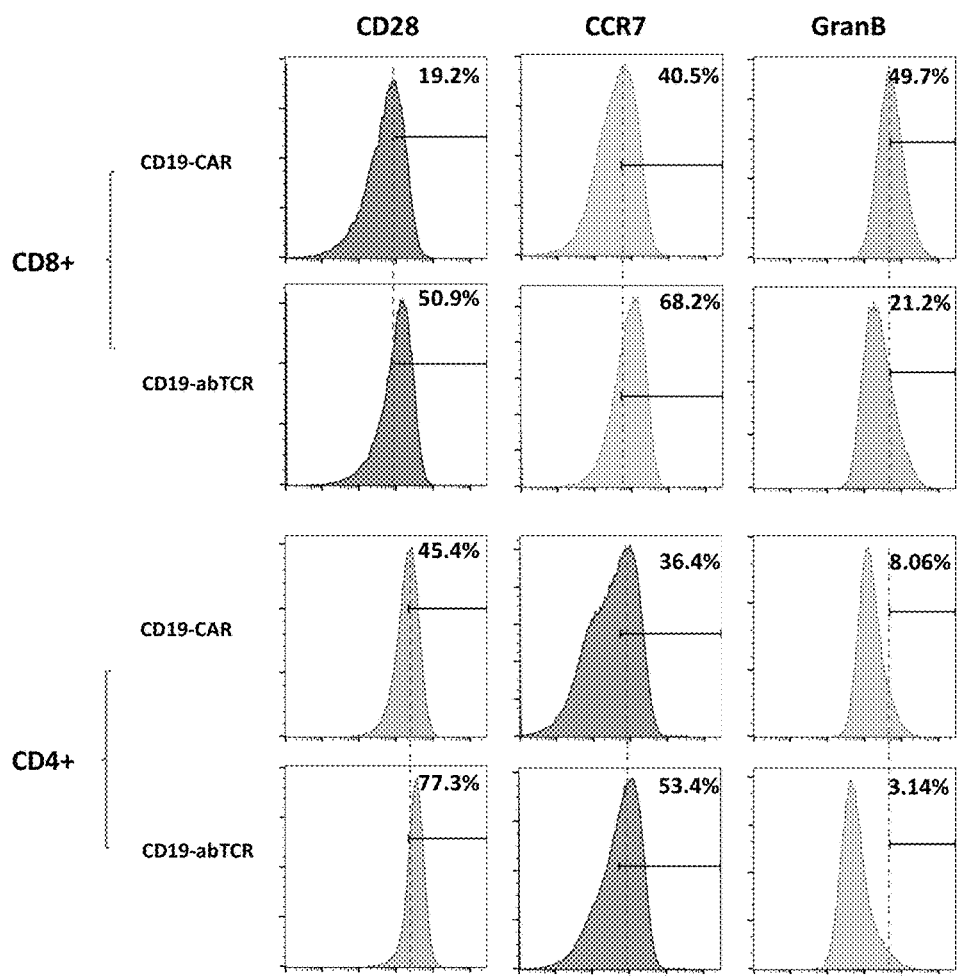
FIG. 20 shows flow cytometry analysis of T cell differentiation markers CD28, CCR7 and granzyme B on CAR- or abTCR-transduced T cells, both having the same anti-CD19 binding moiety variable domains, upon exposure to antigen-positive or -negative target cells.

To determine if anti-CD19 abTCRs can delay the differentiation of T cells during in vitro expansion, we measured the cell surface expression of three T cell differentiation markers, memory T cell markers CCR7 and CD28, and terminal differentiation marker Granzyme B. T cells were transduced with Clone 5-13 abTCR-6MD or a CAR having the same anti-CD19 variable domains, stained with antibodies against these markers, and analyzed by flow cytometry at day 10-12 after viral transduction (FIG. 20). The results show that for both CD4$^+$ and CD8$^+$ T cells, the abTCR T cells expressed more CCR7 and CD28, but less Granzyme B, than the CAR T cells, suggesting that the Clone 5-13 abTCR T cells were less differentiated than the corresponding CAR T cells after T cell expansion in vitro, in agreement with what was observed for anti-AFP158 chimeric receptors.

Proliferation of abTCR and CAR T Cells

Figure 21:
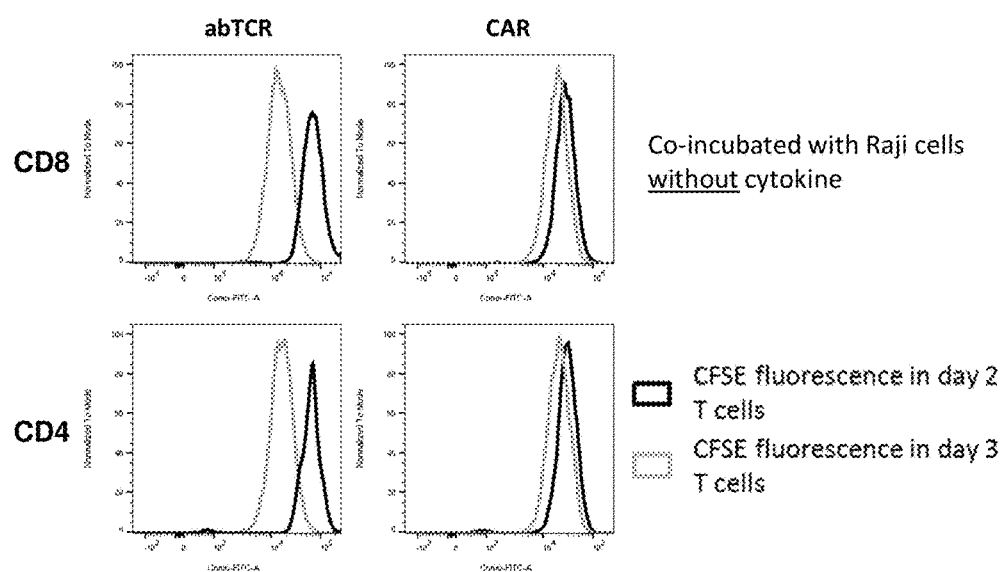
FIG. 21 shows proliferation of CAR- or abTCR-transduced CD4$^+$ or CD8$^+$ T cells, both chimeric receptors having the same anti-CD19 binding moiety variable domains, during exposure to antigen-positive target cells, as assessed by dye dilution from day 2 to day 3 following initiation of exposure.

To further determine if abTCR T cells are less differentiated and have higher proliferation potential than CAR T cells, we monitored the change in CFSE fluorescence, an indicator of cell division, of abTCR and CAR T cells after their engagement with antigen-positive cancer cells. The T cells were labeled with CFSE dye at day 10 after viral transduction with Clone 5-13 abTCR-6MD or a CAR having the same anti-CD19 variable domains, and baseline fluorescence was recorded by flow cytometry. The labeled T cells were incubated with Raji cells (a CD19+ cancer cell line) in cytokine-free medium. The CFSE fluorescence was measured by flow cytometry at day 2 and day 3 for CD4+ and CD8+ T cells (FIG. 21). The decrease in CFSE fluorescence intensity between day 2 and day 3, indicating amount of cell proliferation, was significantly higher in abTCR T cells than CAR T cells, indicating that the Clone 5-13 abTCR T cells undergo more cell divisions than the corresponding CAR T cells.

Chimeric Receptor Internalization of abTCR and CAR T Cells

Figure 22:
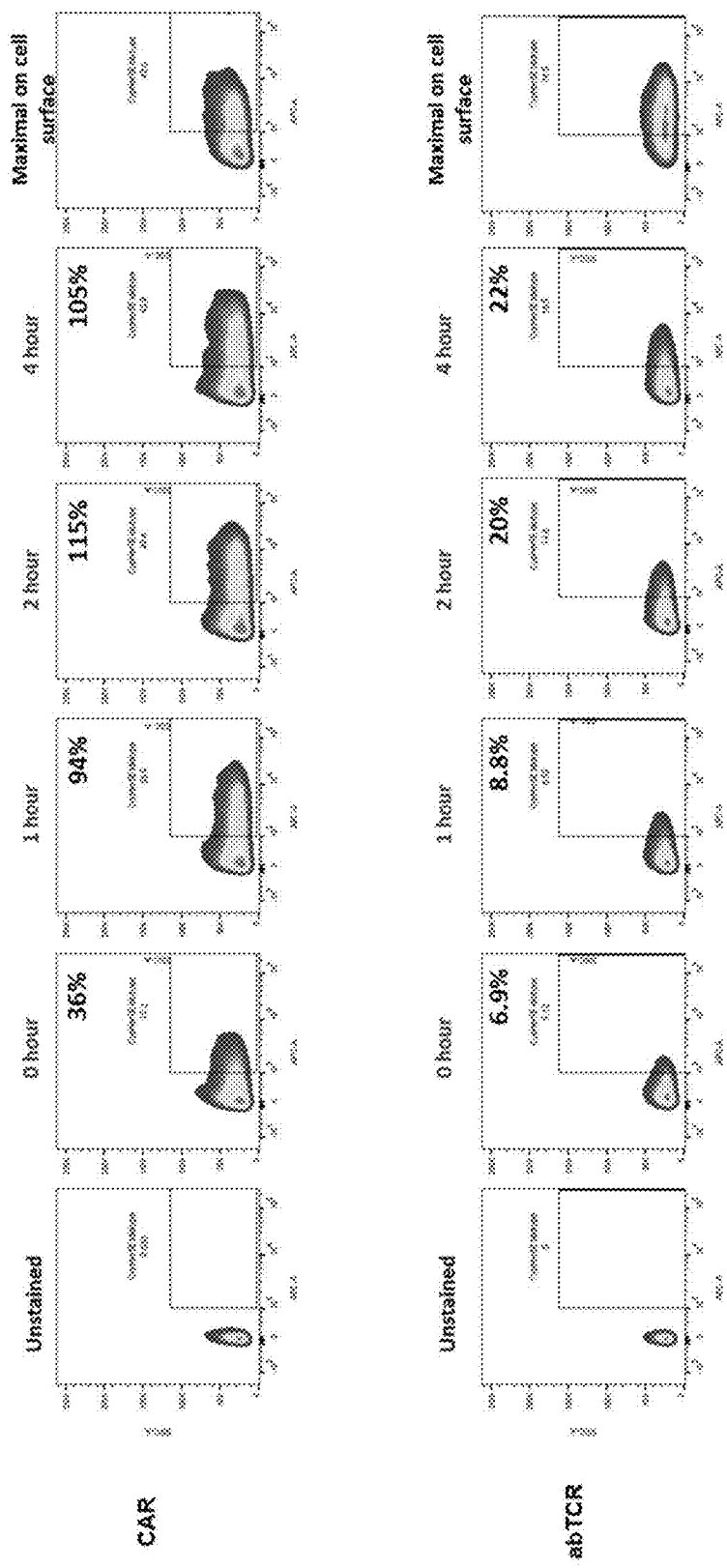
FIG. 22 shows internalization of chimeric receptors on CAR- or abTCR-transduced T cells, both chimeric receptors having the same anti-CD19 binding moiety variable domains, at the indicated time points as assessed by flow cytometry analysis of cells stained for surface chimeric receptors with an anti-idiotype antibody targeting the anti-CD19 binding moiety.

To compare the internalization rate of T cell surface abTCRs and CARs, T cells were transduced with Clone 5-13 abTCR-6MD or a CAR containing the same anti-CD19 variable domains, and stained on ice for 30 minutes with an anti-idiotype antibody recognizing the anti-CD19 binding moiety labeled with CypHer5E, a pH sensitive dye that emits fluorescence at acidic pH 6.5. The cells were then incubated at 37° C. for the indicated amount of time, fixed, and analyzed by flow cytometry for granularity and chimeric receptor expression (FIG. 22, Y-axis is side scattering, X-axis is CypHer5E staining). The results show that almost all the CAR was internalized by 90 minutes after staining. In contrast, the abTCR was internalized at a much slower rate, and most of the abTCR remained on the cell surface even at 90 minutes.

Comparison of Anti-CD19 abTCR and cTCR Constructs

Figure 23A:
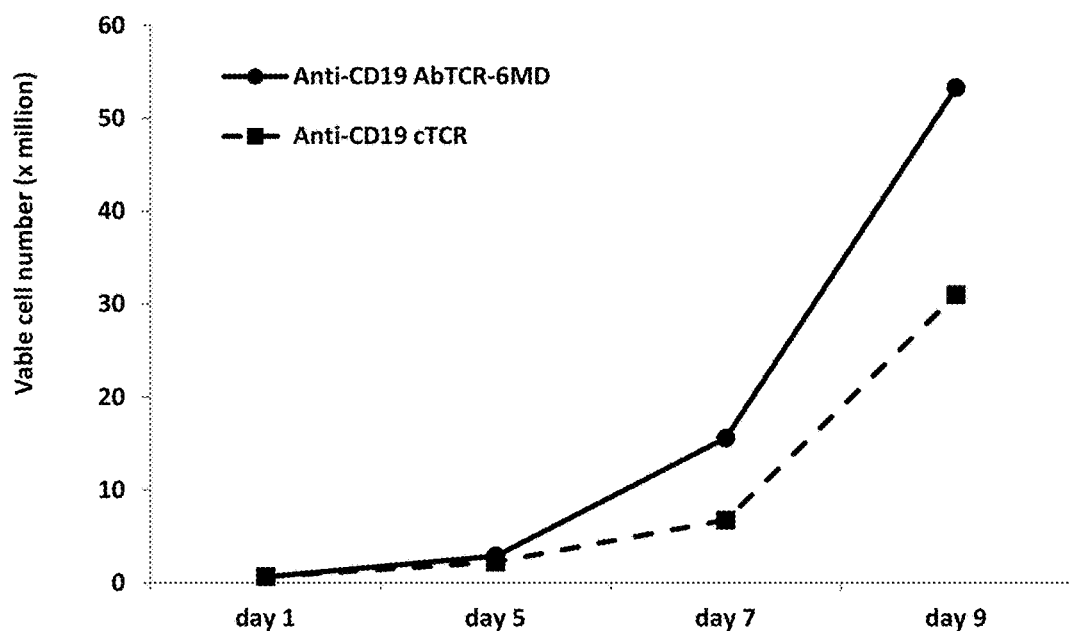
FIGS. 23A and 23B show the characterization of T cells transduced with either an abTCR (anti-CD19 abTCR-6MD) or cTCR (anti-CD19-cTCR), both having the same anti-CD19 binding moiety variable domains.

The cell growth of primary T cells transduced to express an anti-CD19 abTCR-6MD was compared with that of T cells transduced with an anti-CD19 chimeric construct (cTCR) having the same antibody variable domains and transmembrane domains but with constant regions from TCRδ and TCRγ polypeptides. 6.7×10$^5$ T cells were activated by αCD3/αCD28 beads (1:1 ratio) in the presence of 100 U/ml IL-2 on day 0. Activated T cells were transduced with either a lentiviral vector encoding the anti-CD19 abTCR-6MD (TCRδ chimera subunit having the amino acid sequence of SEQ ID NO: 56 and TCRγ chimera subunit having the amino acid sequence of SEQ ID NO: 54) or a lentiviral vector encoding the anti-CD19 cTCR (TCRδ chimera subunit having the amino acid sequence of SEQ ID NO: 75 and TCRγ chimera subunit having the amino acid sequence of SEQ ID NO: 76) at MOI 4 on day 1. Transduced T cells were then cultured and expanded in the presence of IL-2 for 9-10 days. Cell numbers were counted on day 1, day 5, day 7, and day 9. As shown in FIG. 23A, the abTCR-transduced T cells grew faster than the cTCR-transduced T cells, with more than 1.7 times as many viable cells counted at day 9.

Figure 23B:
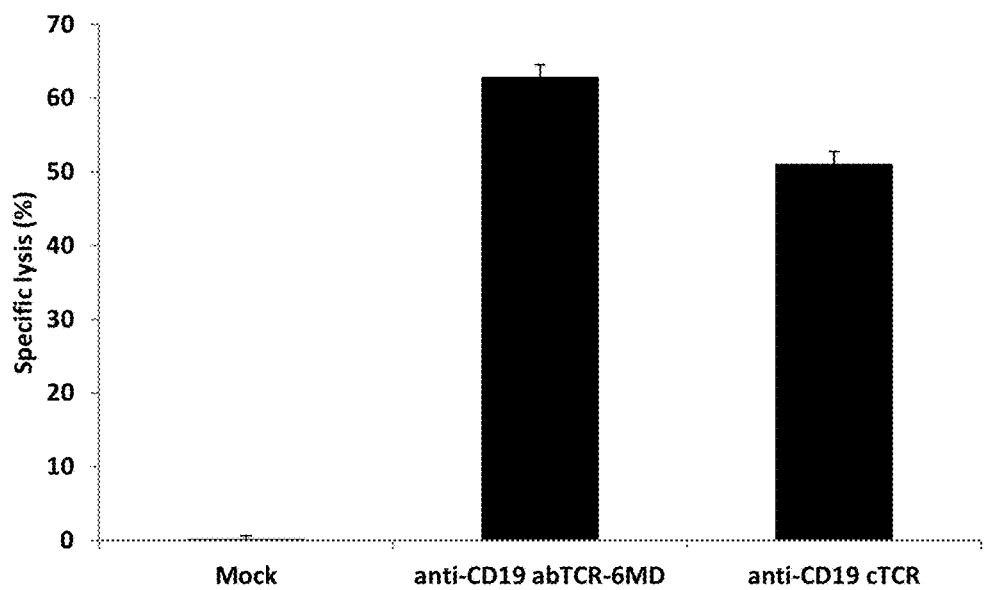

The target-cell killing activity of the anti-CD19 abTCR T cells was compared to that of the anti-CD19 cTCR T cells. Primary T cells were mock-transduced or transduced with lentiviral vectors encoding either the anti-CD19 abTCR-6MD or the anti-CD19 cTCR. T cells transduced with the abTCR or cTCR were tested for their ability to kill CD19-positive target cell line Nalm-6 at an effector-to-target ratio of 5:1. The level of specific killing was measured at 16 hours as described above. As shown in FIG. 23B the abTCR-6MD construct with the anti-CD19 binding moiety directed greater specific lysis of CD19-positive Nalm-6 cells than the cTCR with the same anti-CD19 variable domains.

Figure 24:
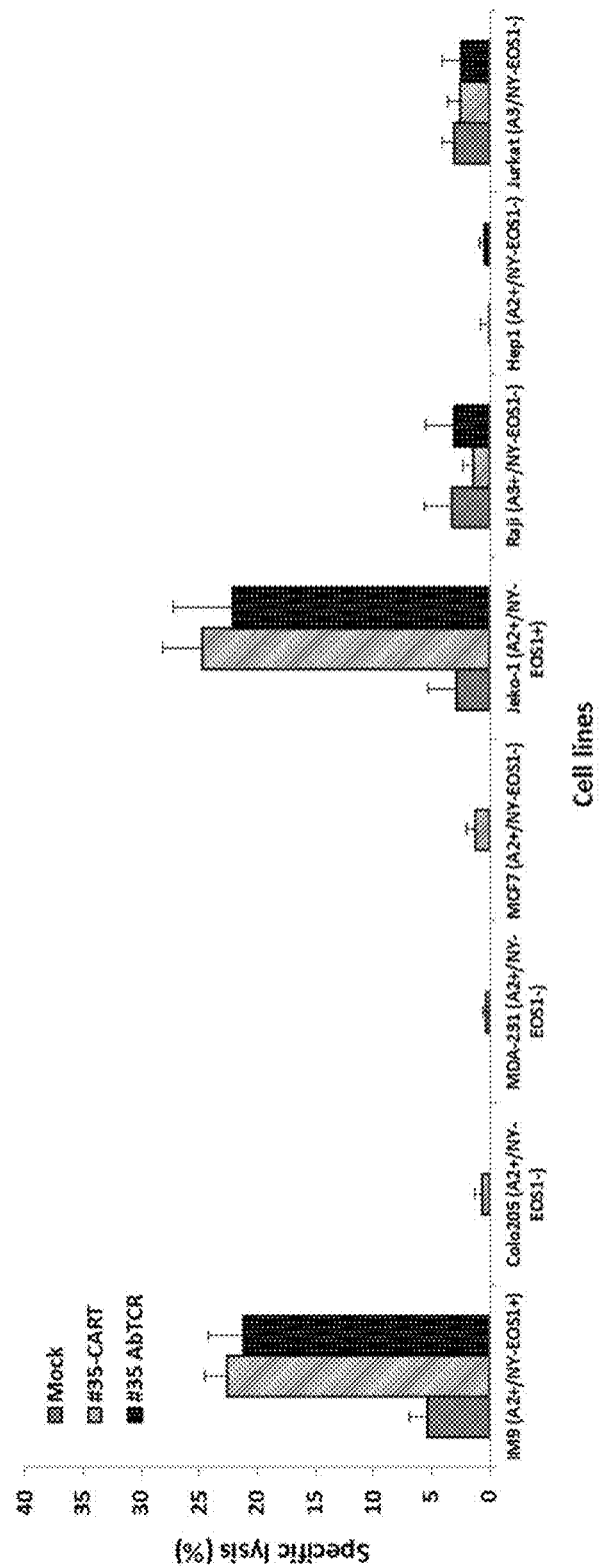
FIG. 24 shows killing of cancer cell lines IM9, Colo205, MDA-231, MCF7, JeKo-1, Raji, Hep1, and Jurkat, mediated by mock-transduced T cells or T cells transduced with either a CAR (#35 CAR) or an abTCR-6MD (#35 abTCR), both having the same anti-NY-ESO-1 binding moiety variable domains.

Example 6. Characterizing Biological Activities of T Cells Transduced with abTCR-6MD and CAR Constructs Having the Same Anti-NY-ESO-1/HLA-A*02:01 Variable Domains Anti-NY-ESO-1/HLA-A*02:01 abTCR-Transduced T Cells can Kill NY-ESO-1-Positive Cancer Cells Primary T cells were mock-transduced or transduced to express either a CAR or abTCR-6MD containing an anti-NY-ESO-1/HLA-A*02:01 binding moiety comprising an IgV$_L$ domain having the amino acid sequence of SEQ ID NO: 73 and an IgV$_H$ domain having the amino acid sequence of SEQ ID NO: 72. The CAR comprised an scFv having, from N-terminus to C-terminus, the IgV$_L$ domain, a linker (SEQ ID NO: 74), and the IgV$_H$ domain. T cells transduced with the CAR or abTCR expressed their respective chimeric receptor at similar levels as assayed by flow cytometry and were used to test their abilities to kill cell lines IM9 (HLA-A2$^+$, NY-ESO-1$^+$), Colo205 (HLA-A2$^+$, NY-ESO-1$^-$), MDA-231 (HLA-A2$^+$, NY-ESO-1$^-$), MCF7 (HLA-A2$^+$, NY-ESO-1$^-$), JeKo-1 (HLA-A2$^+$, NY-ESO-1$^+$), Raji (HLA-A2$^+$, NY-ESO-1$^-$), Hep1 (HLA-A2$^+$, NY-ESO-1$^-$), and Jurkat (HLA-A2$^+$, NY-ESO-1$^-$) at an effector-to-target ratio of 5:1. The level of specific killing was measured at 16 hours using the same methods described above. As shown in FIG. 24, both the CAR and abTCR-6MD with the anti-NY-ESO-1/HLA-A*02:01 binding moiety directed killing of NY-ESO-1-positive JeKo-1 and IM9 cells at similar levels, but did not kill the other cells, which are NY-ESO-1-negative.

Cytokine Secretion by abTCR and CAR T Cells in Tumor Cell Killing

The same transduced T cell populations as used in the cancer killing experiment above were used in a cytokine release assay by co-incubating them with IM9, Colo205, MDA-231, MCF7, JeKo-1, Hep1, and Jurkat cells. A panel of four human cytokines (IL-2, GM-CSF, IFN-γ, TNF-α) was measured after 16 hours. All cytokines tested were detected in the media of CAR- and abTCR-transduced T cells upon co-incubation with NY-ESO-1$^+$ target cells, but not most NY-ESO-1$^-$ cells (data not shown). Importantly, the levels of cytokines released from most of the tested NY-ESO-1$^+$ target cells by abTCR-transduced T cell co-incubation were significantly lower than by CAR-transduced T cell co-incubation (data not shown).

Figure 25A:
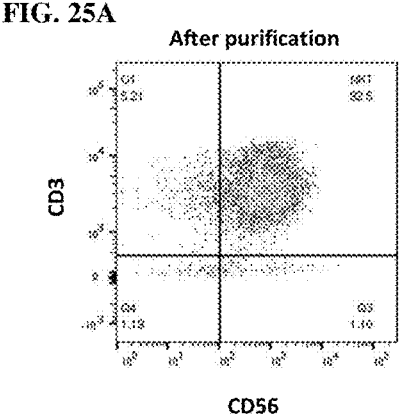
FIG. 25A shows flow cytometry analysis of the expression of CD3 and CD56 on a subset of NKT cells purified from human PBMCs.
Figure 25B:
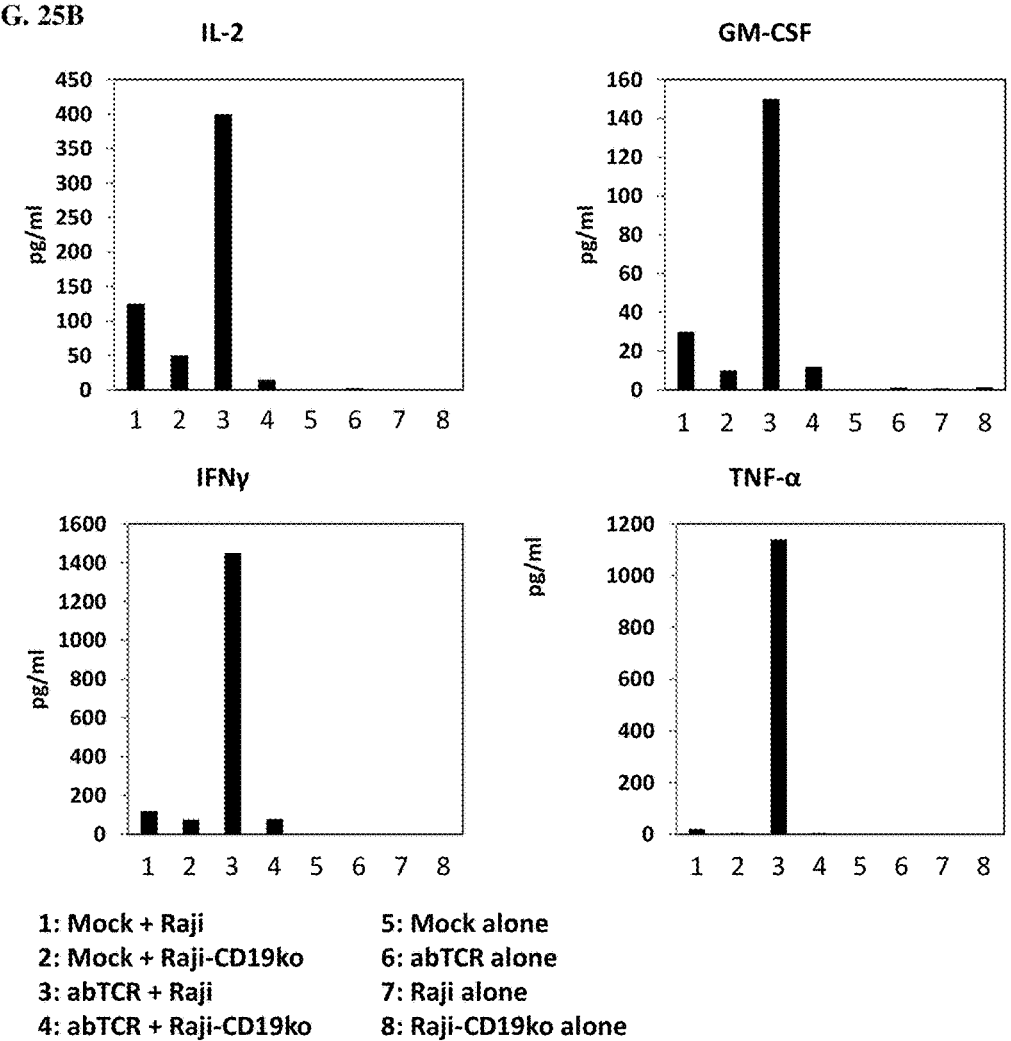
FIG. 25B shows the level of secretion of cytokines IL-2, GM-CSF, IFNγ, and TNFα by mock-transduced T cells or T cells transduced with an abTCR-6MD having an anti-CD19 binding moiety, co-cultured with Raji or Raji-CD19ko cell lines. Controls included mock-transduced or abTCR-transduced T cells alone, and Raji or Raji-CD19ko cells alone.

Example 7. Characterizing Biological Activities of Natural Killer T (NKT) Cells and Regulatory T (Treg) Cells Transduced with abTCR-6MD Constructs anti-CD19 abTCR-Transduced NKT Cells NKT cells were isolated from human PBMCs by indirect magnetic labelling of non-CD3$^+$/CD56$^+$ cells (non-NKT cells) with a biotin-antibody cocktail and anti-biotin microbeads, and depleting the non-NKT cells to enrich for CD3$^+$/CD56$^+$ NKT cells. The surface expression of CD3 and CD56 for the enriched NKT cell population was assessed by flow cytometry and is shown in FIG. 25A. The NKT cells were activated by anti-CD3/anti-CD28 beads, transduced with lentivirus encoding the anti-CD19 abTCR, and expanded in RPMI-1640 containing 10% FBS and IL-2 (100 U/ml). Transduction efficiency was greater than 80% as measured by flow cytometry with an anti-idiotype antibody specific for the anti-CD19 binding moiety. The NKT cells were co-incubated with CD19-expressing Raji or Raji CD19-knockout (CD19ko) cancer cell lines at an effector-to-target ratio of 5:1 for 16 hours followed by measurement of cytokine release (IL-2, GM-CSF, IFNγ, TNFα) in the media (FIG. 25B). The anti-CD19 abTCR-transduced NKT cells, but not mock-transduced NKT cells, were activated to release each of the cytokines tested when incubated with the CD19-positive Raji cells, but not the CD19-negative Raji CD19ko cells, indicating that NKT cells can be specifically activated through binding of the transduced abTCR with the CD19 antigen on cancer cells.

Anti-CD19 abTCR-Transduced Treg Cells

Figure 26A:
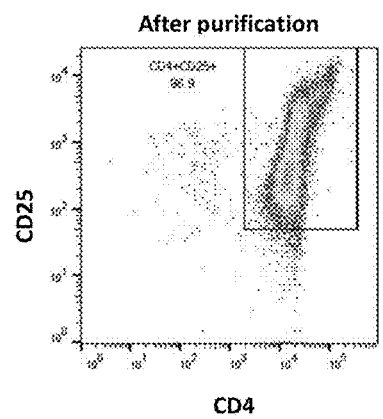
FIG. 26A shows flow cytometry analysis of the expression of CD25 and CD4 on a subset of Treg cells purified from human PBMCs.
Figure 26B:
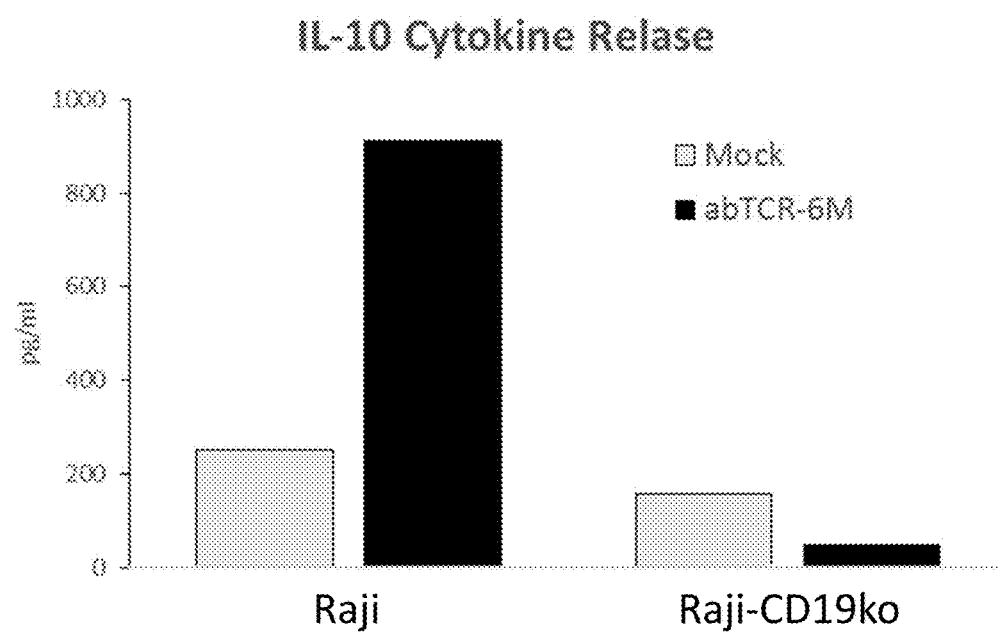
FIG. 26B shows the level of secretion of cytokines IL-2, GM-CSF, IFNγ, and TNFα by mock-transduced T cells or T cells transduced with an abTCR-6MD having an anti-CD19 binding moiety, co-cultured with Raji or Raji-CD19ko cell lines.

Treg cells were isolated from human PBMCs by direct magnetic labelling of CD4+/CD25+ Treg cells. The surface expression of CD4 and CD25 for the isolated Treg cell population was assessed by flow cytometry and is shown in FIG. 26A. The Treg cells were activated by anti-CD3/anti-CD28 beads, transduced with lentivirus encoding the anti-CD19 abTCR, and expanded in RPMI-1640 containing 10% FBS and IL-2 (100 U/ml). Transduction efficiency was 80% as measured by flow cytometry with an anti-idiotype antibody specific for the anti-CD19 binding moiety. The Treg cells were co-incubated with CD19-expressing Raji or Raji CD19-knockout (CD19ko) cancer cell lines at an effector-to-target ratio of 5:1 for 16 hours followed by measurement of IL-10 cytokine release in the media (FIG. 26B). The anti-CD19 abTCR-transduced Treg cells, but not mock-transduced Treg cells, were activated to release IL-10 when incubated with the CD19-positive Raji cells, but not the CD19-negative Raji CD19ko cells, indicating that Treg cells can be specifically activated through binding of the transduced abTCR with the CD19 antigen on cancer cells.

Figure 27:
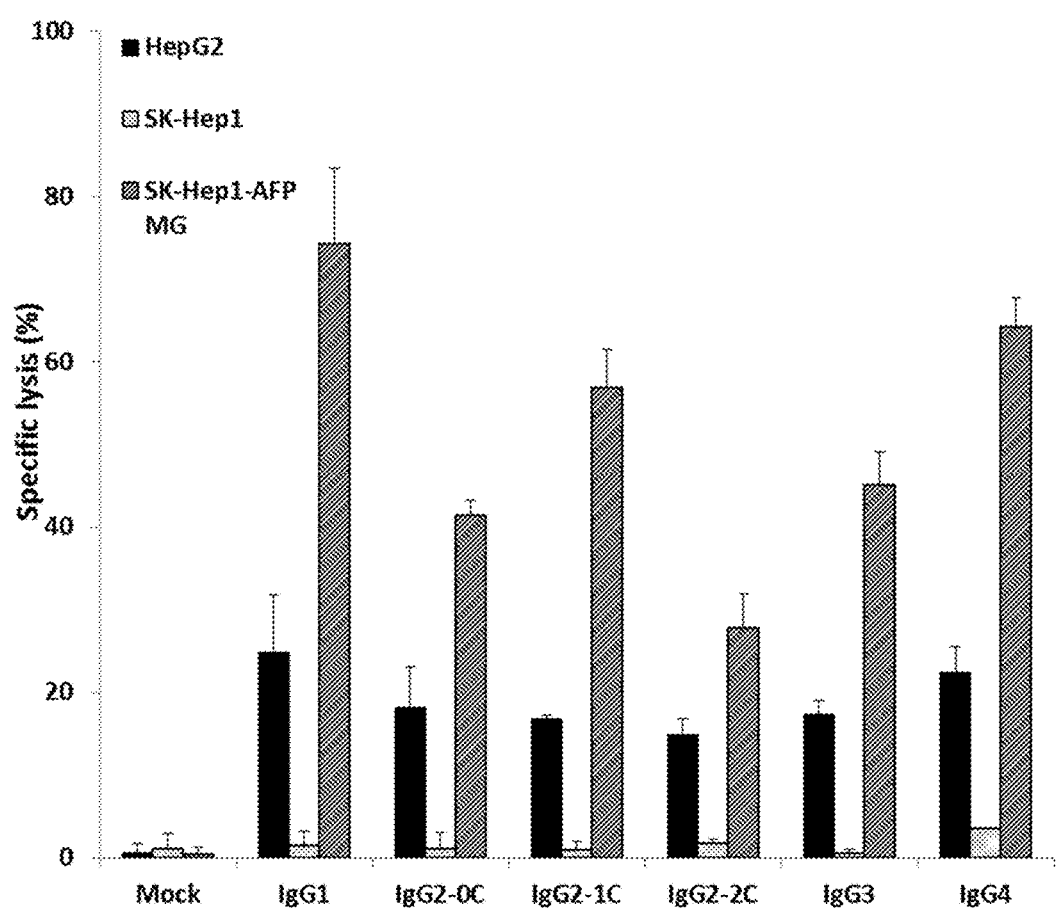
FIG. 27 shows killing of cancer cell lines HepG2, SK-Hep1, and SK-Hep1-AFP MG, mediated by mock-transduced T cells or T cells transduced with abTCRs having various immunoglobulin CH1 domains, each having the same anti-AFP binding moiety.

Example 8. Characterizing Biological Activities of T Cells Transduced with abTCRs Having Different Antibody Heavy Chain Constant Domains In the previous examples, the antibody moieties used in the abTCR constructs contained an IgG1 CH1 domain having the amino acid sequence of SEQ ID NO: 39. To demonstrate that abTCR designs also work with CH1 domains from other immunoglobulin heavy chains, target-cell killing assays were carried out as described above using constructs based on an anti-AFP158/HLA-A*02:01 antibody having CH1 domains from either IgG1 (SEQ ID NO: 39), IgG2 (SEQ ID NO: 60, 61, or 62), IgG3 (SEQ ID NO: 63), or IgG4 (SEQ ID NO: 64). T cells transduced with the abTCRs were assayed for AFP158 tetramer binding as an indication of surface expression (Table 4) and tested for their ability to kill HepG2 (AFP+/HLA-A2+), SK-HEP-1 (AFP-/HLA-A2+), and SK-HEP-1-AFP-MG (SK-HEP-1 transduced with an AFP minigene) cells. Specific lysis was measured after 16 hr incubation using the Cytox 96 Non-radioactive Cytotoxicity Assay (Promega). As shown in FIG. 27, T cells transduced with any of the abTCRs bearing the anti-AFP158/HLA-A*02:01 binding moiety directed killing of antigen-positive cell lines HepG2 and SK-HEP-1-AFP-MG, but did not lead to killing of antigen-negative cell line SK-HEP-1. Importantly, even though surface expression of the abTCRs containing non-IgG1 CH1 domains was lower compared to the abTCR containing IgG1 CH1 (see Table 4), they resulted in similar levels of target cell killing, suggesting they may have enhanced functional properties.

TABLE 4

| abTCR surface expression | |
|---|---|
| abTCR | AFP158 tetramer+ (percent) |
| Mock | 0.3 |
| IgG1 | 64.5 |
| IgG2-0C | 9.58 |
| IgG2-1C | 18.2 |
| IgG2-2C | 7.36 |
| IgG3 | 13.6 |
| IgG4 | 22.2 |

Figure 28:
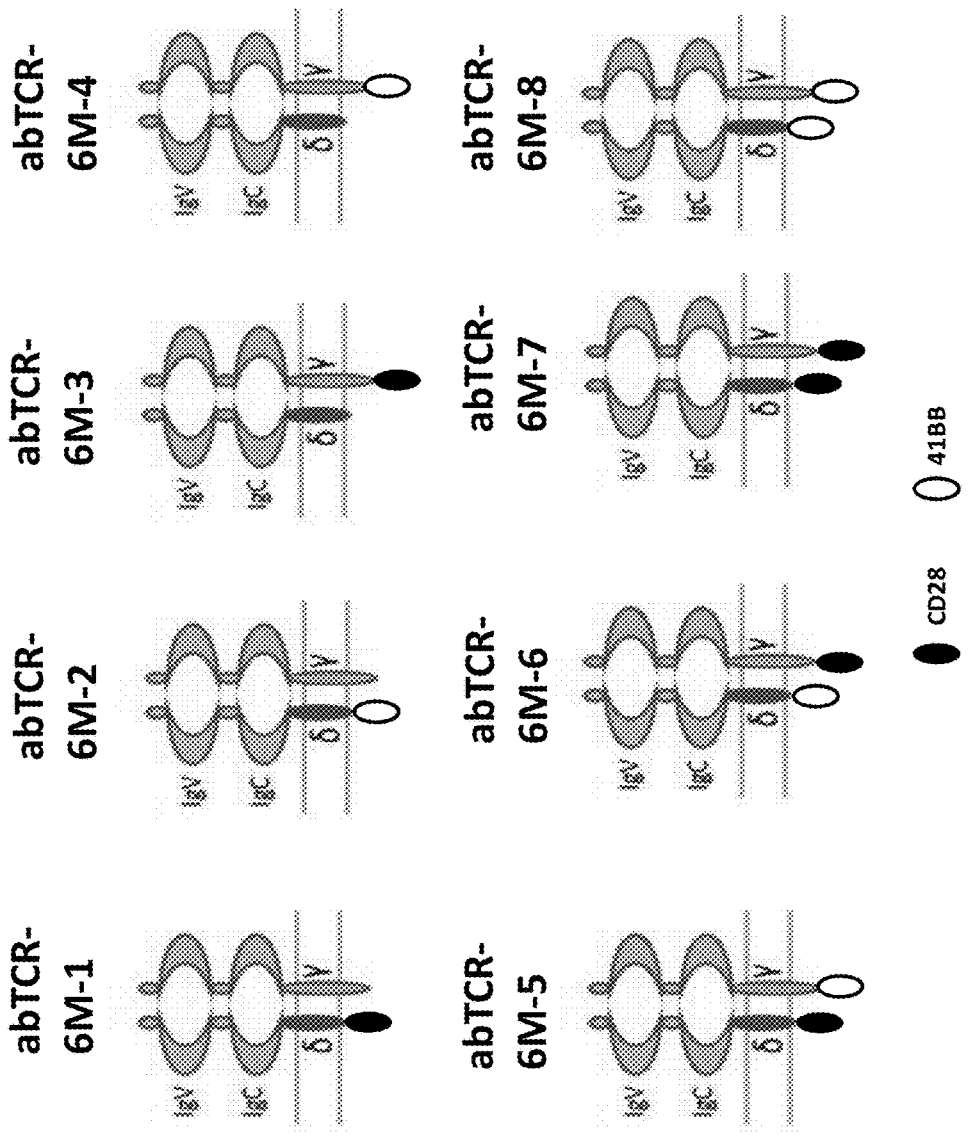
FIG. 28 shows a schematic representation of the various abTCR construct designs containing one or more co-stimulatory domains (abTCR-6M-1, abTCR-6M-2, abTCR-6M-3, abTCR-6M-4, abTCR-6M-5, abTCR-6M-6, abTCR-6M-7, abTCR-6M-8).
Figure 29:
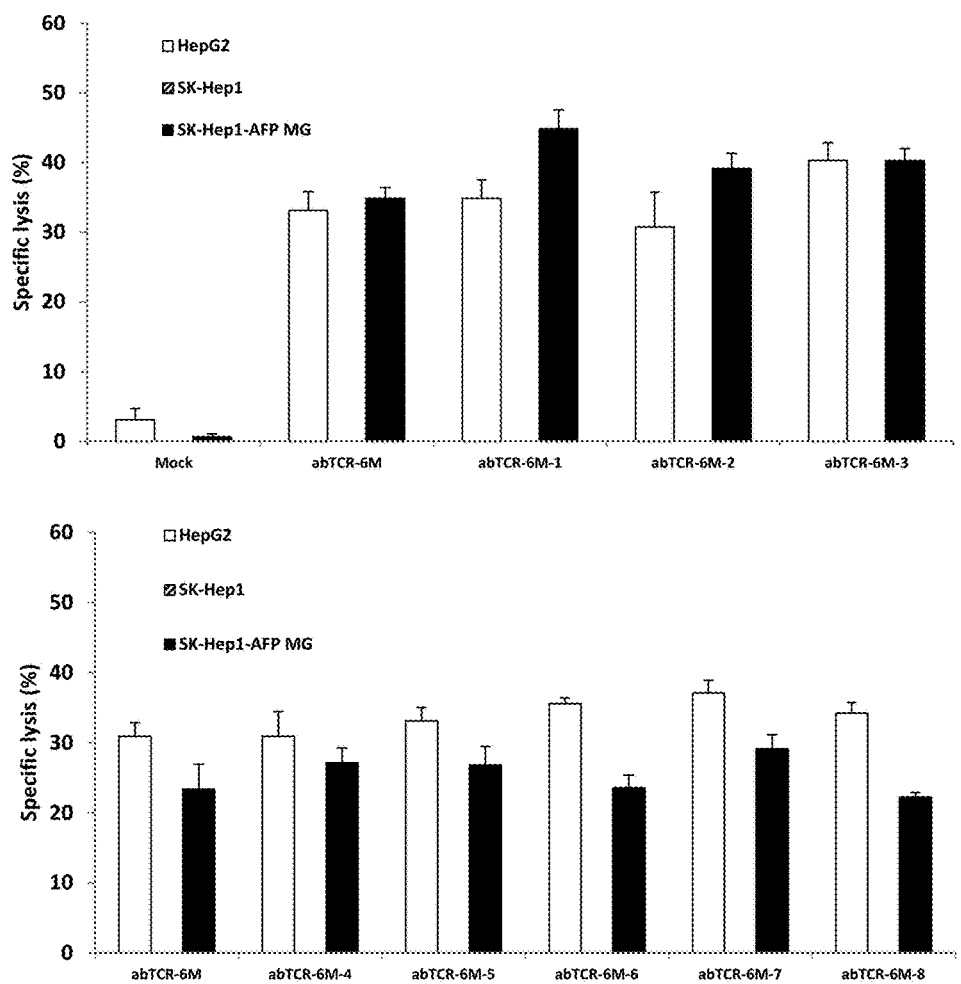
FIG. 29 shows killing of cancer cell lines HepG2, SK-Hep1, and SK-Hep1-AFP MG, mediated by mock-transduced T cells or T cells transduced with various abTCRs having one or more C-terminal co-stimulatory domains, each having the same anti-AFP binding moiety.

Example 9. Characterizing Biological Activities of T Cells Transduced with abTCRs Containing Co-Stimulatory Domains To demonstrate the feasibility of abTCR designs including C-terminal co-stimulatory domains, various anti-AFP158/HLA-A*02:01 abTCR constructs were designed using co-stimulatory fragments derived from CD28 and/or 4-1BB (FIG. 28). The abTCRs consisted of a TCRγ chimeric subunit containing the amino acid sequence of SEQ ID NO: 36 and a TCRδ chimeric subunit containing the amino acid sequence of SEQ ID NO: 35. The abTCR subunits having a CD28 co-stimulatory domain had the amino acid sequence of SEQ ID NO: 70 fused to their C-terminus, and subunits having a 4-1BB co-stimulatory domain had the amino acid sequence of SEQ ID NO: 71 fused to their C-terminus. The abTCR constructs were transduced into J.RT3-R3.5 cells, and abTCR expression and CD3 surface expression rescue was assayed as described above using flow cytometry. The results are summarized in Table 5. The expression of the abTCRs and their ability to rescue CD3 expression was similar between the various abTCR constructs with and without co-stimulatory domains. In another experiment, primary T cells were transduced with the abTCR constructs and assayed by flow cytometry for CD8 expression and AFP158 tetramer binding (Table 6). Primary T cells transduced with the abTCRs were gated for AFP158 tetramer binding and either CD4 or CD8 expression and assayed by flow cytometry for expression of CCR7, CD45RA, CD28, and Granzyme B (Table 7). These results show that viral transduction and differentiation of transduced T cells was similar between the various abTCR constructs with and without co-stimulatory domains. Target-cell killing assays were carried out as described above using the abTCR constructs. T cells transduced with the abTCRs were assayed for their ability to kill HepG2 (AFP+/HLA-A2+), SK-HEP-1 (AFP-/HLA-A2+), and SK-HEP-1-AFP-MG (SK-HEP-1 transduced with an AFP minigene) cells. As shown in FIG. 29, T cells transduced with any of the abTCRs directed killing of antigen-positive cell lines HepG2 and SK-HEP-1-AFP-MG, but did not lead to killing of antigen-negative cell line SK-HEP-1.

Figure 30:
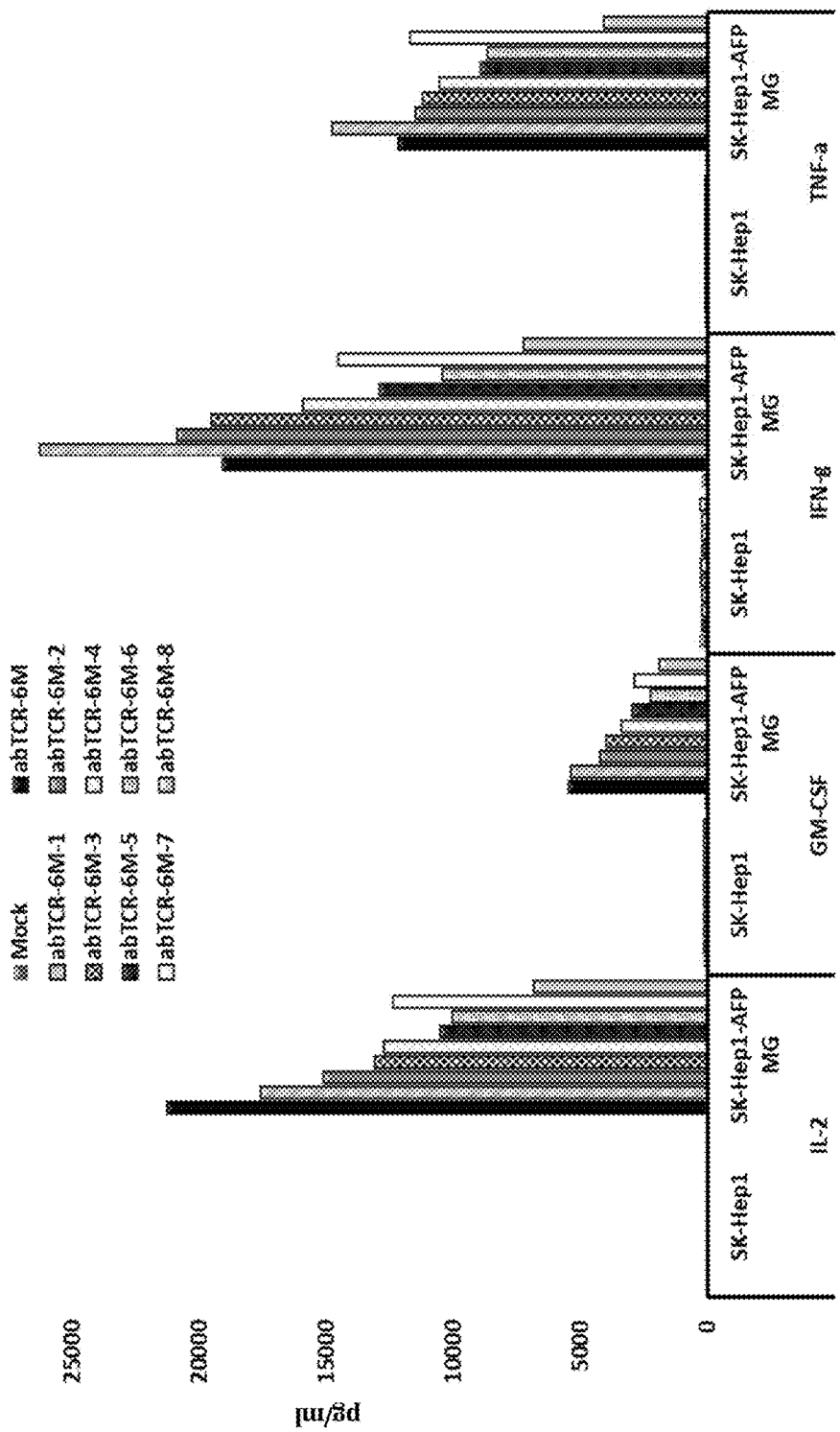
FIG. 30 shows the level of secretion of cytokines IL-2, GM-CSF, IFNγ, and TNFα by mock-transduced T cells or T cells transduced with various abTCRs having one or more C-terminal co-stimulatory domains, each having the same anti-AFP binding moiety, co-cultured with SK-Hep1 or SK-Hep1-AFP MG cell lines.

To further characterize the abTCR constructs containing co-stimulatory domains, T cells transduced with the various abTCRs were gated into 4 different populations (CD8+/abTCR+; CD8+/abTCR-; CD4+/abTCR+; CD4+/abTCR-) and assayed by flow cytometry for expression of the T cell exhaustion markers PD-1, TIM-3, and LAG-3 following incubation with HepG2, SK-HEP-1, and SK-HEP-1-AFP-MG cells. T cells transduced with the various abTCRs containing C-terminal co-stimulatory domains did not show significantly increased T cell exhaustion following activation by the target-positive cells HepG2 and SK-HEP-1-AFP-MG as compared to the T cells transduced with the abTCR lacking any co-stimulatory domains (data not shown). T cells transduced with the various abTCRs were used in a cytokine release assay as described above by co-incubating them with SK-HEP-1 and SK-HEP-1-AFP-MG cells. A panel of four human cytokines (IL-2, GM-CSF, IFN-γ, TNF-α) was measured after 16 hours. All cytokines tested were detected in the media of abTCR-transduced T cells upon co-incubation with AFP+ SK-HEP-1-AFP-MG cells, but not AFP− SK-HEP-1 cells (FIG. 30). T cells transduced with the various abTCRs containing C-terminal co-stimulatory domains did not show significantly increased cytokine release following activation by the target-positive SK-HEP-1-AFP-MG cells as compared to the T cells transduced with the abTCR lacking any co-stimulatory domains, and in some cases showed reduced cytokine release.

Figure 31:
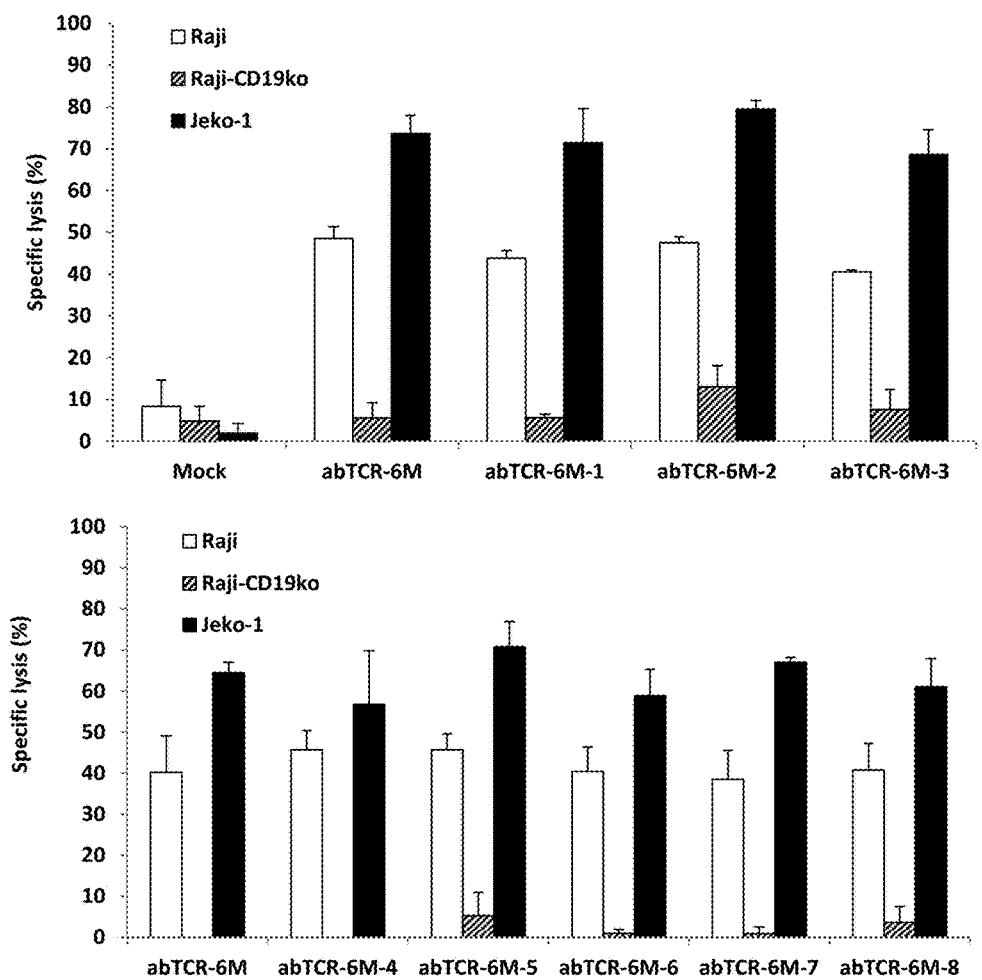
FIG. 31 shows killing of cancer cell lines Raji, Raji-CD19ko, and JeKo-1, mediated by mock-transduced T cells or T cells transduced with various abTCRs having one or more C-terminal co-stimulatory domains, each having the same anti-CD19 binding moiety.
Figure 32:
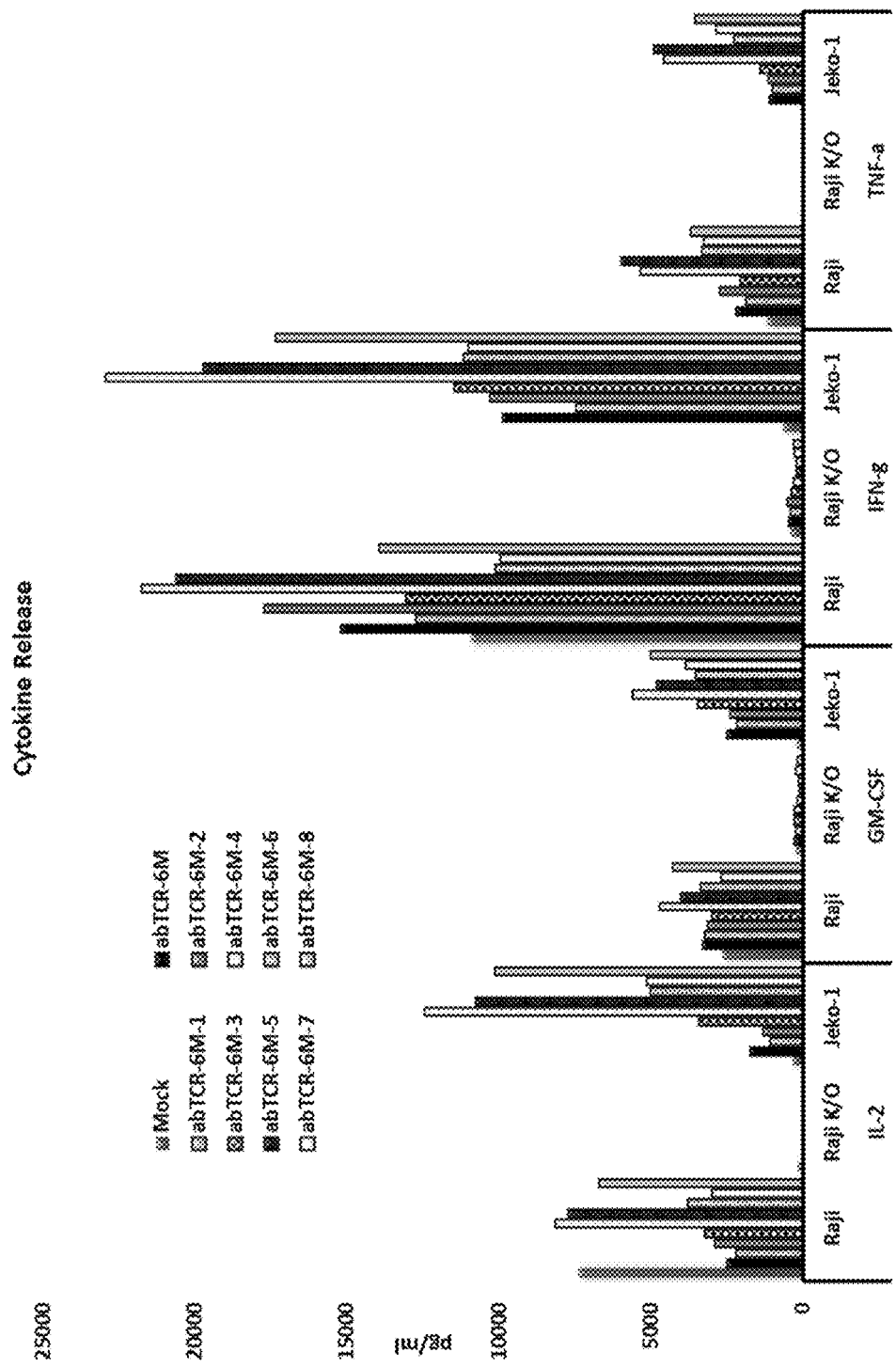
FIG. 32 shows the level of secretion of cytokines IL-2, GM-CSF, IFNγ, and TNFα by mock-transduced T cells or T cells transduced with various abTCRs having one or more C-terminal co-stimulatory domains, each having the same anti-CD19 binding moiety, co-cultured with Raji, Raji-CD19ko, or JeKo-1 cells.

The target-cell killing, T cell exhaustion, and cytokine release experiments were repeated using anti-CD19 abTCR constructs designed using co-stimulatory fragments derived from CD28 and/or 4-1BB as described above and depicted in FIG. 28. The abTCRs consisted of a TCRγ chimeric subunit containing the amino acid sequence of SEQ ID NO: 54 and a TCRδ chimeric subunit containing the amino acid sequence of SEQ ID NO: 56. As with the anti-AFP158/HLA-A*02:01 abTCR constructs, the T cells transduced with the anti-CD19 abTCRs containing co-stimulatory domains behaved similarly to T cells transduced with the anti-CD19 abTCR construct without any co-stimulatory domains (FIGS. 31 and 32).

TABLE 5 abTCR and CD3 surface expression

| abTCR | abTCR+/CD3− (percent) | abTCR−/CD3+ (percent) | abTCR+/CD3+ (percent) |
|---|---|---|---|
| Mock | 0.02 | 2.49 | 0.03 |
| abTCR-6M | 1.11 | 0.217 | 93.8 |
| abTCR-6M-1 | 1.11 | 0.217 | 93.8 |
| abTCR-6M-2 | 1.31 | 0.259 | 93.5 |
| abTCR-6M-3 | 2.8 | 0.418 | 83.5 |
| abTCR-6M-4 | 4.43 | 0.682 | 77.6 |
| abTCR-6M-5 | 3.51 | 0.685 | 81.3 |
| abTCR-6M-6 | 2.91 | 0.738 | 77.3 |
| abTCR-6M-7 | 2.8 | 1.17 | 66.4 |
| abTCR-6M-8 | 3.68 | 0.892 | 75.5 |

TABLE 6

CD8 and abTCR surface expression

| abTCR | CD8+/tetramer+ | CD8−/tetramer+ |
|---|---|---|
| Mock | 0.068 | 0.013 |
| abTCR-6M | 20.6 | 38.3 |
| abTCR-6M-1 | 28.0 | 44.7 |
| abTCR-6M-2 | 23.1 | 39.2 |
| abTCR-6M-3 | 24.9 | 40.0 |
| abTCR-6M-4 | 18.2 | 37.1 |
| abTCR-6M-5 | 14.3 | 33.3 |
| abTCR-6M-6 | 16.1 | 32.6 |
| abTCR-6M-7 | 19.6 | 38.8 |
| abTCR-6M-8 | 7.79 | 19.6 |

TABLE 7

CCR7, CD45RA, CD28, and Granzyme B surface expression on CD4+ and CD8+ abTCR T cells

| | Percent Expression (CD4+/tetramer+-gated) | | | Percent Expression (CD8+/tetramer+-gated) | | |
|---|---|---|---|---|---|---|
| abTCR | CD28 | CCR7 | Granzyme B | CD28 | CCR7 | Granzyme B |
| abTCR-6M | 60 | 56 | 2.4 | 52 | 26.5 | 23.3 |
| abTCR-6M-1 | 65.9 | 53.7 | 2.31 | 57.1 | 20.9 | 21.6 |
| abTCR-6M-2 | 60.3 | 53.8 | 2.41 | 57.1 | 19.1 | 28.5 |
| abTCR-6M-3 | 60.1 | 53.7 | 2.96 | 54.6 | 18.9 | 29.1 |
| abTCR-6M-4 | 63 | 52.5 | 3.11 | 58.6 | 20.2 | 30.1 |
| abTCR-6M-5 | 56.1 | 54 | 3.74 | 52.2 | 19.1 | 34.1 |
| abTCR-6M-6 | 62.3 | 54.8 | 3.1 | 54.5 | 19 | 33.4 |
| abTCR-6M-7 | 63 | 52.2 | 2.4 | 57.7 | 18.4 | 28.1 |
| abTCR-6M-8 | 55.6 | 54.1 | 2.44 | 57.7 | 22.8 | 34.2 |

Example 10. In Vivo Efficacy Studies of abTCR-Transduced T Cells

Figure 33:
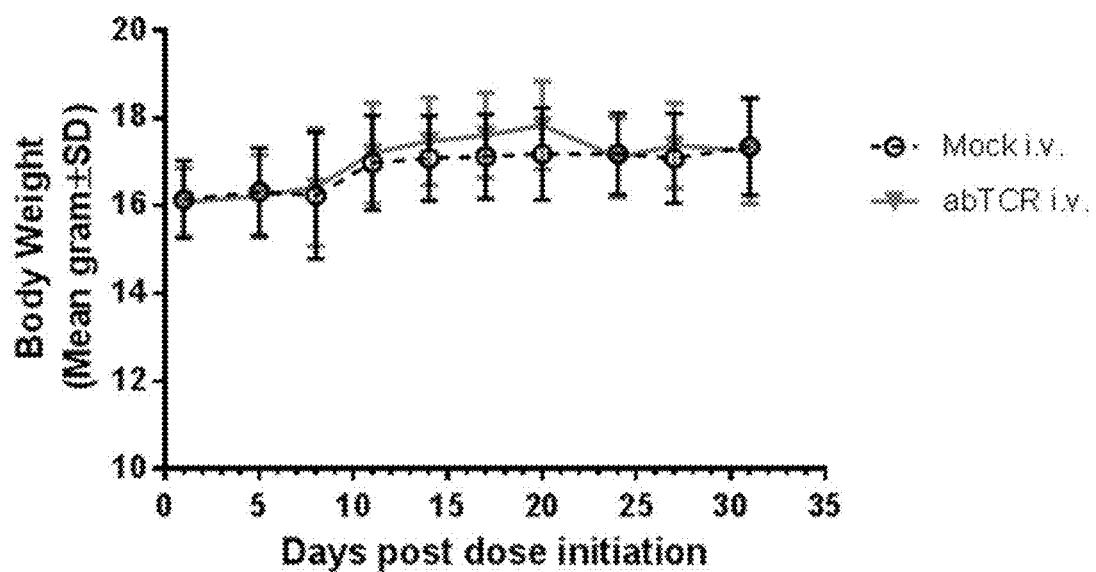
FIG. 33 shows the body weight change over time in a subcutaneous mouse xenograft model of SK-HEP-1-AFP-MG treated with intravenous injection of either mock-transduced T cells or T cells transduced with an abTCR-6MD having an anti-AFP158/HLA-A*02:01 binding moiety.
Figure 34A:
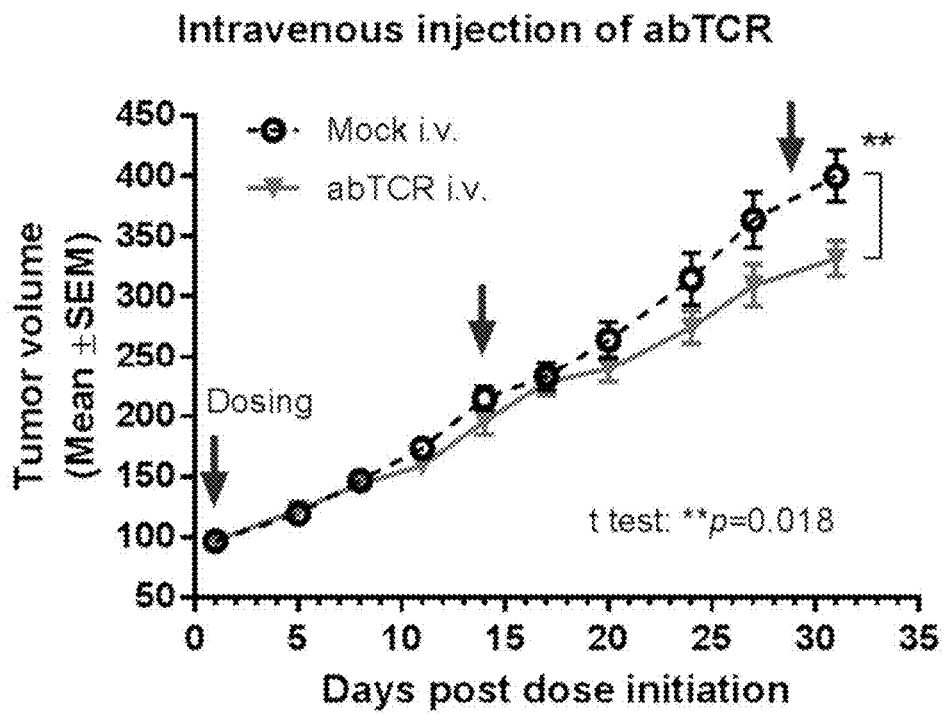
FIG. 34A shows the tumor growth in a subcutaneous mouse model of SK-HEP-1-AFP-MG treated with intravenous injection of either mock-transduced T cells or T cells transduced with an abTCR-6MD having an anti-AFP158/HLA-A*02:01 binding moiety.

In Vivo Antitumor Activity for Anti-AFP158/HLA-A*02:01 Antibody in a Human Hepatocellular Carcinoma Xenograft Model The in vivo antitumor activity of T cells transduced with abTCR-6MD constructs containing an anti-AFP158/HLA-A*02:01 binding moiety (SEQ ID NOs: 35 and 36) was tested using a subcutaneous (s.c.) model of SK-HEP-1-AFP-MG in SCID-beige mice. The SK-HEP-1-AFP-MG cells were s.c. implanted over the right flank of the SCID-beige mice at $5 \times 10^6$ cells per mouse. When average tumor volume reached 100 mm$^3$, animals were randomized based on tumor volume to two groups (with 8 mice per group) receiving: (i) mock-transduced T cells and (ii) abTCR-transduced T cells. The animals were treated immediately after randomization by injecting $10^7$ mock or abTCR-transduced per mouse, intravenously (i.v.) once every two weeks, for three doses. The mice were closely monitored for general health condition, possible adverse response, if any, and changes in tumor volume. Both mock and the abTCR-transduced T cells were well-tolerated at the current dose and schedule. No dosing-related body weight change was observed throughout the study (FIG. 33). While SK-HEP-1-AFP-MG tumors continued to grow after i.v. administration of mock or abTCR-transduced T cells, the growth rate of abTCR-transduced T cell treated tumors was slower compared to mock T-treated tumors. As shown in FIG. 34A, the separation of the tumor growth curves started at 20 days post dosing initiation. On day 31, 23% growth inhibition in abTCR-transduced T cell treated tumors were observed (t test, p=0.018).

Figure 34B:
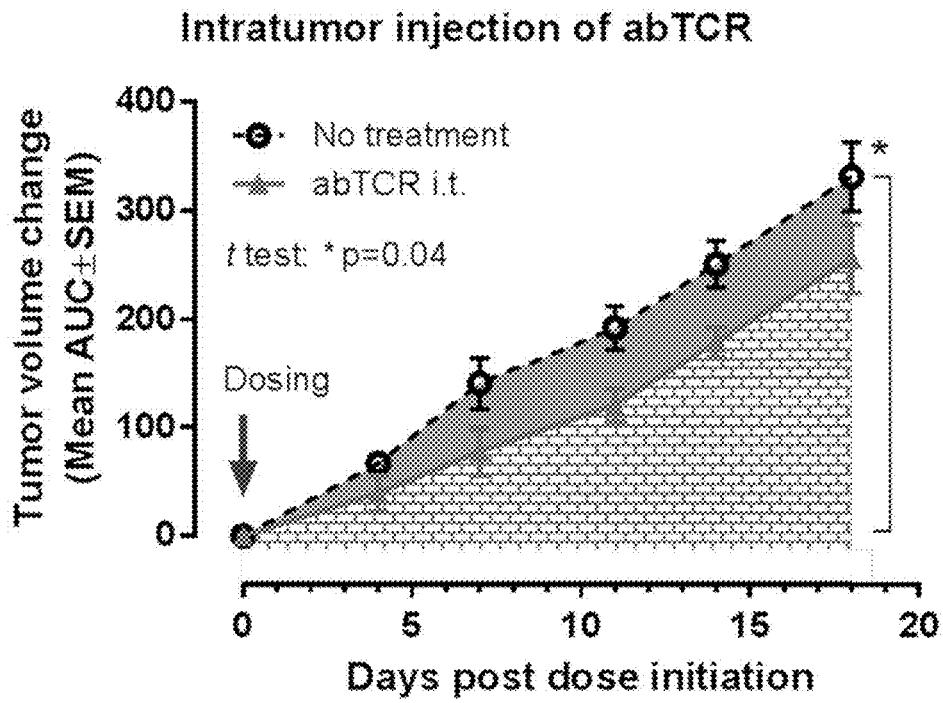
FIG. 34B shows the tumor growth in a subcutaneous mouse model of SK-HEP-1-AFP-MG with no treatment or with a single intratumoral injection of T cells transduced with an abTCR-6MD having an anti-AFP158/HLA-A*02:01 binding moiety when the average tumor volume reached 300 mm³.

The antitumor activity of abTCR-transduced T cells was further evaluated in larger SK-HEP-1-AFP-MG s.c. tumors. In a study with SK-HEP-1-AFP-MG tumor-bearing mice, animals were randomized into two groups when average tumor volume reached 300 mm$^3$ (n=4 mice per group). Animals received either no treatment or a single intratumoral (i.t.) injection of $10^7$ abTCR-transduced T cells per mouse. As shown in FIG. 34B, i.t. delivery of abTCR-transduced T cells slowed down the growth of large SK-HEP-1-AFP-MG tumors as measured by change in tumor volume over time. Comparison of the areas under the curve between untreated and abTCR-transduced T cell-treated large SK-HEP-1-AFP-MG tumors showed a statistically significant difference between the two groups (two tailed t test, p=0.04). Taken together, both i.v. and i.t.

administration of abTCR-transduced T cells significantly inhibited the growth of established s.c. xenografts of SK-HEP-1-AFP-MG.

In Vivo Antitumor Activity for Anti-CD19 Antibody in a Lymphoma Xenograft Model

The in vivo antitumor activity of T cells transduced with CAR and abTCR with an exemplary anti-hCD19 antibody binding moiety are tested in CD19 positive human lymphoma xenograft model in NOD SCID gamma (NSG) mice. Raji-luc-GFP cells are purchased from Comparative Biosciences, Inc. (Sunnyville, Calif. 94085) and are cultured in RPMI Medium+10% FBS and 1% L-Glutamine at 37° C. in a humidified atmosphere with 5% CO2. The Raji-luc-GFP cells are derived from the CD19-positive Burkitt lymphoma cell line, Raji, after stable transfection with dual reporter genes encoding both firefly luciferase (luc) and green fluorescent protein, resulting in cells that can be traced in vivo using bioluminescent imaging. NSG mice are purchased from Jackson Laboratories (Bar Harbor, Me. USA 04609) and are acclimated for at least 7 days prior to the experiment. Raji-luc-GFP cells are re-suspended in PBS and implanted intravenously (i.v.) into NSG mice through tail vein at $1 \times 10^6$ cells/100 µl/mouse. Five days post tumor implantation, animals are imaged using Xenogen IVIS imaging system for assessment of tumor burden. Mice are randomized based on the photon emission into the following four groups at average photon emission of $6.7 \times 10^5$ photons (n=6 mice per group): (i) no treatment, (ii) mock-transduced human T cells, (iii) anti-CD19 CAR-T treated and (iv) anti-hCD19 abTCR T cells treated. The animals are treated i.v. with mock or anti-CD19 CAR-T cells immediately after randomization at a dose of $10^7$ cells per mouse, once every two weeks for 3 doses.

Animals are closely monitored after dosing. Bioluminescent imaging using Xenogen IVIS system is taken once a week for up to 8 weeks.

Animal studies were carried out as described above to evaluate in vivo anti-tumor capabilities of T cells transduced with abTCR-6MD having anti-CD19 binding moieties.

6-8 weeks old female NSG mice were used in this study. The Raji-luc-GFP cell line was cultured in RPMI Medium+10% FBS and 1% L-Glutamine at 37° C. in a humidified atmosphere with 5% CO2. Raji-luc-GFP cells were re-suspended in PBS and implanted i.v. into 40 NSG mice at $1 \times 10^6$ cells/100 µl/mouse.

At four days post tumor implantation, the mice were imaged using the Ivis Spectrum to confirm tumor growth. The mice were then randomized, based on the photon emission, into six groups for the following treatments (n=6 mice/group): 1) Vehicle (PBS); 2) Mock ($8 \times 10^6$ mock-transduced T cells); 3) Clone 5 abTCR ($8 \times 10^6$ T cells transduced with an abTCR-6MD having anti-CD19 clone 5 binding moiety which comprises amino acid sequences of SEQ ID NOs: 42 and 54); 4) Clone 5-3 abTCR ($8 \times 10^6$ T cells transduced with an abTCR-6MD having anti-CD19 clone 5-3 binding moiety which comprises amino acid sequences of SEQ ID NOs: 42 and 43); 5) Clone 5-9 abTCR ($8 \times 10^6$ T cells transduced with an abTCR-6MD having anti-CD19 clone 5-9 binding moiety which comprises amino acid sequences of SEQ ID NOs: 55 and 54); and 6) Clone 5-13 abTCR ($8 \times 10^6$ T cells transduced with an abTCR-6MD having anti-CD19 clone 5-13 binding moiety which comprises amino acid sequences of SEQ ID NOs: 56 and 54).

Animals were closely monitored after tumor implantation and dosing with 8 million receptor-positive T cells. Animals were weighed and Xenogen imaging was conducted twice a week for the duration of the study. Animals showing the following conditions were euthanized and recorded as "conditional death": a) acute adverse response: labored breathing, tremor, passive behavior (loss of appetite and lethargy); b) body weight loss more than 25% initial body weight; and c) limb paralysis that affect mouse movement.

Figure 35:
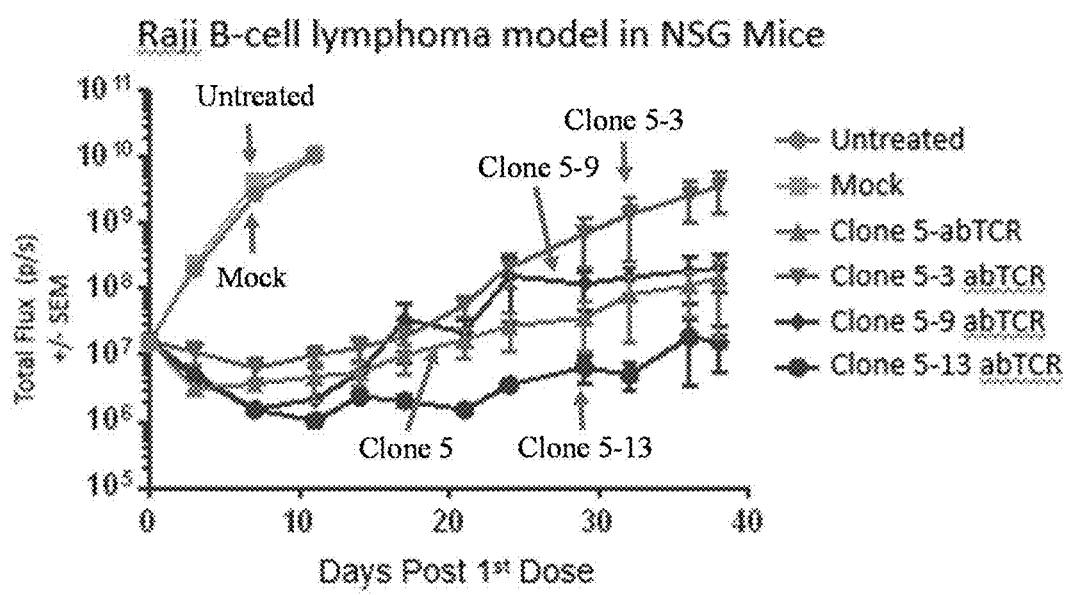
FIG. 35 shows tumor growth in reporter Raji intravenous xenograft mice treated with T cells transduced with various anti-CD19 abTCRs (clones 5, 5-3, 5-9, and 5-14). Mock-transduced T-cells and no T cell treatment were included as controls.

The results of this experiment are depicted in FIG. 35, which plots total flux emission from the tumor vs. days post dosing with abTCR cells or controls. All 4 of the CD19-abTCR T cells targeted and lysed the CD19 positive Raji tumors in vivo, demonstrating efficacy of anti-CD19 antibodies in the abTCR platform to inhibit tumor growth.

In another experiment, NSG mice with no implanted tumors were treated with $8 \times 10^6$ T cells transduced with an anti-CD19 abTCR-6MD or an anti-CD19 CAR with the same binding sequences, and the effect of these transduced T cells in vivo were compared. The mice treated with the anti-CD19 CAR T cells died within 24 hours, while the mice treated with the anti-CD19 abTCR T cells survived after 5 weeks. This result indicates that T cells expressing abTCR constructs are safer than those expressing CARs.

Comparison of Anti-CD19 abTCR and Anti-CD19 CAR

Figure 36:
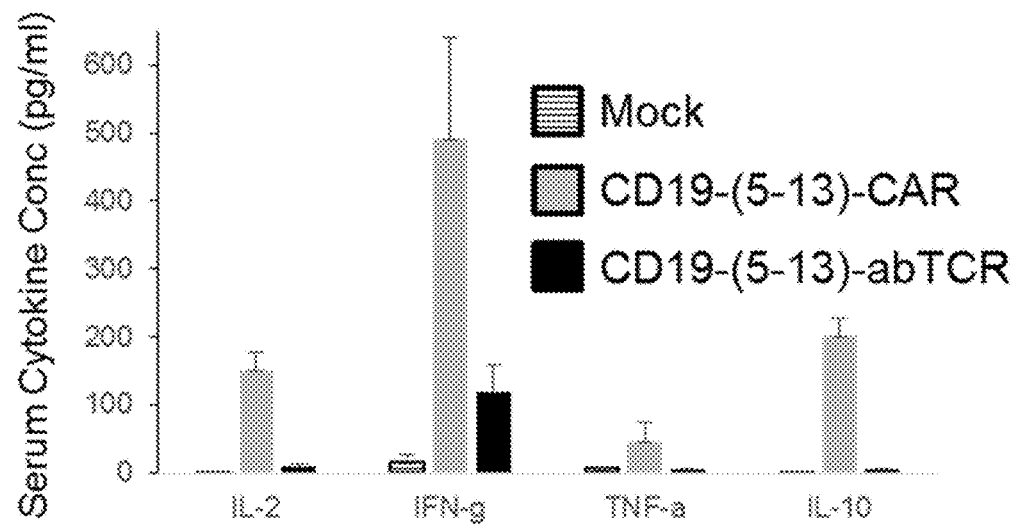
FIG. 36 shows the serum level of IL-2, IFN-γ, TNF-α, and IL-10 in Raji xenograft mice injected with mock-transduced T cells or T cells transduced with either a CAR or an abTCR-6MD, both having the Clone 5-13 anti-CD19 binding moiety variable domains.
Figure 37:
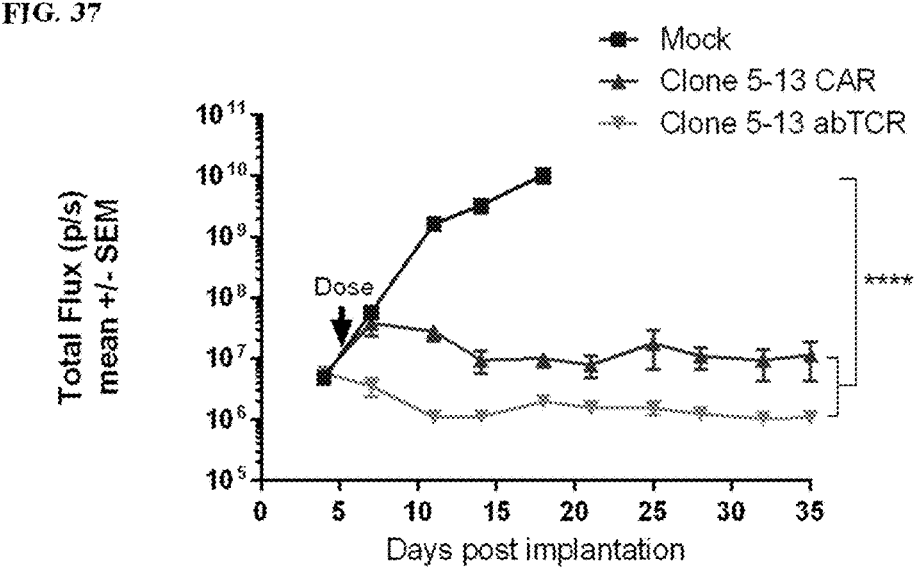
FIG. 37 shows quantitation of tumor growth in reporter Raji xenograft mice treated with T cells transduced with either a CAR or an abTCR-6MD, both having the Clone 5-13 anti-CD19 binding moiety variable domains. Mock-transduced T-cells were included as controls.
Figure 38:
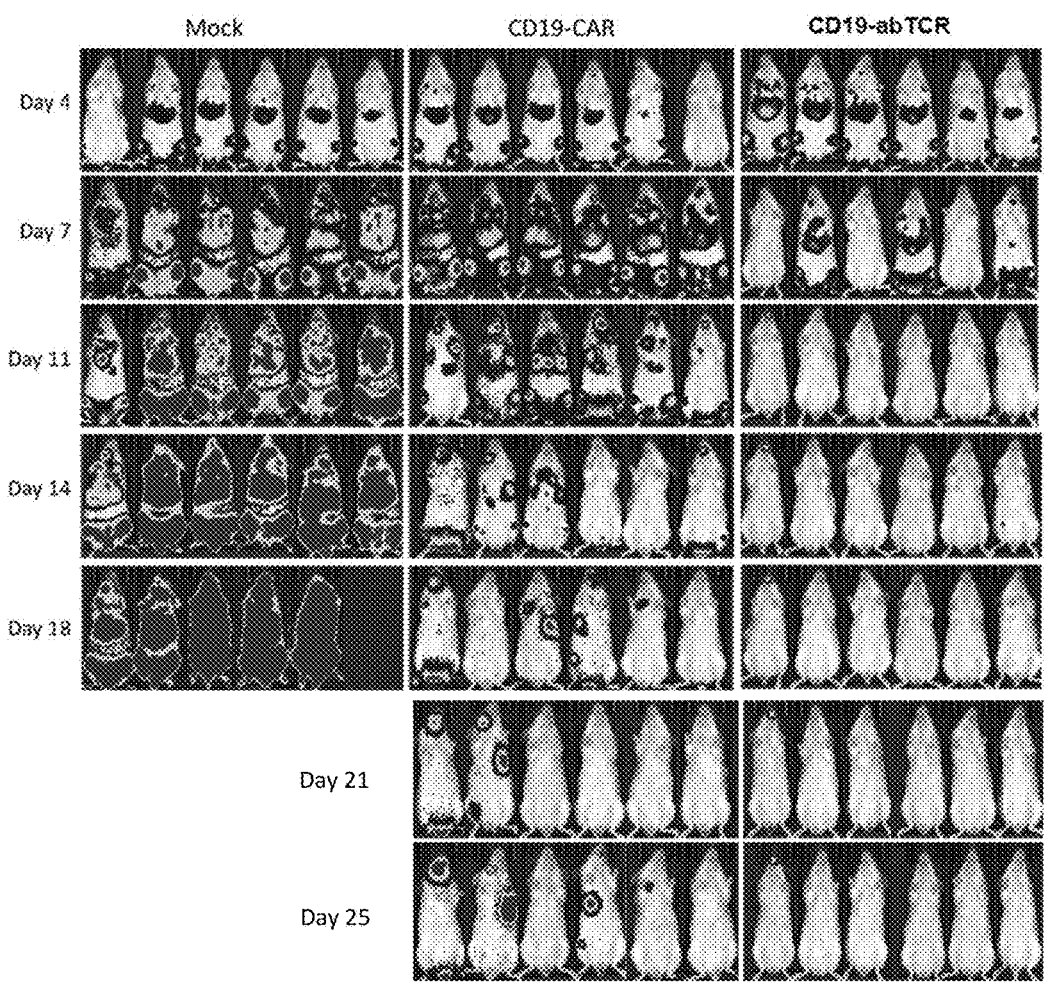
FIG. 38 shows imaging results for tumor-derived bioluminescence in reporter Raji xenograft mice treated with T cells transduced with either a CAR or an abTCR-6MD, both having the Clone 5-13 anti-CD19 binding moiety variable domains. Mock-transduced T-cells were included as controls. The grey-scale converted heatmap indicates total photons per second at the location of tumors, which appear as dark spots overlaid on the mouse images.

Raji B-cell lymphoma Raji-luc-GFP cells were implanted into NSG mice as described above. Mice were then injected with $5 \times 10^6$ abTCR T cells transduced with Clone 5-13 abTCR-6MD (abTCR-6MD having anti-CD19 clone 5-13 binding moiety which comprises amino acid sequences of SEQ ID NOs: 56 and 54), $5 \times 10^6$ CAR$^+$ T cells transduced with Clone 5-13 CAR (CAR having anti-CD19 clone 5-13 binding moiety), or $5 \times 10^6$ mock T cells in groups of eight mice per injection sample. Serum was collected 24 hours after T cell implantation and the concentration of human cytokines within the serum was measured using the Luminex Magpix machine as described above. The cytokine measurement results are shown in FIG. 36. Tumor burden was measured by luciferase activity as previously described and results are shown in FIGS. 37 (quantitation) and 27 (imaging).

In a head to head comparison between Clone 5-13 CAR and Clone 5-13 abTCR T cells, abTCR T cells injected into mice resulted in rapid tumor regression compared to CAR T cells at early time points, while mice injected with CAR T cells did not show tumor regression until after about five days. Throughout the course of this experiment, Clone 5-13 abTCR T cells showed higher in vivo tumor inhibition efficacy than Clone 5-13 CAR T cells. The cytokine measurement results at 24 hrs indicate that mice treated with Clone 5-13 abTCR T cells also had reduced cytokine secretion levels than CAR T cell-treated mice. These results provide evidence that anti-tumor efficacy does not necessitate over-production of cytokines, as abTCR T cells have higher tumor inhibition potency yet lower cytokine-secreting effects than CAR T cells.

Figure 39:
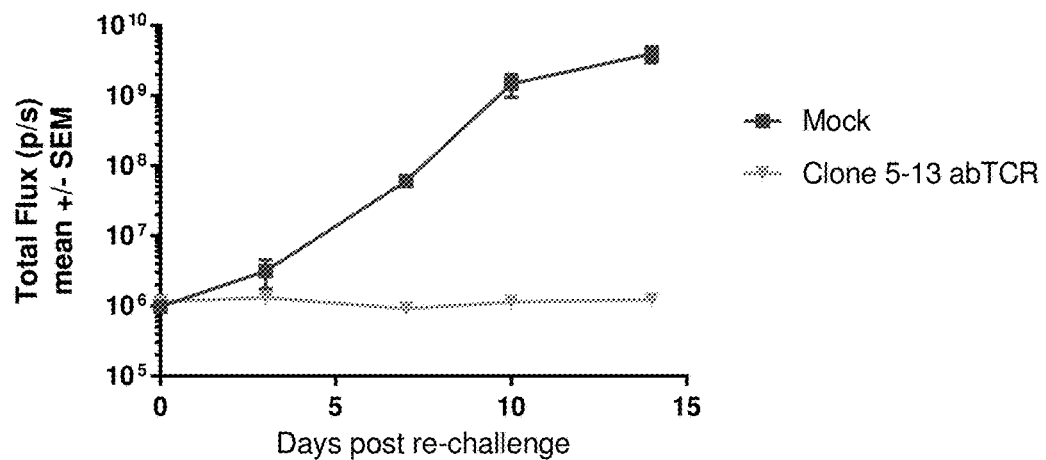
FIG. 39 shows quantitation of tumor growth in reporter Raji xenograft mice re-challenged with tumor cells 7 weeks following initial tumor cell implantation and treatment with T cells transduced with Clone 5-13 anti-CD19 abTCR-6MD. Mock-transduced T-cells were included as controls.

At 7 weeks following tumor implantation, none of the mice treated with Clone 5-13 abTCR T cells had detectable tumors. At this time, 3 mice from the mock T cell treated group and 3 mice from the Clone 5-13 abTCR T cell treated group were re-challenged by i.v. implantation with $5 \times 10^5$ Raji lymphoma cells. Tumor burden was measured by luciferase activity as previously described and results are shown in FIG. 39. While tumors grew rapidly in mice from the mock T cell treated group, the prior treatment with Clone 5-13 abTCR-transduced T cells prevented the growth of tumors following re-challenge with Raji lymphoma cell implantation, indicating that the abTCR-transduced T cells persisted and maintained their ability to respond to antigen.

In another experiment, serum was collected from NSG mice 24 hours after injection of either $5 \times 10^6$ Clone 5-3 abTCR-6MD (abTCR-6MD having anti-CD19 clone 5-3 binding moiety which comprises amino acid sequences of SEQ ID NOs: 42 and 43) T cells or 5×10⁶ Clone 5-3 CAR (CAR having anti-CD19 clone 5-3 binding moiety, SEQ ID NO: 44) T cells. The concentration of cytokines in the mouse serum was measured as described above. High levels of T cell-derived human cytokines and mouse-derived IL-6 were found in mice treated with Clone 5-3 CAR T cells. In contrast, mice treated with Clone 5-3 abTCR displayed dramatically lower serum cytokine levels (data not shown), providing further evidence of the reduced effect on cytokine overproduction for abTCR T cells.

In Vivo Antitumor Activity for Anti-CD19 Antibody in a Leukemia Xenograft Model

The in vivo antitumor activity of T cells transduced with a CAR or abTCR containing an exemplary anti-hCD19 antibody binding moiety were tested in a CD19 positive human leukemia xenograft model in NSG mice. NALM-6-luc-GFP cells were a gift from Eric Smith's Lab at Memorial Sloan Kettering Cancer Center and were cultured in RPMI Medium+10% FBS at 37° C. in a humidified atmosphere with 5% CO2. NALM-6-luc-GFP cells are derived from the CD19-positive acute lymphoblastic leukemia cell line, NALM-6, after stable transfection with dual reporter genes encoding both firefly luciferase (luc) and green fluorescent protein, resulting in cells that can be traced in vivo using bioluminescent imaging. NSG mice were purchased from Jackson Laboratories (Bar Harbor, Me. USA 04609) and acclimated for at least 3 days prior to the experiment. NALM-6-luc-GFP cells were re-suspended in PBS and implanted intravenously (i.v.) into thirty 6-8 week-old female NSG mice through tail vein at 5×10⁵ cells/100 µl/mouse. Four days post tumor implantation, animals were imaged using Xenogen IVIS imaging system for assessment of tumor burden. Mice were randomized based on the photon emission into the following four groups: (i) Vehicle, PBS only (n=6 mice); (ii) 10×10⁶ mock-transduced human T cells (n=6 mice); (iii) 5×10⁶ Clone 5-13 CAR T cells (T cells transduced with a CAR having anti-CD19 clone 5-13 binding moiety) (n=8 mice); and (iv) 5×10⁶ Clone 5-13 abTCR-6MD T cells (T cells transduced with an abTCR-6MD having anti-CD19 clone 5-13 binding moiety which comprises amino acid sequences of SEQ ID NOs: 56 and 54) (n=8 mice).

Animals were closely monitored after tumor implantation and dosing with receptor-positive T cells. Animals were weighed and Xenogen imaging was conducted twice a week for the duration of the study. Animals showing the following conditions were euthanized and recorded as "conditional death": a) acute adverse response: labored breathing, tremor, passive behavior (loss of appetite and lethargy); b) body weight loss more than 25% initial body weight; and c) limb paralysis that affect mouse movement.

Figure 40:
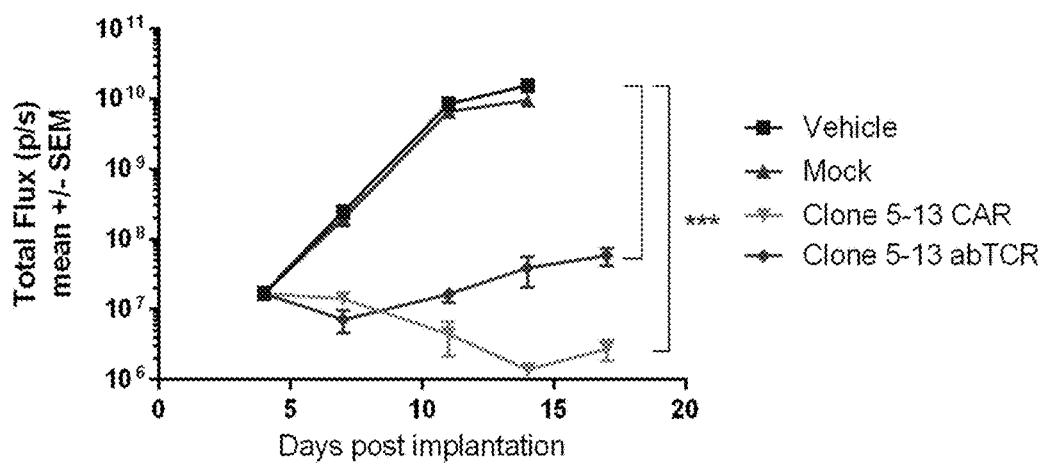
FIG. 40 shows tumor growth in reporter NALM-6 intravenous xenograft mice treated with T cells transduced with either a CAR or an abTCR-6MD, both having the Clone 5-13 anti-CD19 binding moiety variable domains. Mock-transduced T-cells and no T cell treatment were included as controls.

The results of this experiment are depicted in FIG. 40, which plots the average tumor-derived total flux emissions for each treatment arm vs. days post treatment. Both the Clone 5-13 abTCR T cells and Clone 5-13 CAR T cells targeted and lysed the CD19 positive NALM-6 tumors in vivo, demonstrating the efficacy of anti-CD19 antibodies in the abTCR platform to inhibit tumor growth in multiple cancer models.

Figure 41:
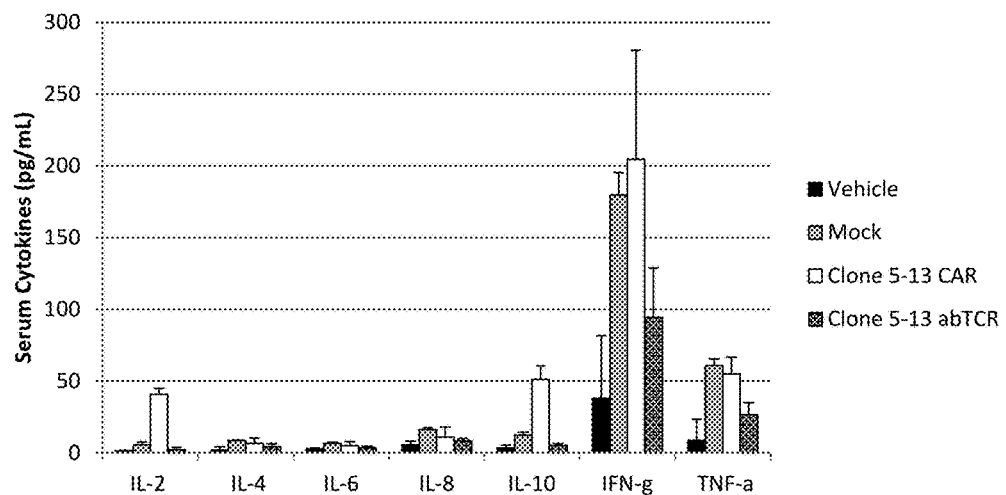
FIG. 41 shows the serum level of IL-2, IL-4, IL-6, IL-8, IL-10, IFN-γ, and TNF-α in NALM-6 xenograft mice injected with cells transduced with either a CAR or an abTCR-6MD, both having the Clone 5-13 anti-CD19 binding moiety variable domains. Mock-transduced T-cells and no T cell treatment were included as controls.

At 24-hours post treatment, blood was collected from 3 mice per group for cytokine measurements, and the results are shown in FIG. 41. As with the lymphoma xenograft model, treatment with anti-CD19 abTCR T cells in this leukemia xenograft model resulted in lower levels of cytokine secretion than treatment with anti-CD19 CAR T cells.

At 7 days and 13 days post treatment, blood was collected from representative mice from each group and analyzed by flow cytometry using the "123count eBeads" kit from Affymetrix eBioscience, Inc. to determine the numbers of CD3+ T cells, CAR/abTCR-expressing T cells, and tumor cells per µl of blood, and the level of PD-1 expression on T cells. At 13 days post treatment, 2 mice per group were euthanized and bone marrow extracts were analyzed by flow cytometry for CD3+/CAR/abTCR T cells, the presence of tumor cells, and PD-1 expression levels on T cells.

Figure 42:
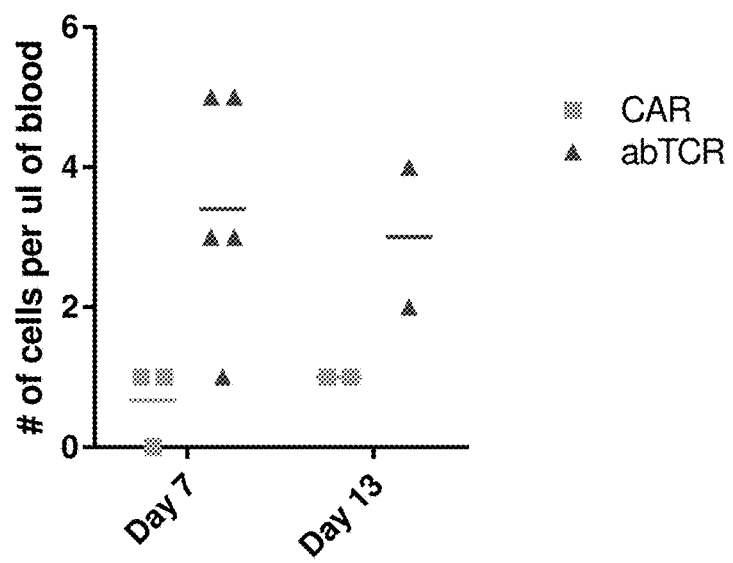
FIG. 42 shows the amount of chimeric receptor-positive T cells in blood from NALM-6 xenograft mice injected with cells transduced with either a CAR or an abTCR-6MD, both having the Clone 5-13 anti-CD19 binding moiety variable domains, at 7 and 13 days post-treatment.
Figure 43:
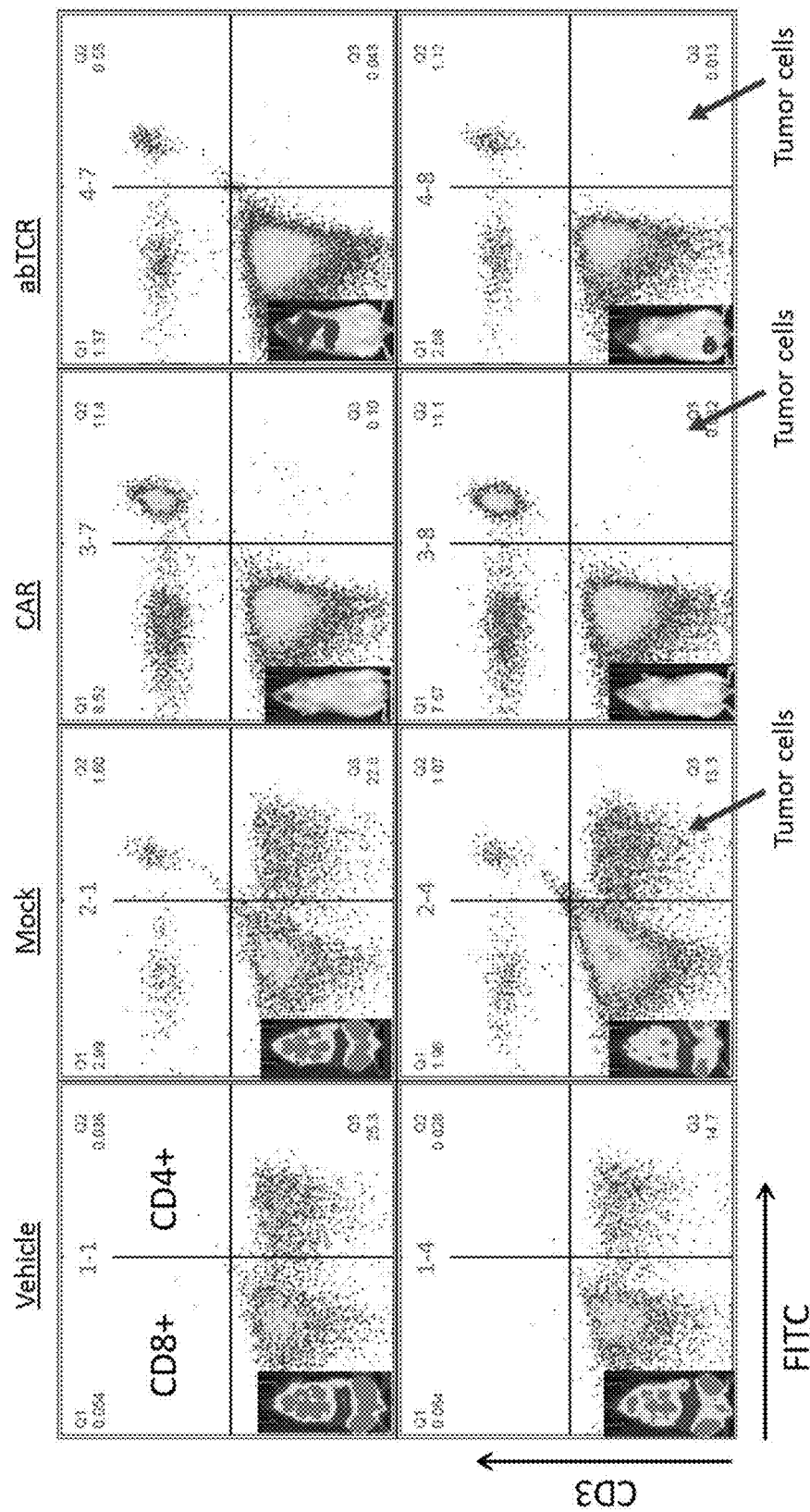
FIG. 43 shows flow cytometry analysis for tumor cells in blood from NALM-6 xenograft mice injected with cells transduced with either a CAR or an abTCR-6MD, both having the Clone 5-13 anti-CD19 binding moiety variable domains, at 13 days post-treatment.
Figure 44:
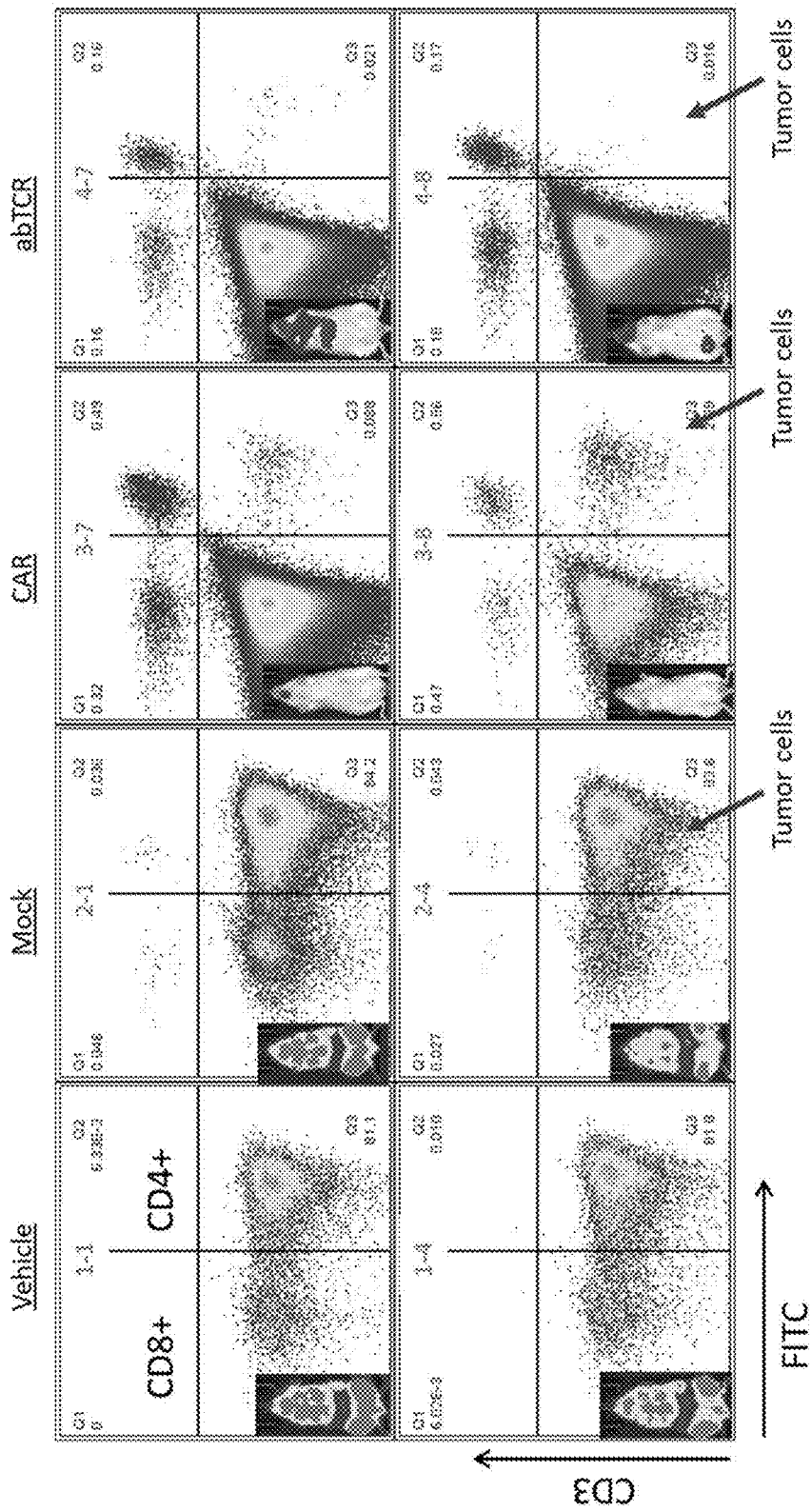
FIG. 44 shows flow cytometry analysis for tumor cells in bone marrow from NALM-6 xenograft mice injected with cells transduced with either a CAR or an abTCR-6MD, both having the Clone 5-13 anti-CD19 binding moiety variable domains, at 13 days post-treatment.
Figure 45:
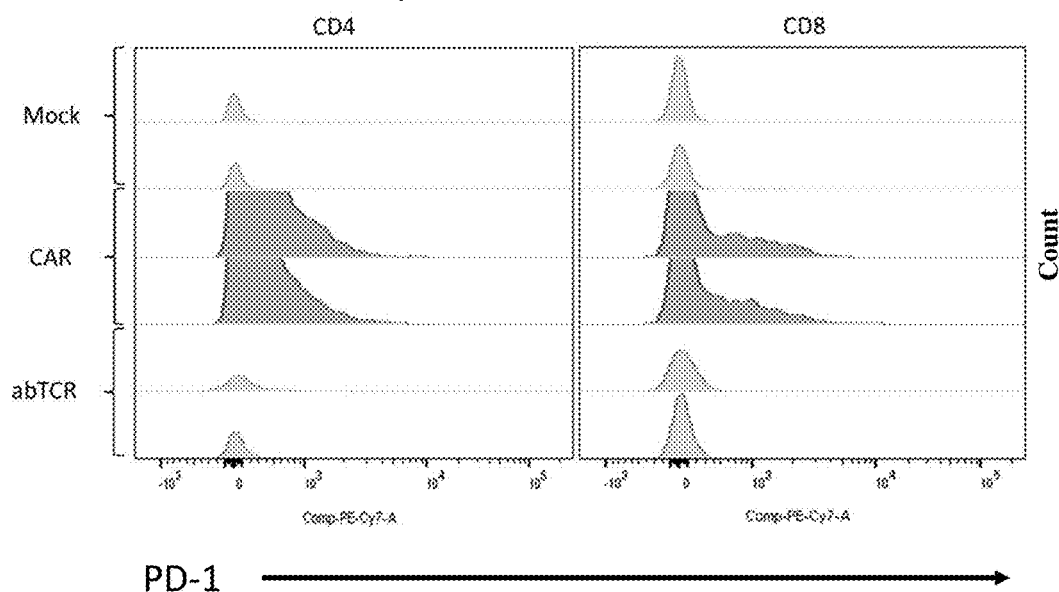
FIG. 45 shows flow cytometry analysis for PD-1 expression on CD3⁺ T cells that are either CD4⁺ or CD8⁺ in blood from NALM-6 xenograft mice injected with cells transduced with either a CAR or an abTCR-6MD, both having the Clone 5-13 anti-CD19 binding moiety variable domains.
Figure 46:
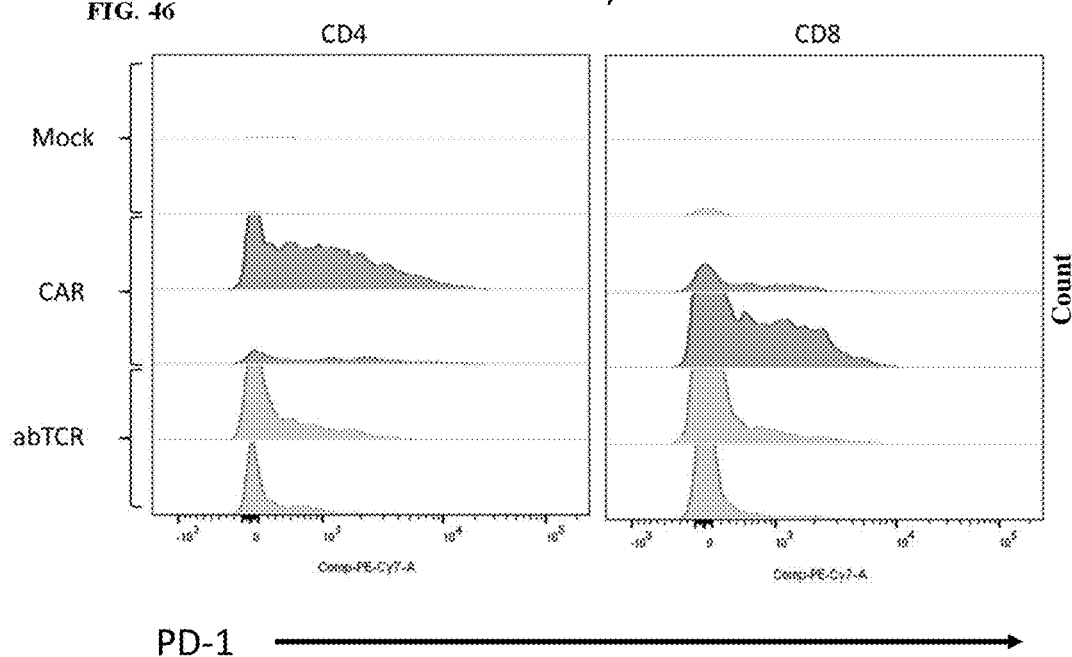
FIG. 46 shows flow cytometry analysis for PD-1 expression on CD3⁺ T cells that are either CD4⁺ or CD8⁺ in bone marrow from NALM-6 xenograft mice injected with cells transduced with either a CAR or an abTCR-6MD, both having the Clone 5-13 anti-CD19 binding moiety variable domains.

Mice administered abTCR T cells had higher levels of chimeric receptor-expressing T cells in their blood at both day 7 and 13 following administration than was observed for mice administered CAR T cells (FIG. 42), indicating that abTCR T cells had higher levels of viability and/or proliferation than their counterpart CAR T cells in this model. As shown in FIGS. 43 and 44, while mice treated with either CAR T cells or abTCR T cells showed a reduction in tumor cells (indicated by FITC staining) in both peripheral blood and bone marrow compared to vehicle- and mock-treated control animals at 13 days post treatment, the reduction in tumor cells in both peripheral blood and bone marrow was greater for animals treated with abTCR T cells. As shown in FIGS. 45 and 46, the expression level of PD-1, a T cell exhaustion marker, on the surface of T cells from both peripheral blood and bone marrow was lower in mice treated with abTCR T cells than those treated with CAR T cells, and comparable to levels observed in mock-treated mice, for both CD4+ and CD8+ T cells. These results suggest that abTCR-expressing T cells may be less likely to become exhausted than CAR-expressing T cells.

Sequence Listing

| SEQ ID NO | Description | Sequence |
|---|---|---|
| 1 | TCRα transmembrane domain | ILLLKVAGFNLLMTLRLWSS |
| 2 | TCRβ transmembrane domain | TILYEILLGKATLYAVLVSALVL |
| 3 | TCRδ transmembrane domain | MLFAKTVAVNFLLTAKLFFL |
| 4 | TCRγ transmembrane domain | YYMYLLLLLKSVVYFAIITCCLL |
| 5 | TCRα connecting peptide | ESSCDVKLVEKSFETDTNLNFQNLSVIGFR |

| SEQ ID NO | Description | Sequence |
|---|---|---|
| 6 | TCRβ connecting peptide | ADCGFTSVSYQQGVLSA |
| 7 | TCRδ connecting peptide | DHVKPKETENTKQPSKSCHKPKAIVHTEKVNMMSLTVLGLR |
| 8 | TCRγ connecting peptide | MDPKDNCSKDANDTLLLQLTNTSA |
| 9 | TCRα connecting peptide MD | IPEDTFFPSPESSCDVKLVEKSFETDTNLNFQNLSVIGFR |
| 10 | TCRβ connecting peptide MD | GRADCGFTSVSYQQGVLSA |
| 11 | TCRδ connecting peptide MD | EVKTDSTDHVKPKETENTKQPSKSCHKPKAIVHTEKVNMMSLTVLGLR |
| 12 | TCRγ connecting peptide MD | PIKTDVITMDPKDNCSKDANDTLLLQLTNTSA |
| 13 | TCRβ intracellular domain | MAMVKRKDF |
| 14 | TCRγ intracellular domain | RRTAFCCNGEKS |
| 15 | TCRD alpha | ESSCDVKLVEKSFETDTNLNFQNLSVIGFRILLLKVAGFNLLMTLRLWSS |
| 16 | TCRD beta | ADCGFTSVSYQQGVLSATILYEILLGKATLYAVLVSALVLMAMVKRKDF |
| 17 | TCRD alpha MD | IPEDTFFPSPESSCDVKLVEKSFETDTNLNFQNLSVIGFRILLLKVAGFNLLMTLRLWSS |
| 18 | TCRD beta MD | GRADCGFTSVSYQQGVLSATILYEILLGKATLYAVLVSALVLMAMVKRKDF |
| 19 | TCRD delta | DHVKPKETENTKQPSKSCHKPKAIVHTEKVNMMSLTVLGLRMLFAKTVAVNFLLTAKLFFL |
| 20 | TCRD gamma | MDPKDNCSKDANDTLLLQLTNTSAYYMYLLLLLKSVVYFAIITCCLLRRTAFCCNGEKS |
| 21 | TCRD delta MD | EVKTDSTDHVKPKETENTKQPSKSCHKPKAIVHTEKVNMMSLTVLGLRMLFAKTVAVNFLLTAKLFFL |
| 22 | TCRD gamma MD | PIKTDVITMDPKDNCSKDANDTLLLQLTNTSAYYMYLLLLLKSVVYFAIITCCLLRRTAFCCNGEKS |
| 23 | anti-AFP158/HLA-A*02:01-abTCR-3 alpha | EVQLVQSGAEVKKPGESLTISCKASGYSFPNYWITWVRQMSGGGLEWMGRIDPGDSYTTYNPSFQGHVTISIDKSTNTAYLHWNSLKASDTAMYYCARYYVSLVDIVVGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCESSCDVKLVEKSFETDTNLNFQNLSVIGFRILLLKVAGFNLLMTLRLWSS |
| 24 | anti-AFP158/HLA-A*02:01-abTCR-3 beta | QSVLTQPASVSGSPGQSITISCTGTSSDVGGYNYVSWYQQHPGKAPKLMIYDVNNRPSEVSNRFSGSKSGNTASLTISGLQAEDEADYYCSSYTTGSRAVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECSADCGFTSVSYQQGVLSATILYEILLGKATLYAVLVSALVLMAMVKRKDF |
| 25 | anti-AFP158/HLA-A*02:01-abTCR-4 alpha | QSVLTQPASVSGSPGQSITISCTGTSSDVGGYNYVSWYQQHPGKAPKLMIYDVNNRPSEVSNRFSGSKSGNTASLTISGLQAEDEADYYCSSYTTGSRAVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECSESSCDVKLVEKSFETDTNLNFQNLSVIGFRILLLKVAGFNLLMTLRLWSS |

| SEQ ID NO | Description | Sequence |
|---|---|---|
| 26 | anti-AFP158/HLA-A*02:01-abTCR-4 beta | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCADCGFTSVSYQQ GVLSATILYEILLGKATLYAVLVSALVLMAMVKRKDF |
| 27 | anti-AFP158/HLA-A*02:01-abTCR-4MD alpha | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGQPKANPTVTLFPPSSEELQANKATLVCLIS DFYPGAVTVAWKADGSPVKAGVETTKPSKQSNNKYAASSYLSLTPE QWKSHRSYSCQVTHEGSTVEKTVAPTECSIPEDTFFPSPESSCDVKLV EKSFETDTNLNFQNLSVIGFRILLLKVAGFNLLMTLRLWSS |
| 28 | anti-AFP158/HLA-A*02:01-abTCR-4MD beta | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCGRADCGFTSVSY QQGVLSATILYEILLGKATLYAVLVSALVLMAMVKRKDF |
| 29 | anti-AFP158/HLA-A*02:01-abTCR-5 delta | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGQPKANPTVTLFPPSSEELQANKATLVCLIS DFYPGAVTVAWKADGSPVKAGVETTKPSKQSNNKYAASSYLSLTPE QWKSHRSYSCQVTHEGSTVEKTVAPTECSDHVKPKETENTKQPSKS CHKPKAIVHTEKVNMMSLTVLGLRMLFAKTVAVNFLLTAKLFFL |
| 30 | anti-AFP158/HLA-A*02:01-abTCR-5 gamma | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCMDPKDNCSKDA NDTLLLQLTNTSAYYMYLLLLLKSVVYFAIITCCLLRRTAFCCNGEK S |
| 31 | anti-AFP158/HLA-A*02:01-abTCR-5MD delta | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGQPKANPTVTLFPPSSEELQANKATLVCLIS DFYPGAVTVAWKADGSPVKAGVETTKPSKQSNNKYAASSYLSLTPE QWKSHRSYSCQVTHEGSTVEKTVAPTECSEVKTDSTDHVKPKETEN TKQPSKSCHKPKAIVHTEKVNMMSLTVLGLRMLFAKTVAVNFLLTA KLFFL |
| 32 | anti-AFP158/HLA-A*02:01-abTCR-5MD gamma | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCPIKTDVITMDPK DNCSKDANDTLLLQLTNTSAYYMYLLLLLKSVVYFAIITCCLLRRTA FCCNGEKS |
| 33 | anti-AFP158/HLA-A*02:01-abTCR-6 delta | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCDHVKPKETENT KQPSKSCHKPKAIVHTEKVNMMSLTVLGLRMLFAKTVAVNFLLTA KLFFL |
| 34 | anti-AFP158/HLA-A*02:01-abTCR-6 gamma | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGQPKANPTVTLFPPSSEELQANKATLVCLIS DFYPGAVTVAWKADGSPVKAGVETTKPSKQSNNKYAASSYLSLTPE QWKSHRSYSCQVTHEGSTVEKTVAPTECSMDPKDNCSKDANDTLL LQLTNTSAYYMYLLLLLKSVVYFAIITCCLLRRTAFCCNGEKS |
| 35 | anti-AFP158/HLA-A*02:01-abTCR-6MD delta | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKRVEPKSCEVKTDSTDHVKP KETENTKQPSKSCHKPKAIVHTEKVNMMSLTVLGLRMLFAKTVAV NFLLTAKLFFL |

| SEQ ID NO | Description | Sequence |
|---|---|---|
| 36 | anti-AFP158/HLA-A*02:01-abTCR-6MD gamma | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGQPKANPTVTLFPPSSEELQANKATLVCLIS DFYPGAVTVAWKADGSPVKAGVETTKPSKQSNNKYAASSYLSLTPE QWKSHRSYSCQVTHEGSTVEKTVAPTECSPIKTDVITMDPKDNCSK DANDTLLLQLTNTSAYYMYLLLLLKSVVYFAIITCCLLRRTAFCCNG EKS |
| 37 | anti-AFP158/HLA-A*02:01-scFv CAR | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLGSRGGGGSGGGGSGGGGSLEMAEVQLVQS GAEVKKPGESLTISCKASGYSFPNYWITWVRQMSGGGLEWMGRIDP GDSYTTYNPSFQGHVTISIDKSTNTAYLHWNSLKASDTAMYYCARY YVSLVDIWGQGTLVTVSSAAAIEVMYPPPYLDNEKSNGTIIHVKGKH LCPSPLFPGPSKPFVVVLVVVGGVLACYSLLVTVAFIIFVVVRSKRSRLL HSDYMNMTPRRPGPTRKHYQPYAPPRDFAAYRSRVKFSRSADAPA YQQGQNQLYNELNLGRREEYDVLDKRRGRDPEMGGKPRRKNPQE GLYNELQKDKMAEAYSEIGMKGERRRGKGHDGLYQGLSTATKDTY DALHMQALPPR |
| 38 | IgVH domain of anti-AFP158/HLA-A*02:01 antibody | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTVSS |
| 39 | IgG1 CH1 domain | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSC |
| 40 | IgVL domain of AFP158/HLA-A*02:01 antibody | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVL |
| 41 | IgCL domain | GQPKANPTVTLFPPSSEELQANKATLVCLISDFYPGAVTVAWKADG SPVKAGVETTKPSKQSNNKYAASSYLSLTPEQWKSHRSYSCQVTHE GSTVEKTVAPTECS |
| 42 | anti-CD19-abTCR-6MD delta | EVQLVQSGAEVKKPGESLKISCKGSGYSFTSYWIGWVRQMPGKGLE WMGIIYPGDSDTRYSPSFQGQVTISADKSISTAYLQWSSLKASDTAM YYCARQVWGWQGGMYPRSNWWYNMDSWGQGTLVTVSSASTKGP SVFPLAPSSKSTSGGTAALGCLVKDYFPEPVTVSWNSGALTSGVHTF PAVLQSSGLYSLSSVVTVPSSSLGTQTYICNVNHKPSNTKVDKRVEP KSCEVKTDSTDHVKPKETENTKQPSKSCHKPKAIVHTEKVNMMSLT VLGLRMLFAKTVAVNFLLTAKLFFL |
| 43 | anti-CD19-abTCR-6MD gamma | LPVLTQPPSVSVAPGKTARITCGGNNIGSKSVHWYQQKPGQAPVLV VYDDSNRPSGIPERFSGSNSGNTATLTISRVEAGDEADYYCQVWDSS SEYVVFGGGTKLTVLGQPKANPTVTLFPPSSEELQANKATLVCLISD FYPGAVTVAWKADGSPVKAGVETTKPSKQSNNKYAASSYLSLTPEQ WKSHRSYSCQVTHEGSTVEKTVAPTECSPIKTDVITMDPKDNCSKD ANDTLLLQLTNTSAYYMYLLLLLKSVVYFAIITCCLLRRTAFCCNGE KS |
| 44 | anti-CD19-scFv CAR | LPVLTQPPSVSVAPGKTARITCGGNNIGSKSVHWYQQKPGQAPVLV VYDDSNRPSGIPERFSGSNSGNTATLTISRVEAGDEADYYCQVWDSS SEYVVFGGGTKLTVLGSRGGGGSGGGGSGGGGSLEMAEVQLVQSG AEVKKPGESLKISCKGSGYSFTSYWIGWVRQMPGKGLEWMGIIYPG DSDTRYSPSFQGQVTISADKSISTAYLQWSSLKASDTAMYYCARQV WGWQGGMYPRSNVVWYNMDSWGQGTLVTVSSAAAIEVMYPPPYL DNEKSNGTIIHVKGKHLCPSPLFPGPSKPFVVVLVVVGGVLACYSLLV TVAFIIFVVVRSKRSRLLHSDYMNMTPRRPGPTRKHYQPYAPPRDFA AYRSRVKFSRSADAPAYQQGQNQLYNELNLGRREEYDVLDKRRGR DPEMGGKPRRKNPQEGLYNELQKDKMAEAYSEIGMKGERRRGKG HDGLYQGLSTATKDTYDALHMQALPPR |
| 45 | IgVH domain of anti-CD19 antibody | EVQLVQSGAEVKKPGESLKISCKGSGYSFTSYWIGWVRQMPGKGLE WMGIIYPGDSDTRYSPSFQGQVTISADKSISTAYLQWSSLKASDTAM YYCARQVWGWQGGMYPRSNWWYNMDSWGQGTLVTVSS |
| 46 | IgVL domain of anti-CD19 antibody | LPVLTQPPSVSVAPGKTARITCGGNNIGSKSVHWYQQKPGQAPVLV VYDDSNRPSGIPERFSGSNSGNTATLTISRVEAGDEADYYCQVWDSS SEYVVFGGGTKLTVL |

Sequence Listing

| SEQ ID NO | Description | Sequence |
|---|---|---|
| 47 | fragment of CD28 | IEVMYPPPYLDNEKSNGTIIHVKGKHLCPSPLFPGPSKPFVVVLVVVG GVLACYSLLVTVAFIIFVVVRSKRSRLLHSDYMNMTPRRPGPTRKHY QPYAPPRDFAAYRS |
| 48 | fragment of CD3-zeta | RVKFSRSADAPAYQQGQNQLYNELNLGRREEYDVLDKRRGRDPEM GGKPRRKNPQEGLYNELQKDKMAEAYSEIGMKGERRRGKGHDGL YQGLSTATKDTYDALHMQALPPR |
| 49 | Signal peptide | METDTLLLWVLLLWVPGSTG |
| 50 | HA tag | YPYDVPDYA |
| 51 | 3x Flag tag | DYKDHDGDYKDHDIDYKDDDDK |
| 52 | myc tag | EQKLISEEDL |
| 53 | AFP158 | FMNKFIYEI |
| 54 | anti-CD19 clone 5 abTCR-6MD gamma | LPVLTQPPSVSVAPGKTARITCGGNNIGSKSVHWYQQKPGQAPVLV VYDDSDRPSGIPERFSGSNSGNTATLTISRVEAGDEADYYCQVWDSS SDYVVFGGGTKLTVLGQPKANPTVTLFPPSSEELQANKATLVCLISD FYPGAVTVAWKADGSPVKAGVETTKPSKQSNNKYAASSYLSLTPEQ WKSHRSYSCQVTHEGSTVEKTVAPTECSPIKTDVITMDPKDNCSKD ANDTLLLQLTNTSAYYMYLLLLLKSVVYFAIITCCLLRRTAFCCNGE KS |
| 55 | anti-CD19 clone 5-9 abTCR-6MD delta | EVQLVQSGAEVKKPGESLKISCKGSGYSFTSYWIGWVRQMPGKGLE WMGIIYPGDSDTRYSPFFQGQVTISADKSISTAYLQWSSLKASDTAM YYCARQVWGWQGGMYPRSNWWYNMDSWGQGTLVTVSSASTKGP SVFPLAPSSKSTSGGTAALGCLVKDYFPEPVTVSWNSGALTSGVHTF PAVLQSSGLYSLSSVVTVPSSSLGTQTYICNVNHKPSNTKVDKRVEP KSCEVKTDSTDHVKPKETENTKQPSKSCHKPKAIVHTEKVNMMSLT VLGLRMLFAKTVAVNFLLTAKLFFL |
| 56 | anti-CD19 clone 5-13 abTCR-6MD delta | EVQLVQSGAEVKKPGESLKISCKGSGYSFTSYWIGWVRQMPGKGLE WMGIIYPGDSDTRYSPSFQGQVTISADKSISTAYLQWSSLKASDTAM YYCARQVWGWQGGMYPRSNWWYNLDSWGQGTLVTVSSASTKGP SVFPLAPSSKSTSGGTAALGCLVKDYFPEPVTVSWNSGALTSGVHTF PAVLQSSGLYSLSSVVTVPSSSLGTQTYICNVNHKPSNTKVDKRVEP KSCEVKTDSTDHVKPKETENTKQPSKSCHKPKAIVHTEKVNMMSLT VLGLRMLFAKTVAVNFLLTAKLFFL |
| 57 | IgVL domain of anti-CD19 antibody clone 5 | LPVLTQPPSVSVAPGKTARITCGGNNIGSKSVHWYQQKPGQAPVLV VYDDSDRPSGIPERFSGSNSGNTATLTISRVEAGDEADYYCQVWDSS SDYVVFGGGTKLTVL |
| 58 | IgVH domain of anti-CD19 antibody clone 5-9 | EVQLVQSGAEVKKPGESLKISCKGSGYSFTSYWIGWVRQMPGKGLE WMGIIYPGDSDTRYSPFFQGQVTISADKSISTAYLQWSSLKASDTAM YYCARQVWGWQGGMYPRSNWWYNMDSWGQGTLVTVSS |
| 59 | IgVH domain of anti-CD19 antibody clone 5-13 | EVQLVQSGAEVKKPGESLKISCKGSGYSFTSYWIGWVRQMPGKGLE WMGIIYPGDSDTRYSPSFQGQVTISADKSISTAYLQWSSLKASDTAM YYCARQVWGWQGGMYPRSNWWYNLDSWGQGTLVTVSS |
| 60 | IgG2-0C CH1 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERK |
| 61 | IgG2-1C CH1 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKC |
| 62 | IgG2-2C CH1 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCC |
| 63 | IgG3 CH1 | ASTKGPSVFPLAPCSRSTSGGTAALGCLVKDYFPEPVTVSWNSGALT SGVHTFPAVLQSSGLYSLSSVVTVPSSSLGTQTYTCNVNHKPSNTKV DKRVELKTP |
| 64 | IgG4 CH1 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYG |

Sequence Listing

| SEQ ID NO | Description | Sequence |
|---|---|---|
| 65 | IgA1 CH1 | ASPTSPKVFPLSLCSTQPDGNVVIACLVQGFFPQEPLSVTWSESGQGV TARNFPPSQDASGDLYTTSSQLTLPATQCLAGKSVTCHVKHYTNPSQ DVTVPCPVPSTPPTPSPSTPPTPSPS |
| 66 | IgA2 CH1 | ASPTSPKVFPLSLDSTPQDGNVVVACLVQGFFPQEPLSVTWSESGQN VTARNFPPSQDASGDLYTTSSQLTLPATQCPDGKSVTCHVKHYTNPS QDVTVPCPVPPPPP |
| 67 | IgD CH1 | APTKAPDVFPIISGCRHPKDNSPVVLACLITGYHPTSVTVTWYMGTQ SQPQRTFPEIQRRDSYYMTSSQLSTPLQQWRQGEYKCVVQHTASKS KKEIFRWPESPKAQASSVPTAQPQAEGSLAKATTAPATTRNTGRGGE EKKKEKEKEEQEERETKTP |
| 68 | IgE CH1 | ASTQSPSVFPLTRCCKNIPSNATSVTLGCLATGYFPEPVMVTWDTGS LNGTTMTLPATTLTLSGHYATISLLTVSGAWAKQMFTCRVAHTPSS TDWVDNKTFS |
| 69 | IgM CH1 | GSASAPTLFPLVSCENSPSDTSSVAVGCLAQDFLPDSITLSWKYKNNS DISSTRGFPSVLRGGKYAATSQVLLPSKDVMQGTDEHVVCKVQHPN GNKEKNVPLP |
| 70 | CD28 co-stimulatory fragment | RSKRSRLLHSDYMNMTPRRPGPTRKHYQPYAPPRDFAAYRS |
| 71 | 4-1BB co-stimulatory fragment | KRGRKKLLYIFKQPFMRPVQTTQEEDGCSCRFPEEEEGGCEL |
| 72 | IgVH domain of anti-NY-ESO-1/HLA-A*02:01 antibody clone 35 | QVQLVQSGAEVKKPGSSVKVSCKASGDTFSSYSISWVRQAPGQGLE WMGRIIPILGIANYAQKYQGRVTLSADKSTSTSYMELNSLRSEDTAV YYCARDWSYSIDYWGQGTLVTVSS |
| 73 | IgVL domain of anti-NY-ESO-1/HLA-A*02:01 antibody clone 35 | QSVVTQPPSVSAAPGQKVTISCSGSSSNIGNNYVSWYQQLPGTAPKL LIYDNNKRPSGIPDRFSGSKSGTSATLGITGLQTGDEADYYCGTWDS SLSAWVFGGGTKLTVLG |
| 74 | scFv linker | SRGGGGSGGGGSGGGGSLEMA |
| 75 | anti-CD19-cTCR delta | EVQLVQSGAEVKKPGESLKISCKGSGYSFTSYWIGWVRQMPGKGLE WMGIIYPGDSDTRYSPSFQGQVTISADKSISTAYLQWSSLKASDTAM YYCARQVWGWQGGMYPRSNWWYNLDSWGQGTLVTVSSRSQPHT KPSVFVMKNGTNVACLVKEFYPKDIRINLVSSKKITEFDPAIVISPSG KYNAVKLGKYEDSNSVTCSVQHDNKTVHSTDFEVKTDSTDHVKPK ETENTKQPSKSCHKPKAIVHTEKVNMMSLTVLGLRMLFAKTVAVNF LLTAKLFFL |
| 76 | anti-CD19-cTCR gamma | LPVLTQPPSVSVAPGKTARITCGGNNIGSKSVHWYQQKPGQAPVLV VYDDSDRPSGIPERFSGSNSGNTATLTISRVEAGDEADYYCQVWDSS SDYVVFGGGTKLTVLGDKQLDADVSPKPTIFLPSIAETKLQKAGTYL CLLEKFFPDVIKIHWQEKKSNTILGSQEGNTMKTNDTYMKFSWLTV PEKSLDKEHRCIVRHENNKNGVDQEIIFPPIKTDVITMDPKDNCSKDA NDTLLLQLTNTSAYYMYLLLLLKSVVYFAIITCCLLRRTAFCCNGEK S |
| 77 | TCRα constant domain | PNIQNPDPAVYQLRDSKSSDKSVCLFTDFDSQTNVSQSKDSDVYITD KTVLDMRSMDFKSNSAVAWSNKSDFACANAFNNSIIPEDTFFPSPES SCDVKLVEKSFETDTNLNFQNLSVIGFRILLLKVAGFNLLMTLRLWS S |
| 78 | TCRβ constant domain | EDLNKVFPPEVAVFEPSEAEISHTQKATLVCLATGFFPDHVELSWWV NGKEVHSGVSTDPQPLKEQPALNDSRYCLSSRLRVSATFWVQNPRNH FRCQVQFYGLSENDEWTQDRAKPVTQIVSAEAWGRADCGFTSVSY QQGVLSATILYEILLGKATLYAVLVSALVLMAMVKRKDF |
| 79 | TCRδ constant domain | SQPHTKPSVFVMKNGTNVACLVKEFYPKDIRINLVSSKKITEFDPAIV ISPSGKYNAVKLGKYEDSNSVTCSVQHDNKTVHSTDFEVKTDSTDH VKPKETENTKQPSKSCHKPKAIVHTEKVNMMSLTVLGRMLFAKTV AVNFLLTAKLFFL |
| 80 | TCRγ constant domain | DKQLDADVSPKPTIFLPSIAETKLQKAGTYLCLLEKFFPDVIKIHWQE KKSNTILGSQEGNTMKTNDTYMKFSWLTVPEKSLDKEHRCIVRHEN NKNGVDQEIIFPPIKTDVITMDPKDNCSKDANDTLLLQLTNTSAYYM YLLLLLKSVVYFAIITCCLLRRTAFCCNGEKS |

Sequence Listing

| SEQ ID NO | Description | Sequence |
|---|---|---|
| 81 | anti-AFP158/HLA-A*02:01 abTCR-7 delta | EVQLVQSGAEVKKPGESLTISCKASGYSFPNYWITWVRQMSGGGLE WMGRIDPGDSYTTYNPSFQGHVTISIDKSTNTAYLHWNSLKASDTA MYYCARYYVSLVDIVVGQGTLVTSSRSQPHTKPSVFVMKNGTNVA CLVKEFYPKDIRINLVSSKKITEFDPAIVISPSGKYNAVKLGKYEDSNS VTCSVQHDNKTVHSTDFEVKTDSTDHVKPKETENTKQPSKSCHKPK AIVHTEKVNMMSLTVLGLRMLFAKTVAVNFLLTAKLFFL |
| 82 | anti-AFP158/HLA-A*02:01 abTCR-7 gamma | QSVLTQPASVSGSPGQSITISCTGTSSDVGGYNYVSWYQQHPGKAPK LMIYDVNNRPSEVSNRFSGSKSGNTASLTISGLQAEDEADYYCSSYT TGSRAVFGGGTKLTVLDKQLDADVSPKPTIFLPSIAETKLQKAGTYL CLLEKFFPDVIKIHWQEKKSNTILGSQEGNTMKTNDTYMKFSWLTV PEKSLDKEHRCIVRHENNKNGVDQEIIFPPIKTDVITMDPKDNCSKDA NDTLLLQLTNTSAYYMYLLLLLKSVVYFAIITCCLLRRTAFCCNGEK S |

What is claimed is:

1. An antibody-T cell receptor (TCR) chimeric molecule (abTCR) that specifically binds to CD19, comprising:
    a) a first polypeptide chain comprising a first antigen-binding domain comprising $V_H$ and $C_H1$ antibody domains and a first T cell receptor domain (TCRD) comprising a first transmembrane domain of a first TCR subunit; and
    b) a second polypeptide chain comprising a second antigen-binding domain comprising $V_L$ and $C_L$ antibody domains and a second TCRD comprising a second transmembrane domain of a second TCR subunit,
wherein the $V_H$ and $C_H1$ domains of the first antigen-binding domain and the $V_L$ and $C_L$ domains of the second antigen-binding domain form an antigen-binding module that specifically binds to CD19,
wherein the first TCRD and the second TCRD form a T cell receptor module (TCRM) that is capable of recruiting at least one TCR-associated signaling module,
wherein i) the first TCR subunit is a TCR γ chain, and the second TCR subunit is a TCR δ chain, or ii) the first TCR subunit is a TCR δ chain, and the second TCR subunit is a TCR γ chain,
wherein the CH1 antibody domain comprises the amino acid sequence of SEQ ID NO: 39 and the CL antibody domain comprises the amino acid sequence of SEQ ID NO: 41, and wherein the $V_H$ antibody domain comprises the amino acid sequence of SEQ ID NO: 59 and the $V_L$ antibody domain comprises the amino acid sequence of SEQ ID NO: 57.

2. The abTCR of claim 1, wherein the first TCR subunit is a TCR γ chain, and the second TCR subunit is a TCR δ chain.

3. The abTCR of claim 1, wherein the first TCR subunit is a TCR δ chain, and the second TCR subunit is a TCR γ chain.

4. The abTCR of claim 1, wherein the first polypeptide chain further comprises a first peptide linker between the first antigen-binding domain and the first TCRD and the second polypeptide chain further comprises a second peptide linker between the second antigen-binding domain and the second TCRD.

5. The abTCR of claim 1, wherein the first TCRD further comprises a first connecting peptide or fragment thereof of a TCR subunit N-terminal to the first transmembrane domain and the second TCRD further comprises a second connecting peptide or fragment thereof of a TCR subunit N-terminal to the second transmembrane domain.

6. The abTCR of claim 1, wherein the transmembrane domain of a TCR δ chain comprises the amino acid sequence of SEQ ID NO: 3 and the transmembrane domain of a TCR γ chain comprises the amino acid sequence of SEQ ID NO: 4.

7. The abTCR of claim 5, wherein the connecting peptide of the TCRD comprising a transmembrane domain of a TCR δ chain comprises the amino acid sequence of SEQ ID NO: 7 and the connecting peptide of the TCRD comprising a transmembrane domain of a TCR γ chain comprises the amino acid sequence of SEQ ID NO: 8.

8. The abTCR of claim 7, wherein the connecting peptide of the TCRD comprising a transmembrane domain of a TCR δ chain comprises the amino acid sequence of SEQ ID NO: 11 and the connecting peptide of the TCRD comprising a transmembrane domain of a TCR γ chain comprises the amino acid sequence of SEQ ID NO: 12.

9. The abTCR of claim 7, wherein the transmembrane domain of a TCR δ chain comprises the amino acid sequence of SEQ ID NO: 3 and the transmembrane domain of a TCR γ chain comprises the amino acid sequence of SEQ ID NO: 4.

10. A composition comprising nucleic acid(s) encoding the first and second polypeptide chains of the abTCR of claim 1.

11. A complex comprising the abTCR of claim 1 and at least one TCR-associated signaling module selected from the group consisting of CD3δε, CD3γε, and ζζ.

12. An effector cell presenting on its surface the abTCR of claim 1.

13. An effector cell comprising the nucleic acid(s) of the composition of claim 10.

14. The effector cell of claim 12, wherein the effector cell does not express TCRγ and/or TCRδ.

15. The effector cell of claim 14, wherein the effector cell is an αβ T cell.

16. The effector cell of claim 12, wherein the effector cell is modified to block or decrease the expression of a first endogenous TCR subunit and/or a second endogenous TCR subunit.

17. The effector cell of claim 12, wherein the effector cell is selected from the group consisting of a cytotoxic T cell, a helper T cell, a natural killer T cell, and a suppressor T cell.

18. The effector cell of claim 12, comprising a vector comprising a first nucleic acid sequence encoding the first polypeptide chain of the abTCR and a second nucleic acid sequence encoding the second polypeptide chain of the abTCR.

19. A pharmaceutical composition comprising the effector cell of claim 12.

20. A method of treating a CD19-associated disease in an individual in need thereof comprising administering to the individual an effective amount of the pharmaceutical composition of claim 19.

21. The method of claim 20, wherein the CD19-associated disease is cancer.

22. The method of claim 21, wherein the cancer is lymphoma, or leukemia.

23. The abTCR of claim 1, wherein the first polypeptide chain comprises the amino acid sequence of SEQ ID NO: 56, and the second polypeptide chain comprises the amino acid sequence of SEQ ID NO: 54.

24. An antibody-T cell receptor (TCR) chimeric molecule (abTCR) that specifically binds to a complex comprising an AFP peptide and a major histocompatibility complex (MHC) protein, comprising:
 a) a first polypeptide chain comprising a first antigen-binding domain comprising $V_H$ and $C_H1$ antibody domains and a first T cell receptor domain (TCRD) comprising a first transmembrane domain of a first TCR subunit; and
 b) a second polypeptide chain comprising a second antigen-binding domain comprising $V_L$ and $C_L$ antibody domains and a second TCRD comprising a second transmembrane domain of a second TCR subunit,
wherein the $V_H$ and $C_H1$ domains of the first antigen-binding domain and the $V_L$ and $C_L$ domains of the second antigen-binding domain form an antigen-binding module that specifically binds to the complex comprising the AFP peptide and the MHC protein,
wherein the first TCRD and the second TCRD form a T cell receptor module (TCRM) that is capable of recruiting at least one TCR-associated signaling module,
wherein i) the first TCR subunit is a TCR γ chain, and the second TCR subunit is a TCR δ chain, or ii) the first TCR subunit is a TCR δ chain, and the second TCR subunit is a TCR γ chain, wherein the CH1 antibody domain comprises the amino acid sequence of SEQ ID NO: 39 and the CL antibody domain comprises the amino acid sequence of SEQ ID NO: 41,
and wherein the $V_H$ antibody domain comprises the amino acid sequence of SEQ ID NO: 38 and the $V_L$ antibody domain comprises the amino acid sequence of SEQ ID NO: 40.

25. The abTCR of claim 24, wherein the first TCR subunit is a TCR γ chain, and the second TCR subunit is a TCR δ chain.

26. The abTCR of claim 24, wherein the first TCR subunit is a TCR δ chain, and the second TCR subunit is a TCR γ chain.

27. The abTCR of claim 24, wherein the first polypeptide chain further comprises a first peptide linker between the first antigen-binding domain and the first TCRD and the second polypeptide chain further comprises a second peptide linker between the second antigen-binding domain and the second TCRD.

28. The abTCR of claim 24, wherein the first TCRD further comprises a first connecting peptide or fragment thereof of a TCR subunit N-terminal to the first transmembrane domain and the second TCRD further comprises a second connecting peptide or fragment thereof of a TCR subunit N-terminal to the second transmembrane domain.

29. The abTCR of claim 24, wherein the transmembrane domain of a TCR δ chain comprises the amino acid sequence of SEQ ID NO: 3 and the transmembrane domain of a TCR γ chain comprises the amino acid sequence of SEQ ID NO: 4.

30. The abTCR of claim 28, wherein the connecting peptide of the TCRD comprising a transmembrane domain of a TCR δ chain comprises the amino acid sequence of SEQ ID NO: 7 and the connecting peptide of the TCRD comprising a transmembrane domain of a TCR γ chain comprises the amino acid sequence of SEQ ID NO: 8.

31. The abTCR of claim 30, wherein the connecting peptide of the TCRD comprising a transmembrane domain of a TCR δ chain comprises the amino acid sequence of SEQ ID NO: 11 and the connecting peptide of the TCRD comprising a transmembrane domain of a TCR γ chain comprises the amino acid sequence of SEQ ID NO: 12.

32. The abTCR of claim 30, wherein the transmembrane domain of a TCR δ chain comprises the amino acid sequence of SEQ ID NO: 3 and the transmembrane domain of a TCR γ chain comprises the amino acid sequence of SEQ ID NO: 4.

33. The abTCR of claim 24, wherein the first polypeptide chain comprises the amino acid sequence of SEQ ID NO: 35, and the second polypeptide chain comprises the amino acid sequence of SEQ ID NO: 36.

34. A composition comprising nucleic acid(s) encoding the first and second polypeptide chains of the abTCR of claim 24.

35. A complex comprising the abTCR of claim 24 and at least one TCR-associated signaling module selected from the group consisting of CD3δε, CD3γε, and ζζ.

36. An effector cell presenting on its surface the abTCR of claim 24.

37. An effector cell comprising the nucleic acid(s) of the composition of claim 34.

38. The effector cell of claim 36, wherein the effector cell does not express TCRγ and/or TCRδ.

39. The effector cell of claim 38, wherein the effector cell is an αβ T cell.

40. The effector cell of claim 36, wherein the effector cell is modified to block or decrease the expression of a first endogenous TCR subunit and/or a second endogenous TCR subunit.

41. The effector cell of claim 36, wherein the effector cell is selected from the group consisting of a cytotoxic T cell, a helper T cell, a natural killer T cell, and a suppressor T cell.

42. The effector cell of claim 36, comprising a vector comprising a first nucleic acid sequence encoding the first polypeptide chain of the abTCR and a second nucleic acid sequence encoding the second polypeptide chain of the abTCR.

43. A pharmaceutical composition comprising the effector cell of claim 36.

44. A method of treating an AFP-associated disease in an individual in need thereof comprising administering to the individual an effective amount of the pharmaceutical composition of claim 43.

45. The method of claim 44, wherein the AFP-associated disease is cancer.

46. The method of claim 45, wherein the cancer is hepatocellular carcinoma.

* * * * *

```
                          SEQUENCE LISTING

<160> NUMBER OF SEQ ID NOS: 82

<210> SEQ ID NO 1
<211> LENGTH: 20
<212> TYPE: PRT
<213> ORGANISM: Homo sapiens
<220> FEATURE:
<223> OTHER INFORMATION: TCRalpha transmembrane domain

<400> SEQUENCE: 1

Ile Leu Leu Leu Lys Val Ala Gly Phe Asn Leu Leu Met Thr Leu Arg
 1               5                  10                  15

Leu Trp Ser Ser
            20

<210> SEQ ID NO 2
<211> LENGTH: 23
<212> TYPE: PRT
<213> ORGANISM: Homo sapiens
<220> FEATURE:
<223> OTHER INFORMATION: TCRbeta transmembrane domain

<400> SEQUENCE: 2

Thr Ile Leu Tyr Glu Ile Leu Leu Gly Lys Ala Thr Leu Tyr Ala Val
 1               5                  10                  15

Leu Val Ser Ala Leu Val Leu
            20

<210> SEQ ID NO 3
<211> LENGTH: 20
<212> TYPE: PRT
<213> ORGANISM: Homo sapiens
<220> FEATURE:
<223> OTHER INFORMATION: TCRdelta transmembrane domain

<400> SEQUENCE: 3

Met Leu Phe Ala Lys Thr Val Ala Val Asn Phe Leu Leu Thr Ala Lys
 1               5                  10                  15

Leu Phe Phe Leu
            20

<210> SEQ ID NO 4
<211> LENGTH: 23
```

```
<212> TYPE: PRT
<213> ORGANISM: Homo sapiens
<220> FEATURE:
<223> OTHER INFORMATION: TCRgamma transmembrane domain

<400> SEQUENCE: 4

Tyr Tyr Met Tyr Leu Leu Leu Leu Lys Ser Val Val Tyr Phe Ala
 1               5                  10                  15

Ile Ile Thr Cys Cys Leu Leu
            20

<210> SEQ ID NO 5
<211> LENGTH: 30
<212> TYPE: PRT
<213> ORGANISM: Homo sapiens
<220> FEATURE:
<223> OTHER INFORMATION: TCRalpha connecting peptide

<400> SEQUENCE: 5

Glu Ser Ser Cys Asp Val Lys Leu Val Glu Lys Ser Phe Glu Thr Asp
 1               5                  10                  15

Thr Asn Leu Asn Phe Gln Asn Leu Ser Val Ile Gly Phe Arg
            20                  25                  30

<210> SEQ ID NO 6
<211> LENGTH: 17
<212> TYPE: PRT
<213> ORGANISM: Homo sapiens
<220> FEATURE:
<223> OTHER INFORMATION: TCRbeta connecting peptide

<400> SEQUENCE: 6

Ala Asp Cys Gly Phe Thr Ser Val Ser Tyr Gln Gln Gly Val Leu Ser
 1               5                  10                  15

Ala

<210> SEQ ID NO 7
<211> LENGTH: 41
<212> TYPE: PRT
<213> ORGANISM: Homo sapiens
<220> FEATURE:
<223> OTHER INFORMATION: TCRdelta connecting peptide

<400> SEQUENCE: 7

Asp His Val Lys Pro Lys Glu Thr Glu Asn Thr Lys Gln Pro Ser Lys
 1               5                  10                  15

Ser Cys His Lys Pro Lys Ala Ile Val His Thr Glu Lys Val Asn Met
            20                  25                  30

Met Ser Leu Thr Val Leu Gly Leu Arg
            35                  40

<210> SEQ ID NO 8
<211> LENGTH: 24
<212> TYPE: PRT
<213> ORGANISM: Homo sapiens
<220> FEATURE:
<223> OTHER INFORMATION: TCRgamma connecting peptide

<400> SEQUENCE: 8

Met Asp Pro Lys Asp Asn Cys Ser Lys Asp Ala Asn Asp Thr Leu Leu
 1               5                  10                  15

Leu Gln Leu Thr Asn Thr Ser Ala
            20
```

<210> SEQ ID NO 9
<211> LENGTH: 40
<212> TYPE: PRT
<213> ORGANISM: Homo sapiens
<220> FEATURE:
<223> OTHER INFORMATION: TCRalpha connecting peptide MD

<400> SEQUENCE: 9

Ile Pro Glu Asp Thr Phe Phe Pro Ser Pro Glu Ser Ser Cys Asp Val
1               5                   10                  15

Lys Leu Val Glu Lys Ser Phe Glu Thr Asp Thr Asn Leu Asn Phe Gln
            20                  25                  30

Asn Leu Ser Val Ile Gly Phe Arg
        35                  40

<210> SEQ ID NO 10
<211> LENGTH: 19
<212> TYPE: PRT
<213> ORGANISM: Homo sapiens
<220> FEATURE:
<223> OTHER INFORMATION: TCRbeta connecting peptide MD

<400> SEQUENCE: 10

Gly Arg Ala Asp Cys Gly Phe Thr Ser Val Ser Tyr Gln Gln Gly Val
1               5                   10                  15

Leu Ser Ala

<210> SEQ ID NO 11
<211> LENGTH: 48
<212> TYPE: PRT
<213> ORGANISM: Homo sapiens
<220> FEATURE:
<223> OTHER INFORMATION: TCRdelta connecting peptide MD

<400> SEQUENCE: 11

Glu Val Lys Thr Asp Ser Thr Asp His Val Lys Pro Lys Glu Thr Glu
1               5                   10                  15

Asn Thr Lys Gln Pro Ser Lys Ser Cys His Lys Pro Lys Ala Ile Val
            20                  25                  30

His Thr Glu Lys Val Asn Met Met Ser Leu Thr Val Leu Gly Leu Arg
        35                  40                  45

<210> SEQ ID NO 12
<211> LENGTH: 32
<212> TYPE: PRT
<213> ORGANISM: Homo sapiens
<220> FEATURE:
<223> OTHER INFORMATION: TCRgamma connecting peptide MD

<400> SEQUENCE: 12

Pro Ile Lys Thr Asp Val Ile Thr Met Asp Pro Lys Asp Asn Cys Ser
1               5                   10                  15

Lys Asp Ala Asn Asp Thr Leu Leu Leu Gln Leu Thr Asn Thr Ser Ala
            20                  25                  30

<210> SEQ ID NO 13
<211> LENGTH: 9
<212> TYPE: PRT
<213> ORGANISM: Homo sapiens
<220> FEATURE:
<223> OTHER INFORMATION: TCRbeta intracellular domain

<400> SEQUENCE: 13

```
Met Ala Met Val Lys Arg Lys Asp Phe
1               5
```

<210> SEQ ID NO 14
<211> LENGTH: 12
<212> TYPE: PRT
<213> ORGANISM: Homo sapiens
<220> FEATURE:
<223> OTHER INFORMATION: TCRgamma intracellular domain

<400> SEQUENCE: 14

```
Arg Arg Thr Ala Phe Cys Cys Asn Gly Glu Lys Ser
1               5                   10
```

<210> SEQ ID NO 15
<211> LENGTH: 50
<212> TYPE: PRT
<213> ORGANISM: Homo sapiens
<220> FEATURE:
<223> OTHER INFORMATION: TCRD alpha

<400> SEQUENCE: 15

```
Glu Ser Ser Cys Asp Val Lys Leu Val Glu Lys Ser Phe Glu Thr Asp
1               5                   10                  15

Thr Asn Leu Asn Phe Gln Asn Leu Ser Val Ile Gly Phe Arg Ile Leu
            20                  25                  30

Leu Leu Lys Val Ala Gly Phe Asn Leu Leu Met Thr Leu Arg Leu Trp
        35                  40                  45

Ser Ser
    50
```

<210> SEQ ID NO 16
<211> LENGTH: 49
<212> TYPE: PRT
<213> ORGANISM: Homo sapiens
<220> FEATURE:
<223> OTHER INFORMATION: TCRD beta

<400> SEQUENCE: 16

```
Ala Asp Cys Gly Phe Thr Ser Val Ser Tyr Gln Gln Gly Val Leu Ser
1               5                   10                  15

Ala Thr Ile Leu Tyr Glu Ile Leu Leu Gly Lys Ala Thr Leu Tyr Ala
            20                  25                  30

Val Leu Val Ser Ala Leu Val Leu Met Ala Met Val Lys Arg Lys Asp
        35                  40                  45

Phe
```

<210> SEQ ID NO 17
<211> LENGTH: 60
<212> TYPE: PRT
<213> ORGANISM: Homo sapiens
<220> FEATURE:
<223> OTHER INFORMATION: TCRD alpha MD

<400> SEQUENCE: 17

```
Ile Pro Glu Asp Thr Phe Phe Pro Ser Pro Glu Ser Ser Cys Asp Val
1               5                   10                  15

Lys Leu Val Glu Lys Ser Phe Glu Thr Asp Thr Asn Leu Asn Phe Gln
            20                  25                  30

Asn Leu Ser Val Ile Gly Phe Arg Ile Leu Leu Leu Lys Val Ala Gly
        35                  40                  45

Phe Asn Leu Leu Met Thr Leu Arg Leu Trp Ser Ser
```

<210> SEQ ID NO 18
<211> LENGTH: 51
<212> TYPE: PRT
<213> ORGANISM: Homo sapiens
<220> FEATURE:
<223> OTHER INFORMATION: TCRD beta MD

<400> SEQUENCE: 18

Gly Arg Ala Asp Cys Gly Phe Thr Ser Val Ser Tyr Gln Gln Gly Val
1               5                   10                  15

Leu Ser Ala Thr Ile Leu Tyr Glu Ile Leu Leu Gly Lys Ala Thr Leu
            20                  25                  30

Tyr Ala Val Leu Val Ser Ala Leu Val Leu Met Ala Met Val Lys Arg
        35                  40                  45

Lys Asp Phe
    50

<210> SEQ ID NO 19
<211> LENGTH: 61
<212> TYPE: PRT
<213> ORGANISM: Homo sapiens
<220> FEATURE:
<223> OTHER INFORMATION: TCRD delta

<400> SEQUENCE: 19

Asp His Val Lys Pro Lys Glu Thr Glu Asn Thr Lys Gln Pro Ser Lys
1               5                   10                  15

Ser Cys His Lys Pro Lys Ala Ile Val His Thr Glu Lys Val Asn Met
            20                  25                  30

Met Ser Leu Thr Val Leu Gly Leu Arg Met Leu Phe Ala Lys Thr Val
            35                  40                  45

Ala Val Asn Phe Leu Leu Thr Ala Lys Leu Phe Phe Leu
        50                  55                  60

<210> SEQ ID NO 20
<211> LENGTH: 59
<212> TYPE: PRT
<213> ORGANISM: Homo sapiens
<220> FEATURE:
<223> OTHER INFORMATION: TCRD gamma

<400> SEQUENCE: 20

Met Asp Pro Lys Asp Asn Cys Ser Lys Asp Ala Asn Asp Thr Leu Leu
1               5                   10                  15

Leu Gln Leu Thr Asn Thr Ser Ala Tyr Tyr Met Tyr Leu Leu Leu Leu
            20                  25                  30

Leu Lys Ser Val Val Tyr Phe Ala Ile Ile Thr Cys Cys Leu Leu Arg
        35                  40                  45

Arg Thr Ala Phe Cys Cys Asn Gly Glu Lys Ser
    50                  55

<210> SEQ ID NO 21
<211> LENGTH: 68
<212> TYPE: PRT
<213> ORGANISM: Homo sapiens
<220> FEATURE:
<223> OTHER INFORMATION: TCRD delta MD

<400> SEQUENCE: 21

Glu Val Lys Thr Asp Ser Thr Asp His Val Lys Pro Lys Glu Thr Glu

```
                1               5              10              15

Asn Thr Lys Gln Pro Ser Lys Ser Cys His Lys Pro Lys Ala Ile Val
                            20              25              30

His Thr Glu Lys Val Asn Met Met Ser Leu Thr Val Leu Gly Leu Arg
                        35              40              45

Met Leu Phe Ala Lys Thr Val Ala Val Asn Phe Leu Leu Thr Ala Lys
                        50              55              60

Leu Phe Phe Leu
            65

<210> SEQ ID NO 22
            <211> LENGTH: 67
            <212> TYPE: PRT
            <213> ORGANISM: Homo sapiens
            <220> FEATURE:
            <223> OTHER INFORMATION: TCRD gamma MD

<400> SEQUENCE: 22

Pro Ile Lys Thr Asp Val Ile Thr Met Asp Pro Lys Asp Asn Cys Ser
            1               5                  10                  15

Lys Asp Ala Asn Asp Thr Leu Leu Gln Leu Thr Asn Thr Ser Ala
                        20              25              30

Tyr Tyr Met Tyr Leu Leu Leu Leu Lys Ser Val Val Tyr Phe Ala
                        35              40              45

Ile Ile Thr Cys Cys Leu Leu Arg Arg Thr Ala Phe Cys Cys Asn Gly
                        50              55              60

Glu Lys Ser
            65

<210> SEQ ID NO 23
            <211> LENGTH: 270
            <212> TYPE: PRT
            <213> ORGANISM: Artificial Sequence
            <220> FEATURE:
            <223> OTHER INFORMATION: anti-AFP158/HLA-A*02:01-abTCR-3 alpha

<400> SEQUENCE: 23

Glu Val Gln Leu Val Gln Ser Gly Ala Glu Val Lys Lys Pro Gly Glu
            1               5                  10                  15

Ser Leu Thr Ile Ser Cys Lys Ala Ser Gly Tyr Ser Phe Pro Asn Tyr
                        20              25              30

Trp Ile Thr Trp Val Arg Gln Met Ser Gly Gly Leu Glu Trp Met
                        35              40              45

Gly Arg Ile Asp Pro Gly Asp Ser Tyr Thr Thr Tyr Asn Pro Ser Phe
                        50              55              60

Gln Gly His Val Thr Ile Ser Ile Asp Lys Ser Thr Asn Thr Ala Tyr
            65              70                  75                  80

Leu His Trp Asn Ser Leu Lys Ala Ser Asp Thr Ala Met Tyr Cys
                        85              90              95

Ala Arg Tyr Tyr Val Ser Leu Val Asp Ile Trp Gly Gln Gly Thr Leu
                        100             105             110

Val Thr Val Ser Ser Ala Ser Thr Lys Gly Pro Ser Val Phe Pro Leu
                        115             120             125

Ala Pro Ser Ser Lys Ser Thr Ser Gly Gly Thr Ala Ala Leu Gly Cys
                        130             135             140

Leu Val Lys Asp Tyr Phe Pro Glu Pro Val Thr Val Ser Trp Asn Ser
            145             150             155             160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
            245                 250                 255

Ala Gly Phe Asn Leu Leu Met Thr Leu Arg Leu Trp Ser Ser
            260                 265                 270

<210> SEQ ID NO 24
<211> LENGTH: 265
<212> TYPE: PRT
<213> ORGANISM: Artificial Sequence
<220> FEATURE:
<223> OTHER INFORMATION: anti-AFP158/HLA-A*02:01-abTCR-3 beta

<400> SEQUENCE: 24

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Ala Asp Cys Gly Phe Thr Ser Val
210                 215                 220

Ser Tyr Gln Gln Gly Val Leu Ser Ala Thr Ile Leu Tyr Glu Ile Leu
225                 230                 235                 240

Leu Gly Lys Ala Thr Leu Tyr Ala Val Leu Val Ser Ala Leu Val Leu
            245                 250                 255
```

```
Met Ala Met Val Lys Arg Lys Asp Phe
            260                 265
```

<210> SEQ ID NO 25
<211> LENGTH: 266
<212> TYPE: PRT
<213> ORGANISM: Artificial Sequence
<220> FEATURE:
<223> OTHER INFORMATION: anti-AFP158/HLA-A*02:01-abTCR-4 alpha

<400> SEQUENCE: 25

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Glu Ser Ser Cys Asp Val Lys Leu
    210                 215                 220

Val Glu Lys Ser Phe Glu Thr Asp Thr Asn Leu Asn Phe Gln Asn Leu
225                 230                 235                 240

Ser Val Ile Gly Phe Arg Ile Leu Leu Leu Lys Val Ala Gly Phe Asn
                245                 250                 255

Leu Leu Met Thr Leu Arg Leu Trp Ser Ser
            260                 265
```

<210> SEQ ID NO 26
<211> LENGTH: 269
<212> TYPE: PRT
<213> ORGANISM: Artificial Sequence
<220> FEATURE:
<223> OTHER INFORMATION: anti-AFP158/HLA-A*02:01-abTCR-4 beta

<400> SEQUENCE: 26

```
Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30
```

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
50                      55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Ala Asp Cys Gly
210                 215                 220

Phe Thr Ser Val Ser Tyr Gln Gln Gly Val Leu Ser Ala Thr Ile Leu
225                 230                 235                 240

Tyr Glu Ile Leu Leu Gly Lys Ala Thr Leu Tyr Ala Val Leu Val Ser
                245                 250                 255

Ala Leu Val Leu Met Ala Met Val Lys Arg Lys Asp Phe
            260                 265

<210> SEQ ID NO 27
<211> LENGTH: 276
<212> TYPE: PRT
<213> ORGANISM: Artificial Sequence
<220> FEATURE:
<223> OTHER INFORMATION: anti-AFP158/HLA-A*02:01-abTCR-4MD alpha

<400> SEQUENCE: 27

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

```
Leu Gln Ala Asn Lys Ala Thr Leu Val Cys Leu Ile Ser Asp Phe Tyr
            130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser Ile Pro Glu Asp Thr Phe Phe Pro
210                 215                 220
Ser Pro Glu Ser Ser Cys Asp Val Lys Leu Val Glu Lys Ser Phe Glu
225                 230                 235                 240
Thr Asp Thr Asn Leu Asn Phe Gln Asn Leu Ser Val Ile Gly Phe Arg
                245                 250                 255
Ile Leu Leu Leu Lys Val Ala Gly Phe Asn Leu Leu Met Thr Leu Arg
            260                 265                 270
Leu Trp Ser Ser
            275
```

<210> SEQ ID NO 28
<211> LENGTH: 271
<212> TYPE: PRT
<213> ORGANISM: Artificial Sequence
<220> FEATURE:
<223> OTHER INFORMATION: anti-AFP158/HLA-A*02:01-abTCR-4MD beta

<400> SEQUENCE: 28

```
Glu Val Gln Leu Val Gln Ser Gly Ala Glu Val Lys Lys Pro Gly Glu
1               5                   10                  15
Ser Leu Thr Ile Ser Cys Lys Ala Ser Gly Tyr Ser Phe Pro Asn Tyr
            20                  25                  30
Trp Ile Thr Trp Val Arg Gln Met Ser Gly Gly Leu Glu Trp Met
            35                  40                  45
Gly Arg Ile Asp Pro Gly Asp Ser Tyr Thr Thr Tyr Asn Pro Ser Phe
50                  55                  60
Gln Gly His Val Thr Ile Ser Ile Asp Lys Ser Thr Asn Thr Ala Tyr
65                  70                  75                  80
Leu His Trp Asn Ser Leu Lys Ala Ser Asp Thr Ala Met Tyr Tyr Cys
                85                  90                  95
Ala Arg Tyr Tyr Val Ser Leu Val Asp Ile Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
```

```
Thr Lys Val Asp Lys Arg Val Glu Pro Lys Ser Cys Gly Arg Ala Asp
    210             215                 220
Cys Gly Phe Thr Ser Val Ser Tyr Gln Gln Gly Val Leu Ser Ala Thr
225             230                 235                 240
Ile Leu Tyr Glu Ile Leu Leu Gly Lys Ala Thr Leu Tyr Ala Val Leu
                245                 250                 255
Val Ser Ala Leu Val Leu Met Ala Met Val Lys Arg Lys Asp Phe
            260                 265                 270
```

<210> SEQ ID NO 29
<211> LENGTH: 277
<212> TYPE: PRT
<213> ORGANISM: Artificial Sequence
<220> FEATURE:
<223> OTHER INFORMATION: anti-AFP158/HLA-A*02:01-abTCR-5 delta

<400> SEQUENCE: 29

```
Gln Ser Val Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Asn Asn Arg Pro Ser Glu Val Ser Asn Arg Phe
 50                 55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Thr Gly
                85                  90                  95
Ser Arg Ala Val Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser Asp His Val Lys Pro Lys Glu Thr
    210                 215                 220
Glu Asn Thr Lys Gln Pro Ser Lys Ser Cys His Lys Pro Lys Ala Ile
225                 230                 235                 240
Val His Thr Glu Lys Val Asn Met Met Ser Leu Thr Val Leu Gly Leu
                245                 250                 255
Arg Met Leu Phe Ala Lys Thr Val Ala Val Asn Phe Leu Leu Thr Ala
            260                 265                 270
Lys Leu Phe Phe Leu
        275
```

<210> SEQ ID NO 30

<211> LENGTH: 279
<212> TYPE: PRT
<213> ORGANISM: Artificial Sequence
<220> FEATURE:
<223> OTHER INFORMATION: anti-AFP158/HLA-A*02:01-abTCR-5 gamma

<400> SEQUENCE: 30

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Gly Leu Glu Trp Met
        35                  40                  45

Gly Arg Ile Asp Pro Gly Asp Ser Tyr Thr Thr Tyr Asn Pro Ser Phe
50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Met Asp Pro Lys
210                 215                 220

Asp Asn Cys Ser Lys Asp Ala Asn Asp Thr Leu Leu Leu Gln Leu Thr
225                 230                 235                 240

Asn Thr Ser Ala Tyr Tyr Met Tyr Leu Leu Leu Leu Leu Lys Ser Val
                245                 250                 255

Val Tyr Phe Ala Ile Ile Thr Cys Cys Leu Leu Arg Arg Thr Ala Phe
            260                 265                 270

Cys Cys Asn Gly Glu Lys Ser
        275

<210> SEQ ID NO 31
<211> LENGTH: 284
<212> TYPE: PRT
<213> ORGANISM: Artificial Sequence
<220> FEATURE:
<223> OTHER INFORMATION: anti-AFP158/HLA-A*02:01-abTCR-5MD delta

<400> SEQUENCE: 31

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu

```
                35                  40                  45
Met Ile Tyr Asp Val Asn Asn Arg Pro Ser Glu Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Gly
                 85                  90                  95

Ser Arg Ala Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Glu Val Lys Thr Asp Ser Thr Asp
210                 215                 220

His Val Lys Pro Lys Glu Thr Glu Asn Thr Lys Gln Pro Ser Lys Ser
225                 230                 235                 240

Cys His Lys Pro Lys Ala Ile Val His Thr Glu Lys Val Asn Met Met
                245                 250                 255

Ser Leu Thr Val Leu Gly Leu Arg Met Leu Phe Ala Lys Thr Val Ala
            260                 265                 270

Val Asn Phe Leu Leu Thr Ala Lys Leu Phe Phe Leu
        275                 280

<210> SEQ ID NO 32
<211> LENGTH: 287
<212> TYPE: PRT
<213> ORGANISM: Artificial Sequence
<220> FEATURE:
<223> OTHER INFORMATION: anti-AFP158/HLA-A*02:01-abTCR-5MD gamma

<400> SEQUENCE: 32

Glu Val Gln Leu Val Gln Ser Gly Ala Glu Val Lys Lys Pro Gly Glu
 1                   5                  10                  15

Ser Leu Thr Ile Ser Cys Lys Ala Ser Gly Tyr Ser Phe Pro Asn Tyr
                 20                  25                  30

Trp Ile Thr Trp Val Arg Gln Met Ser Gly Gly Leu Glu Trp Met
             35                  40                  45

Gly Arg Ile Asp Pro Gly Asp Ser Tyr Thr Thr Tyr Asn Pro Ser Phe
         50                  55                  60

Gln Gly His Val Thr Ile Ser Ile Asp Lys Ser Thr Asn Thr Ala Tyr
 65                  70                  75                  80

Leu His Trp Asn Ser Leu Lys Ala Ser Asp Thr Ala Met Tyr Tyr Cys
                 85                  90                  95

Ala Arg Tyr Tyr Val Ser Leu Val Asp Ile Trp Gly Gln Gly Thr Leu
                100                 105                 110

Val Thr Val Ser Ser Ala Ser Thr Lys Gly Pro Ser Val Phe Pro Leu
```

```
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Pro Ile Lys Thr
210                 215                 220
Asp Val Ile Thr Met Asp Pro Lys Asp Asn Cys Ser Lys Asp Ala Asn
225                 230                 235                 240
Asp Thr Leu Leu Leu Gln Leu Thr Asn Thr Ser Ala Tyr Tyr Met Tyr
                245                 250                 255
Leu Leu Leu Leu Lys Ser Val Val Tyr Phe Ala Ile Ile Thr Cys
            260                 265                 270
Cys Leu Leu Arg Arg Thr Ala Phe Cys Cys Asn Gly Glu Lys Ser
        275                 280                 285
```

<210> SEQ ID NO 33
<211> LENGTH: 281
<212> TYPE: PRT
<213> ORGANISM: Artificial Sequence
<220> FEATURE:
<223> OTHER INFORMATION: anti-AFP158/HLA-A*02:01-abTCR-6 delta

<400> SEQUENCE: 33

```
Glu Val Gln Leu Val Gln Ser Gly Ala Glu Val Lys Lys Pro Gly Glu
1               5                   10                  15
Ser Leu Thr Ile Ser Cys Lys Ala Ser Gly Tyr Ser Phe Pro Asn Tyr
            20                  25                  30
Trp Ile Thr Trp Val Arg Gln Met Ser Gly Gly Gly Leu Glu Trp Met
        35                  40                  45
Gly Arg Ile Asp Pro Gly Asp Ser Tyr Thr Thr Tyr Asn Pro Ser Phe
    50                  55                  60
Gln Gly His Val Thr Ile Ser Ile Asp Lys Ser Thr Asn Thr Ala Tyr
65                  70                  75                  80
Leu His Trp Asn Ser Leu Lys Ala Ser Asp Thr Ala Met Tyr Tyr Cys
                85                  90                  95
Ala Arg Tyr Tyr Val Ser Leu Val Asp Ile Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
```

```
              195                 200                 205
Thr Lys Val Asp Lys Arg Val Glu Pro Lys Ser Cys Asp His Val Lys
    210                 215                 220

Pro Lys Glu Thr Glu Asn Thr Lys Gln Pro Ser Lys Ser Cys His Lys
225                 230                 235                 240

Pro Lys Ala Ile Val His Thr Glu Lys Val Asn Met Met Ser Leu Thr
                245                 250                 255

Val Leu Gly Leu Arg Met Leu Phe Ala Lys Thr Val Ala Val Asn Phe
            260                 265                 270

Leu Leu Thr Ala Lys Leu Phe Phe Leu
            275                 280

<210> SEQ ID NO 34
<211> LENGTH: 275
<212> TYPE: PRT
<213> ORGANISM: Artificial Sequence
<220> FEATURE:
<223> OTHER INFORMATION: anti-AFP158/HLA-A*02:01-abTCR-6 gamma

<400> SEQUENCE: 34

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Met Asp Pro Lys Asn Cys Ser
    210                 215                 220

Lys Asp Ala Asn Asp Thr Leu Leu Leu Gln Leu Thr Asn Thr Ser Ala
225                 230                 235                 240

Tyr Tyr Met Tyr Leu Leu Leu Leu Lys Ser Val Val Tyr Phe Ala
                245                 250                 255

Ile Ile Thr Cys Cys Leu Leu Arg Arg Thr Ala Phe Cys Cys Asn Gly
            260                 265                 270

Glu Lys Ser
```

<210> SEQ ID NO 35
<211> LENGTH: 288
<212> TYPE: PRT
<213> ORGANISM: Artificial Sequence
<220> FEATURE:
<223> OTHER INFORMATION: anti-AFP158/HLA-A*02:01-abTCR-6MD delta

<400> SEQUENCE: 35

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Gly Leu Glu Trp Met
        35                  40                  45

Gly Arg Ile Asp Pro Gly Asp Ser Tyr Thr Thr Tyr Asn Pro Ser Phe
    50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Met Leu Phe Ala
            260                 265                 270

Lys Thr Val Ala Val Asn Phe Leu Leu Thr Ala Lys Leu Phe Phe Leu
        275                 280                 285

<210> SEQ ID NO 36
<211> LENGTH: 283
<212> TYPE: PRT
<213> ORGANISM: Artificial Sequence
<220> FEATURE:
<223> OTHER INFORMATION: anti-AFP158/HLA-A*02:01-abTCR-6MD gamma

<400> SEQUENCE: 36

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Glu Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Pro Ile Lys Thr Asp Val Ile Thr
        210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
            275                 280

<210> SEQ ID NO 37
<211> LENGTH: 471
<212> TYPE: PRT
<213> ORGANISM: Artificial Sequence
<220> FEATURE:
<223> OTHER INFORMATION: anti-AFP158/HLA-A*02:01-scFv CAR

<400> SEQUENCE: 37

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Glu Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Gly
                85                  90                  95

```
Ser Arg Ala Val Phe Gly Gly Thr Lys Leu Thr Val Leu Gly Ser
            100                 105                 110

Arg Gly Gly Gly Ser Gly Gly Gly Ser Gly Gly Gly Ser
    115                 120                 125

Leu Glu Met Ala Glu Val Gln Leu Val Gln Ser Gly Ala Glu Val Lys
130                 135                 140

Lys Pro Gly Glu Ser Leu Thr Ile Ser Cys Lys Ala Ser Gly Tyr Ser
145                 150                 155                 160

Phe Pro Asn Tyr Trp Ile Thr Trp Val Arg Gln Met Ser Gly Gly Gly
                165                 170                 175

Leu Glu Trp Met Gly Arg Ile Asp Pro Gly Asp Ser Tyr Thr Thr Tyr
            180                 185                 190

Asn Pro Ser Phe Gln Gly His Val Thr Ile Ser Ile Asp Lys Ser Thr
        195                 200                 205

Asn Thr Ala Tyr Leu His Trp Asn Ser Leu Lys Ala Ser Asp Thr Ala
        210                 215                 220

Met Tyr Tyr Cys Ala Arg Tyr Tyr Val Ser Leu Val Asp Ile Trp Gly
225                 230                 235                 240

Gln Gly Thr Leu Val Thr Val Ser Ser Ala Ala Ile Glu Val Met
            245                 250                 255

Tyr Pro Pro Pro Tyr Leu Asp Asn Glu Lys Ser Asn Gly Thr Ile Ile
            260                 265                 270

His Val Lys Gly Lys His Leu Cys Pro Ser Pro Leu Phe Pro Gly Pro
                275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
            355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 38
<211> LENGTH: 117
<212> TYPE: PRT
<213> ORGANISM: Artificial Sequence
<220> FEATURE:
<223> OTHER INFORMATION: IgVH domain of anti-AFP158/HLA-A*02:01 antibody
```

<400> SEQUENCE: 38

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
                20                  25                  30

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
        50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
                100                 105                 110

Val Thr Val Ser Ser
            115

<210> SEQ ID NO 39
<211> LENGTH: 103
<212> TYPE: PRT
<213> ORGANISM: Homo sapiens
<220> FEATURE:
<223> OTHER INFORMATION: IgG1 CH1 domain

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
                100

<210> SEQ ID NO 40
<211> LENGTH: 110
<212> TYPE: PRT
<213> ORGANISM: Artificial Sequence
<220> FEATURE:
<223> OTHER INFORMATION: IgVL domain of AFP158/HLA-A*02:01 antibody

<400> SEQUENCE: 40

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Glu Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu
            100                 105                 110

<210> SEQ ID NO 41
<211> LENGTH: 106
<212> TYPE: PRT
<213> ORGANISM: Homo sapiens
<220> FEATURE:
<223> OTHER INFORMATION: IgCL domain

<400> SEQUENCE: 41

Gly Gln Pro Lys Ala Asn Pro Thr Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 42
<211> LENGTH: 301
<212> TYPE: PRT
<213> ORGANISM: Artificial Sequence
<220> FEATURE:
<223> OTHER INFORMATION: anti-CD19-abTCR-6MD delta

<400> SEQUENCE: 42

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Met Asp Ser Trp Gly Gln Gly Thr Leu Val Thr Val
            115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys

```
                145                 150                 155                 160
Asp Tyr Phe Pro Glu Pro Val Thr Val Ser Trp Asn Ser Gly Ala Leu
                    165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
                195                 200                 205

Gln Thr Tyr Ile Cys Asn Val Asn His Lys Pro Ser Asn Thr Lys Val
            210                 215                 220

Asp Lys Arg Val Glu Pro Lys Ser Cys Glu Val Lys Thr Asp Ser Thr
225                 230                 235                 240

Asp His Val Lys Pro Lys Glu Thr Glu Asn Thr Lys Gln Pro Ser Lys
                    245                 250                 255

Ser Cys His Lys Pro Lys Ala Ile Val His Thr Glu Lys Val Asn Met
                260                 265                 270

Met Ser Leu Thr Val Leu Gly Leu Arg Met Leu Phe Ala Lys Thr Val
                275                 280                 285

Ala Val Asn Phe Leu Leu Thr Ala Lys Leu Phe Phe Leu
                290                 295                 300

<210> SEQ ID NO 43
<211> LENGTH: 281
<212> TYPE: PRT
<213> ORGANISM: Artificial Sequence
<220> FEATURE:
<223> OTHER INFORMATION: anti-CD19-abTCR-6MD gamma

<400> SEQUENCE: 43

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
                85                  90                  95

Val Val Phe Gly Gly Gly Thr Lys Leu Thr Val Leu Gly Gln Pro Lys
                100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser Pro Ile Lys Thr Asp Val Ile Thr Met Asp
```

```
                210               215                220
Pro Lys Asp Asn Cys Ser Lys Asp Ala Asn Asp Thr Leu Leu Leu Gln
225                230                235                240

Leu Thr Asn Thr Ser Ala Tyr Tyr Met Tyr Leu Leu Leu Leu Leu Lys
                245                250                255

Ser Val Val Tyr Phe Ala Ile Ile Thr Cys Cys Leu Leu Arg Arg Thr
                260                265                270

Ala Phe Cys Cys Asn Gly Glu Lys Ser
                275                280
```

<210> SEQ ID NO 44
<211> LENGTH: 482
<212> TYPE: PRT
<213> ORGANISM: Artificial Sequence
<220> FEATURE:
<223> OTHER INFORMATION: anti-CD19-scFv CAR

<400> SEQUENCE: 44

```
Leu Pro Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
                85                  90                  95

Val Val Phe Gly Gly Gly Thr Lys Leu Thr Val Leu Gly Ser Arg Gly
                100                 105                 110

Gly Gly Gly Ser Gly Gly Gly Gly Ser Gly Gly Gly Gly Ser Leu Glu
            115                 120                 125

Met Ala Glu Val Gln Leu Val Gln Ser Gly Ala Glu Val Lys Lys Pro
130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
                180                 185                 190

Ser Phe Gln Gly Gln Val Thr Ile Ser Ala Asp Lys Ser Ile Ser Thr
            195                 200                 205

Ala Tyr Leu Gln Trp Ser Ser Leu Lys Ala Ser Asp Thr Ala Met Tyr
        210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser Ala Ala Ala Ile Glu Val Met Tyr Pro Pro Pro Tyr
                260                 265                 270

Leu Asp Asn Glu Lys Ser Asn Gly Thr Ile Ile His Val Lys Gly Lys
            275                 280                 285

His Leu Cys Pro Ser Pro Leu Phe Pro Gly Pro Ser Lys Pro Phe Trp
```

```
                290                 295                 300
Val Leu Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
                340                 345                 350

Arg Lys His Tyr Gln Pro Tyr Ala Pro Pro Arg Asp Phe Ala Ala Tyr
                355                 360                 365

Arg Ser Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 45
<211> LENGTH: 130
<212> TYPE: PRT
<213> ORGANISM: Artificial Sequence
<220> FEATURE:
<223> OTHER INFORMATION: IgVH domain of anti-CD19 antibody

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
                100                 105                 110

Trp Trp Tyr Asn Met Asp Ser Trp Gly Gln Gly Thr Leu Val Thr Val
            115                 120                 125

Ser Ser
    130

<210> SEQ ID NO 46
<211> LENGTH: 108
<212> TYPE: PRT
<213> ORGANISM: Artificial Sequence
```

<220> FEATURE:
<223> OTHER INFORMATION: IgVL domain of anti-CD19 antibody

<400> SEQUENCE: 46

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
                85                  90                  95

Val Val Phe Gly Gly Gly Thr Lys Leu Thr Val Leu
            100                 105

<210> SEQ ID NO 47
<211> LENGTH: 107
<212> TYPE: PRT
<213> ORGANISM: Homo sapiens
<220> FEATURE:
<223> OTHER INFORMATION: fragment of CD28

<400> SEQUENCE: 47

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 48
<211> LENGTH: 112
<212> TYPE: PRT
<213> ORGANISM: Homo sapiens
<220> FEATURE:
<223> OTHER INFORMATION: fragment of CD3-zeta

<400> SEQUENCE: 48

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

```
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 49
<211> LENGTH: 20
<212> TYPE: PRT
<213> ORGANISM: Homo sapiens
<220> FEATURE:
<223> OTHER INFORMATION: Signal peptide

<400> SEQUENCE: 49

Met Glu Thr Asp Thr Leu Leu Leu Trp Val Leu Leu Leu Trp Val Pro
  1               5                  10                  15

Gly Ser Thr Gly
             20

<210> SEQ ID NO 50
<211> LENGTH: 9
<212> TYPE: PRT
<213> ORGANISM: Artificial Sequence
<220> FEATURE:
<223> OTHER INFORMATION: HA tag

<400> SEQUENCE: 50

Tyr Pro Tyr Asp Val Pro Asp Tyr Ala
  1               5

<210> SEQ ID NO 51
<211> LENGTH: 22
<212> TYPE: PRT
<213> ORGANISM: Artificial Sequence
<220> FEATURE:
<223> OTHER INFORMATION: 3x Flag tag

<400> SEQUENCE: 51

Asp Tyr Lys Asp His Asp Gly Asp Tyr Lys Asp His Asp Ile Asp Tyr
  1               5                  10                  15

Lys Asp Asp Asp Asp Lys
             20

<210> SEQ ID NO 52
<211> LENGTH: 10
<212> TYPE: PRT
<213> ORGANISM: Artificial Sequence
<220> FEATURE:
<223> OTHER INFORMATION: myc tag

<400> SEQUENCE: 52

Glu Gln Lys Leu Ile Ser Glu Glu Asp Leu
  1               5                  10

<210> SEQ ID NO 53
<211> LENGTH: 9
<212> TYPE: PRT
<213> ORGANISM: Homo sapiens
<220> FEATURE:
<223> OTHER INFORMATION: AFP158

<400> SEQUENCE: 53

Phe Met Asn Lys Phe Ile Tyr Glu Ile
  1               5
```

<210> SEQ ID NO 54
<211> LENGTH: 281
<212> TYPE: PRT
<213> ORGANISM: Artificial Sequence
<220> FEATURE:
<223> OTHER INFORMATION: anti-CD19 clone 5 abTCR-6MD gamma

<400> SEQUENCE: 54

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Pro Ile Lys Thr Asp Val Ile Thr Met Asp
    210                 215                 220

Pro Lys Asp Asn Cys Ser Lys Asp Ala Asn Asp Thr Leu Leu Leu Gln
225                 230                 235                 240

Leu Thr Asn Thr Ser Ala Tyr Tyr Met Tyr Leu Leu Leu Leu Leu Lys
                245                 250                 255

Ser Val Val Tyr Phe Ala Ile Ile Thr Cys Cys Leu Leu Arg Arg Thr
            260                 265                 270

Ala Phe Cys Cys Asn Gly Glu Lys Ser
        275                 280

<210> SEQ ID NO 55
<211> LENGTH: 301
<212> TYPE: PRT
<213> ORGANISM: Artificial Sequence
<220> FEATURE:
<223> OTHER INFORMATION: anti-CD19 clone 5-9 abTCR-6MD delta

<400> SEQUENCE: 55

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr

```
            20                  25                  30
Trp Ile Gly Trp Val Arg Gln Met Pro Gly Lys Gly Leu Glu Trp Met
         35                  40                  45
Gly Ile Ile Tyr Pro Gly Asp Ser Asp Thr Arg Tyr Ser Pro Phe Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gln Val Trp Gly Trp Gln Gly Gly Met Tyr Pro Arg Ser Asn
             100                 105                 110
Trp Trp Tyr Asn Met Asp Ser Trp Gly Gln Gly Thr Leu Val Thr Val
         115                 120                 125
Ser Ser Ala Ser Thr Lys Gly Pro Ser Val Phe Pro Leu Ala Pro Ser
     130                 135                 140
Ser Lys Ser Thr Ser Gly Gly Thr Ala Ala Leu Gly Cys Leu Val Lys
145                 150                 155                 160
Asp Tyr Phe Pro Glu Pro Val Thr Val Ser Trp Asn Ser Gly Ala Leu
             165                 170                 175
Thr Ser Gly Val His Thr Phe Pro Ala Val Leu Gln Ser Ser Gly Leu
         180                 185                 190
Tyr Ser Leu Ser Ser Val Val Thr Val Pro Ser Ser Ser Leu Gly Thr
     195                 200                 205
Gln Thr Tyr Ile Cys Asn Val Asn His Lys Pro Ser Asn Thr Lys Val
 210                 215                 220
Asp Lys Arg Val Glu Pro Lys Ser Cys Glu Val Lys Thr Asp Ser Thr
225                 230                 235                 240
Asp His Val Lys Pro Lys Glu Thr Glu Asn Thr Lys Gln Pro Ser Lys
             245                 250                 255
Ser Cys His Lys Pro Lys Ala Ile Val His Thr Glu Lys Val Asn Met
         260                 265                 270
Met Ser Leu Thr Val Leu Gly Leu Arg Met Leu Phe Ala Lys Thr Val
     275                 280                 285
Ala Val Asn Phe Leu Leu Thr Ala Lys Leu Phe Phe Leu
 290                 295                 300

<210> SEQ ID NO 56
<211> LENGTH: 301
<212> TYPE: PRT
<213> ORGANISM: Artificial Sequence
<220> FEATURE:
<223> OTHER INFORMATION: anti-CD19 clone 5-13 abTCR-6MD delta

<400> SEQUENCE: 56

Glu Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Thr Ser Tyr
             20                  25                  30
Trp Ile Gly Trp Val Arg Gln Met Pro Gly Lys Gly Leu Glu Trp Met
         35                  40                  45
Gly Ile Ile Tyr Pro Gly Asp Ser Asp Thr Arg Tyr Ser Pro Ser Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
```

```
                         85                  90                  95
Ala Arg Gln Val Trp Gly Trp Gln Gly Gly Met Tyr Pro Arg Ser Asn
                100                 105                 110

Trp Trp Tyr Asn Leu Asp Ser Trp Gly Gln Gly Thr Leu Val Thr Val
                115                 120                 125

Ser Ser Ala Ser Thr Lys Gly Pro Ser Val Phe Pro Leu Ala Pro Ser
            130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
                195                 200                 205

Gln Thr Tyr Ile Cys Asn Val Asn His Lys Pro Ser Asn Thr Lys Val
                210                 215                 220

Asp Lys Arg Val Glu Pro Lys Ser Cys Glu Val Lys Thr Asp Ser Thr
225                 230                 235                 240

Asp His Val Lys Pro Lys Glu Thr Glu Asn Thr Lys Gln Pro Ser Lys
                245                 250                 255

Ser Cys His Lys Pro Lys Ala Ile Val His Thr Glu Lys Val Asn Met
                260                 265                 270

Met Ser Leu Thr Val Leu Gly Leu Arg Met Leu Phe Ala Lys Thr Val
                275                 280                 285

Ala Val Asn Phe Leu Leu Thr Ala Lys Leu Phe Phe Leu
                290                 295                 300

<210> SEQ ID NO 57
<211> LENGTH: 108
<212> TYPE: PRT
<213> ORGANISM: Artificial Sequence
<220> FEATURE:
<223> OTHER INFORMATION: IgVL domain of anti-CD19 antibody clone 5

<400> SEQUENCE: 57

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu
                100                 105

<210> SEQ ID NO 58
<211> LENGTH: 130
<212> TYPE: PRT
<213> ORGANISM: Artificial Sequence
<220> FEATURE:
<223> OTHER INFORMATION: IgVH domain of anti-CD19 antibody clone 5-9
```

<400> SEQUENCE: 58

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Phe Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Met Asp Ser Trp Gly Gln Gly Thr Leu Val Thr Val
        115                 120                 125

Ser Ser
130

<210> SEQ ID NO 59
<211> LENGTH: 130
<212> TYPE: PRT
<213> ORGANISM: Artificial Sequence
<220> FEATURE:
<223> OTHER INFORMATION: IgVH domain of anti-CD19 antibody clone 5-13

<400> SEQUENCE: 59

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Leu Asp Ser Trp Gly Gln Gly Thr Leu Val Thr Val
        115                 120                 125

Ser Ser
130

<210> SEQ ID NO 60
<211> LENGTH: 101
<212> TYPE: PRT
<213> ORGANISM: Homo sapiens
<220> FEATURE:
<223> OTHER INFORMATION: IgG2-0C CH1

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 61
<211> LENGTH: 102
<212> TYPE: PRT
<213> ORGANISM: Homo sapiens
<220> FEATURE:
<223> OTHER INFORMATION: IgG2-1C CH1

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys
            100

<210> SEQ ID NO 62
<211> LENGTH: 103
<212> TYPE: PRT
<213> ORGANISM: Homo sapiens
<220> FEATURE:
<223> OTHER INFORMATION: IgG2-2C CH1

<400> SEQUENCE: 62

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys

<210> SEQ ID NO 63
<211> LENGTH: 103
<212> TYPE: PRT
<213> ORGANISM: Homo sapiens
<220> FEATURE:
<223> OTHER INFORMATION: IgG3 CH1

<400> SEQUENCE: 63

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro
            100

<210> SEQ ID NO 64
<211> LENGTH: 103
<212> TYPE: PRT
<213> ORGANISM: Homo sapiens
<220> FEATURE:
<223> OTHER INFORMATION: IgG4 CH1

<400> SEQUENCE: 64

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly
            100

<210> SEQ ID NO 65
<211> LENGTH: 121
<212> TYPE: PRT
<213> ORGANISM: Homo sapiens
<220> FEATURE:
<223> OTHER INFORMATION: IgA1 CH1

<400> SEQUENCE: 65

Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
             20                  25                  30

```
Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser
            115                 120
```

```
<210> SEQ ID NO 66
<211> LENGTH: 108
<212> TYPE: PRT
<213> ORGANISM: Homo sapiens
<220> FEATURE:
<223> OTHER INFORMATION: IgA2 CH1

<400> SEQUENCE: 66

Ala Ser Pro Thr Ser Pro Lys Val Phe Pro Leu Ser Leu Asp Ser Thr
  1               5                  10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Pro Asp Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Pro Pro Pro
                100                 105
```

```
<210> SEQ ID NO 67
<211> LENGTH: 159
<212> TYPE: PRT
<213> ORGANISM: Homo sapiens
<220> FEATURE:
<223> OTHER INFORMATION: IgD CH1

<400> SEQUENCE: 67

Ala Pro Thr Lys Ala Pro Asp Val Phe Pro Ile Ile Ser Gly Cys Arg
  1               5                  10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
 50                  55                  60

Met Thr Ser Ser Gln Leu Ser Thr Pro Leu Gln Trp Arg Gln Gly
 65                  70                  75                  80

Glu Tyr Lys Cys Val Val Gln His Thr Ala Ser Lys Ser Lys Lys Glu
                 85                  90                  95

Ile Phe Arg Trp Pro Glu Ser Pro Lys Ala Gln Ala Ser Ser Val Pro
```

```
                100             105             110
Thr Ala Gln Pro Gln Ala Glu Gly Ser Leu Ala Lys Ala Thr Thr Ala
            115                 120                 125
Pro Ala Thr Thr Arg Asn Thr Gly Arg Gly Gly Glu Glu Lys Lys Lys
            130                 135                 140
Glu Lys Glu Lys Glu Glu Gln Glu Glu Arg Glu Thr Lys Thr Pro
145                 150                 155
```

<210> SEQ ID NO 68
<211> LENGTH: 103
<212> TYPE: PRT
<213> ORGANISM: Homo sapiens
<220> FEATURE:
<223> OTHER INFORMATION: IgE CH1

<400> SEQUENCE: 68

```
Ala Ser Thr Gln Ser Pro Ser Val Phe Pro Leu Thr Arg Cys Cys Lys
  1               5                  10                  15
Asn Ile Pro Ser Asn Ala Thr Ser Val Thr Leu Gly Cys Leu Ala Thr
             20                  25                  30
Gly Tyr Phe Pro Glu Pro Val Met Val Thr Trp Asp Thr Gly Ser Leu
         35                  40                  45
Asn Gly Thr Thr Met Thr Leu Pro Ala Thr Thr Leu Thr Leu Ser Gly
     50                  55                  60
His Tyr Ala Thr Ile Ser Leu Leu Thr Val Ser Gly Ala Trp Ala Lys
 65                  70                  75                  80
Gln Met Phe Thr Cys Arg Val Ala His Thr Pro Ser Ser Thr Asp Trp
                 85                  90                  95
Val Asp Asn Lys Thr Phe Ser
            100
```

<210> SEQ ID NO 69
<211> LENGTH: 104
<212> TYPE: PRT
<213> ORGANISM: Homo sapiens
<220> FEATURE:
<223> OTHER INFORMATION: IgM CH1

<400> SEQUENCE: 69

```
Gly Ser Ala Ser Ala Pro Thr Leu Phe Pro Leu Val Ser Cys Glu Asn
  1               5                  10                  15
Ser Pro Ser Asp Thr Ser Ser Val Ala Val Gly Cys Leu Ala Gln Asp
             20                  25                  30
Phe Leu Pro Asp Ser Ile Thr Leu Ser Trp Lys Tyr Lys Asn Asn Ser
         35                  40                  45
Asp Ile Ser Ser Thr Arg Gly Phe Pro Ser Val Leu Arg Gly Gly Lys
     50                  55                  60
Tyr Ala Ala Thr Ser Gln Val Leu Leu Pro Ser Lys Asp Val Met Gln
 65                  70                  75                  80
Gly Thr Asp Glu His Val Val Cys Lys Val Gln His Pro Asn Gly Asn
                 85                  90                  95
Lys Glu Lys Asn Val Pro Leu Pro
            100
```

<210> SEQ ID NO 70
<211> LENGTH: 41
<212> TYPE: PRT
<213> ORGANISM: Homo sapiens
<220> FEATURE:

<223> OTHER INFORMATION: CD28 co-stimulatory fragment

<400> SEQUENCE: 70

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 71
<211> LENGTH: 42
<212> TYPE: PRT
<213> ORGANISM: Homo sapiens
<220> FEATURE:
<223> OTHER INFORMATION: 4-1BB co-stimulatory fragment

<400> SEQUENCE: 71

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 72
<211> LENGTH: 117
<212> TYPE: PRT
<213> ORGANISM: Artificial Sequence
<220> FEATURE:
<223> OTHER INFORMATION: IgVH domain of anti-NY-ESO-1/HLA-A*02:01
      antibody clone 35

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ser Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Tyr
    50                  55                  60

Gln Gly Arg Val Thr Leu Ser Ala Asp Lys Ser Thr Ser Thr Ser Tyr
65                  70                  75                  80

Met Glu Leu Asn Ser Leu Arg Ser Glu Asp Thr Ala Val Tyr Tyr Cys
                85                  90                  95

Ala Arg Asp Trp Ser Tyr Ser Ile Asp Tyr Trp Gly Gln Gly Thr Leu
            100                 105                 110

Val Thr Val Ser Ser
        115

<210> SEQ ID NO 73
<211> LENGTH: 111
<212> TYPE: PRT
<213> ORGANISM: Artificial Sequence
<220> FEATURE:
<223> OTHER INFORMATION: IgVL domain of anti-NY-ESO-1/HLA-A*02:01
      antibody clone 35

<400> SEQUENCE: 73

Gln Ser Val Val Thr Gln Pro Pro Ser Val Ser Ala Ala Pro Gly Gln

```
                1               5                   10                  15
            Lys Val Thr Ile Ser Cys Ser Gly Ser Ser Asn Ile Gly Asn Asn
                            20                  25                  30

Tyr Val Ser Trp Tyr Gln Gln Leu Pro Gly Thr Ala Pro Lys Leu Leu
                            35                  40                  45

Ile Tyr Asp Asn Asn Lys Arg Pro Ser Gly Ile Pro Asp Arg Phe Ser
                        50                  55                  60

Gly Ser Lys Ser Gly Thr Ser Ala Thr Leu Gly Ile Thr Gly Leu Gln
             65                 70                  75                  80

Thr Gly Asp Glu Ala Asp Tyr Tyr Cys Gly Thr Trp Asp Ser Ser Leu
                            85                  90                  95

Ser Ala Trp Val Phe Gly Gly Gly Thr Lys Leu Thr Val Leu Gly
                        100                 105                 110

<210> SEQ ID NO 74
<211> LENGTH: 21
<212> TYPE: PRT
<213> ORGANISM: Artificial Sequence
<220> FEATURE:
<223> OTHER INFORMATION: scFv linker

<400> SEQUENCE: 74

Ser Arg Gly Gly Gly Gly Ser Gly Gly Gly Ser Gly Gly Gly Gly
             1              5                   10                  15

Ser Leu Glu Met Ala
                        20

<210> SEQ ID NO 75
<211> LENGTH: 284
<212> TYPE: PRT
<213> ORGANISM: Artificial Sequence
<220> FEATURE:
<223> OTHER INFORMATION: anti-CD19-cTCR delta

<400> SEQUENCE: 75

Glu Val Gln Leu Val Gln Ser Gly Ala Glu Val Lys Lys Pro Gly Glu
             1              5                   10                  15

Ser Leu Lys Ile Ser Cys Lys Gly Ser Gly Tyr Ser Phe Thr Ser Tyr
                            20                  25                  30

Trp Ile Gly Trp Val Arg Gln Met Pro Gly Lys Gly Leu Glu Trp Met
                            35                  40                  45

Gly Ile Ile Tyr Pro Gly Asp Ser Asp Thr Arg Tyr Ser Pro Ser Phe
                        50                  55                  60

Gln Gly Gln Val Thr Ile Ser Ala Asp Lys Ser Ile Ser Thr Ala Tyr
             65                 70                  75                  80

Leu Gln Trp Ser Ser Leu Lys Ala Ser Asp Thr Ala Met Tyr Tyr Cys
                            85                  90                  95

Ala Arg Gln Val Trp Gly Trp Gln Gly Gly Met Tyr Pro Arg Ser Asn
                        100                 105                 110

Trp Trp Tyr Asn Leu Asp Ser Trp Gly Gln Gly Thr Leu Val Thr Val
                        115                 120                 125

Ser Ser Arg Ser Gln Pro His Thr Lys Pro Ser Val Phe Val Met Lys
                        130                 135                 140

Asn Gly Thr Asn Val Ala Cys Leu Val Lys Glu Phe Tyr Pro Lys Asp
             145                150                 155                 160

Ile Arg Ile Asn Leu Val Ser Ser Lys Lys Ile Thr Glu Phe Asp Pro
                            165                 170                 175
```

Ala Ile Val Ile Ser Pro Ser Gly Lys Tyr Asn Ala Val Lys Leu Gly
            180                 185                 190

Lys Tyr Glu Asp Ser Asn Ser Val Thr Cys Ser Val Gln His Asp Asn
        195                 200                 205

Lys Thr Val His Ser Thr Asp Phe Glu Val Lys Thr Asp Ser Thr Asp
    210                 215                 220

His Val Lys Pro Lys Glu Thr Glu Asn Thr Lys Gln Pro Ser Lys Ser
225                 230                 235                 240

Cys His Lys Pro Lys Ala Ile Val His Thr Glu Lys Val Asn Met Met
                245                 250                 255

Ser Leu Thr Val Leu Gly Leu Arg Met Leu Phe Ala Lys Thr Val Ala
            260                 265                 270

Val Asn Phe Leu Leu Thr Ala Lys Leu Phe Phe Leu
        275                 280

<210> SEQ ID NO 76
<211> LENGTH: 282
<212> TYPE: PRT
<213> ORGANISM: Artificial Sequence
<220> FEATURE:
<223> OTHER INFORMATION: anti-CD19-cTCR gamma

<400> SEQUENCE: 76

Leu Pro Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Tyr
                 85                  90                  95

Val Val Phe Gly Gly Gly Thr Lys Leu Thr Val Leu Gly Asp Lys Gln
            100                 105                 110

Leu Asp Ala Asp Val Ser Pro Lys Pro Thr Ile Phe Leu Pro Ser Ile
        115                 120                 125

Ala Glu Thr Lys Leu Gln Lys Ala Gly Thr Tyr Leu Cys Leu Leu Glu
    130                 135                 140

Lys Phe Phe Pro Asp Val Ile Lys Ile His Trp Gln Glu Lys Lys Ser
145                 150                 155                 160

Asn Thr Ile Leu Gly Ser Gln Glu Gly Asn Thr Met Lys Thr Asn Asp
                165                 170                 175

Thr Tyr Met Lys Phe Ser Trp Leu Thr Val Pro Glu Lys Ser Leu Asp
            180                 185                 190

Lys Glu His Arg Cys Ile Val Arg His Glu Asn Asn Lys Asn Gly Val
        195                 200                 205

Asp Gln Glu Ile Ile Phe Pro Pro Ile Lys Thr Asp Val Ile Thr Met
    210                 215                 220

Asp Pro Lys Asp Asn Cys Ser Lys Asp Ala Asn Asp Thr Leu Leu Leu
225                 230                 235                 240

Gln Leu Thr Asn Thr Ser Ala Tyr Tyr Met Tyr Leu Leu Leu Leu Leu
                245                 250                 255

```
Lys Ser Val Val Tyr Phe Ala Ile Ile Thr Cys Cys Leu Leu Arg Arg
            260                 265                 270

Thr Ala Phe Cys Cys Asn Gly Glu Lys Ser
            275                 280

<210> SEQ ID NO 77
<211> LENGTH: 142
<212> TYPE: PRT
<213> ORGANISM: Homo sapiens
<220> FEATURE:
<223> OTHER INFORMATION: TCRalpha constant domain

<400> SEQUENCE: 77

Pro Asn Ile Gln Asn Pro Asp Pro Ala Val Tyr Gln Leu Arg Asp Ser
  1               5                  10                  15

Lys Ser Ser Asp Lys Ser Val Cys Leu Phe Thr Asp Phe Asp Ser Gln
             20                  25                  30

Thr Asn Val Ser Gln Ser Lys Asp Ser Asp Val Tyr Ile Thr Asp Lys
         35                  40                  45

Thr Val Leu Asp Met Arg Ser Met Asp Phe Lys Ser Asn Ser Ala Val
     50                  55                  60

Ala Trp Ser Asn Lys Ser Asp Phe Ala Cys Ala Asn Ala Phe Asn Asn
 65                  70                  75                  80

Ser Ile Ile Pro Glu Asp Thr Phe Phe Pro Ser Pro Glu Ser Ser Cys
                 85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 78
<211> LENGTH: 177
<212> TYPE: PRT
<213> ORGANISM: Homo sapiens
<220> FEATURE:
<223> OTHER INFORMATION: TCRbeta constant domain

<400> SEQUENCE: 78

Glu Asp Leu Asn Lys Val Phe Pro Pro Glu Val Ala Val Phe Glu Pro
  1               5                  10                  15

Ser Glu Ala Glu Ile Ser His Thr Gln Lys Ala Thr Leu Val Cys Leu
             20                  25                  30

Ala Thr Gly Phe Phe Pro Asp His Val Glu Leu Ser Trp Trp Val Asn
         35                  40                  45

Gly Lys Glu Val His Ser Gly Val Ser Thr Asp Pro Gln Pro Leu Lys
     50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140
```

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 79
<211> LENGTH: 153
<212> TYPE: PRT
<213> ORGANISM: Homo sapiens
<220> FEATURE:
<223> OTHER INFORMATION: TCRdelta constant domain

<400> SEQUENCE: 79

Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
                20                  25                  30

Asn Leu Val Ser Ser Lys Lys Ile Thr Glu Phe Asp Pro Ala Ile Val
            35                  40                  45

Ile Ser Pro Ser Gly Lys Tyr Asn Ala Val Lys Leu Gly Lys Tyr Glu
50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
            100                 105                 110

Pro Lys Ala Ile Val His Thr Glu Lys Val Asn Met Met Ser Leu Thr
        115                 120                 125

Val Leu Gly Leu Arg Met Leu Phe Ala Lys Thr Val Ala Val Asn Phe
130                 135                 140

Leu Leu Thr Ala Lys Leu Phe Phe Leu
145                 150

<210> SEQ ID NO 80
<211> LENGTH: 173
<212> TYPE: PRT
<213> ORGANISM: Homo sapiens
<220> FEATURE:
<223> OTHER INFORMATION: TCRgamma constant domain

<400> SEQUENCE: 80

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
                20                  25                  30

Leu Leu Glu Lys Phe Phe Pro Asp Val Ile Lys Ile His Trp Gln Glu
            35                  40                  45

Lys Lys Ser Asn Thr Ile Leu Gly Ser Gln Glu Gly Asn Thr Met Lys
50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

```
Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170
```

<210> SEQ ID NO 81
<211> LENGTH: 271
<212> TYPE: PRT
<213> ORGANISM: Artificial Sequence
<220> FEATURE:
<223> OTHER INFORMATION: anti-AFP158/HLA-A*02:01-cTCR delta

<400> SEQUENCE: 81

```
Glu Val Gln Leu Val Gln Ser Gly Ala Glu Val Lys Lys Pro Gly Glu
  1               5                  10                  15

Ser Leu Thr Ile Ser Cys Lys Ala Ser Gly Tyr Ser Phe Pro Asn Tyr
             20                  25                  30

Trp Ile Thr Trp Val Arg Gln Met Ser Gly Gly Leu Glu Trp Met
         35                  40                  45

Gly Arg Ile Asp Pro Gly Asp Ser Tyr Thr Thr Tyr Asn Pro Ser Phe
 50                  55                  60

Gln Gly His Val Thr Ile Ser Ile Asp Lys Ser Thr Asn Thr Ala Tyr
 65                  70                  75                  80

Leu His Trp Asn Ser Leu Lys Ala Ser Asp Thr Ala Met Tyr Tyr Cys
                 85                  90                  95

Ala Arg Tyr Tyr Val Ser Leu Val Asp Ile Trp Gly Gln Gly Thr Leu
            100                 105                 110

Val Thr Val Ser Ser Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser Cys His Lys Pro Lys Ala Ile Val His Thr Glu Lys Val
225                 230                 235                 240

Asn Met Met Ser Leu Thr Val Leu Gly Leu Arg Met Leu Phe Ala Lys
                245                 250                 255

Thr Val Ala Val Asn Phe Leu Leu Thr Ala Lys Leu Phe Phe Leu
            260                 265                 270
```

<210> SEQ ID NO 82
<211> LENGTH: 283
<212> TYPE: PRT
<213> ORGANISM: Artificial Sequence
<220> FEATURE:
<223> OTHER INFORMATION: anti-AFP158/HLA-A*02:01-cTCR gamma

<400> SEQUENCE: 82

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Asp Lys
            100                 105                 110

Gln Leu Asp Ala Asp Val Ser Pro Lys Pro Thr Ile Phe Leu Pro Ser
        115                 120                 125

Ile Ala Glu Thr Lys Leu Gln Lys Ala Gly Thr Tyr Leu Cys Leu Leu
    130                 135                 140

Glu Lys Phe Phe Pro Asp Val Ile Lys Ile His Trp Gln Glu Lys Lys
145                 150                 155                 160

Ser Asn Thr Ile Leu Gly Ser Gln Glu Gly Asn Thr Met Lys Thr Asn
                165                 170                 175

Asp Thr Tyr Met Lys Phe Ser Trp Leu Thr Val Pro Glu Lys Ser Leu
            180                 185                 190

Asp Lys Glu His Arg Cys Ile Val Arg His Glu Asn Asn Lys Asn Gly
        195                 200                 205

Val Asp Gln Glu Ile Ile Phe Pro Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
        275                 280
```